United States Patent
Sugawara

(10) Patent No.: US 7,863,408 B2
(45) Date of Patent: Jan. 4, 2011

(54) BODY FLUID COMPATIBLE AND BIOCOMPATIBLE RESIN

(75) Inventor: Shuichi Sugawara, Fuji (JP)

(73) Assignee: Asahi Kasei Kabushiki Kaisha, Osaka (JP)

(*) Notice: Subject to any disclaimer, the term of this patent is extended or adjusted under 35 U.S.C. 154(b) by 511 days.

(21) Appl. No.: 11/028,185

(22) Filed: Jan. 4, 2005

(65) Prior Publication Data

US 2005/0113560 A1    May 26, 2005

Related U.S. Application Data

(63) Continuation-in-part of application No. PCT/JP03/08565, filed on Jul. 4, 2003.

(30) Foreign Application Priority Data

Jul. 5, 2002    (JP)    ............................. 2002-197308
Dec. 20, 2002   (JP)    ............................. 2002-369933

(51) Int. Cl.
    *C08G 65/34*    (2006.01)
(52) U.S. Cl. .................. 528/425; 424/78.27; 424/85.2; 424/426; 525/54.1; 528/245; 527/205
(58) Field of Classification Search ................ 528/220, 528/425, 245; 424/78.27, 85.2, 426; 525/54.1; 527/205
    See application file for complete search history.

(56) References Cited

U.S. PATENT DOCUMENTS

| | | | | |
|---|---|---|---|---|
| 4,125,369 A | * | 11/1978 | Reder-James et al. | ........ 8/115.6 |
| 5,811,510 A | * | 9/1998 | Papisov | ...................... 528/230 |
| 2002/0142039 A1 | * | 10/2002 | Claude | ...................... 424/486 |

FOREIGN PATENT DOCUMENTS

| | | |
|---|---|---|
| JP | 4-108819 A | 4/1992 |
| JP | 2806510 B2 | 7/1998 |
| JP | 2001-533 A | 1/2001 |
| WO | WO96/32419 A1 | 10/1996 |
| WO | WO02/22739 A1 | 3/2002 |

OTHER PUBLICATIONS

Dimitrov et al (Polymer, 43(2002), p. 7171-7178).*
Dworak et al (Reactive and functional polymers, 42(1999), 31-36).*
STIC sturcture search, USPTO.*
www.peg-drug.com/pegulation.html, 2006.*
STIC structure search, USPTO, Jun. 4, 2007.*
Maeda, H., Advanced Drug Delivery Reviews, vol. 6, pp. 181-202, (1991).
Vandenberg, E. J., J. Polym. Sci. Polym. Chem. Ed., vol. 23, pp. 915-949, (1985).
Vandenberg et al., J. Polym. Sci., Part A, vol. 27, pp. 3113-3149, (1989).
Hase et al., J. Biochem., vol. 98, pp. 863-874, (1985).
Larm et al., Carbohyd. Res., vol. 20, pp. 39-48, (1971).
English language Abstract of JP 4-152952 (May 26, 1992).

* cited by examiner

*Primary Examiner*—James Seidleck
*Assistant Examiner*—Gregory Listvoyb
(74) *Attorney, Agent, or Firm*—Birch, Stewart, Kolasch & Birch, LLP

(57) ABSTRACT

A body fluid compatible and biocompatible resin for use in a medical treatment involving a contact of said resin with at least one member selected from the group consisting of a body fluid and a biological tissue, which comprises at least one substituted oxyalkylene polymer having a weight average molecular weight of from 1,000 to 1,000,000 and represented by the following formula (1):

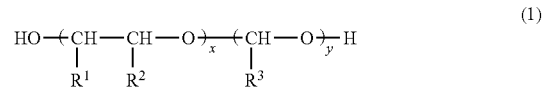

(1)

wherein each of $R^1$, $R^2$ and $R^3$ independently represents a hydrogen atom or a —$CH_2R^4$ group, and each $R^4$ independently represents a hydroxyl group or a —$OR^5$ group (wherein $R^5$ represents a group selected from the group consisting of a $C_1$-$C_{10}$ aliphatic hydrocarbyl group, a $C_6$-$C_{10}$ aryl group, a —$R^6COOH$ group and a derivative thereof, and a —$CH_2$—O—$CH_2$—CH(OH)—$CH_2$—$OR^7$ group, wherein $R^6$ represents a $C_1$-$C_{10}$ aliphatic hydrocarbylene group and $R^7$ represents a $C_1$-$C_{10}$ aliphatic hydrocarbyl group or a $C_6$-$C_{10}$ aryl group), provided that all of $R^1$, $R^2$, and $R^3$ are not simultaneously hydrogen atoms; and $10 \leq x \leq 10,000$ and $0 \leq y \leq 10,000$.

3 Claims, 65 Drawing Sheets

BODY FLUID COMPATIBLE AND BIOCOMPATIBLE RESIN

This application is a Continuation-In-Part of copending Application No. PCT/JP03/08565 filed on Jul. 4, 2003. This Nonprovisional application claims priority under 35 U.S.C. §119(a) on Patent Application No(s). 2002-197308 & 2002-369933 filed in Japan on Jul. 5, 2002 & Dec. 20, 2002; respectively, the entire contents of which are hereby incorporated by reference and for which priority is claimed under 35 U.S.C. §120.

BACKGROUND OF THE INVENTION

1. Field of the Invention

The present invention relates to a body fluid compatible and biocompatible resin. More particularly, the present invention is concerned with a body fluid compatible and biocompatible resin for use in a medical treatment involving a contact of the resin with at least one member selected from the group consisting of a body fluid and a biological tissue, which comprises at least one substituted oxyalkylene polymer having a specific structure and having a weight average molecular weight of from 1,000 to 1,000,000. The body fluid compatible and biocompatible resin of the present invention is advantageous not only in that the adhesion of biological substances (such as a biological tissue, a cell and a platelet) to the resin can be suppressed, and the activation of a platelet, a complement and the like by the resin can also be suppressed, but also in that the resin of the present invention is highly safe for living organisms and remains stable in a body fluid for a long time. Therefore, the body fluid compatible and biocompatible resin of the present invention can be advantageously used as an ingredient, a molding material or a coating material in the production of various biological and medical products. Specific examples of biological and medical products include a membrane for an artificial kidney, a plasma separation membrane, a membrane for an artificial lung, an artificial blood vessel, an anti-adhesion membrane, a wound dressing, an artificial skin, a virus removal membrane and a leukocyte removal membrane.

Further, the resin of the present invention is amphipathic and, hence, is soluble not only in water but also in organic solvents, such as an alcohol, an ether, an ester and an aromatic hydrocarbon. Therefore, the resin of the present invention can be used in a wide variety of medical application fields. For example, the resin of the present invention in the form of a film can be used for covering external wounds, such as bedsore, burn and ulcer, and can also be used for covering wounds caused by destruction of internal tissues, such as a corium, a hypoderm, a muscle, a tendon, an articulation and a bone. Further, by utilizing the hydrophilicity and moisture retention property of the resin, the resin of the present invention can be used for producing cosmetics, and can also be used for fiber treatments. Furthermore, by utilizing the ability of the resin to prevent adsorption of a protein thereto as well as the hydrophilicity of the resin, the resin of the present invention can also be used as a component of a contact lens washing solution.

As applications other than mentioned above, for example, the resin of the present invention can be used for various treatments of a polypeptide and a protein which are derived from organisms, such as a human, a mammal, a reptile, a microbe and an insect, wherein the treatments include a separation, a purification, a concentration, a filtration, a desalting/concentration and the like. Further, the resin of the present invention can also be used for treating a medicine, an active pharmaceutical ingredient of a medicine and a raw material for a medicine, which contain the above-mentioned polypeptide or protein, wherein the treatments include a separation, a purification, a concentration, a filtration, a desalting/concentration and the like. Furthermore, the resin of the present invention can also be used as an additive for raw materials for producing an equipment used for the above-mentioned treatments or as a coating material for such an equipment.

When a compound having a pharmaceutical activity is bonded to the resin of the present invention through an amino acid or a peptide (i.e., the so-called "linker") to form a drug complex, such a drug complex enables the delivery of the compound having a pharmaceutical activity to a target tissue without being recognized by a biological tissue when the drug complex is administered to a living body.

2. Prior Art

In recent years, studies have been made on polymeric materials having body fluid compatibility and/or biocompatibility (hereinafter, referred to as "body fluid compatible/biocompatible materials"), and the development of the application of body fluid compatible/biocompatible materials in the fields of various biological and medical products (such as a membrane for an artificial kidney, a plasma separation membrane, a catheter, a membrane for an artificial lung, an artificial blood vessel, an anti-adhesion membrane, a wound dressing and an artificial skin) is expected. In the fields of the above-exemplified biological and medical products, the body fluid compatible/biocompatible material (e.g., a synthetic polymeric material), which is foreign to a living body, is contacted with a biological tissue and/or a body fluid during the use thereof. Therefore, the body fluid compatible/biocompatible material is required to possess a satisfactory body fluid compatibility and/or biocompatibility such that interaction and/or interference is not caused between the body fluid compatible/biocompatible material and a biological tissue and/or a body fluid.

The level of body fluid compatibility and/or biocompatibility which is required of a body fluid compatible/biocompatible material depends on the use of the material and the method for using the material. Further, when a body fluid compatible/biocompatible material is used, for example, as a material which is contacted with blood, such a body fluid compatible/biocompatible material is required to have the abilities to suppress the adsorption of a protein thereto, the blood coagulation, the adhesion of a platelet thereto, the activation of a platelet and a complement, and the like.

For example, Unexamined Japanese Patent Application Laid-Open Specification No. Hei 4-152952 describes an acrylate-type biocompatible material. However, conventional acrylate-type biocompatible materials pose problems in that the monomer used as a raw material is toxic, so that the acrylate-type biocompatible material exhibits toxicity when the monomer is not completely removed from the material, and in that the acrylate-type biocompatible material which is a polymeric material cannot be decomposed at all in a living body, so that the material remains and is accumulated in a living body.

Further, a polyalkoxyalkyl (meth)acrylate, which is one of the above-mentioned acrylate-type biocompatible materials, is known to have the abilities to suppress the adhesion of a platelet thereto, and the activation of a platelet and a complement, thereby exhibiting excellent blood compatibility. However, when the polyalkoxyalkyl (meth)acrylate is accumulated in an organ, such as a liver or a spleen, there is a danger that the organ is damaged by the accumulated polyalkoxyalkyl (meth)acrylate. Specifically, there is a danger that the polyalkoxyalkyl (meth)acrylate is separated from a substrate (e.g., by delamination of a polyalkoxyalkyl (meth)acrylate film from a substrate), so that the separated polyalkoxyalkyl (meth)acrylate is released into a body fluid and accumulated in an organ, such as a liver or a spleen. Conventionally, with respect to the polyalkoxyalkyl (meth)acrylate, only the abilities thereof to suppress the adhesion and activation of a platelet and the activation of a complement have been considered important, and the above-mentioned danger of damage to an organ has not been considered seriously. In an attempt to solve this problem, Unexamined Japanese Patent Application Laid-Open Specification No. 2001-000533 proposes a polyalkoxyalkyl (meth)acrylate product containing a specific amount of a polyalkoxyalkyl (meth)acrylate molecule having a specific high molecular weight. However, even such a polyalkoxyalkyl (meth)acrylate product is not free from the above-mentioned danger of damage to an organ and, hence, is not suitable as a biocompatible material.

WO02/22739 proposes to use an alkylene oxide copolymer in a medical equipment by utilizing the lubricity of an alkylene oxide copolymer, wherein the lubricity is exhibited due to the hydrophilicity and swelling property of the copolymer. More specifically, in this patent document, a medical equipment, a catheter and an implant are mentioned side-by-side with shaving devices and the like as examples of the use of an alkylene oxide copolymer. However, in the working example of this patent document in which the above-mentioned copolymer is synthesized, only the lubricity of the copolymer is evaluated, and there is no teaching or suggestion about the body fluid compatibility and biocompatibility of the copolymer.

Further, as an example of biodegradable and biocompatible polyacetal polymers, Japanese Patent Application prior-to-examination Publication (Tokuhyo) No. Hei 11-503481 describes the production of a polyacetal polymer obtained from an oxidized polysaccharide. This patent document describes that the polyacetal polymer has biodegradability and biocompatibility. However, in this patent document, the polyacetal polymer is only evaluated with respect to the degradability thereof using hydrochloric acid, and there is no teaching or suggestion about the biodegradability, body fluid compatibility and biocompatibility of the polymer.

On the other hand, an unsubstituted ethylene glycol homopolymer is a highly safe compound which has conventionally been used in the medical application fields. However, an unsubstituted ethylene glycol homopolymer is disadvantageous in that a drug can be introduced into this polymer only at the terminals thereof. That is, an unsubstituted ethylene glycol homopolymer is disadvantageous in that the maximum number of a drug compound which can be introduced per molecular chain of the polymer is as small as 2 (two). Therefore, when a drug complex is produced using the unsubstituted ethylene glycol homopolymer, the effective dose of the drug complex contains too large an amount of the unsubstituted ethylene glycol homopolymer such that the administration of the drug complex is practically impossible due to a heavy load on the patient. Further, an unsubstituted ethylene glycol homopolymer is generally water-soluble, so that, when used as a coating material for a shaped article, the unsubstituted ethylene glycol homopolymer is likely to dissolve out from the shaped article. Furthermore, when a mixture of an unsubstituted ethylene glycol homopolymer with a resin other than an unsubstituted ethylene glycol homopolymer is used to produce a shaped article, problems are likely to be caused due to the lack of a lipophilic subsituent in the unsubstituted ethylene glycol homopolymer, i.e., problems in that the compatibility of the unsubstituted ethylene glycol homopolymer and the other resin is poor, and in that, even when the unsubstituted ethylene glycol homopolymer and the other resin are compatibilized, the unsubstituted ethylene glycol homopolymer is likely to dissolve out from the shaped article.

With respect to a body fluid compatible/biocompatible material, not only is it demanded that the material has body fluid compatibility and biocompatibility which are appropriate for the intended use of the material and the method for using the material, but also the material is desired to be highly safe for living organisms. The reason for this is as follows. For example, when a body fluid compatible/biocompatible material is coated on a substrate and the resultant is in contact with a body fluid over a long period of time, a portion of the body fluid compatible/biocompatible material may be delaminated from the substrate and released into the body fluid. Therefore, even when the material has excellent body fluid compatibility, there is still a danger that the material is accumulated in an organ to damage the organ. Therefore, it has been desired to develop a body fluid compatible/biocompatible material which not only has the abilities to suppress blood coagulation, platelet adhesion, platelet activation and complement activation, but also exhibits high biological safety.

SUMMARY OF THE INVENTION

In this situation, the present inventor has made extensive and intensive studies with a view toward developing a resin having excellent body fluid compatibility and biocompatibility. As a result, it has unexpectedly been found that a resin which comprises at least one substituted oxyalkylene polymer having a specific structure and having a weight average molecular weight of from 1,000 to 1,000,000 has excellent body fluid compatibility and biocompatibility (that is, the resin is advantageous not only in that the resin is capable of suppressing the adsorption of a protein thereto, the adhesion of biological substances (such as a biological tissue, a cell and a platelet) thereto, and the activation of a platelet, a complement and the like, but also in that the resin exhibits high biological safety), and that, hence, the resin can be advantageously used in a medical treatment involving a contact of the resin with at least one member selected from the group consisting of a body fluid and a biological tissue. The present invention has been completed, based on these novel findings.

Accordingly, it is an object of the present invention to provide a body fluid compatible and biocompatible resin for use in a medical treatment involving a contact of said resin with at least one member selected from the group consisting of a body fluid and a biological tissue.

It is another object of the present invention to provide a resin composition comprising the above-mentioned body fluid compatible and biocompatible resin and a resin other than the body fluid compatible and biocompatible resin.

It is still another object of the present invention to provide use of the resin of the present invention in various treatments of a polypeptide and a protein which are derived from organisms, such as a human, a mammal, a reptile, a microbe and an insect, wherein the treatments include a separation, a purification, a concentration, a filtration, a desalting/concentration and the like, and to provide use of the resin of the present invention in treatments of a medicine, an active pharmaceutical ingredient of a medicine and a raw material for a medicine, which contain the above-mentioned polypeptide or protein, wherein the treatments include a separation, a purification, a concentration, a filtration, a desalting/concentration and the like.

The foregoing and other objects, features and advantages of the present invention will be apparent from the following description and appended claims taken in connection with the accompanying drawings.

DETAILED DESCRIPTION OF THE INVENTION

Figure 1:
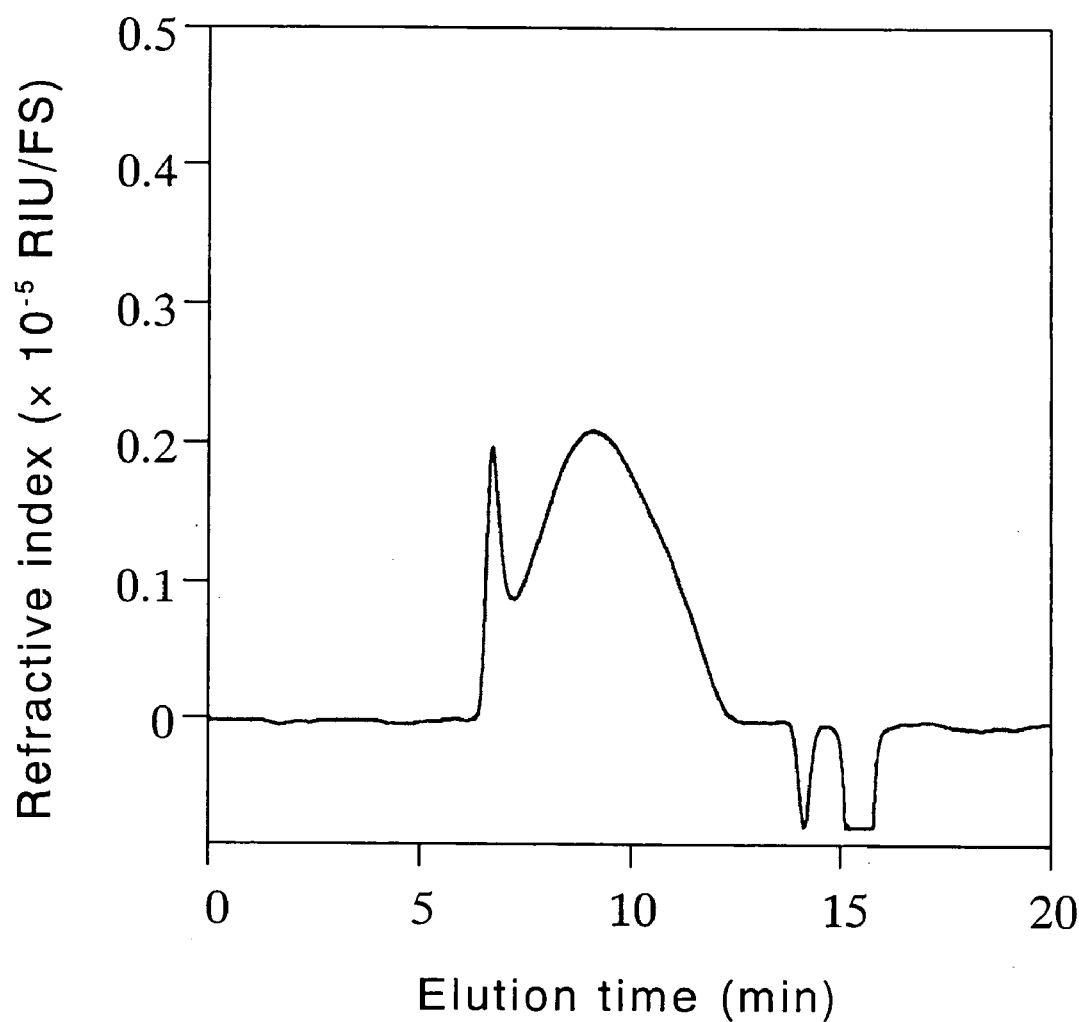
FIG. 1 is a GPC chart which is obtained with respect to resin (86) of the present invention produced in Example 30.

According to the present invention, there is provided a body fluid compatible and biocompatible resin for use in a medical treatment involving a contact of the resin with at least one member selected from the group consisting of a body fluid and a biological tissue, which comprises at least one substituted oxyalkylene polymer represented by the following formula (1):

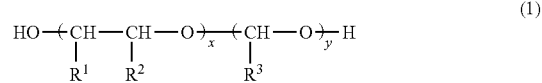

wherein:
each of $R^1$, $R^2$ and $R^3$ independently represents a hydrogen atom or a —$CH_2R^4$ group,
wherein each $R^4$ independently represents a hydroxyl group or a —$OR^5$ group, wherein $R^5$ represents a group selected from the group consisting of a $C_1$-$C_{10}$ aliphatic hydrocarbyl group, a $C_6$-$C_{10}$ aryl group, a —$R^6COOH$ group and a derivative thereof, and a —$CH_2$—O—$CH_2$—CH(OH)—$CH_2$—$OR^7$ group, wherein $R^6$ represents a $C_1$-$C_{10}$ aliphatic hydrocarbylene group and $R^7$ represents a group selected from the group consisting of a $C_1$-$C_{10}$ aliphatic hydrocarbyl group and a $C_6$-$C_{10}$ aryl group,
provided that all of $R^1$, $R^2$, and $R^3$ are not simultaneously hydrogen atoms; and
x and y represent integers which satisfy the following requirements:
$10 \leq x \leq 10,000$ and
$0 \leq y \leq 10,000$,
the at least one substituted oxyalkylene polymer having a weight average molecular weight of from 1,000 to 1,000,000 as measured by gel permeation chromatography (GPC) using a calibration curve obtained with respect to standard polyethylene glycol (PEG) samples, each having a narrow molecular weight distribution.

For easy understanding of the present invention, the essential features and various preferred embodiments of the present invention are enumerated below.

1. A body fluid compatible and biocompatible resin for use in a medical treatment involving a contact of the resin with at least one member selected from the group consisting of a body fluid and a biological tissue, which comprises at least one substituted oxyalkylene polymer represented by the following formula (1):

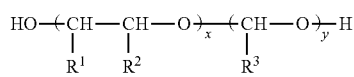 (1)

wherein:
each of $R^1$, $R^2$ and $R^3$ independently represents a hydrogen atom or a $-CH_2R^4$ group,
wherein each $R^4$ independently represents a hydroxyl group or a $-OR^5$ group, wherein $R^5$ represents a group selected from the group consisting of a $C_1$-$C_{10}$ aliphatic hydrocarbyl group, a $C_6$-$C_{10}$ aryl group, a $-R^6COOH$ group and a derivative thereof, and a $-CH_2-O-CH_2-CH(OH)-CH_2-OR^7$ group, wherein $R^6$ represents a $C_1$-$C_{10}$ aliphatic hydrocarbylene group and $R^7$ represents a group selected from the group consisting of a $C_1$-$C_{10}$ aliphatic hydrocarbyl group and a $C_6$-$C_{10}$ aryl group,
provided that all of $R^1$, $R^2$, and $R^3$ are not simultaneously hydrogen atoms; and
x and y represent integers which satisfy the following requirements:
$10 \leq x \leq 10,000$ and
$0 \leq y \leq 10,000$,
the at least one substituted oxyalkylene polymer having a weight average molecular weight of from 1,000 to 1,000,000 as measured by gel permeation chromatography (GPC) using a calibration curve obtained with respect to standard polyethylene glycol (PEG) samples, each having a narrow molecular weight distribution.

2. The body fluid compatible and biocompatible resin according to item 1 above, wherein x and y in the formula (1) satisfy the following requirements:
x=y,
$10 \leq x \leq 10,000$ and
$10 \leq y \leq 10,000$, and
wherein the amount of the $-CH_2R^4$ group as any of $R^1$, $R^2$ and $R^3$ is from 0.01 to 2.5 mole, per mole of the total of $-(CHR^1-CHR^2-O-)$ unit and $-(CHR^1-CHR^2-O-)$ unit of the at least one substituted oxyalkylene polymer.

3. The body fluid compatible and biocompatible resin according to item 1 above, wherein the at least one substituted oxyalkylene polymer is a homopolymer.

4. The body fluid compatible and biocompatible resin according to item 1 above, wherein the at least one substituted oxyalkylene polymer is a copolymer.

5. The body fluid compatible and biocompatible resin according to item 2 above, wherein the at least one substituted oxyalkylene polymer is a copolymer comprised mainly of recurring units represented by formula (2) and formula (3);

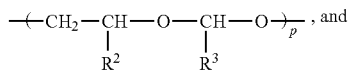 (2)

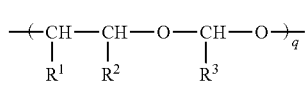 (3)

wherein:
$R^2$ and $R^3$ are as defined for formula (1),
wherein $R^1$ represents a $-CH_2R^4$ group, and
p and q are integers which satisfy the following requirements:
$10 \leq p \leq 10,000$ and
$10 \leq q \leq 10,000$,
wherein the molar ratio of recurring unit of formula (2) to recurring unit of formula (3) is 0.5.

6. The body fluid compatible and biocompatible resin according to item 1 above, wherein the at least one substituted oxyalkylene polymer is obtained by polymerizing an ethylene oxide derivative or by polymerizing an ethylene oxide derivative, followed by treatment with an acid.

7. The body fluid compatible and biocompatible resin according to item 1 above, wherein the at least one substituted oxyalkylene polymer is crosslinked by a crosslinking agent.

8. The body fluid compatible and biocompatible resin according to item 7 above, wherein the crosslinking agent is at least one compound selected form the group consisting of ethylene glycol diglycidyl ether and butanediol diglycidyl ether.

9. The body fluid compatible and biocompatible resin according to item 7 above, wherein the crosslinking agent is at least one compound selected form the group consisting of epichlorohydrin and epibromohydrin.

10. The body fluid compatible and biocompatible resin according to item 7 above, wherein the crosslinking agent is used in an amount of from 10 to 120% by weight, based on the weight of the at least one substituted oxyalkylene polymer.

11. The body fluid compatible and biocompatible resin according to item 1 above, wherein the at least one substituted oxyalkylene polymer is produced from a polysaccharide.

12. The body fluid compatible and biocompatible resin according to item 11 above, wherein the polysaccharide is a dextran or pullulan.

13. The body fluid compatible and biocompatible resin according to item 1 above, which is in the form of a film for preventing adhesion of a biological tissue or covering a wound.

14. The body fluid compatible and biocompatible resin according to any one of items 1, 3, 4 and 6 above, wherein y is 0, each $R^1$ is a hydrogen atom and each $R^2$ independently represents a $-CH_2R^8$ group,
wherein each $R^8$ independently represents a hydroxyl group, a $-O-CH_2COOH$ group, a $-O-CH_2COONa$ group or a $-O-CH_2COOR^{11}$ group, wherein $R^{11}$ represents a group comprising an amino acid or peptide having bonded thereto a compound having a pharmaceutical activity.

15. The body fluid compatible and biocompatible resin according to any one of items 1, 3, 4 and 6 above, wherein a copolymer is represented by the following formula (4):

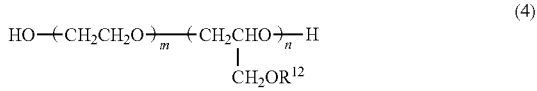

(4)

wherein:
each $R^{12}$ independently represents a hydrogen atom, a —$CH_2COOH$ group, a —$CH_2COONa$ group or a —$CH_2COOR^{13}$ group, wherein each $R^{13}$ represents a group comprising an amino acid or peptide having bonded thereto a compound having a pharmaceutical activity; and m and n are integers which satisfy the following requirements:
$10 \leq m \leq 10,000$ and
$10 \leq n \leq 10,000$.

16. The body fluid compatible and biocompatible resin according to item 14 above, wherein the compound having a pharmaceutical activity is a compound having an anticancer activity.

17. The body fluid compatible and biocompatible resin according to item 15 above, wherein the compound having a pharmaceutical activity is a compound having an anticancer activity.

18. The body fluid compatible and biocompatible resin according to item 14 above, wherein the compound having a pharmaceutical activity is an adrenocortical hormone, a vasodilator or an enzyme inhibitor.

19. The body fluid compatible and biocompatible resin according to item 15 above, wherein the compound having a pharmaceutical activity is an adrenocortical hormone, a vasodilator or an enzyme inhibitor.

20. The body fluid compatible and biocompatible resin according to item 4 above, wherein the at least one substituted oxyalkylene polymer is a copolymer having different $R^2$ groups, wherein each y is 0, each $R^1$ is a hydrogen atom and each $R^2$ independently represents a —$CH_2OH$ group, a —$CH_2OCH_3$ group, a —$CH_2OCH_2CH_2CH_3$ group or a —$CH_2OC_6H_5$ group.

21. The body fluid compatible and biocompatible resin according to item 1 above, wherein each y is 0, each $R^1$ is a hydrogen atom and each $R^2$ represents a —$CH_2OH$ group, wherein the —OH group in $R^2$ is formed by hydrolysis of a group selected from the group consisting of a tertiary butyl group, a trimethylsilyl group, a 1-ethoxyethyl group, a tetrahydropyranyl group and an acetyl group.

22. The body fluid compatible and biocompatible resin according to item 1 above, wherein the at least one substituted oxyalkylene polymer is a homopolymer obtained by subjecting an alkyl glycidyl ether or an aryl glycidyl ether to ring opening polymerization.

23. The body fluid compatible and biocompatible resin according to item 4 or 5 above, wherein the at least one substituted oxyalkylene polymer is a copolymer obtained by subjecting at least two different glycidyl ethers selected from the group consisting of an alkyl glycidyl ether and an aryl glycidyl ether to ring opening copolymerization.

24. The body fluid compatible and biocompatible resin according to item 1 above, which is for use as a coating material for a shaped article of a resin other than the body fluid compatible and biocompatible resin.

25. The body fluid compatible and biocompatible resin according to item 24 above, wherein the coating material is used in an amount of from 0.01 to 20% by weight, based on the weight of the resin other than the body fluid compatible and biocompatible resin.

26. The body fluid compatible and biocompatible resin according to item 24 or 25 above, wherein the resin other than the body fluid compatible and biocompatible resin is selected from the group consisting of a polyester, a polyamide, a polyimide, a polyether sulfone and a polysulfone.

27. A resin composition comprising the body fluid compatible and biocompatible resin of item 1 above, and a resin other than the body fluid compatible and biocompatible resin.

28. The resin composition according to item 27 above, wherein the resin other than the body fluid compatible and biocompatible resin is selected from the group consisting of a polyester, a polyamide, a polyimide a polyether sulfone and a polysulfone.

29. A body fluid compatible and biocompatible resin for use in a medical treatment involving a contact of the resin with at least one member selected from the group consisting of a body fluid and a biological tissue, which comprises at least one substituted oxyalkylene polymer represented by the following formula (5):

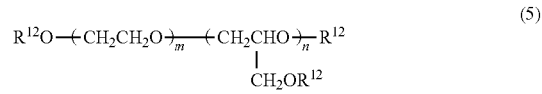

(5)

wherein:
each $R^{12}$ independently represents a hydrogen atom, a-$CH_2COOH$ group, a-$CH_2COONa$ group or a —$CH_2COOR^{14}$ group, wherein each $R^{14}$ represents a group comprising an amino acid or peptide having bonded thereto a compound having a pharmaceutical activity; and m and n are integers which satisfy the following requirements:
$10 \leq m \leq 10,000$ and
$10 \leq n \leq 10,000$, the at least one substituted oxyalkylene polymer having a weight average molecular weight of from 1,000 to 1,000,000 as measured by gel permeation chromatography (GPC) using a calibration curve obtained with respect to standard polyethylene glycol (PEG) samples, each having a narrow molecular weight distribution.

30. The body fluid compatible and biocompatible resin according to item 29 above, wherein the at least one substituted oxyalkylene polymer is obtained by polymerizing an ethylene oxide derivative or by polymerizing an ethylene oxide derivative, followed by treatment with an acid.

31. The body fluid compatible and biocompatible resin according to item 29 or 30 above, wherein the compound having a pharmaceutical activity is a compound having an anticancer activity.

32. The body fluid compatible and biocompatible resin according to item 29 or 30 above, wherein the compound having a pharmaceutical activity is an adrenocortical hormone, a vasodilator or an enzyme inhibitor.

33. A resin composition comprising the body fluid compatible and biocompatible resin of item 29 above, and a resin other than the body fluid compatible and biocompatible resin.

34. The resin composition according to item 33 above, wherein the resin other than the body fluid compatible and biocompatible resin is selected from the group consisting of a polyester, a polyamide, a polyimide a polyether sulfone and a polysulfone.

Hereinbelow, the present invention is described in detail.

The body fluid compatible and biocompatible resin of the present invention is a resin which comprises at least one substituted oxyalkylene polymer represented by the following formula (1):

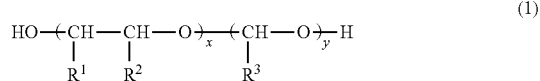
(1)

wherein:
each of $R^1$, $R^2$ and $R^3$ independently represents a hydrogen atom or a —$CH_2R^4$ group,
wherein each $R^4$ independently represents a hydroxyl group or a —$OR^5$ group, wherein $R^5$ represents a group selected from the group consisting of a $C_1$-$C_{10}$ aliphatic hydrocarbyl group, a $C_6$-$C_{10}$ aryl group, a —$R^6COOH$ group and a derivative thereof, and a —$CH_2$—O—$CH_2$—CH(OH)—$CH_2$—$OR^7$ group, wherein $R^6$ represents a $C_1$-$C_{10}$ aliphatic hydrocarbylene group and $R^7$ represents a group selected from the group consisting of a $C_1$-$C_{10}$ aliphatic hydrocarbyl group and a $C_6$-$C_{10}$ aryl group,
provided that all of $R^1$, $R^2$, and $R^3$ are not simultaneously hydrogen atoms; and
x and y represent integers which satisfy the following requirements:
$10 \leq x \leq 10,000$ and
$0 \leq y \leq 10,000$,
the at least one substituted oxyalkylene polymer having a weight average molecular weight of from 1,000 to 1,000,000 as measured by gel permeation chromatography (GPC) using a calibration curve obtained with respect to standard polyethylene glycol (PEG) samples, each having a narrow molecular weight distribution.

The body fluid compatible and biocompatible resin of the present invention has features that the resin has a specific molecular weight and that the resin comprises at least one substituted oxyalkylene polymer mentioned above, which has a specific substituent. By virtue of such features, the resin of the present invention exhibits excellent body fluid compatibility and excellent biocompatibility. Therefore, the resin of the present invention can be advantageously used for a medical treatment involving a contact of the resin with at least one member selected from the group consisting of a body fluid and a biological tissue. Specific examples of body fluids include a blood, a lymph, a lacrimal fluid, an articulation fluid and a cerebrospinal fluid. Examples of biological tissues include various tissues other than an epidermis tissue. More specific examples of biological tissues include tissues of internal organs (such as a liver, a pancreas, a kidney and a spleen), an epithelial tissue, a connective tissue, a blood cell tissue, a myeloid tissue, a muscular tissue, a bone, a cartilage, a blood vessel, an eyeball, an adipose tissue, an alimentary tract, an alimentary tract mucosa and a nervous tissue.

The substituted oxyalkylene polymer contained in the resin of the present invention has a weight average molecular weight of from 1,000 to 1,000,000 as measured by GPC using a calibration curve obtained with respect to standard polyethylene glycol samples, each having a narrow molecular weight distribution (hereinafter, the thus measured weight average molecular weight is frequently referred to as a "weight average molecular weight determined by GPC using a PEG calibration curve"). When the weight average molecular weight of the polymer is less than 1,000, the solubility of the polymer in water becomes too high, thereby causing a disadvantage that, when the resin containing such a low molecular weight polymer is used for coating a shaped article produced from a hydrophobic resin other than the resin of the present invention, such a low molecular weight polymer is likely to get dissolved into a body fluid or the like. On the other hand, when the weight average molecular weight of the polymer is more than 1,000,000, the solubility of the polymer in water becomes too low, thereby causing a disadvantage that the body fluid compatibility and biocompatibility of a resin containing such a high molecular weight polymer is lowered. From the viewpoint of the coatability of the resin of the present invention to a substrate (such as the above-mentioned shaped article produced from a resin other than the resin of the present invention) and the miscibility of a resin other than the resin of the present invention (which is used to form a resin composition containing the resin of the present invention) with the resin of the present invention, it is preferred that the weight average molecular weight of the polymer contained in the resin of the present invention is in the range of from 1,000 to 500,000. Further, when the weight average molecular weight of the polymer contained in the resin of the present invention is measured by GPC using a calibration curve obtained with respect to standard pullulan samples, it is preferred that the weight average molecular weight is in the same range as in the case of the above-mentioned weight average molecular weight determined by GPC using a PEG calibration curve.

As mentioned above, from the viewpoint of the coatability of the resin of the present invention to a substrate and the miscibility of a resin other than the resin of the present invention with the resin of the present invention, it is preferred that the weight average molecular weight of the substituted oxyalkylene polymer contained in the resin of the present invention is in the range of from 1,000 to 500,000, as determined by GPC using a PEG calibration curve. The weight average molecular weight of the polymer is more preferably in the range of from 1,000 to 150,000, still more preferably from 1,000 to 100,000. From the viewpoint of the miscibility of the resin of the present invention with a resin other than the resin of the present invention, and the safety of the resin of the present invention for living organisms in the case where the resin of the present invention gets dissolved out from the substrate, it is preferred that the weight average molecular weight of the polymer is in the range of from 1,000 to 100,000, more advantageously from 1,000 to 65,000, as determined by GPC using a PEG calibration curve.

The above-mentioned preferred range of the weight average molecular weight influences the "biocompatibility" of the resin of the present invention, and is especially advantageous for achieving the high safety of the resin of the present invention. That is, in the present invention, the "biocompatible" resin means that the resin not only has less interaction and interference with living organisms, but also has a specific molecular weight which enables the rapid excretion of the resin from the kidney, so that the accumulation of the resin in organs and the like can be suppressed and the resin exhibits high safety. The reason for the high safety of the resin of the present invention is as follows. For example, when the resin of the present invention is released into a body fluid, a polymer having a weight average molecular weight which is lower than the molecular weight (about 67,000) of a blood plasma albumin present in a living organism can be rapidly excreted from the living organism. For this reason, the above-mentioned preferred range of the weight average molecular weight is especially advantageous for the renal excretion.

As examples of the method for controlling the weight average molecular weight of the polymer (determined by GPC using a PEG calibration curve) to be in the range of from 1,000 to 1,000,000, there can be mentioned a method in which raw materials are purified, and a method in which a high molecular weight fraction and/or a low molecular weight fraction is removed after the polymerization reaction for producing the resin of the present invention. With respect to the reaction conditions for producing the resin of the present invention, the type and amount of a polymerization initiator, the type and amount of a reaction solvent (if any), the reaction temperature, the reaction time, the concentrations of the raw materials, the polymerization initiator concentration, the reaction atmosphere, the reaction pressure, the manner of stirring, the stirring rate and the like can be appropriately selected so as to obtain a polymer having a desired weight average molecular weight. With respect to the above-mentioned method in which a high molecular weight fraction and/or a low molecular weight fraction is removed after the polymerization reaction, the fractionation of the polymer can be performed by various methods. Examples of methods for fractionation of the polymer include a chromatography, such as size exclusion chromatography (SEC); ultrafiltration with a UF module or the like; ultracentrifuge; a precipitation fractionation using a solvent or the like.

The weight average molecular weight determined by GPC using a PEG calibration curve means a molecular weight as measured by GPC using a calibration curve obtained with respect to standard polyethylene glycol (PEG) samples, each having a narrow molecular weight distribution. PEG is soluble not only in water but also in organic solvents and, hence, PEG is generally used as a standard substance for measuring a molecular weight of a hydrophobic polymer.

It is preferred that the substituted oxyalkylene polymer contained in the resin of the present invention has a molecular weight distribution of from 1.2 to 2.5 in terms of the Mw/Mn ratio, wherein Mw represents the weight average molecular weight (determined by GPC using a PEG calibration curve) of the polymer and Mn represents the number average molecular weight (determined by GPC using a PEG calibration curve) of the polymer. For surely achieving the desired excellent properties of the resin of the present invention, it is more preferred that the molecular weight distribution is in the range of from 1.2 to 2.2, still more advantageously from 1.2 to 2.0, most advantageously from 1.0 to 1.8. When the molecular weight distribution of the polymer is more than 2.5, such a polymer becomes a collection of high molecular polymer chains having widely varied molecular weights which range from a low molecular weight to a high molecular weight, so that it becomes difficult to surely obtain a resin having a satisfactory biocompatibility. On the other hand, with respect to the lower limit (1.0) of the molecular weight distribution, the production of a polyether having such a low molecular weight distribution is technically difficult.

Examples of raw material monomers used for producing the resin of the present invention which comprises the substituted oxyalkylene polymer represented by formula (1) include epoxy group-containing $C_3$-$C_{100}$ compounds, such as ethylene oxide, an aliphatic hydrocarbon glycidyl ether (e.g., a $C_1$-$C_{12}$ alkyl glycidyl ether) and an aromatic hydrocarbon glycidyl ether (e.g., a $C_6$-$C_{12}$ aryl glycidyl ether). Specific examples of alkyl glycidyl ethers include methyl glydidyl ether, ethyl glycidyl ether, n-propyl glycidyl ether, i-propyl glycidyl ether, n-butyl glycidyl ether, i-butyl glycidyl ether, t-butyl glycidyl ether, allyl glycidyl ether, 2-ethylhexyl glycidyl ether, 2-methyloctyl glycidyl ether, ethylene glycol diglycidyl ether, butanediol diglycidyl ether, glycerol triglycidyl ether, acetyl glycidol (which is a reaction product of glycidol and acetyl chloride) and glycidyl methacrylate. These glycidyl ethers may be used individually or in combination. Specific examples of aryl glycidyl ethers include phenyl glycidyl ether and benzyl glycidyl ether. Further examples of raw material monomers include an alkylene oxide (such as propylene oxide), epichlorohydrin and epibromohydrin. For example, when epichlorohydrin is used as the raw material monomer, the resin of the present invention can be produced as follows. Epichlorohydrin is polymerized to produce a polyepichlorohydrin. The produced polyepichlorohydrin is dissolved in a solvent, such as diethylene glycol methyl ether and, then, potassium acetate is added to the resultant solution, followed by heating at 100 to 150° C., thereby converting chloromethyl groups of the polyepichlorohydrin to acetyloxy groups. Subsequently, the resultant is hydrolyzed with an aqueous sodium hydroxide solution at room temperature to convert the acetyloxy groups to hydroxyl groups, thereby producing a resin comprising the substituted oxyalkylene polymer represented by formula (1). Further, the resin comprising the substituted oxyalkylene polymer having alkyloxy groups introduced thereto can be produced in substantially the same manner as mentioned above, except that a potassium alkoxide or a sodium alkoxide is used instead of potassium acetate.

As examples of structures of the substituted oxyalkylene polymer represented by formula (1), there can be mentioned (i) a homopolymer, (ii) a copolymer comprised of the different recurring units which are, respectively, represented by formula (1), and (iii) a copolymer containing the recurring units of formula (1) and a monomer unit other than the recurring unit of formula (1). When the substituted oxyalkylene polymer represented by formula (1) is a copolymer of item (iii) above, the molar fraction of the monomer unit other than the recurring units of formula (1) present in the copolymer is preferably 80% or less, more preferably 60% or less, still more preferably 40% or less, based on the total molar amount of the recurring units of formula (1) and the monomer unit other than the recurring units of formula (1). As specific examples of monomer units other than the recurring units of formula (1), there can be mentioned monomer units which are, respectively, derived from an acrylic ester, a methacrylic ester, glycidyl methacrylate and vinyl ether. The copolymer of item (iii) above can be produced as follows. For example, the substituted oxyalkylene polymer represented by formula (1), wherein y is 0, and $R_1$ and $R_2$ are a hydrogen atom and a —$CH_2OCH_2CHCH_2$ group, respectively, is prepared. Then, the resultant polymer is subjected to radical polymerization with an acrylic acid, in which a double bond in the aryl group contained in $R_2$ is reacted with a double bond in the acrylic acid, thereby obtaining a copolymer of item (iii) above.

When the at least one substituted oxyalkylene polymer is a copolymer, the ratio of different monomer units constituting the copolymer can be controlled by appropriately adjusting the types and amounts of raw materials, the type and amount of a polymerization initiator, the type and amount of a reaction solvent (if any), the reaction temperature, the reaction time, the concentrations of raw materials, the polymerization initiator concentration, the reaction atmosphere, the reaction pressure, the manner of stirring, the stirring rate and the like.

When an ethylene oxide derivative is used to obtain the resin of the present invention, the production of the resin may be performed by any of the following methods: a method in which an ethylene oxide derivative is polymerized; and a method in which a polymer obtained by polymerization of an ethylene oxide derivative is treated in an organic solvent (such as dioxane) with hydrogen chloride or an acidic aqueous solution, such as hydrochloric acid (e.g., 4 N HCl), or with a basic aqueous solution, such as 1 N aqueous sodium hydroxide solution.

The mechanism of various functions of the resin of the present invention is as follows. In the substituted oxyalkylene polymer contained in the resin of the present invention, the main chain and the hydrophilic side chain (having a primary hydroxyl group etc.) not only suppresses the adhesion of a polypeptide, a protein, a cell and a platelet to the resin, and the activation of platelet by the resin, but also improves efficiencies of various treatments (such as a separation, a removal and a recovery) for a polypeptide, a protein and a cell, and a platelet recovery. On the other hand, the presence of the hydrophobic group introduced into the side chain improves the liposolubility of the resin of the present invention, thereby rendering easy the mixing the resin of the present invention with a resin other than the resin of the present invention, or the coating of an equipment (used for the above-mentioned treatments) with the resin of the present invention.

In the resin of the present invention, the substituted oxyalkylene polymer may be a copolymer having a structure represented by the following formula (4):

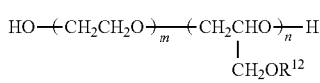
(4)

wherein:
  each $R^{12}$ independently represents a hydrogen atom, a —$CH_2COOH$ group, a —$CH_2COONa$ group or a —$CH_2COOR^{13}$ group, wherein each $R^{13}$ represents a group comprising an amino acid or peptide having bonded thereto a compound having a pharmaceutical activity; and
  m and n are integers which satisfy the following requirements:
    $10 \leq m \leq 10,000$ and
    $10 \leq n \leq 10,000$.

Further, the terminals of the substituted oxyalkylene polymer may be modified to form a copolymer having a structure represented the following formula (5):

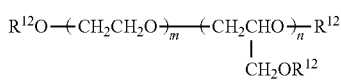
(5)

wherein:
  each $R^{12}$ independently represents a hydrogen atom, a-$CH_2COOH$ group, a-$CH_2COONa$ group or a —$CH_2COOR^{14}$ group, wherein each $R^{14}$ represents a group comprising an amino acid or peptide having bonded thereto a compound having a pharmaceutical activity; and
  m and n are integers which satisfy the following requirements:
    $10 \leq m \leq 10,000$ and
    $10 \leq n \leq 10,000$.

Each of the copolymers of formulae (4) and (5) can be produced by introducing a functional group into the terminal(s) of a side chain and/or a main chain of a substituted oxyalkylene polymer obtained from ethylene oxide and an epoxy group-containing $C_3$-$C_{100}$ compound. Further, in each of the copolymers of formulae (4) and (5), ethylene oxide is used as a raw material and, hence, the number of the side chains can be reduced, thereby simplifying the structure of the copolymer. As examples of functional groups introduced into the terminal(s) of a side chain and/or a main chain of the substituted oxyalkylene polymer, there can be mentioned a hydrocarbyl group and a carboxymethyl group. The carboxymethyl group introduced into the copolymer represented by formula (4) or (5) can be used for binding a compound having a pharmaceutical activity (e.g., anti-cancer activity) to the copolymer through a linker, to form a drug complex. When such a drug complex is administered to a living organism, the resin of the present invention exhibits a characteristic that an interaction and interference of the drug complex with a biological tissue or body fluid do not occur. Specifically, as shown in the working example of the present specification, the resin of the present invention exhibits an advantage that the resin is not accumulated in an organ (such as a liver, a spleen or a bone marrow) in which side effects are caused by a drug metabolism and a drug. Further, by utilizing characteristics of a tumor tissue, such as EPR effect (see, Maeda, H., Advanced Drug Delivery Reviews, 6, pp. 181-202 (1991)), it becomes possible to deliver a drug selectively to a tumor site or an inflammatory site by administering the drug in the form of a drug complex which contains the copolymer represented by formula (4) or (5) to a living organism. The weight average molecular weight (determined by GPC using a PEG calibration curve) of the copolymer represented by formula (4) or (5) is in the range of from 1,000 to 1,000,000, preferably from 1,000 to 500,000. However, from the viewpoint of administration of the copolymer, the weight average molecular weight of the copolymer is more preferably in the range of from 1,000 to 150,000. Further, from the viewpoint of the safety of the copolymer to a living organism, it is preferred that the weight average molecular weight of the copolymer is in the range of from 1,000 to 100,000, more advantageously from 1,000 to 65,000. It is preferred that the copolymer represented by formula (4) or (5) has a molecular weight distribution of from 1.2 to 2.5, in terms of the Mw/Mn ratio, wherein Mw represents the weight average molecular weight (determined by GPC using a PEG calibration curve) of the polymer and Mn represents the number average molecular weight (determined by GPC using a PEG calibration curve) of the polymer. For surely achieving the desired excellent properties of the resin of the present invention, it is more preferred that the molecular weight distribution is in the range of from 1.2 to 2.2, still more advantageously from 1.2 to 2.0, most advantageously from 1.0 to 1.8. Further, with respect to the molar ratio (%) of the monomer units present in the copolymer of formula (4) or (5), the molar ratio ("m" in formula (4) or (5)) of ethylene oxide units is in the range of from 0.01 to 99.99%, and the molar ratio "n" in formula (4) or (5)) of an epoxy group-containing $C_3$-$C_{100}$ compound units is in the range of from 99.99 to 0.01%, each based on the total molar amount of the ethylene oxide units and the epoxy group-containing $C_3$-$C_{100}$ compound units.

The resin of the present invention, which contains the copolymer of formula (4) or (5), can be produced as follows. For example, the introduction of a carboxymethyl group into a side chain of the polymer represented by formula (1) can be performed by a method in which ethyl bromoacetate is reacted with the polymer represented by formula (1) in a solvent (such as toluene) in the presence of potassium t-butoxide and 18-crown-6-ether, and the ester linkage in the resultant reaction product is hydrolyzed with an alkali, thereby obtaining a polymer represented by formula (1) having introduced thereto a carboxymethyl group. Further, the introduction of a carboxymethyl group into a side chain of the polymer represented by formula (1) can also be performed by a method in which sodium chloroacetic acid is reacted with the polymer of formula (1) in an aqueous solution thereof in the presence of a base, such as sodium hydroxide, thereby introducing the carboxymethyl group into the polymer represented by formula (1).

The substituted oxyalkylene polymer contained in the resin of the present invention may have a crosslinked structure. The crosslinked structure can be formed by a crosslinking agent. For example, the resin of the present invention which comprises a substituted oxyalkylene polymer having a side chain to which a hydrocarbyl group is introduced by an acid or base treatment can be crosslinked by various crosslinking agents, such as a crosslinking agent containing at least two epoxy groups in a molecule thereof, a crosslinking agent containing at least two carboxyl groups in a molecule thereof and a crosslinking agent containing at least two isocyanate groups in a molecule thereof. As preferred examples of copolymers to which a hydrocarbyl group is introduced at a side chain thereof by an acid or base treatment, there can be mentioned a copolymer of at least one member selected from the group consisting of t-butyl glycidyl ether, glycidyl trimethylsilyl ether, glycidyl tetrahydropyranyl ether, acetyl glycidol, glycidyl methacrylate and (1-ethoxy) ethyl glycidyl ether, with ethylene oxide or an epoxy group-containing $C_3$-$C_{100}$ compound.

As preferred examples of crosslinking agents used for crosslinking the substituted oxyalkylene polymer contained in the resin of the present invention, there can be mentioned diglycidyl ether, a triglycidyl ether derivative, a dicarboxylic acid derivative, a tricarboxylic acid derivative, a diisocyanate and a triisocyanate. Examples of diglycidyl ethers include ethylene glycol diglycidyl ether and butandiol diglycidyl ether. Examples of carboxylic acids include polycarboxylic acids, such as succinic acid, malic acid, citric acid and adipic acid, and examples of isocyanates include tolylene diisocyanate and xylylene diisocyanate. As further examples of crosslinking agents, there can be mentioned epichlorohydrin and epibromohydrin. In general, when a polymer is reacted with the crosslinking agent as mentioned above, the resultant crosslinked product forms a gel. However, the hardness and swelling of the gel depend on the degree of a crosslinking and, hence, the hardness and swelling of the gel can be adjusted by appropriately selecting the type of the crosslinking agent and the reaction conditions. Further, the gel is transparent, and the water-solubility and strength of the gel can also be adjusted by appropriately selecting the crosslinking conditions. In the present invention, the crosslinking agent is used in an amount of from 5 to 300% by weight, preferably from 5 to 150% by weight, more preferably from 10 to 120% by weight, still more preferably from 25 to 75% by weight, based on the weight of the substituted oxyalkylene polymer. When the crosslinking agent is used in an amount within the above-mentioned range, the resultant crosslinked resin of the present invention is especially effective for suppressing the adhesion of biological substances (such as a biological tissue, a protein, a cell and a platelet) to the resin and the activation of platelet by the resin. Hereinbelow, an explanation is made with respect to a method for producing a crosslinked product of the resin of the present invention. In the explanation, resins produced from raw materials other than polysaccharide are taken as examples; however, the crosslinking method explained below can also be applicable to the hydrocarbyl group-containing resins of the present invention produced by oxidation reaction of a polysaccharide.

(1) Crosslinking of a Copolymer Having a Hydrocarbyl Group at a Side Chain Thereof:

For example, when the resin of the present invention comprises a copolymer obtained by copolymerizing t-butyl glycidyl ether as a protective monomer with ethylene oxide as a hydrophilic monomer, the copolymer is subjected to a conventional treatment for removing a protective group (t-butyl group), such as a treatment using a solution of hydrogen chloride in dioxane, hydrochloric acid or an ion exchange resin, thereby removing the t-butyl group from the copolymer. As a result, a copolymer having a side chain having a hydroxymethyl group (which has a primary hydroxyl group) is obtained. The obtained copolymer can be crosslinked using the below-mentioned crosslinking agent under various reaction conditions. By the crosslinking of the copolymer, for example, a hydrophilic or hydrophobic gel can be obtained. Also in the case where the protective monomer is glycidyl trimethylsilyl ether, glycidyl tetrahydropyranyl ether or (1-ethoxy)ethyl glycidyl ether, the protective group can be removed from the copolymer by the above-mentioned treatment with an acid, such as a solution of hydrogen chloride in dioxane, hydrochloric acid or an ion exchange resin, thereby obtaining a copolymer having a side chain to which a primary hydroxyl group is introduced. The thus obtained copolymer also can be crosslinked using the above-mentioned crosslinking agent.

On the other hand, when the protective monomer is a glycidyl carboxylate (such as acetyl glycidol) or a glycidyl ester of (meth)acrylic acid (such as glycidyl methacrylate), a copolymer obtained by a reaction between the protective monomer and the hydrophilic monomer is treated with a base solution, such as an aqueous sodium hydroxide solution or an aqueous potassium hydroxide solution, to remove an acetyl group from the copolymer, thereby obtaining a copolymer having a side chain having a hydroxymethyl group which has a primary hydroxyl group. The thus obtained copolymer also can be crosslinked using the above-mentioned crosslinking agent.

A glycidyl ether preferably used as the crosslinking agent is a diglycidyl ether having two epoxy groups in a molecule thereof or a triglycidyl ether having three epoxy groups in a molecule thereof. As examples of diglycidyl ethers, there can be mentioned ethylene glycol diglycidyl ether, diethylene glycol diglycidyl ether, propylene glycol diglycidyl ether, butandiol diglycidyl ether, 1,6-hexanediol diglycidyl ether and $C_8$-$C_{20}$ diglycidyl ethers. Further, as examples of triglycidyl esters, there can be mentioned glycerol triglycidyl ether.

Among those which are exemplified above, from the viewpoint of the yield of a crosslinked product and the balance between the hydrophilicity and hydrophobicity of a crosslinked product, preferred are diglycidyl ethers, such as ethylene glycol diglycidyl ether, diethylene glycol diglycidyl ether and butanediol diglycidyl ether. The reason why these crosslinking agents are preferred is as follows. By using a crosslinking agent having an epoxy group, a hydroxyl group is generated after the crosslinking reaction and, hence, an increase in the liposolubility of the crosslinked product can be suppressed, thereby maintaining excellent body fluid compatibility and biocompatibility of the resin of the present invention even after the crosslinking reaction.

In the crosslinking reaction, the degree of crosslinking can be adjusted by appropriately selecting reaction conditions, such as the concentration of a copolymer having a side chain to which a hydroxymehtyl group (having a primary hydroxyl group) is introduced, the amount of a crosslinking agent, the type of a solvent, the amount of a crosslinking catalyst (such as an acid or a base) and the reaction temperature. Further, the hydrophobicity of the crosslinked product can be adjusted by controlling the degree of crosslinking. That is, the degree of crosslinking can be changed by changing the amount of a crosslinking agent used for the crosslinking reaction, and the change in the degree of crosslinking leads to a change in the hydrophobicity of the crosslinked product. Therefore, a crosslinked product having a desired hydrophobicity can be obtained by using an appropriate amount of the crosslinking agent. It is even possible to obtain a crosslinked product in the form of a gel which has a poor water-solubility. Further, the crosslinked product can be molded into a film or a sheet.

Examples of bases which can be used as a crosslinking catalyst include potassium hydroxide, sodium hydroxide, cesium hydroxide, potassium carbonate, sodium methoxide, sodium ethoxide, sodium propoxide, sodium t-butoxide, potassium propoxide, potassium t-butoxide and potassium t-2-methyl-2-butoxide.

The crosslinking agent is used in an amount of from 5 to 300% by weight, preferably from 5 to 150% by weight, more preferably from 10 to 120% by weight, still more preferably from 25 to 75% by weight, based on the weight of the copolymer having a side chain to which a hydroxymethyl group (having a primary hydroxyl group) is introduced. When the crosslinked product of the resin of the present invention is produced using the crosslinking agent in an amount within the range mentioned above, the resin of the present invention exhibits especially excellent body fluid compatibility and biocompatibility, that is, the resin of the present invention is especially effective for suppressing the adhesion of biological substances (such as a biological tissue, a protein, a cell and a platelet) to the resin and the activation of platelet by the resin. Further, when such a crosslinked product is in the form of a film, such a film can be advantageously used for preventing the adhesion of a biological tissue, and can also be used for covering external wounds (such as bedsore, burn and ulcer) and for covering wounds caused by destruction of internal tissues (such as a corium, a hypoderm, a muscle, a tendon, an articulation and a bone).

(2) Crosslinking Reaction Performed Simultaneously with Copolymerization Reaction:

As another method for producing a crosslinked product of the resin of the present invention, there can be mentioned the following method. In the production of the body fluid compatible and biocompatible resin of the present invention, for example, when ethylene oxide and ethylene glycol diglycidyl ether or butanediol diglycidyl ether are used as raw material monomers, both of the raw material monomers are introduced into a pressure resistant reaction vessel and, then, subjected to ring opening copolymerization by a conventional method (such as a method described in E. J. Vandenberg, J. Polym. Sci., Polym. Chem. Ed., 23, 915-949 (1985); or E. J. Vandenberg, J. C. Mullis, R. S. Juvet, Jr., T. Miller and R. A. Nieman, J. Polym. Sci., Part A, 27, 3113-3149 (1989)), wherein the ring opening copolymerization is performed in the presence or absence of a reaction solvent (such as toluene, hexane, bis(2-methoxyethyl) ether, ethylene glycol dimethyl ether or ethylene glycol diethyl ether), in the presence of a polymerization initiator, on ice, at room temperature (if necessary, while heating) and under atmospheric pressure or superatmospheric pressure, thereby obtaining a copolymer in the form of a crosslinked product. As examples of polymerization initiators, there can be mentioned Lewis acid (such as tributylaluminum) and a strong base (such as a potassium t-butyl alcohol).

When a crosslinking reaction is performed simultaneously with a copolymerization reaction, the larger the amount of the crosslinking agent used, the higher the degree of crosslinking and the higher the hydrophobicity of a reaction product. It is even possible to obtain a crosslinked product in the form of a gel which has a poor water-solubility. It is preferred that the crosslinking agent is used in an amount of from 0.1 to 100% by weight, more advantageously from 0.1 to 50% by weight, based on the weight of the substituted oxyalkylene polymer. When the crosslinked product exhibits a poor water-insolubility, the crosslinked product may be melted by heating and shaped into a film. Thus obtained film also exhibits excellent body fluid compatibility and biocompatibility, that is, the film is especially effective for suppressing the adhesion of biological substances (such as a biological tissue, a protein, a cell and a platelet) to the resin and the activation of platelet by the resin. Further, the film can be advantageously used for preventing the adhesion of a biological tissue, and can also be used for covering external wounds (such as bedsore, burn and ulcer) and for covering wounds caused by destruction of internal tissues (such as a corium, a hypoderm, a muscle, a tendon, an articulation and a bone). With respect to the use of the resin of the present invention, it is possible to produce a medical equipment using only the resin of the present invention as a raw material. Alternatively, the resin of the present invention can be used as an additive for a resin composition used in the production of a medical equipment, or as a coating material for coating a portion of a medical equipment, which portion is contacted with a body fluid or a biological tissue.

The resin of the present invention may be produced from a polysaccharide. For example, the resin of the present invention may be produced from a natural polysaccharide, such as dextran or pullulan, by the so-called "Smith Degradation" which is a conventional method generally employed in the structural analysis of polysaccharides (with respect to the reaction conditions of the Smith Degradation, see, for example, S. Hase, N. Kikuchi, T. Ikenaka, K. Inoue, J. Biochem., Vol. 98 (1985), p. 863). Specifically, the resin of the present invention may be produced as follows. A polysaccharide is treated with an oxidizing agent (e.g., an excess amount of sodium metaperiodate) under conditions wherein the pH is appropriately adjusted to a weakly acidic value using an acetic acid buffer solution or the like, the temperature is from 4 to 40° C., the reaction time is from 4 hours to 1 week, and light is shielded, to thereby obtain a desired polyaldehyde. Then, the oxidizing agent is deactivated using ethylene glycol or the like, and the obtained polyaldehyde is subjected to reduction with sodium boron hydride, thereby obtaining the resin of the present invention.

The substituted oxyalkylene polymer of formula (1) which is present in the thus obtained resin of the present invention generally satisfies the following requirements:

$x=y$, $10 \leq x \leq 10,000$ and $10 \leq y \leq 10,000$, and the amount of the $—CH_2R^4$ group as any of $R^1$, $R^2$ and $R^3$ is from 0.01 to 2.5 mole, per mole of $—(CHR^1—CHR^2—O—)$ unit of the substituted oxyalkylene polymer.

As mentioned above, the polysaccharides which are preferably used for producing the resin of the present invention are natural polysaccharides. Therefore, the produced resin tends to have a non-uniform structure. For example, in O. Larm, B. Lindberg, S. Sevensson, Carbohyd. Res., Vol. 20 (1971), pp. 39-48, it is reported that, with respect to dextran manufactured and sold by Pharmacia, Sweden, (which is a polysaccharide preferably used in the present invention), 5% of the recurring units thereof form not only an ordinary linkage (i.e., 1,6-α-D-glucan linkage), but also a branch linkage at the O-3 position.

With respect to a saccharide residue having such a branch linkage at the O-3 position, a cleavage reaction (i.e., ring opening polymerization) by an oxidizing agent (e.g., sodium metaperiodate) does not proceed. Therefore, a polymer comprised only of recurring units shown in formula (1) above cannot be obtained from a natural polysaccharide. For example, when a substituted oxyalkylene polymer is produced from the above-mentioned dextran (manufactured and sold by Pharmacia, Sweden), the produced polymer has a structure in which an uncleaved saccharide residue is sandwiched between recurring units shown in formula (1) above. In formula (1) above, such an uncleaved saccharide residue is not shown; however, the resin of the present invention may contain such an uncleaved saccharide residue.

When a substituted oxyalkylene polymer is produced from pullulan, due to the structural characteristics of pullulan, the polymer produced by the cleavage reaction using an oxidizing agent (e.g., sodium metaperiodate) is theoretically comprised mainly of recurring units represented by the following formulae (2) and (3);

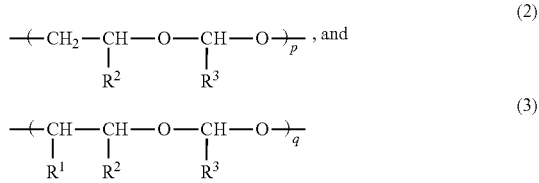

wherein $R^1$, $R^2$ and $R^3$ are as defined for formula (1),
wherein p and q are integers which satisfy the following requirements:
$10 \leq p \leq 10,000$ and
$10 \leq q \leq 10,000$, wherein the molar ratio of recurring unit of formula (2) to recurring unit of formula (3) is 0.5.

When the substituted oxyalkylene polymer represented by formula (1) above is reacted with any of the crosslinking agents exemplified above, the resultant product forms a gel. The thus obtained gel exhibits not only hydrophilicity and water regain, but also biocompatibility, thereby reducing adsorption of a protein, a cell and the like, which adsorption occur when the gel is contacted with a body fluid. Further, the gel is advantageous in that it has low toxicity, and in that the adhesion of a biological tissue to the gel is reduced. Therefore, the gel can be used in the form of a film for preventing the adhesion of a biological tissue or covering a wound. When such a film is used for covering a heat wound, such as a burn, the film exhibits effects of cooling the heat wound due to the hydrophilicity and water regain of the gel. Further, when such a film is used for covering a heat wound, the film absorbs an excess amount of a transudate from the wound so as to provide an appropriate moisture to the wound, thereby promoting the healing of the wound. Furthermore, the film is advantageous in that the patient feels less pain during the peeling off of the film from the wound.

With respect to the thickness of the above-mentioned film, there is no particular limitation. The thickness of the film is generally from 0.1 to 10 mm, preferably from 0.1 to 5 mm, more preferably from 0.2 to 1 mm. The film can be advantageously used as a medical product (e.g., an anti-adhesion membrane for use after an operation, and a wound dressing) and for producing cosmetics.

The resin of the present invention can be used in the form of a drug complex in which a compound having a pharmaceutical activity is bonded to the resin of the present invention through a linker, such as an amino acid or a peptide. Since such a drug complex has only an extremely weak interaction with living organisms, the drug complex enables the delivery of a compound having a pharmaceutical activity to a target tissue (e.g., a tumor cell, an inflamed tissue and a damaged tissue) without being recognized by a biological tissue when administered to a living body.

For example, when the resin of the present invention comprises a polymer which has a carboxyl group introduced thereto, sodium can be introduced to the carboxyl group by an ion exchange resin, to thereby improve the water-solubility of a drug complex which is produced by introducing a drug into the resin of the present invention.

Examples of the above-mentioned compounds having a pharmaceutical activity include compounds having an anti-cancer activity, such as compounds having a hydroxyl group or an amino group, and anti-cancer drug derivatives which have the above-mentioned functional group introduced thereto. Specific examples of compounds having an anti-cancer activity include taxanes and derivatives thereof, such as paclitaxel and docetaxel; anthracycline antibody drugs and derivatives thereof, such as doxorubicine; platinum anti-tumor drugs and derivatives thereof, such as mitomycin C and cisplatin; camptothecine and derivatives thereof; and anti-tumor drugs and derivatives thereof other than mentioned above, such as fluoropyrimidine antimetabolites, vinca alkaloids and folic acid antagonists. Further examples of compounds having a pharmaceutical activity include adrenocortical hormones, such as prednisolone and dexamethasone; vasolidators, such as nifedipine and dipyridamole; and enzyme inhibitors, such as angiotensin converting enzyme inhibitors (e.g., captoril) and HMG-CoA reductase inhibitors (e.g., mevalotin and lovastatin).

Examples of the above-mentioned linkers include amino acids and peptides having 2 to 4 amino acid residues. Specific examples of linkers include amino acids, such as glycine (gly), alanine (Ala), leucine (Leu), isoleucine (Ile) and phenylalanine (Phe); peptides having 2 amino acid residues, such as Phe-Gly, Ala-Gly and Leu-Gly; peptides having 3 amino acid residues, such as Gly-Phe-Gly and Gly-Gly-Gly; and peptides having 4 amino acid residues, such as Gly-Gly-Phe-Gly.

With respect to the above-mentioned compound having a pharmaceutical activity, in view of the ability of the drug complex to migrate into a tumor cell, the introduction ratio thereof is preferably from 0.001 to 30 mol %, more preferably from 0.01 to 30 mol %, still more preferably from 0.01 to 10 mol %, based on the total molar amount of recurring units shown in formula (1) above. Further, it is preferred that the amount of the above-mentioned compound having a pharmaceutical activity is from 0.1 to 50% by weight, more advantageously from 1 to 20% by weight, based on the weight of the polymer having the compound bonded thereto.

The dose and form of the drug complex and the schedule of administration of the drug complex are not particularly limited, and may vary depending on the type of the drug complex used. Further, with respect to the manner of administration of the drug complex, there is no particular limitation; however, it is preferred to employ a non-oral administration. Especially in the case of paclitaxel, it is preferred that the dose of the drug complex is from 20 to 1000 mg/m² (mg/body surface area) per adult, in terms of the amount of paclitaxel contained in the drug complex. However, in actuality, the appropriate dose of the drug complex depends on the composition of the drug complex, the manner of administration, the body portion to which the drug complex is delivered, and the type of tumor to be treated. Further, with respect to the dose of the drug complex, it is required to consider various factors, such as the age, weight, gender, diet and physical condition of the patient, which factors may affect the drug action of the drug complex.

The resin of the present invention which comprises the substituted oxyalkylene polymer represented by formula (1) above may be produced, for example, by subjecting ethylene oxide and/or at least one alkyl or aryl glycidyl ether to a ring opening polymerization, if desired, in a solvent (such as toluene, bis(2-methoxyethyl) ether, ethylene glycol dimethyl ether or hexane) in the presence of a conventional polymerization initiator, such as a catalytic amount of a Lewis acid (e.g., tributyllithium aluminum), a potassium salt of a tertiary alcohol (e.g., a potassium salt of t-butanol) or a mixture thereof, wherein the ring opening polymerization is performed at room temperature or while cooling with ice or heating. Herein, the "catalytic amount" means an amount of from 0.001 to 30 mol %, preferably 0.01 to 20 mol %, based on the total molar amount of all monomers used in the ring opening polymerization (i.e., ethylene oxide and/or at least one alkyl or aryl glycidyl ether).

With respect to a substituted oxyalkylene polymer, it is reported that, when a glycidyl ether (such as an alkyl glycidyl ether and an aryl glycidyl ether) and ethylene oxide are used as raw material monomers, a 3-hydroxyoxetane derivative may be by-produced in a very small amount depending on the type of glycidyl ether used, the type of polymerization initiator used, the type of solvent and the reaction conditions (see, for example, E. J. Vandenberg, J. Polym. Sci., Polym. Chem. Ed., Vol. 23 (1985), pp. 915-949 and E. J. Vandenberg, J. C. Mullis, R. S. Juvet, Jr., T. Miller and R. A. Nieman, J. Polym. Sci., Part A, Vol. 27 (1989), pp. 3113-3149). However, the excellent effects of the resin of the present invention are achieved by the presence of the substituted oxyalkylene polymer, and are not adversely affected by such a 3-hydroxyoxetan derivative which is by-produced in a very small amount.

With respect to the body fluid compatible/biocompatible resin of the present invention, the hydrophilicity or hydrophobicity thereof can be adjusted by appropriately selecting the raw materials (e.g., a glycidyl ether, such as an alkyl glycidyl ether and an aryl glycidyl ether, and ethylene oxide) for producing the resin of the present invention. For example, when the resin of the present invention which is produced from an alkyl or aryl glycidyl ether having a highly lipophilic group (e.g., propyl glycidyl ether, butyl glycidyl ether or phenyl glycidyl ether) is coated on a shaped article of a hydrophobic resin other than the resin of the present invention, it is possible to prevent the resin of the present invention from being delaminated from the shaped article.

Specifically, when the resin of the present invention is produced from an alkyl or aryl glycidyl ether having a highly lipophilic group (e.g., propyl glycidyl ether, butyl glycidyl ether or phenyl glycidyl ether) for improving the compatibility of the resin of the present invention with a polyethylene terephthalate (PET) film, it becomes possible to prevent the resin of the present invention from being delaminated from the PET film over a long period of time, namely, for about 5 hours while vibrating the PET film, and for about 12 hours when the PET film is allowed to stand. Further, as shown in the working examples of the present invention, when the resin of the present invention is produced from an alkylene glycidyl ether having a highly lipophilic group, the produced resin is advantageous in that it has the abilities to suppress the adsorption of a protein and/or a cell thereto, the platelet adhesion and the platelet activation, even when it is coated on a shaped article of a resin other than the resin of the present invention.

Alternatively, when a substituted oxyalkylene polymer is produced from a polysaccharide, the saccharide structure of a large part of polysaccharide molecules are broken to form a large number of primary hydroxyl groups, so that the structural freedom of the produced polymer is increased. As a result, the produced polymer becomes highly hydrophilic. Therefore, when the substituted oxyalkylene polymer produced from a polysaccharide is coated on a shaped article of a hydrophobic resin other than the resin of the present invention, the substituted oxyalkylene polymer is delaminated from the shaped article due to the high hydrophilicity thereof, so that the excellent effects of the present invention cannot be achieved. Specifically, for example, when a substituted oxyalkylene polymer is produced from dextran is coated on a PET film and the coated PET film is vibrated in a physiological saline, the substituted oxyalkylene polymer is delaminated from the PET film (i.e., the hydrophilicity of the coated film surface is impaired) in about 3 hours, so that the abilities of the coated film to suppress the adsorption of a protein and/or a cell thereto, the platelet adhesion and the platelet activation are impaired. For preventing the resin of the present invention (produced from a polysaccharide) from being delaminated from a PET film, it is preferred to introduce a lipophilic group to the resin produced from a polysaccharide, to thereby improve the compatibility of the resin and the surface of the PET film. By introducing a lipophilic group to the resin of the present invention, it becomes possible to prevent the resin from being delaminated from the PET film over a long period of time, namely, for about 5 hours while vibrating the PET film, and for 12 hours or more when the PET film is allowed to stand. Examples of lipophilic groups include a propyl group, a butyl group and a phenyl group.

When the resin of the present invention is produced from a polysaccharide, a lipophilic group can be introduced thereto by alkylation reaction. When the alkylation reaction is performed using an alkyl halide and a basic compound, it is necessary to dissolve a hydrophilic polymer obtained from the polysaccharide and the alkyl halide (which is hydrophobic) simultaneously, so that it is difficult to introduce a long chain alkyl group to the polymer, which long chain alkyl group has a low solubility. However, by reacting a glycidyl ether derivative (e.g., butyl glycidyl ether or phenyl glycidyl ether) with the polymer produced from a polysaccharide, in the presence of a basic compound, it becomes possible to introduce a long chain alkyl group to the polymer produced from a polysaccharide. By the introduction of such a long chain alkyl group, it has, for the first time, become possible to impart a resin produced from a polysaccharide with excellent abilities to prevent the adsorption of a protein and/or a cell thereto, the platelet adhesion and the platelet activation (see the working examples).

When the resin of the present invention comprises the substituted oxyalkylene polymer of formula (1) above which is a copolymer comprising two types of recurring units, namely, a recurring unit in which $R^2$ is a methyl group, and a recurring unit in which $R^2$ is a butyl group, there is a tendency that the hydrophilicity of the copolymer increases in accordance with the increase in the molar ratio of methyl groups to all $R^2$ groups, thereby increasing the solubility of the copolymer in water, whereas the hydrophobicity of the copolymer increases in accordance with the increase in the molar ratio of butyl groups to all $R^2$ groups, thereby lowering the solubility of the copolymer in water. Specifically, when the molar amount of butyl groups, based on the total molar amount of all $R^2$ groups, is extremely high, for example, as high as 95 mol % or more, the liposolubility of the copolymer is improved, thereby improving the coatability of the resin of the present invention to a resin other than the resin of the present invention; however, disadvantages are caused in that the amount of plasma protein is increased, and in that occurrence of platelet adhesion is increased. On the other hand, when the molar amount of methyl groups, based on the total molar amount of all $R^2$ groups, is extremely high, for example, as high as 95 mol % or more, the suppression of the adsorption of plasma protein and platelet adhesion is remarkably improved; however, disadvantages are caused in that the copolymer is rendered water-soluble, so that the coatability of the resin of the present invention is lowered, and that, hence, the resin is likely to be delaminated from a substrate. Therefore, for achieving the satisfactory effects of suppressing the adsorption of a protein/or a cell, the platelet adhesion and the platelet activation, it is important that the copolymer has both of a hydrophilic group (e.g., a hydroxyl group or a methyl group) and a hydrophobic group (e.g., a butyl group or a phenyl group) in an appropriate ratio.

In the present invention, when the resin of the present invention which comprises the substituted oxyalkylene polymer of formula (1) above is produced from, for example, ethylene oxide and n-butyl glycidyl ether, there is a tendency that the hydrophilicity of the resin increases in accordance with the increase in the molar ratio of ethylene oxide to n-butyl glycidyl ether, thereby increasing the solubility of the resin in water, whereas the hydrophobicity of the resin increases in accordance with the increase in the molar ratio of n-butyl glycidyl ether to ethylene oxide, thereby lowering the solubility of the resin in water. Specifically, when the molar amount of n-butyl glycidyl ether, based on the total molar amount of n-butyl glycidyl ether and ethylene oxide, is extremely high, for example, as high as 95 mol % or more, the liposolubility of the resin of the present invention is improved, thereby improving the coatability of the resin to a medical equipment at a portion which is contacted with a body fluid or a biological tissue and improving the compatibility of the resin of the present invention with a resin other than the resin of the present invention; however, disadvantages are caused in that the amount of plasma protein adsorbed by the medical equipment is increased, and in that occurrence of platelet adhesion is increased. On the other hand, when the molar amount of ethylene oxide, based on the total molar amount of ethylene oxide and n-butyl glycidyl ether, is extremely high, for example, as high as 95 mol % or more, the suppression of the adsorption of a polypeptide, a protein and a cell, and the suppression of platelet adhesion are remarkably improved; however, disadvantages are caused in that the resin is rendered water-soluble, so that the coatability of the resin to a substrate is lowered, and that, hence, the resin is likely to be delaminated from the substrate.

Therefore, for satisfactorily suppressing the adsorption of a protein and a cell, the platelet adhesion and the platelet activation, it is important that the resin of the present invention has a good balance with respect to the amounts of a hydrophilic group (e.g., a group containing ethylene oxide) and a hydrophobic group (e.g., a group containing n-butyl glycidyl ether). For example, when it is intended to apply the resin of the present invention (produced from hydrophilic monomer (A) (e.g., ethylene oxide) and a hydrophobic monomer (B) (e.g., n-butyl glycidyl ether)) onto a substrate, a hydrophobic group which is suitable for obtaining a resin to be coated on a substrate can be introduced to the resin of the present invention by producing the resin using an appropriate amount of hydrophobic monomer (B). By introducing appropriate hydrophobic monomer (B) to the resin of the present invention in an appropriate amount, it becomes possible to obtain the resin of the present invention, which, in the form of a mixture thereof with a resin other than the resin of the present invention or in the form of a coating formed on a substrate, exhibits excellent desired properties, i.e., excellent abilities to suppress adsorption of a polypeptide, a protein and a cell, platelet adhesion and platelet activation, excellent ability to separate, remove and recover a polypeptide, a protein and a cell, and excellent ability to recover a platelet). In the present invention, the molar ratio of hydrophobic monomer (B) to the total of hydrophilic monomer (A) and hydrophobic monomer (B), i.e., (B)/((A)+(B)), is from 0.001 to 0.5, preferably from 0.025 to 0.5. Similarly, with respect to the substituted oxyalkylene polymer represented by formula (4) above, the molar ratio of m to the total of m and n (i.e., m/(m+n)) is from 0.001 to 0.500, preferably from 0.025 to 0.500.

The body fluid compatible and biocompatible resin of the present invention can be advantageously used as an ingredient, a molding material or a coating material in the production of various biological and medical products. Specific examples of biological and medical products include a membrane for an artificial kidney, a membrane for an artificial spleen, a membrane for an artificial liver, a plasma separation membrane, a membrane for an artificial lung, an artificial blood vessel, an artificial skin, a virus removal membrane and a leukocyte removal membrane. Further, the resin of the present invention can be used in the form of a film. The resin of the present invention in the form of a film can be used for covering external wounds, such as bedsore, burn and ulcer, and can also be used for covering wounds caused by destruction of internal tissues, such as a corium, a hypoderm, a muscle, a tendon, an articulation and a bone. Furthermore, the resin of the present invention can also be used as a raw material in a wide variety of medical application fields. For example, the resin can be used for producing an anti-adhesion membrane, a wound dressing, an implant material, a drug complex for use in a drug delivery system (DDS) in which a drug release rate is controlled, a filter for separating and purifying a useful component in blood.

Further, by utilizing the hydrophilicity and moisture retention property of the resin, the resin of the present invention can be used for producing cosmetics, and can also be used for fiber treatments. As applications other than mentioned above, for example, the resin of the present invention can be used for various treatments of a polypeptide and a protein which are derived from organisms, such as a human, a mammal, a reptile, a microbe and an insect, wherein the treatments include a separation, a purification, a concentration, a filtration, a desalting/concentration and the like. Furthermore, the resin of the present invention can also be used for treatments of a medicine, an active pharmaceutical ingredient of a medicine and a raw material for a medicine, which contain the above-mentioned polypeptide or protein, wherein the treatments include a separation, a purification, a concentration, a filtration, a desalting/concentration and the like. Furthermore, the resin of the present invention can also be used as an additive for raw materials for producing an equipment used for the above-mentioned treatments or as a coating material for such an equipment.

Further, by utilizing the moisture retention property of the resin and the ability of the resin to be unrecognized by a living organism (e.g., suppression of a protein adsorption and the like), the resin of the present invention can be used for producing cosmetics, such as an antistatic hair dressing, and a stimulation inhibitory substance for decreasing the stimulation caused by a fibrous material which has a stimulating substance attached thereto. Furthermore, by utilizing the amphipathic property of the resin, the resin of the present invention can be used as a component of a contact lens washing solution, wherein the washing solution can be prepared by dissolving the resin of the present invention in water in a small amount (e.g., 0.001 to 1% by weight, based on the total weight of the washing solution).

In the above-mentioned applications, only the exposed surface of the resin is contacted with a biological tissue or a body fluid, and the exposed surface of the resin exhibits affinity with a biological tissue or a body fluid (e.g., an interaction between the exposed surface of the resin and the biological tissue or the body fluid). The resin of the present invention remains stable at the interface between the resin and the biological tissue or the body fluid, so that the dissolution of the resin into a biological tissue or a body fluid can be suppressed. Therefore, by using the resin of the present invention individually or in the form of a resin composition which is obtained by combining the resin of the present invention with a resin other than the resin of the present invention, a membrane for an artificial organ (e.g., a membrane for an artificial kidney, a membrane for an artificial spleen and a membrane for an artificial liver) can be produced. Alternatively, the resin of the present invention or the above-mentioned resin composition can be used for coating a membrane for an artificial organ produced from a material other than the resin of the present invention. An artificial organ coated with the resin of the present invention or the above mentioned resin composition is advantageous in that an appropriate material (other than the resin of the present invention) can be selected for obtaining a membrane having the characteristics (e.g., satisfactory physical strength) required of a membrane for an artificial organ and the like. That is, in the present invention, there is provided a method for medical treatment involving a contact of the body fluid compatible and biocompatible resin of the present invention with at least one member selected from the group consisting of a body fluid and a biological tissue, wherein the resin of the present invention or a composition comprising the resin of the present invention is used as an ingredient, a molding material or a coating material in the production of various biological and medical products. Specific examples of biological and medical products include a membrane for an artificial kidney, a membrane for an artificial spleen, a membrane for an artificial liver, a plasma separation membrane, a membrane for an artificial lung, an artificial blood vessel, an anti-adhesion membrane, an artificial skin, a wound dressing, an implant material, a drug complex for use in a drug delivery system (DDS) in which a drug release rate is controlled, and a filter for separating and purifying a useful component in blood.

When the resin of the present invention is used as a coating material for a shaped article of a resin other than the resin of the present invention, an appropriate amount of a hydrophobic group can be introduced into the resin of the present invention, which hydrophobic group is necessary for obtaining a satisfactory coatability to the shaped article. By introducing a hydrophobic group which is compatible with the above-mentioned resin other than the resin of the present invention, it becomes possible to obtain the resin of the present invention, which, in the form of a coating formed on the above-mentioned shaped article, can suppress not only the adhesion of biological substances (such as a cell and a platelet) and adsorption of a protein to the resin, but also the activation of a platelet and the like. That is, with respect to the resin of the present invention used as a coating material for a shaped article of a resin other than the resin of the present invention, by virtue of the hydrophilic group present in the resin, the adsorption of a protein to the resin and the adhesion of biological substances (such as a cell and a platelet) to the resin can be suppressed, and the activation of a platelet by the resin can also be suppressed, whereas, by virtue of the hydrophobic group present in the resin, the liposolubility thereof is improved (i.e., the coatability of the resin to the shaped article is improved).

The hydrophilicity of the resin of the present invention can be lowered by crosslinking the resin by a crosslinking agent, such as a compound having a terminal epoxy group. As a result, not only does the coating of a shaped article produced from the resin other than the resin of the present invention with the resin of the present invention become easy, but also the coating ratio of the shaped article can be improved. For example, when the resin of the present invention contains a recurring unit of formula (1) in which $R^4$ represents a hydroxyl group, this hydroxyl group can be used as a functional group for crosslinking the resin.

As crosslinking agents, there can be mentioned the above-mentioned compounds having a terminal epoxy group, such as epichlorohydrin, epibromohydrin, ethylene glycol diglycidyl ether and butanediol diglycidyl ether; and diisocyanate compounds, such as tolylene diisocyanate and xylylene diisocyanate. Among them, from the viewpoint of the yield of a crosslinked product and the balance between the hydrophilicity and hydrophobicity of a crosslinked product, preferred are ethylene glycol diglycidyl ether and butanediol diglycidyl. When these crosslinking agents are used, the degree of crosslinking can be adjusted by appropriately selecting reaction conditions, such as the amount of a crosslinking agent used in the production of the resin, the type of a solvent and the reaction temperature. Further, the hydrophobicity of a crosslinked product can be adjusted by the degree of crosslinking. With respect to the amount of the crosslinking agent, the larger the amount of the crosslinking agent, the higher the degree of crosslinking of the crosslinked product and, hence, the higher the hydrophobicity of the crosslinked product. It is even possible to obtain a crosslinked product in the form of a gel which has a poor water-solubility.

When the resin of the present invention is used as a coating material for a shaped article, the resin of the present invention is generally used in an amount of from 0.001 to 30% by weight, based on the weight of the resin other than the resin of the present invention. However, when the resin of the present invention is used in an amount of from 0.01 to 20% by weight, based on the weight of the resin other than the resin of the present invention, the resin of the present invention exhibits excellent body fluid compatibility and biocompatibility, that is, the resin is advantageous not only in that the adhesion of biological substances (such as a biological tissue, a cell and a platelet) to the resin can be suppressed, but also in that the activation of a platelet, a complement and the like by the resin can be suppressed.

As methods for incorporating the resin of the present invention to a shaped article produced from the resin other than the resin of the present invention, there can be mentioned an addition method and a coating method, which are generally employed. For example, a coating of a shaped article can be performed as follows. A shaped article is coated with a resin solution obtained by diluting the resin of the present invention with a solvent by a conventional method, such as an immersion method, a spray method or a flow coater method, to form a coating, followed by drying the coating. There is no particular limitation with respect to the thickness of the coating; however, it is preferred that the thickness of the coating is 1 mm or less. As examples of solvents for diluting the resin, there can be mentioned ethanol, isopropanol, ethylene glycol and the like.

As the resin other than the resin of the present invention, which is used in the resin composition of the present invention or used in the above-mentioned shaped article, there can be mentioned a polyethylene, a polypropylene, a polyvinyl chloride, a polyvinylidene chloride, a polyvinylidene fluoride, a polytetrafluoroethylene, a halogenated polyolefin, a polyester, a polyamide, a polyimide, a polysulfone, a polycarbonate and the like. Further, as a substrate used when the resin or resin composition of the present invention is used as a coating material, there can be mentioned metals, such as stainless steel, titanium and a titanium alloy; and ceramics, such as a hydroxyapatite, graphite and titanium nitride.

The resin composition of the present invention can be shaped into a film, a yarn or a non-woven fabric. Even in the form of a film, a yarn or a non-woven fabric, the resin composition of the present invention exhibits excellent body fluid compatibility and biocompatibility. Specifically, the resin composition of the present invention in the form of a film, a yarn or a non-woven fabric is advantageous not only in that the adhesion of biological substances (such as a biological tissue, a cell and a platelet) to the resin composition, and the adsorption of a protein to the resin composition can be suppressed, but also in that the activation of a platelet, a complement and the like by the resin composition can be suppressed. For example, the resin of the present invention may be added to a polysulfone which is a material for a hollow yarn used for a module in an artificial kidney (i.e., an addition method), thereby increasing the blood compatibility of the module. The amount of the body fluid compatible and biocompatible resin of the present invention in the resin composition of the present invention is in the range of from 0.01 to 75% by weight, preferably from 1 to 75% by weight, more preferably from 5 to 50% by weight, based on the weight of the resin composition.

As mentioned above, the resin of the present invention remains stable at the interface between the resin and the biological tissue, specifically, the body fluid (e.g., blood) and, hence, the dissolution of the resin into the body fluid can be suppressed. Further, as already mentioned above, the resin of the present invention exhibits excellent body fluid compatibility and biocompatibility. Specifically, the resin of the present invention is advantageous not only in that the adhesion of biological substances (such as a biological tissue and a platelet) to the resin can be suppressed, but also in that the activation of a platelet and the like by the resin can be suppressed. Furthermore, when the resin of the present invention has an aliphatic hydrocarbon group as a side chain functional group, the hydrophilicity of the resin as a whole becomes small. For the above reasons, the resin of the present invention as a whole remains stable at the interface between the resin and the biological tissue without being dissolved into the body fluid. Further, when such a resin having a hydrophobic group at the side chain is used as a coating material, the resin is advantageous in that the coating ratio of a shaped article is improved.

When the body fluid compatible and biocompatible resin of the present invention is administered to a living organism, the resin of the present invention is unlikely to be recognized by the biological tissue. Further, the amount of the resin of the present invention introduced into an organ is reduced and, hence, the resin of the present invention is advantageous in that the resin is unlike to exhibit toxicity in an organ. The crosslinked product of the resin of the present invention is gradually excreted from the living organisms and, hence, the crosslinked product has advantageously high safety.

BEST MODE FOR CARRYING OUT THE INVENTION

Hereinbelow, the present invention will be described in more detail with reference to the following Examples, Reference Example and Comparative Examples, which should not be construed as limiting the scope of the present invention.

Example 1

40 ml of anhydrous dichloromethane was added to 2.5 g (10 mmol) of p-toluenesulfonic acid-pyridinium salt while cooling with ice under an argon atmosphere, and the resultant mixture was stirred for 15 minutes. 6.63 ml (100 mmol) of glycidol (manufactured and sold by Sigma-Aldrich Co., U.S.A.) and 18.3 ml (200 mmol) of 3,4-dihydro-2H-pyran were then added to the above-obtained mixture, followed by stirring at room temperature for 6 days to thereby effect a reaction. After completion of the reaction, the resultant reaction mixture was washed with ethyl acetate and a saturated aqueous sodium hydrogen carbonate solution. The washed reaction mixture was dehydrated and concentrated. The resultant concentrated reaction mixture was purified by silica gel column chromatography (silica gel: 120 g, product no. 9385, manufactured and sold by Merck & Co., Inc, U.S.A.; eluant: a mixed solvent comprised of hexane and ethyl acetate (hexane:ethyl acetate ratio=5:2), thereby obtaining 2.6 g of glycidyl tetrahydropyranyl ether (compound (1)) which was a pale yellow, transparent oil.

Compound (1) was subjected to a $^1$H-NMR analysis using tetramethylsilane as a reference standard and deuterated DMSO (DMSO-d6) as a solvent. The resultant NMR spectrum showed that peaks ascribed to a tetrahydropyranyl group appeared at δ 1.50-1.75 ppm, δ 3.28-3.34 ppm, δ 3.45-3.53 ppm and δ 4.65-4.66 ppm, and that peaks ascribed to a glycidyl group appeared at δ 2.57-2.59 ppm, δ 2.61-2.63 ppm, δ 2.76-2.78, δ 3.14-3.18 ppm, δ 3.67-3.71 ppm, δ 3.75-3.80 ppm and δ 3.86-3.90 ppm.

Example 2

Substantially the same procedure as in the production of compound (1) in Example 1 was repeated, except that 19.1 ml (200 mmol) of ethyl vinyl ether was used instead of 18.3 ml (200 mmol) of 3,4-dihydro-2H-pyran and that the reaction was performed for only 1 day, thereby obtaining 1-ethoxyethyl glycidyl ether (compound (2)) in an amount of 5.0 g. The obtained compound (2) was a colorless, transparent oil.

Compound (2) was subjected to a $^1$H-NMR analysis using tetramethylsilane as a reference standard and deuterated DMSO as a solvent. The resultant NMR spectrum showed that peaks ascribed to an ethoxyethyl group appeared at δ 1.02-1.06 ppm, δ 1.12-1.15 ppm, δ 3.17-3.21 ppm, δ 3.28-3.38 ppm and δ 4.63-4.64 ppm, and that peaks ascribed to a glycidyl group appeared at δ 2.47-2.51 ppm, δ 2.65-2.67 ppm, δ 3.01-3.03 ppm, δ 3.48-3.53 ppm, δ 3.59-3.62 ppm and δ 3.68-3.72 ppm.

Example 3

5 ml of toluene was added to a mixture of 1.4 ml (10 mmol) of t-butyl glycidyl ether (manufactured and sold by Tokyo Kasei Kogyo Co., Ltd., Japan) and 12.9 ml (90 mmol) of n-butyl glycidyl ether (manufactured and sold by Tokyo Kasei Kogyo Co., Ltd., Japan) while cooling with ice under an argon atmosphere, and the resultant mixture was stirred for 20 minutes, thereby obtaining a first mixture. On the other hand, 100 μl of boron trifluoride ether complex and 900 μl of toluene were mixed together to obtain a second mixture, and 800 μl of the obtained second mixture was dropwise added to the first mixture, followed by a reaction at room temperature for 24 hours. After completion of the reaction, the resultant reaction mixture was washed with ethyl acetate and a saturated aqueous sodium hydrogen carbonate solution. The washed reaction mixture was dehydrated with magnesium sulfate and, then, concentrated under reduced pressure, thereby obtaining 10.8 g of the desired product (resin (1)) which was a colorless, transparent oil.

Resin (1) was subjected to a $^1$H-NMR analysis using tetramethylsilane as a reference standard and deuterated DMSO as a solvent. The resultant NMR spectrum showed that multiplet peaks ascribed to an n-butyl group appeared at δ 0.77-0.81 ppm, δ 1.21-1.26 ppm and δ 1.37-1.4 ppm, and that a peak ascribed to a t-butyl group appeared at δ 1.04 ppm. Further, the amount of pendant t-butyl group introduced into the resin was determined by the $^1$H-NMR analysis. The amount of the introduced pendant t-butyl group was 0.086 mol per mol of the recurring unit in formula (1) (i.e., n-butyl group:t-butyl group=0.914:0.086) (the above-mentioned amount of introduced pendant t-butyl group is hereinafter referred to simply as "t-butyl group introduction ratio").

Substantially the same procedure as in the production of resin (1) above was repeated except that the amounts of t-butyl glycidyl ether and n-butyl glycidyl ether were changed as shown in Table 1 below, thereby obtaining resins (2) to (8). The t-butyl group introduction ratio of each of resins (2) to (8) was determined by $^1$H-NMR analysis. The results are also shown in Table 1 below.

TABLE 1

|  | Resin (1) | Resin (2) | Resin (3) | Resin (4) |
|---|---|---|---|---|
| t-butyl glycidyl ether (mmol) | 10 | 20 | 30 | 50 |
| n-butyl glycidyl ether (mmol) | 90 | 80 | 70 | 50 |
| Amount of product (g) | 10.8 | 12.7 | 10.8 | 10.8 |
| t-butyl group introduction ratio | 0.086 | 0.167 | 0.289 | 0.472 |
| n-butyl group introduction ratio | 0.914 | 0.833 | 0.711 | 0.528 |

|  | Resin (5) | Resin (6) | Resin (7) | Resin (8) |
|---|---|---|---|---|
| t-butyl glycidyl ether (mmol) | 60 | 70 | 80 | 90 |
| n-butyl glycidyl ether (mmol) | 40 | 30 | 20 | 10 |
| Amount of product (g) | 11.0 | 11.4 | 11.0 | 10.0 |
| t-butyl group introduction ratio | 0.583 | 0.687 | 0.788 | 0.891 |
| n-butyl group introduction ratio | 0.417 | 0.313 | 0.212 | 0.109 |

Further, in Examples 3 to 29, the weight average molecular weights of the resins obtained were determined by GPC under the following conditions:

Column: G4000PWXL and G5000PWXL (each manufactured and sold by Tosoh Corporation, Japan),
Mobile phase: 20% acetonitrile solution in 50 mM lithium chloride,
Flow rate: 0.8 ml/min,
Column temperature: 40° C.,
Pump: L-6200 (manufactured and sold by Hitachi, Ltd., Japan),
Detector for RI: L-3300 (a differential refractometer, manufactured and sold by Hitachi, Ltd., Japan), and
Detector for UV and visual light absorbance: L-4200 (a spectrophotometer, manufactured and sold by Hitachi, Ltd., Japan).

A calibration curve for calculating the molecular weight was prepared using standard polyethylene glycol samples (4 types of "TSK standard POLY(ETHYLENE OXIDE)" respectively having weight average molecular weights of 24,000, 50,000, 107,000 and 140,000) (manufactured and sold by Tosoh Corporation, Japan).

The weight average molecular weight (Mw) of each of resins (1) to (8) was approximately 20,000.

Example 4

Substantially the same procedure as in the production of resin (1) in Example 3 was repeated except that 1.4 ml (10 mmol) of t-butyl glycidyl ether (manufactured and sold by Tokyo Kasei Kogyo Co., Ltd., Japan) and 8.1 ml (90 mmol) of glycidyl methyl ether (manufactured and sold by Tokyo Kasei Kogyo Co., Ltd., Japan) were used as raw materials, thereby obtaining resin (9) in an amount of 9.8 g. The obtained resin (9) was a pale yellow, transparent oil.

Resin (9) was subjected to a $^1$H-NMR analysis using tetramethylsilane as a reference standard and deuterated DMSO as a solvent. The resultant NMR spectrum showed that a single peak ascribed to a t-butyl group appeared at δ 1.038 ppm and a single peak ascribed to a methyl group appeared at δ 3.164 ppm. Further, the amount of pendant t-butyl group introduced into the resin was determined by the $^1$H-NMR analysis. The amount of the introduced pendant t-butyl group was 0.123 mol per mol of the recurring unit in formula (1).

The weight average molecular weight (Mw) of resin (9) was 20,000.

Example 5

Substantially the same procedure as in the production of resin (1) in Example 3 was repeated except that 2.8 ml (20 mmol) of t-butyl glycidyl ether and 7.18 ml (80 mmol) of glycidyl methyl ether were used as raw materials, thereby obtaining resin (10) in an amount of 9.5 g. The obtained resin (10) was a pale yellow, transparent oil.

The amount of the introduced pendant t-butyl group was 0.242 mol per mol of the recurring unit in formula (1).

The weight average molecular weight (Mw) of resin (10) was 18,000.

Example 6

Substantially the same procedure as in the production of resin (1) in Example 3 was repeated except that 4.0 ml (45 mmol) of glycidyl methyl ether and 0.8 ml (5 mmol) of glycidyl tetrahydropyranyl ether (compound (1)) prepared in Example 1 were used as raw materials, thereby obtaining resin (11) in an amount of 4.1 g. The obtained resin (11) was a pale yellow, transparent oil.

Resin (11) was subjected to a $^1$H-NMR analysis using tetramethylsilane as a reference standard and deuterated DMSO as a solvent. The resultant NMR spectrum showed that a peak ascribed to a tetrahydropyranyl group appeared in the vicinity of δ 1.4 ppm, and that a single peak ascribed to a methyl group appeared at δ 3.166 ppm. Further, the amount of pendant tetrahydropyranyl group introduced into the resin was determined by $^1$H-NMR analysis. The amount of the introduced pendant tetrahydropyranyl group was 0.093 mol per mol of the recurring unit in formula (1).

The weight average molecular weight (Mw) of resin (11) was 18,000.

Example 7

Substantially the same procedure as in the production of resin (1) in Example 3 was repeated except that 4.0 ml (45 mmol) of glycidyl methyl ether and 0.7 ml (5 mmol) of 1-ethoxyethyl glycidyl ether (compound (2)) prepared in Example 2 were used as raw materials, thereby obtaining resin (12) in an amount of 3.6 g. The obtained resin (12) was a pale yellow, transparent oil.

Resin (12) was subjected to a $^1$H-NMR analysis using tetramethylsilane as a reference standard and deuterated DMSO as a solvent. The resultant NMR spectrum showed that multiplet peaks ascribed to a 1-ethoxyethyl group appeared at δ 0.984-1.016 ppm and δ 1.076-1.110 ppm, and that a single peak ascribed to a methyl group appeared at δ 3.166 ppm. Further, the amount of pendant 1-ethoxyethyl group introduced in the resin was determined by $^1$H-NMR analysis. The amount of the introduced pendant 1-ethoxyethyl group was 0.121 mol per mol of the recurring unit in formula (1).

The weight average molecular weight (Mw) of resin (12) was 15,000.

Example 8

Substantially the same procedure as in the production of resin (1) in Example 3 was repeated except that 6.77 ml (50 mmol) of glycidyl phenyl ether alone was used as a raw material, thereby obtaining resin (13) in an amount of 7.2 g. The obtained resin (13) was a colorless, transparent oil. The weight average molecular weight (Mw) of resin (13) was 15,000.

Example 9

Substantially the same procedure as in the production of resin (1) in Example 3 was repeated except that 6.1 ml (45 mmol) of glycidyl phenyl ether and 0.45 ml (5 mmol) of glycidyl methyl ether were used as raw materials, thereby obtaining resin (14) in an amount of 7.2 g. The obtained resin (14) was a colorless, transparent oil.

Resin (14) was subjected to a $^1$H-NMR analysis using tetramethylsilane as a reference standard and deuterated DMSO as a solvent. The resultant NMR spectrum showed that multiplet peaks ascribed to a phenyl group appeared at δ 6.870-6.971 ppm and δ 7.175-7.298 ppm, and that a peak ascribed to a methyl group appeared at δ 3.381 ppm. Further, the amount of pendant methyl group introduced into the resin was determined by $^1$H-NMR analysis. The amount of the introduced pendant methyl group was 0.079 mol per mol of the recurring unit in formula (1) (the above-mentioned amount of introduced methyl group is hereinafter referred to simply as "methyl group introduction ratio").

Substantially the same procedure as in the production of resin (14) above was repeated except that the amounts of glycidyl phenyl ether and glycidyl methyl ether were changed as shown in Table 2 below, thereby obtaining resins (15) to (21). The methyl group introduction ratio of each of resins (15) to (21) was determined by $^1$H-NMR analysis. The results are also shown in Table 2 below.

TABLE 2

|  | Resin (14) | Resin (15) | Resin (16) | Resin (17) |
|---|---|---|---|---|
| Glycidyl phenyl ether (mmol) | 45 | 30 | 20 | 15 |
| Glycidyl methyl ether (mmol) | 5 | 20 | 30 | 35 |
| Amount of product (g) | 7.2 | 6.5 | 3.8 | 4.5 |
| Methyl group introduction ratio | 0.079 | 0.244 | 0.338 | 0.464 |
| Phenyl group introduction ratio | 0.921 | 0.756 | 0.662 | 0.536 |

|  | Resin (18) | Resin (19) | Resin (20) | Resin (21) |
|---|---|---|---|---|
| Glycidyl phenyl ether (mmol) | 10 | 5 | 3.57 | 2.94 |
| Glycidyl methyl ether (mmol) | 40 | 45 | 46.3 | 47.06 |
| Amount of product (g) | 4.2 | 3.0 | 2.6 | 3.0 |
| Methyl group introduction ratio | 0.708 | 0.807 | 0.844 | 0.876 |
| Phenyl group introduction ratio | 0.292 | 0.193 | 0.156 | 0.124 |

The weight average molecular weight (Mw) of each of resins (14) to (21) was approximately 10,000.

Example 10

Substantially the same procedure as in the production of resin (1) in Example 3 was repeated except that 6.1 ml (45 mmol) of glycidyl phenyl ether (manufactured and sold by Tokyo Kasei Kogyo Co., Ltd., Japan) and 0.35 ml (5 mmol) of propylene oxide (manufactured and sold by Tokyo Kasei Kogyo Co., Ltd., Japan) were used as raw materials, thereby obtaining resin (22) in an amount of 6.6 g. The obtained resin (22) was a colorless, transparent oil.

Resin (22) was subjected to a $^1$H-NMR analysis using tetramethylsilane as a reference standard and deuterated DMSO as a solvent. The resultant NMR spectrum showed that a single peak ascribed to a methyl group appeared in the vicinity of δ 1.0 ppm, and that multiplet peaks ascribed to a phenyl group appeared at δ 6.857-6.960 ppm and δ 7.163-7.281 ppm. Further, the amount of pendant methyl group introduced into the resin was determined by $^1$H-NMR analysis. The amount of the introduced pendant methyl group was 0.090 mol per mol of the recurring unit in formula (1). The weight average molecular weight (Mw) of resin (22) was 10,000.

Example 11

Substantially the same procedure as in the production of resin (1) in Example 3 was repeated except that 2.0 ml (15 mmol) of glycidyl phenyl ether and 2.5 ml (35 mmol) of propylene oxide were used as raw materials, thereby obtaining resin (23) in an amount of 3.5 g. The obtained resin (23) was a colorless, transparent oil. The amount of pendant methyl group introduced into the resin was determined by $^1$H-NMR analysis. The amount of the introduced pendant methyl group was 0.621 mol per mol of the recurring unit in formula (1). The weight average molecular weight (Mw) of resin (23) was 8,000.

Example 12

Substantially the same procedure as in the production of resin (1) in Example 3 was repeated except that 12.2 ml (90 mmol) of glycidyl phenyl ether and 1.4 ml (10 mmol) of t-butyl glycidyl ether were used as raw materials, thereby obtaining resin (24) in an amount of 14.2 g. The obtained resin (24) was a colorless, transparent oil.

Resin (24) was subjected to a $^1$H-NMR analysis using tetramethylsilane as a reference standard and deuterated DMSO as a solvent. The resultant NMR spectrum showed that a single peak ascribed to a t-butyl group appeared at δ 1.11 ppm, and that multiplet peaks ascribed to a phenyl group appeared at δ 6.925-6.976 ppm and δ 7.153-7.318 ppm. Further, the amount of pendant t-butyl group introduced into the resin was determined by $^1$H-NMR analysis. The amount of the introduced pendant t-butyl group was 0.095 mol per mol of the recurring unit in formula (1) (the above-mentioned amount of introduced t-butyl group is hereinafter referred to simply as "t-butyl group introduction ratio").

Substantially the same procedure as in the production of resin (24) above was repeated except that the amounts of glycidyl phenyl ether and t-butyl glycidyl ether were changed as shown in Table 3 below, thereby obtaining resins (25) to (31). The t-butyl group introduction ratio of each of resins (25) to (31) was determined by $^1$H-NMR analysis. The results are also shown in Table 3 below.

TABLE 3

|  | Resin (24) | Resin (25) | Resin (26) | Resin (27) |
|---|---|---|---|---|
| Glycidyl phenyl ether (mmol) | 90 | 80 | 70 | 50 |
| t-butyl glycidyl ether (mmol) | 10 | 20 | 30 | 50 |
| Amount of product (g) | 14.2 | 13.0 | 11.4 | 11.0 |
| t-butyl group introduction ratio | 0.095 | 0.165 | 0.294 | 0.484 |
| Phenyl group introduction ratio | 0.905 | 0.835 | 0.706 | 0.516 |

|  | Resin (28) | Resin (29) | Resin (30) | Resin (31) |
|---|---|---|---|---|
| Glycidyl phenyl ether (mmol) | 40 | 30 | 20 | 10 |
| t-butyl glycidyl ether (mmol) | 60 | 70 | 80 | 90 |
| Amount of product (g) | 11.0 | 10.2 | 11.4 | 11.8 |
| t-butyl group introduction ratio | 0.581 | 0.680 | 0.777 | 0.880 |
| Phenyl group introduction ratio | 0.419 | 0.320 | 0.223 | 0.120 |

The weight average molecular weight (Mw) of each of resins (24) to (31) was approximately 20,000.

Example 13

Substantially the same procedure as in the production of resin (1) in Example 3 was repeated except that 7.15 ml (50 mmol) of n-butyl glycidyl ether was used as a raw material, thereby obtaining resin (32) in an amount of 5.4 g. The obtained resin (32) was a colorless, transparent oil. The weight average molecular weight (Mw) of resin (32) was 30,000.

Example 14

Substantially the same procedure as in the production of resin (1) in Example 3 was repeated except that 6.4 ml (45 mmol) of n-butyl glycidyl ether and 0.45 ml (5 mmol) of glycidyl methyl ether were used as raw materials, thereby obtaining resin (33) in an amount of 5.3 g. The obtained resin (33) was a colorless, transparent oil.

Resin (33) was subjected to a $^1$H-NMR analysis using tetramethylsilane as a reference standard and deuterated DMSO as a solvent. The resultant NMR spectrum showed that a single peak ascribed to a methyl group appeared in the vicinity of δ 3.2 ppm, and that multiple peaks ascribed to an n-butyl group appeared at δ 0.857-0.899 ppm, δ 1.294-1.349 ppm and δ 1.452-1.505 ppm. Further, the amount of pendant methyl group introduced into the resin was determined by $^1$H-NMR analysis. The amount of the introduced pendant methyl group was 0.152 mol per mol of the recurring unit in formula (1) (the above-mentioned amount of introduced methyl group is hereinafter referred to simply as "methyl group introduction ratio").

Substantially the same procedure as in the production of resin (33) above was repeated except that the amounts of n-butyl glycidyl ether and glycidyl methyl ether were changed as shown in Table 4 below, thereby obtaining resins (34) to (41). The methyl group introduction ratio of each of resins (34) to (41) was determined by $^1$H-NMR analysis. The results are also shown in Table 4 below.

TABLE 4

|  | Resin (33) | Resin (34) | Resin (35) | Resin (36) | Resin (37) |
|---|---|---|---|---|---|
| n-butyl glycidyl ether (mmol) | 45 | 30 | 25 | 20 | 15 |
| Glycidyl methyl ether (mmol) | 5 | 20 | 25 | 30 | 35 |
| Amount of product (g) | 5.3 | 5.3 | 4.6 | 4.2 | 4.5 |
| Methyl group introduction ratio | 0.152 | 0.275 | 0.380 | 0.462 | 0.554 |
| Butyl group introduction ratio | 0.848 | 0.725 | 0.620 | 0.538 | 0.446 |

TABLE 4-continued

|  | Resin (38) | Resin (39) | Resin (40) | Resin (41) |
|---|---|---|---|---|
| n-butyl glycidyl ether (mmol) | 10 | 5 | 3.57 | 2.94 |
| Glycidyl methyl ether (mmol) | 40 | 45 | 46.3 | 47.06 |
| Amount of product (g) | 3.6 | 2.8 | 2.7 | 2.8 |
| Methyl group introduction ratio | 0.698 | 0.827 | 0.865 | 0.891 |
| Butyl group introduction ratio | 0.302 | 0.173 | 0.135 | 0.109 |

The weight average molecular weight (Mw) of each of resins (33) to (41) was 20,000.

Example 15

Substantially the same procedure as in the production of resin (1) in Example 3 was repeated except that 6.4 ml (45 mmol) of n-butyl glycidyl ether and 0.35 ml (5 mmol) of propylene oxide were used as raw materials, thereby obtaining resin (42) in an amount of 5.6 g. The obtained resin (42) was a colorless, transparent oil.

Resin (42) was subjected to a $^1$H-NMR analysis using tetramethylsilane as a reference standard and deuterated DMSO as a solvent. The resultant NMR spectrum showed that a single peak ascribed to a methyl group appeared at δ 1.0 ppm, and that multiplet peaks ascribed to an n-butyl group appeared at δ 0.855-0.899 ppm, δ 1.274-1.348 ppm and δ 1.450-1.503 ppm. Further, the amount of pendant methyl group introduced into the resin was determined by $^1$H-NMR analysis. The amount of the introduced pendant methyl group was 0.099 mol per mol of the recurring unit in formula (1) (the above-mentioned amount of introduced methyl group is hereinafter referred to simply as "methyl group introduction ratio").

Substantially the same procedure as in the production of resin (42) above was repeated except that the amounts of n-butyl glycidyl ether and propylene oxide were changed as shown in Table 5 below, thereby obtaining resin (43). The methyl group introduction ratio of resin (43) was determined by $^1$H-NMR analysis. The result is also shown in Table 5 below.

TABLE 5

|  | Resin (42) | Resin (43) |
|---|---|---|
| n-butyl glycidyl ether (mmol) | 45 | 15 |
| Propylene oxide (mmol) | 5 | 35 |
| Amount of product (g) | 5.6 | 2.6 |
| Methyl group introduction ratio | 0.099 | 0.657 |
| Butyl group introduction ratio | 0.901 | 0.343 |

The weight average molecular weight (Mw) of each of resins (42) and (43) was approximately 15,000.

Example 16

Substantially the same procedure as in the production of resin (1) in Example 3 was repeated except that 4.48 ml (50 mmol) of glycidyl methyl ether alone was used as a raw material, thereby obtaining resin (44) in an amount of 3.2 g. The obtained resin (44) was a colorless, transparent oil. The weight average molecular weight (Mw) of resin (44) was approximately 10,000.

Example 17

Substantially the same procedure as in the production of resin (1) in Example 3 was repeated except that 14.3 ml (50 mmol) of t-butyl glycidyl ether alone was used as a raw material, thereby obtaining resin (45) in an amount of 4.9 g. The obtained resin (45) was a colorless, transparent oil. The weight average molecular weight (Mw) of resin (45) was 40,000.

Example 18

Resin (1) (which is a glycidol derivative) was used as a starting material. To 5.4 g (50 mmol) of resin (1) cooled in ice was added 25 ml of 4 N hydrogen chloride in 1,4-dioxane (manufactured and sold by KOKUSAN CHEMICAL Co., Ltd, Japan) (amount of hydrogen chloride added: 100 mmol), and the resultant mixture was reacted at room temperature for 2 days. After completion of the reaction, the reaction solvent (1,4-dioxane) was distilled off from the reaction mixture under reduced pressure, thereby obtaining 5.6 g of the desired product (resin (46)) which was a colorless, transparent oil.

Resin (46) was subjected to a $^1$H-NMR analysis using tetramethylsilane as a reference standard and deuterated DMSO as a solvent. The peak ascribed to a t-butyl group of resin (1) (which appeared at δ 1.04 ppm) disappeared from the resultant NMR spectrum of resin (46) and, thus, it was confirmed that the pendant t-butyl groups were eliminated from resin (1) by the reaction with 4 N hydrogen chloride.

Substantially the same procedure as in the production of resin (46) above was repeated except that the resin used as a starting material was changed as shown in Table 6 below, thereby obtaining resins (47) to (63). The resins used as starting materials contained t-butyl groups as a protecting group for a hydroxyl group, but the t-butyl groups were eliminated by the reaction with 4 N hydrogen chloride. The elimination of the t-butyl groups was confirmed by $^1$H-NMR analysis, that is, disappearance of the peak ascribed to the t-butyl group was detected. The amounts of the products obtained are also shown in Table 6 below.

TABLE 6

|  | Resin (46) | Resin (47) | Resin (48) | Resin (49) | Resin (50) |
|---|---|---|---|---|---|
| Starting material | Resin (1) | Resin (2) | Resin (3) | Resin (4) | Resin (5) |
| Amount of starting material weight (g)/moles (mmol) | 5.4/50 | 6.3/50 | 5.4/50 | 5.4/50 | 5.5/50 |
| Amount of 4N—HCl (ml) | 25 | 25 | 25 | 25 | 25 |
| Method for analyzing the product | NMR | NMR | NMR | NMR | NMR |
| Amount of product (g) | 5.6 | 5.7 | 3.2 | 3.3 | 3.3 |

|  | Resin (51) | Resin (52) | Resin (53) | Resin (54) | Resin (55) |
|---|---|---|---|---|---|
| Starting material | Resin (6) | Resin (7) | Resin (8) | Resin (9) | Resin (10) |
| Amount of starting material weight (g)/moles (mmol) | 5.7/50 | 5.5/50 | 5.0/50 | 4.9/50 | 4.7/50 |
| Amount of 4N—HCl (ml) | 25 | 25 | 25 | 25 | 25 |
| Method for analyzing the product | NMR | NMR | NMR | NMR | NMR |
| Amount of product (g) | 2.9 | 2.6 | 2.6 | 3.7 | 3.8 |

|  | Resin (56) | Resin (57) | Resin (58) | Resin (59) | Resin (60) |
|---|---|---|---|---|---|
| Starting material | Resin (25) | Resin (26) | Resin (27) | Resin (28) | Resin (29) |
| Amount of starting material weight (g)/moles (mmol) | 7.1/50 | 6.5/50 | 5.7/50 | 5.5/50 | 5.5/50 |
| Amount of 4N—HCl (ml) | 25 | 25 | 25 | 25 | 25 |
| Method for analyzing the product | NMR | NMR | NMR | NMR | NMR |
| Amount of product (g) | 6.3 | 4.7 | 4.9 | 3.9 | 3.4 |

|  | Resin (61) | Resin (62) | Resin (63) |
|---|---|---|---|
| Starting material | Resin (30) | Resin (31) | Resin (45) |
| Amount of starting material weight (g)/moles (mmol) | 5.1/50 | 5.7/50 | 4.9/50 |
| Amount of 4N—HCl (ml) | 25 | 25 | 25 |
| Method for analyzing the product | NMR | NMR | NMR |
| Amount of product (g) | 2.4 | 2.7 | 1.8 |

The weight average molecular weight (Mw) of each of resins (46) to (63) was approximately 18,000.

Example 19

7 ml of toluene was added to a mixture of 13.49 ml (95 mmol) of t-butyl glycidyl ether and 0.78 ml (5 mmol) of ethylene glycol diglycidyl ether while cooling with ice under an argon atmosphere, and the resultant mixture was stirred for 20 minutes to obtain a first mixture. On the other hand, 100 μl of boron trifluoride ether complex and 900 μl of toluene were mixed together to obtain a second mixture, and 800 μl of the obtained second mixture was dropwise added to the first mixture, followed by a reaction at room temperature for 24 hours. After completion of the reaction, the resultant reaction mixture was concentrated under reduced pressure, thereby obtaining 10.8 g of the desired product (resin (64)) which was a colorless, transparent oil.

Substantially the same procedure as in the production of resin (64) above was repeated except that the amounts of t-butyl glycidyl ether and ethylene glycol diglycidyl ether were changed as shown in Table 7 below, thereby obtaining resins (65) to (69). The amount of each of the products obtained is also shown in Table 7 below.

TABLE 7

|  | Resin(64) | Resin(65) | Resin(66) |
|---|---|---|---|
| t-butyl glycidyl ether (mmol) | 95 | 90 | 85 |
| Ethylene glycol diglycidyl ether (mmol) | 5 | 10 | 15 |
| 10% (v/v) boron trifluoride ether complex (μl) | 900 | 900 | 800 |
| Toluene (ml) | 7 | 7 | 7 |
| Amount of product (g) | 10.8 | 9.3 | 10.5 |
|  | Resin(67) | Resin(68) | Resin(69) |
| t-butyl glycidyl ether (mmol) | 80 | 75 | 70 |
| Ethylene glycol diglycidyl ether (mmol) | 20 | 25 | 30 |
| 10% (v/v) boron trifluoride ether complex (μl) | 800 | 900 | 800 |
| Toluene (ml) | 7 | 7 | 7 |
| Amount of product (g) | 11.2 | 10.2 | 10.9 |

Example 20

7 ml of toluene was added to a mixture of 13.49 ml (95 mmol) of t-butyl glycidyl ether and 0.96 ml (5 mmol) of butanediol diglycidyl ether while cooling with ice under an argon atmosphere, and the resultant mixture was stirred for 10 minutes to obtain a first mixture. On the other hand, 100 μl of boron trifluoride ether complex and 900 μl of toluene were mixed together to obtain a second mixture, and 800 μl of the obtained second mixture was dropwise added to the first mixture, followed by a reaction at room temperature for 24 hours. After completion of the reaction, the resultant reaction mixture was concentrated under reduced pressure, thereby obtaining 9.4 g of the desired product (resin (70)) which was a colorless, transparent oil.

Substantially the same procedure as in the production of resin (70) above was repeated except that the amounts of t-butyl glycidyl ether and butanediol diglycidyl ether were changed as shown in Table 8 below, thereby obtaining resins (71) and (72). The amount of each of the products obtained is also shown in Table 8 below.

TABLE 8

|  | Resin(70) | Resin(71) | Resin(72) |
|---|---|---|---|
| t-butyl glycidyl ether (mmol) | 95 | 85 | 75 |
| Butanediol glycol diglycidyl ether (mmol) | 5 | 15 | 25 |
| 10% (v/v) boron trifluoride ether complex (μl) | 800 | 800 | 800 |
| Toluene (ml) | 7 | 7 | 7 |
| Amount of product (g) | 10.4 | 9.8 | 9.6 |

Example 21

Resin (64) (which is a glycidol derivative) was used as a starting material. To 5.2 g of resin (64) cooled in ice was added 25 ml of 4 N hydrogen chloride in 1,4-dioxane (manufactured and sold by KOKUSAN CHEMICAL Co., Ltd, Japan) (amount of hydrogen chloride added: 100 mmol), and the resultant mixture was reacted at room temperature for 2 days. After completion of the reaction, the reaction solvent (1,4-dioxane) was distilled off from the reaction mixture under reduced pressure, thereby obtaining 4.7 g of the desired product (resin (73)) which was a colorless, transparent oil.

Resin (73) was subjected to a $^1$H-NMR analysis using tetramethylsilane as a reference standard and deuterated DMSO as a solvent. The peak ascribed to a t-butyl group of resin (64) (which appeared at δ 1.04 ppm) disappeared from the resultant NMR spectrum of resin (73) and, thus, it was confirmed that the pendant t-butyl groups were eliminated from resin (64) by the reaction with 4 N hydrogen chloride.

Substantially the same procedure as in the production of resin (73) above was repeated except that the resin used as a starting material was changed as shown in Table 9 below, thereby obtaining resins (74) to (77). The resins used as starting materials contained t-butyl groups as a protecting group for a hydroxyl group, but the t-butyl groups were eliminated by the reaction with 4 N hydrogen chloride. The amounts of the products obtained are also shown in Table 9 below.

TABLE 9

|  | Resin (73) | Resin (74) | Resin (75) | Resin (76) | Resin (77) |
|---|---|---|---|---|---|
| Starting material | Resin (64) | Resin (65) | Resin (67) | Resin (70) | Resin (71) |
| Amount of starting Material (g) | 5.2 | 5.0 | 5.5 | 5.3 | 5.5 |
| Amount of 4N—HCl (ml) | 25 | 25 | 25 | 25 | 25 |
| Method for analyzing the product | NMR | NMR | NMR | NMR | NMR |
| Amount of product (g) | 4.7 | 4.7 | 5.1 | 4.9 | 5.2 |

Example 22

Resin (63) produced in Example 18 was used as a starting material. 1 ml of 1 N aqueous sodium hydroxide was added to 200 mg of resin (63) and, then, 0.15 ml (1 mmol) of ethylene glycol diglycidyl ether was also added thereto, followed by stirring to thereby obtain a reaction mixture. A part of the obtained reaction mixture was taken out and sandwiched between two glass plates, wherein the thickness of the space between the glass plates was adjusted using a vinyl tape. The resultant structure comprised of glass plates having the reaction mixture sandwiched therebetween was allowed to stand still at room temperature for 15 hours to cause crosslinking of the resin, to thereby obtain a gel in the form of a sheet. On the other hand, the remaining reaction mixture was stirred at room temperature for 15 hours to cause crosslinking of the resin, thereby obtaining a gel. In both cases of the crosslinking of the resin, the reaction mixture turned from an opaque liquid into a transparent gel as the crosslinking of the resin proceeded. The obtained gel in the form of a sheet (hereinafter referred to simply as a "gel sheet") was placed in a petri dish and neutralized with an equivalent amount of 1 N aqueous hydrochloric acid. Subsequently, the neutralized gel sheet was shaken in distilled water to thereby desalt the gel sheet.

Substantially the same procedure as in the production of the gel sheet above was repeated except that the amounts of resin (63), ethylene glycol diglycidyl ether and 1 N aqueous sodium hydroxide used were changed as shown in Table 10 below, thereby obtaining gel sheets (resins (78) to (80)). The estimated thickness of each of the obtained gel sheets is also shown in Table 10 below.

TABLE 10

|  | Resin(78) | Resin(79) | Resin(80) |
|---|---|---|---|
| Starting material | Resin(63) | Resin(63) | Resin(63) |
| Amount of starting material (mg) | 110 | 200 | 300 |
| Amount of ethylene glycol diglycidyl ether (ml) | 0.073 | 0.146 | 0.293 |
| Amount of 1 N aqueous sodium hydroxide (ml) | 1 | 1 | 1 |
| Estimated thickness of the gel sheet (mm) | 1 | 1 | 1 |

Example 23

To 3.2 g of resin (63) obtained in Example 18 was added 50 ml of dried toluene and the resultant mixture was refluxed at 110° C. for 1 hour. To the refluxed mixture were added 3.6 g of potassium t-butoxide (tBuOK) and 3.7 g of sodium chloroacetate, followed by a reaction at room temperature for 15 hours while stirring. After completion of the reaction, the reaction solvent was distilled off from the resultant reaction mixture under reduced pressure. The resultant residue was dissolved in 20 ml of water and dialyzed for 2 days against purified water using a dialysis membrane (trade name: Spectra/Por 3, molecular weight cut-off: 3,500) manufactured and sold by Spectrum Laboratories Inc., U.S.A. The resultant dialyzate was filtered through a membrane filter (trade name: MILLEX GP, pore size: 0.22 µm) manufactured and sold by Millipore Corporation, Japan, and the resultant filtrate was lyophilized, thereby obtaining 2.1 g of substituted polyethylene oxide (resin (81)) having a carboxymethyl group introduced therein. The obtained product was subjected to an NMR analysis using deuterated methanol as a solvent and tetramethylsilane as a reference standard. The NMR analysis showed that the amount of the carboxymethyl group introduced into the resin was 3.5 mol %, based on the total molar amount of the recurring unit in formula (1). The weight average molecular weight (Mw) of resin (81) was 40,000.

Example 24

Using paclitaxel (manufactured and sold by Hauser Chemical Research, Inc., Boulder, Colo., U.S.A.) as a starting material, a peptide linker was introduced into the OH group at the 2'-position of the paclitaxel, thereby obtaining 2'-Gly-Gly-Phe-Gly-paclitaxel hydrochloride. The introduction of the peptide linker into the paclitaxel was performed in accordance with the method described in U.S. Pat. No. 6,458,347. The structure of the obtained 2'-Gly-Gly-Phe-Gly-paclitaxel hydrochloride was confirmed by NMR and HRMS (high-resolution mass spectrometry).

Example 25

200 mg of resin (81) produced in Example 23 was dissolved in 8 ml of an aqueous N,N-dimethylformamide (DMF) (water:DMF ratio=1:1). To the resultant solution were added 1 ml of an aqueous DMF (water:DMF ratio=1:1) having 40 mg of 2'-Gly-Gly-Phe-Gly-paclitaxel hydrochloride (prepared in Example 24) dissolved therein and 1 ml of DMF having 0.2 g of 1-ethoxycarbonyl-2-ethoxy-1,2-dihydroquinoline (EEDQ) dissolved therein, and the resultant mixture was stirred at room temperature for 3 hours. The resultant reaction mixture was dialyzed for 2 days against purified water at 4° C. using a dialysis membrane (trade name: Spectra/Por 3, molecular weight cut-off: 3,500) manufactured and sold by Spectrum Laboratories Inc., U.S.A. The resultant dialyzate was filtered through a membrane filter (trade name: MILLEX GP, pore size: 0.22 µm) manufactured and sold by Millipore Corporation, Japan, and the resultant filtrate was lyophilized, thereby obtaining 120 mg of resin (82) having paclitaxel bonded thereto through a peptide linker. The amount of paclitaxel bonded to resin (82) was determined by measuring the absorbance of the obtained resin at 254 nm and comparing the measured absorbance value with a calibration curve prepared using standard samples. The amount of paclitaxel bonded to resin (82) was 1.8 mol %, based on the total molar amount of recurring unit in formula (1). The weight average molecular weight (Mw) of resin (82) was 50,000.

Example 26

100 mg of resin (81) produced in Example 23 was dissolved in 4 ml of an aqueous N,N-dimethylformamide (DMF) (water:DMF ratio=1:1). To the resultant solution were added 1 ml of an aqueous DMF (water:DMF ratio=1:1) having 10 mg of 2'-Gly-Gly-Phe-Gly-paclitaxel hydrochloride (prepared in Example 24) dissolved therein and 1 ml of DMF having 0.1 g of 1-ethoxycarbonyl-2-ethoxy-1,2-dihydroquinoline (EEDQ) dissolved therein, and the resultant mixture was stirred at room temperature for 3 hours. The resultant reaction mixture was dialyzed for 3 days against purified water at 4° C. using a dialysis membrane (trade name: Spectra/Por 3, molecular weight cut-off: 3,500) manufactured and sold by Spectrum Laboratories Inc., U.S.A. The resultant dialyzate was filtered through a membrane filter (trade name: MILLEX GP, pore size: 0.22 µm) manufactured and sold by Millipore Corporation, Japan, and the resultant filtrate was lyophilized, thereby obtaining 105 mg of resin (83) having paclitaxel bonded thereto through a peptide linker. The amount of paclitaxel bonded to resin (83) was determined by NMR analysis using DSS as a reference standard and heavy water as a solvent, and found to be 0.24 mol %, based on the total molar amount of the recurring unit in formula (1). The weight average molecular weight (Mw) of resin (83) was 50,000.

Example 27

100 mg of resin (81) produced in Example 23 was dissolved in 4 ml of an aqueous N,N-dimethylformamide (DMF) (water:DMF ratio=1:1). To the resultant solution were added 1 ml of an aqueous DMF (water:DMF ratio=1:1) having 8 mg of 2'-Gly-Gly-Phe-Gly-paclitaxel hydrochloride (prepared in Example 24) dissolved therein and 1 ml of DMF having 0.1 g of 1-ethoxycarbonyl-2-ethoxy-1,2-dihydroquinoline (EEDQ) dissolved therein, and the resultant mixture was stirred at room temperature for 3 hours. The resultant reaction mixture was dialyzed for 3 days against purified water at 4° C. using a dialysis membrane (trade name: Spectra/Por 3, molecular weight cut-off: 3,500) manufactured and sold by Spectrum Laboratories Inc., U.S.A. The resultant dialyzate was filtered through a membrane filter (trade name: MILLEX GP, pore size: 0.22 µm) manufactured and sold by Millipore Corporation, Japan, and the resultant filtrate was lyophilized, thereby obtaining 98 mg of resin (84) having paclitaxel bonded thereto through a peptide linker. The amount of paclitaxel bonded to resin (84) was determined by NMR analysis using DSS as a reference standard and heavy water as a solvent, and found to be 0.19 mol %, based on the total molar amount of the recurring unit in formula (1). The weight average molecular weight (Mw) of resin (84) was 50,000.

Example 28

Using paclitaxel (manufactured and sold by Hauser Chemical Research, Inc., U.S.A.) as a starting material, 2'-Gly-paclitaxel hydrochloride having an amino acid linker introduced into the OH group at the 2'-position of the paclitaxel was obtained by the following method.

178 mg (0.6 mmol) of Fmoc-Gly, 73 mg (0.6 mmol) of dimethylaminopyridine and 427 mg (0.5 mmol) of paclitaxel (manufactured and sold by Hauser Chemical Research, Inc., U.S.A.) were dissolved in 20 ml of methylene chloride, to thereby obtain a solution. To the obtained solution was added 76 mg (0.6 mmol) of N,N'-diisopropylcarbodiimide, followed by stirring at room temperature overnight to effect a reaction, thereby obtaining a reaction mixture. The reaction solvent (methylene chloride) was distilled off from the obtained reaction mixture under reduced pressure. The resultant residue was purified by silica gel column chromatography (silica gel: Art No. 9385, Silica gel 60, 200-400 mesh, manufactured and sold by Merck KGaA, Germany; column: 4.0× 30 cm; eluant: methylene chloride/acetonitrile ratio=70/30), thereby obtaining 499 mg of 2'-Fmoc-Gly-paclitaxel hydrochloride.

Subsequently, 420 mg of the above-obtained 2'-Fmoc-Gly-paclitaxel was dissolved in 10 ml of N,N-dimethylformamide. To the resultant solution was added 2 ml of piperidine at room temperature, followed by stirring for 5 minutes, and the solvent was distilled off from the resultant mixture under reduced pressure, to thereby remove the Fmoc group from 2'-Fmoc-Gly-paclitaxel hydrochloride. The resultant 2'-Gly-paclitaxel hydrochloride was purified by silica gel column chromatography (silica gel: Art No. 9385, Silica gel 60, 200-400 mesh, manufactured and sold by Merck KGBA, Germany; column: 4.0×50 cm; eluant: acetonitrile/methylene chloride ratio=80/20), thereby obtaining 141 mg of purified 2'-Gly-paclitaxel hydrochloride.

The structure of the obtained 2'-Gly-paclitaxel hydrochloride was confirmed by NMR and HRMS (high-resolution mass spectrometry). The results are as follows.

$^1$H-NMR (solvent: DMSO-d6; reference standard: TMS): δ 1.01 (s, 3H, Me-17), 1.05 (s, 3H, Me-16), 1.52 (dd, 1H, J=14.6, 9.2 Hz, H-14b), 1.51 (s, 3H, Me-19), 1.65 (t, 1H, J=11.6 Hz, H-6b), 1.81 (dd, 1H, J=15.5, 9.6 Hz, H-14a), 1.86 (s, 3H, Me-18), 2.11 (s, 3H, Ac-10), 2.23 (s, 3H, Ac-4), 2.32 (m, 1H, H-6a), 3.58 (d, 1H, J=7.0 Hz, H-3), 3.96-4.07 (m, 3H, GlyCH2, H-20), 4.10 (dd, 1H, J=6.7, 10.7, H-7), 4.63 (s, 1H, OH-1), 4.90 (brs, 1H, OH-7), 4.91 (dd, 1H, J=4.9 Hz, H-5), 5.43 (d, 1H, J=7.0, H-2), 5.46 (d, 1H, J=8.2 Hz, H-2'), 5.58 (t, 1H, J=8.4 Hz, H-3'), 5.87 (t, 1H, J=8.6 Hz, H-13), 6.30 (s, 1H, H-10), 7.19-8.00 (aromatic, 15H), 8.40 (brs, 2H, GlyNH2), 9.25 (d, 1H, J=8.6 Hz, CONH-3')

HRMS: m/z 911.3604 (M+H)$^+$: the molecular weight calculated for $C_{49}H_{55}O_{15}N_2$ was 911.3602

Example 29

100 mg of resin (81) produced in Example 23 was dissolved in 4 ml of an aqueous N,N-dimethylformamide (DMF) (water:DMF ratio=1:1). To the resultant solution were added 1 ml of an aqueous DMF (water:DMF ratio=1:1) having 15 mg of 2'-Gly-paclitaxel hydrochloride (prepared in Example 28) dissolved therein and 1 ml of DMF having 0.1 g of 1-ethoxycarbonyl-2-ethoxy-1,2-dihydroquinoline (EEDQ) dissolved therein, and the resultant mixture was stirred at room temperature for 3 hours. The resultant reaction mixture was dialyzed for 3 days against purified water at 4° C. using a dialysis membrane (trade name: Spectra/Por 3, molecular weight cut-off: 3,500) manufactured and sold by Spectrum Laboratories Inc., U.S.A. The resultant dialyzate was filtered through a membrane filter (trade name: MILLEX GP, pore size: 0.22 μm) manufactured and sold by Millipore Corporation, Japan, and the resultant filtrate was lyophilized, thereby obtaining 86 mg of resin (85) having paclitaxel bonded thereto through a peptide linker. The amount of paclitaxel bonded to resin (85) was determined by NMR analysis using DSS as a reference standard and heavy water as a solvent, and found to be 0.25 mol %, based on the total molar amount of the recurring unit in formula (1). The weight average molecular weight (Mw) of resin (85) was 50,000.

Example 30

(1) Synthesis of Polyether Derivative (86) DexT2000

1.75 L of an aqueous sodium metaperiodate solution containing 132 g (617 mmol) of sodium metaperiodate was added to 1.25 L of an aqueous 0.1 M sodium acetate buffer (pH 5.5) containing 50 g of Dextran T2000 (manufactured and sold by Amersham Biosciences Corp., U.S.A.), followed by a reaction at room temperature for 16 hours, thereby obtaining a first reaction mixture.

52 ml (926 mmol) of ethylene glycol was added to the obtained first reaction mixture, and a reaction was performed at room temperature for 6 hours, thereby inactivating an excess sodium metaperiodate in the first reaction mixture. Then, 70 g (1,851 mmol) of sodium boron hydride was added to the resultant reaction mixture, followed by a reaction at room temperature overnight, thereby obtaining a second reaction mixture. Subsequently, the pH value of the obtained second reaction mixture was adjusted to pH 5 by adding acetic acid thereto, thereby inactivating excess sodium boron hydride in the second reaction mixture.

The resultant reaction mixture was desalted and concentrated by ultrafiltration using an ultrafiltration module (Microza™ SEP-1013; manufactured and sold by Asahi Kasei Chemicals Corporation, Japan), thereby obtaining an aqueous polyether derivative solution. The obtained aqueous polyether derivative solution was filtered using a membrane filter (pore size: 0.22 μm) (DURAPORE™; manufactured and sold by Millipore Corporation, Japan; filter type: 0.22 μm GV, CAT No. GVWPO4700). The resultant filtrate was lyophilized to thereby obtain 34 g of a white amorphous powder which was polyether derivative DexT2000 (86).

(2) Measurement of Molecular Weight

The weight average molecular weight of the polyether derivative obtained was determined by GPC and the resultant GPC chart is shown in FIG. 1. The GPC was performed under the following conditions:

Column: G4000PWXL and G5000PWXL (each manufactured and sold by Tosoh Corporation, Japan), Mobile phase: 20% acetonitrile solution in 50 mM lithium chloride, Flow rate: 0.8 ml/min, Column temperature: 40° C., Pump: L-6200 (manufactured and sold by Hitachi, Ltd., Japan), Detector for RI: L-3300 (a differential refractometer, manufactured and sold by Hitachi, Ltd., Japan), and Detector for UV and visual light absorbance: L-4200 (a spectrophotometer, manufactured and sold by Hitachi, Ltd., Japan).

A calibration curve for calculating the molecular weight distribution was prepared using standard pullulan samples (5 types of "pullulan P-82" respectively having weight average molecular weights of 38.0×10$^4$, 18.6×10$^4$, 10.0×10$^4$, 4.80× 10$^4$ and 2.37×10$^4$) (manufactured and sold by SHOWA DENKO K.K., Japan).

The weight average molecular weight (Mw) of resin (86) was 90,000.

The weight average molecular weight (Mw) of each of the resins obtained in the Examples described below was also measured under the above-mentioned conditions.

(3) Instrumental Analysis

Figure 2:
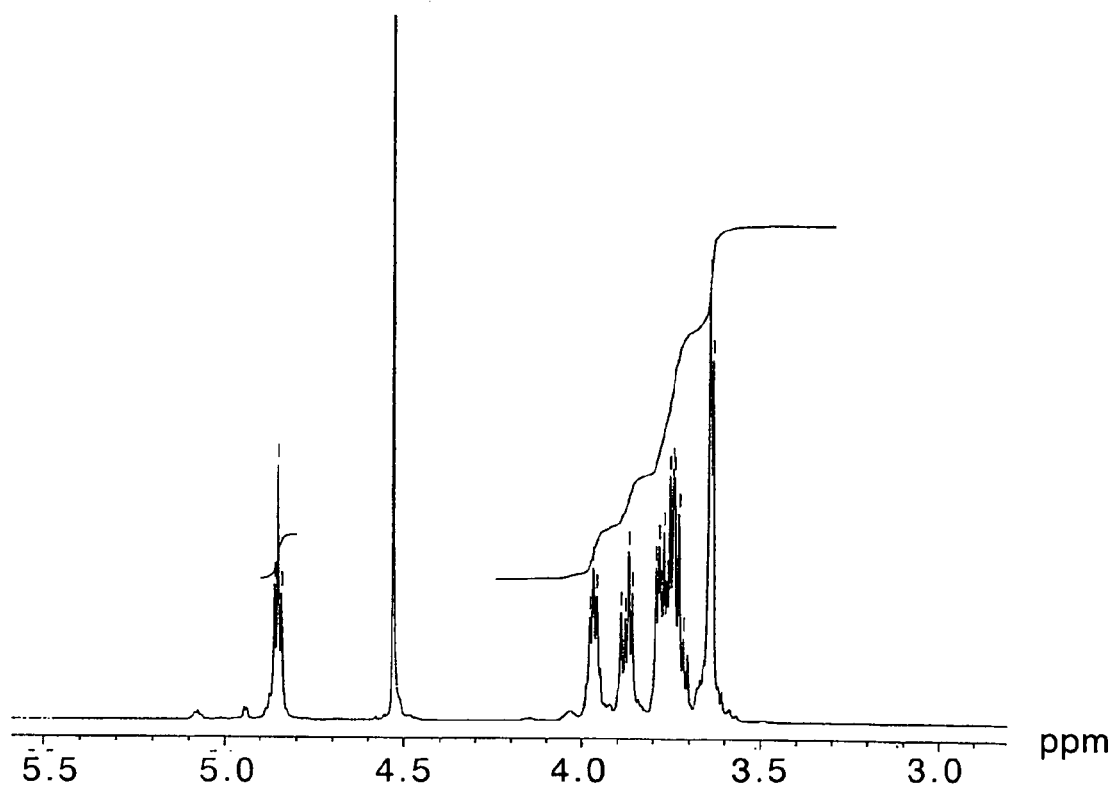
FIG. 2 is a $^1$H-NMR chart which is obtained with respect to resin (86) of the present invention produced in Example 30 (wherein the $^1$H-NMR analysis is performed using heavy water as a solvent)

The obtained polyether derivative was subjected to an instrumental analysis by $^1$H-NMR spectroscopy using heavy water as a solvent and DSS (sodium 2,2-dimethyl-2-silapentane-5-sulfonate) as a reference standard. The results are shown in FIG. 2.

Example 31

(1) Synthesis of Polyether Derivative DexT500 (87)

Substantially the same procedure as in the production of polyether derivative DexT2000 (86) in Example 30 was repeated, except that 50 g of dextran T500 (manufactured and sold by Amersham Biosciences Corp., U.S.A.) was used instead of 50 g of dextran T2000, thereby obtaining 39 g of a white amorphous powder which was polyether derivative DexT500 (87).

(2) Analysis of Polyether Derivative DexT500 (87)

Figure 3:
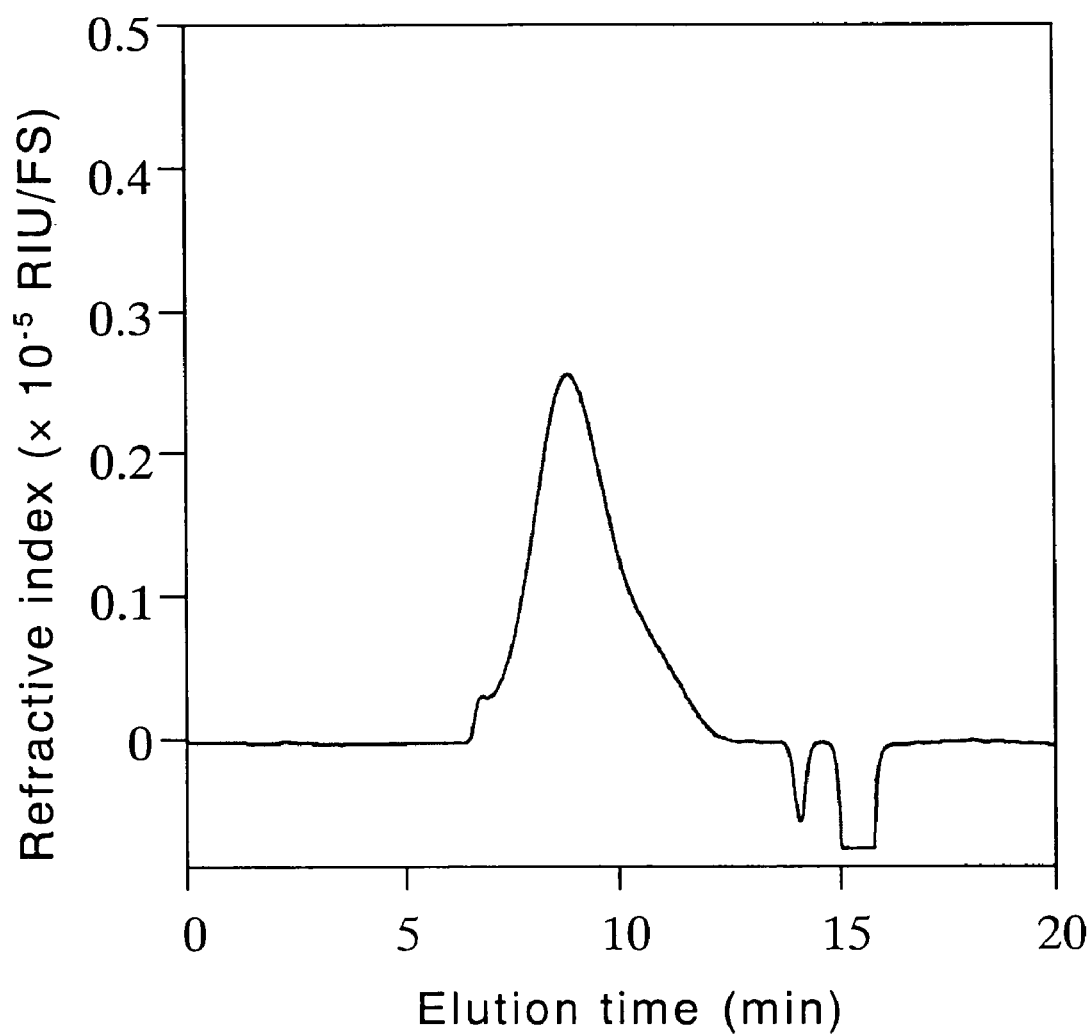
FIG. 3 is a GPC chart which is obtained with respect to resin (87) of the present invention produced in Example 31.
Figure 4:
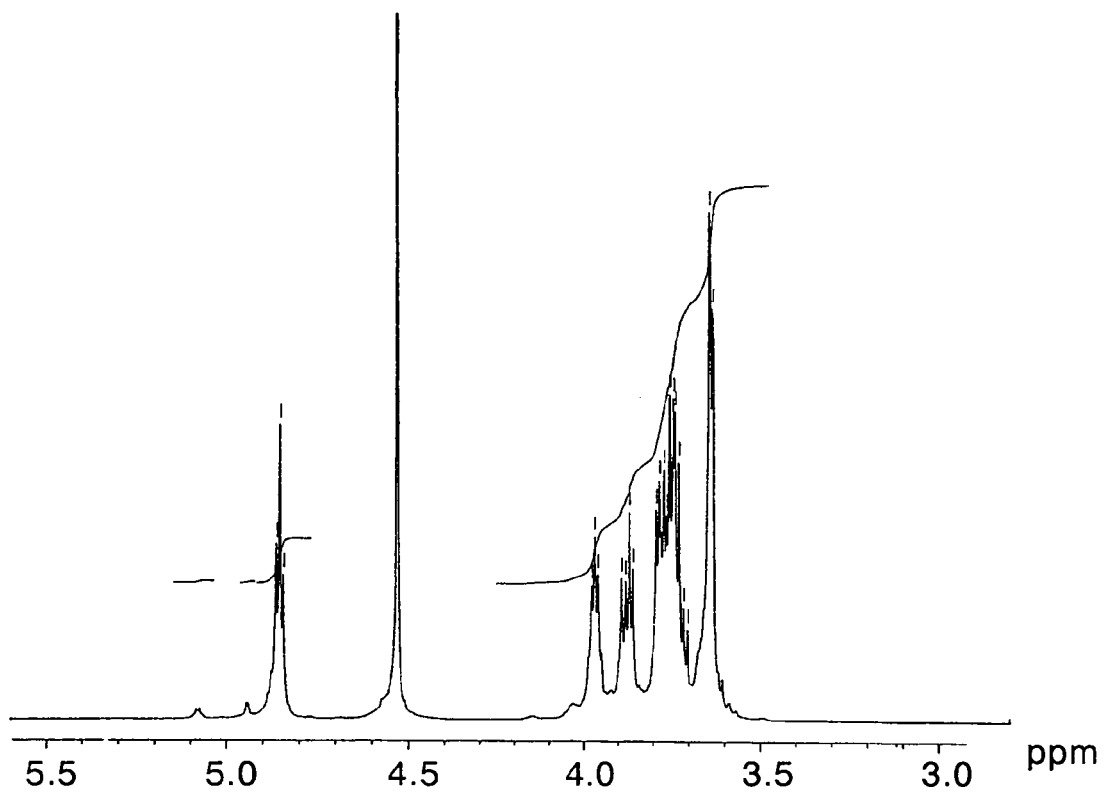
FIG. 4 is a $^1$H-NMR chart which is obtained with respect to resin (87) of the present invention produced in Example 31 (wherein the $^1$H-NMR analysis is performed using heavy water as a solvent)

The weight average molecular weight of the polyether derivative obtained above was determined by GPC under the same conditions as in Example 30, and the resultant GPC chart is shown in FIG. 3. The weight average molecular weight (Mw) of polyether derivative DexT500 (87) was 120,000. The obtained polyether derivative was subjected to an instrumental analysis by $^1$H-NMR spectroscopy in substantially the same manner as in Example 30. The results are shown in FIG. 4.

Example 32

(1) Synthesis of Polyether Derivative (88)

Substantially the same procedure as in the production of polyether derivative DexT2000 (86) in Example 30 was repeated, except that 3 g of pullulan T1600 (manufactured and sold by Showa Denko K.K., Japan) was used instead of 50 g of dextran T2000, thereby obtaining 2.2 g of a white amorphous powder which was polyether derivative (88).

(2) Analysis of Polyether Derivative (88)

Figure 5:
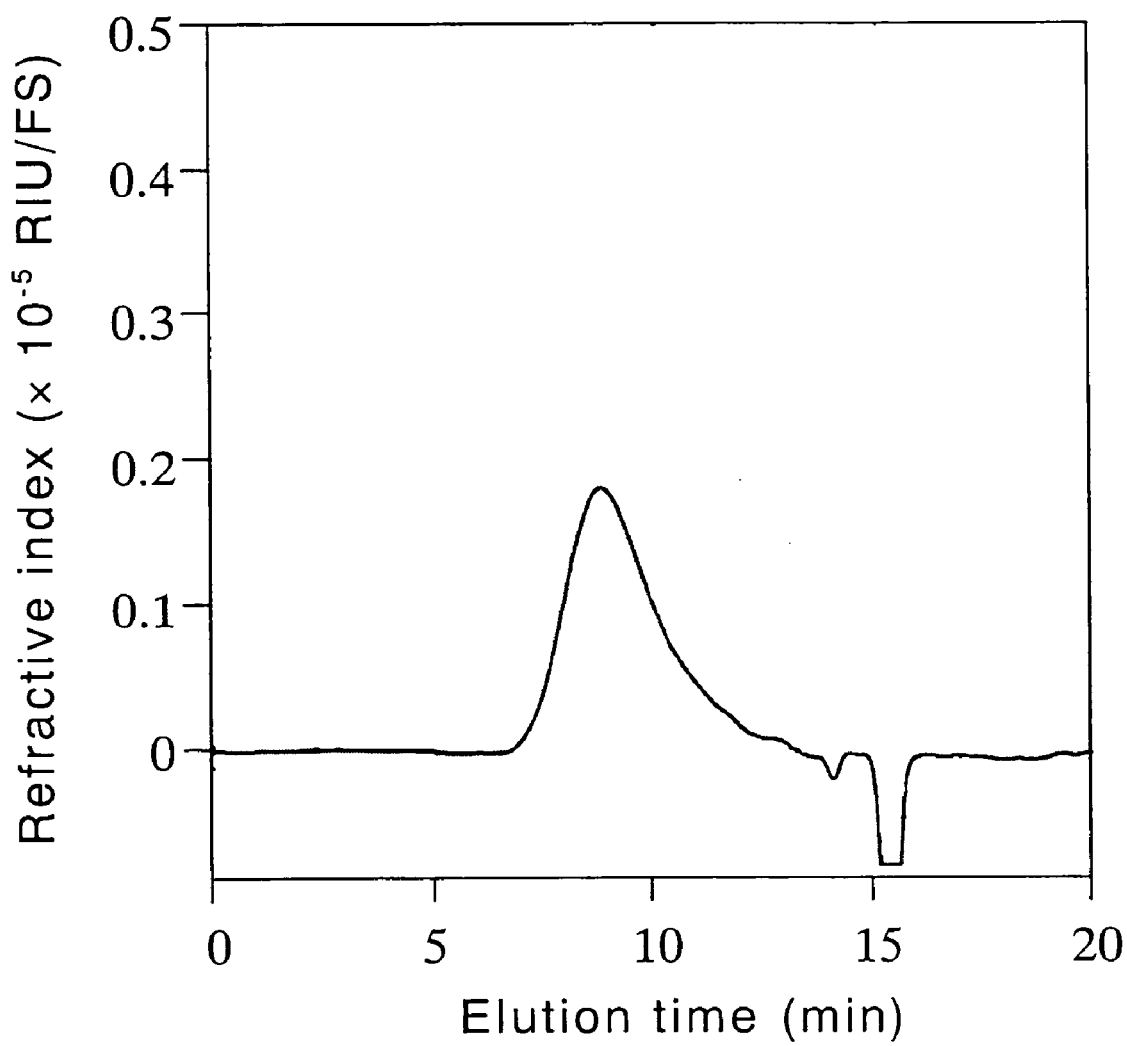
FIG. 5 is a GPC chart which is obtained with respect to resin (88) of the present invention produced in Example 32.
Figure 6:
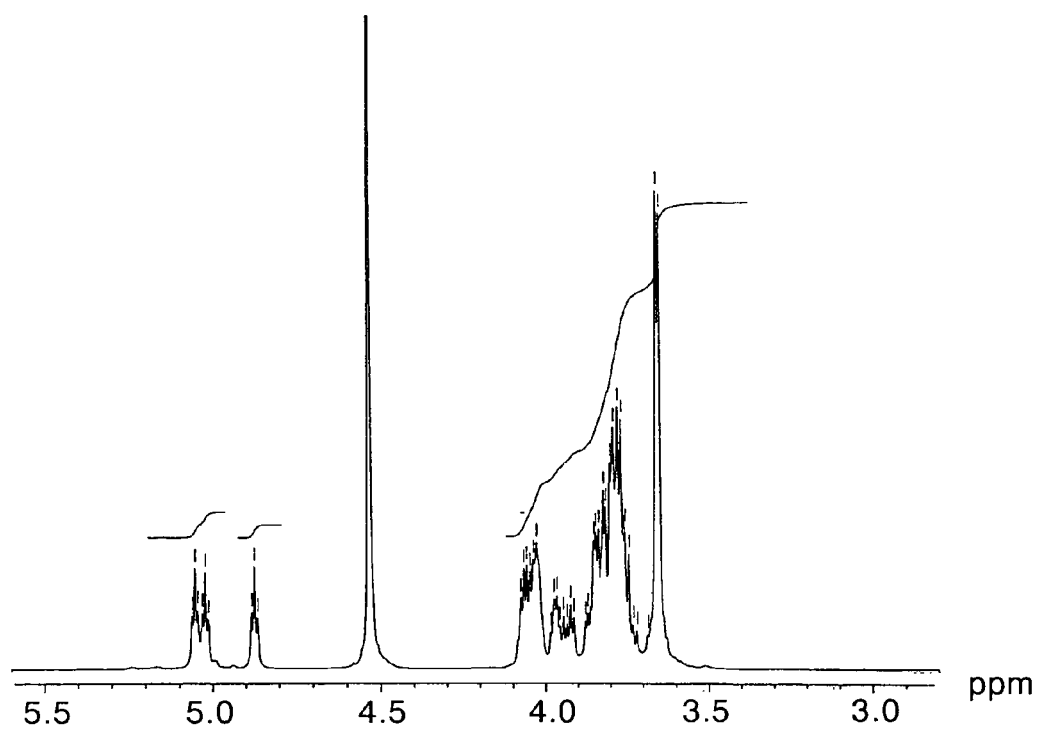
FIG. 6 is a $^1$H-NMR chart which is obtained with respect to resin (88) of the present invention produced in Example 32 (wherein the $^1$H-NMR analysis is performed using heavy water as a solvent)
Figure 7:
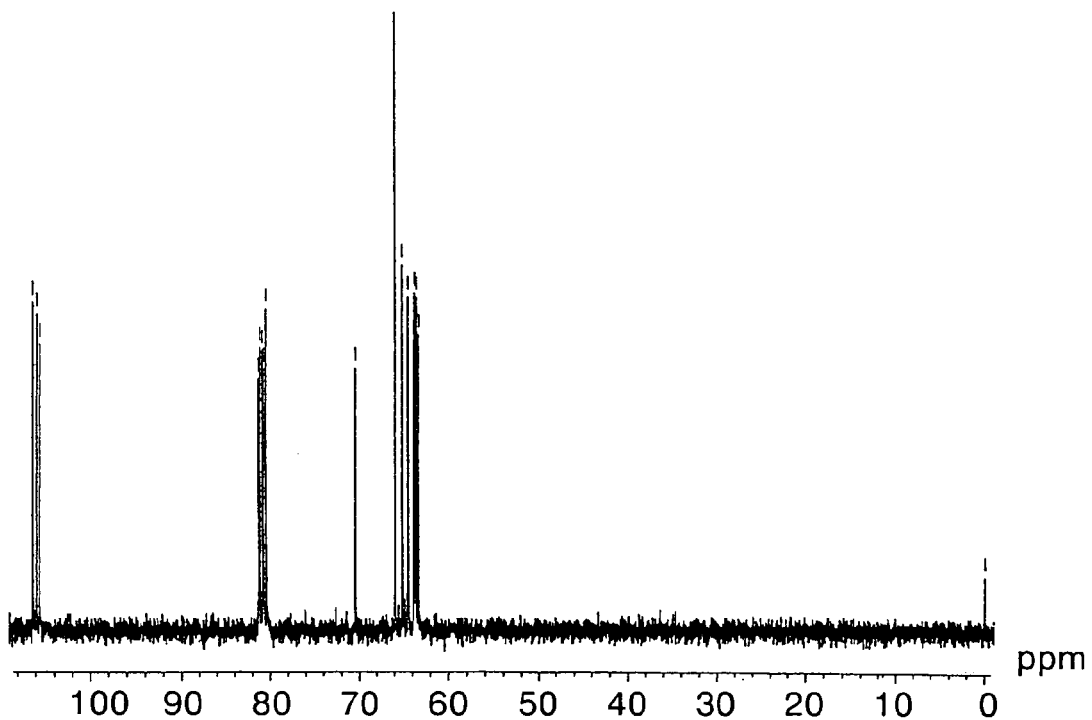
FIG. 7 is a $^{13}$C-NMR chart which is obtained with respect to resin (88) of the present invention produced in Example 32 (wherein the $^{13}$C-NMR analysis is performed using heavy water as a solvent)
Figure 8:
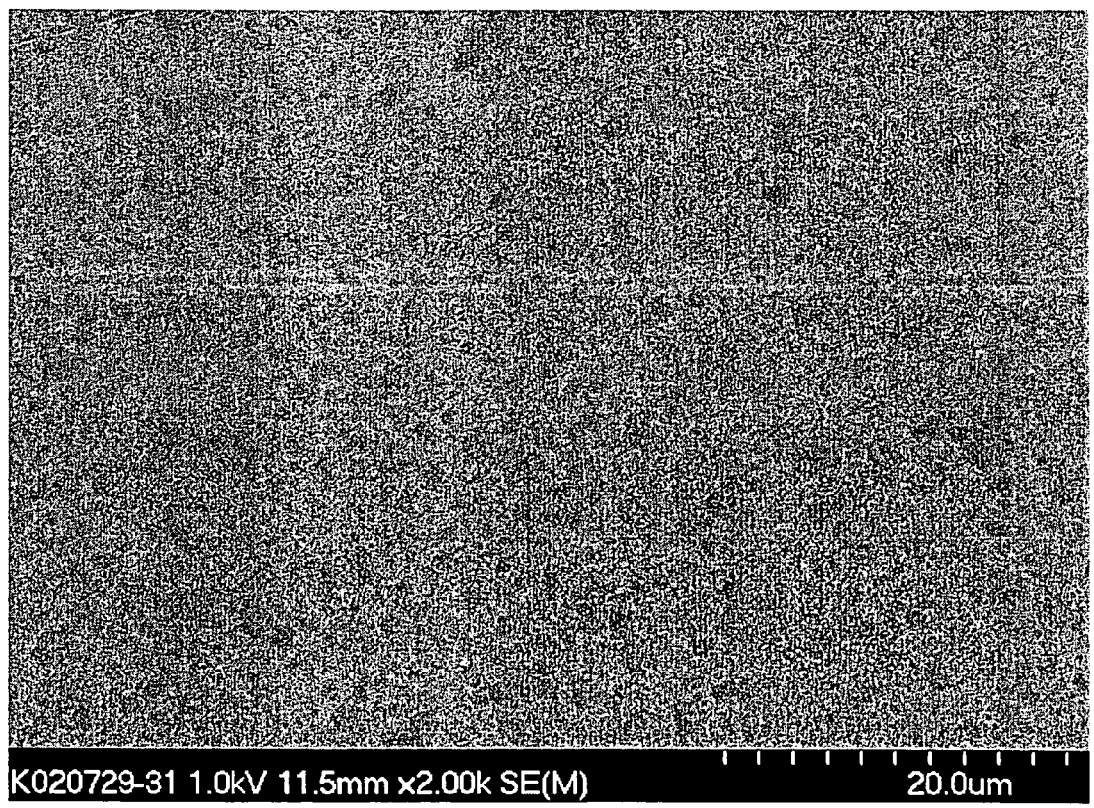
FIG. 8 is an electron photomicrograph of a PET film obtained in Example 68, which PET film is coated with resin (15) of the present invention and has been subjected to a test for evaluating platelet adhesion.
Figure 9:
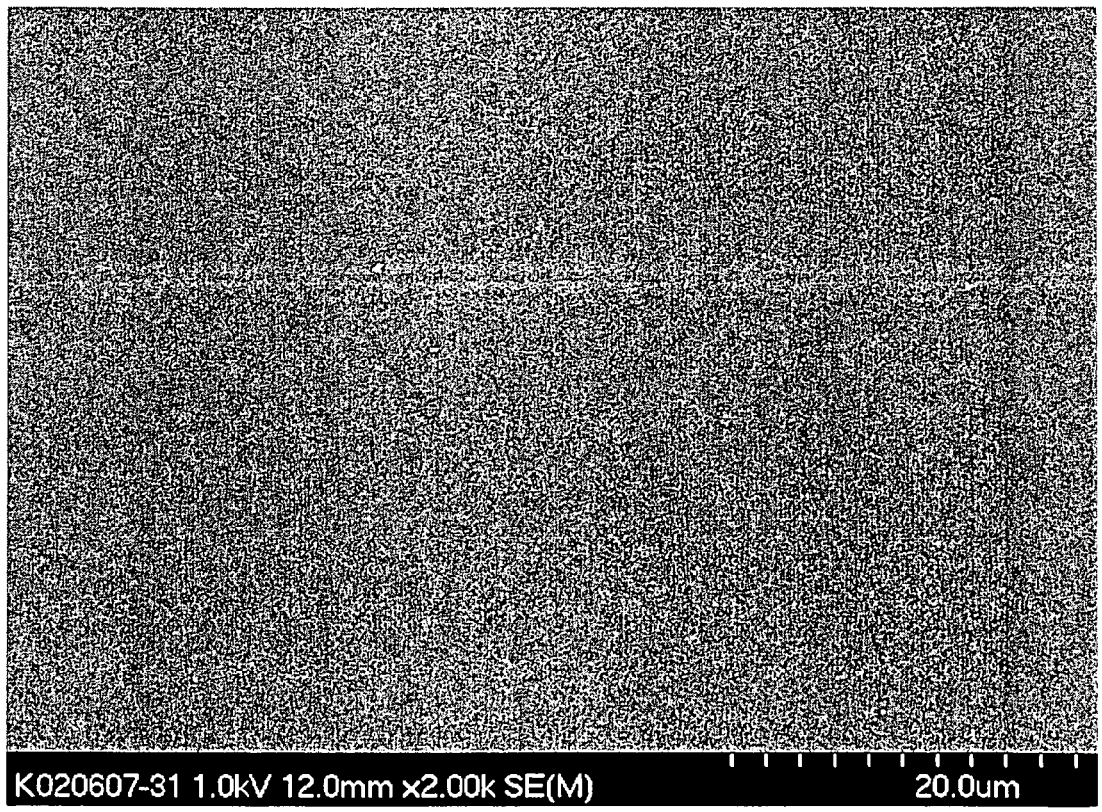
FIG. 9 is an electron photomicrograph of a PET film obtained in Example 68, which PET film is coated with resin (33) of the present invention and has been subjected to a test for evaluating platelet adhesion.
Figure 10:
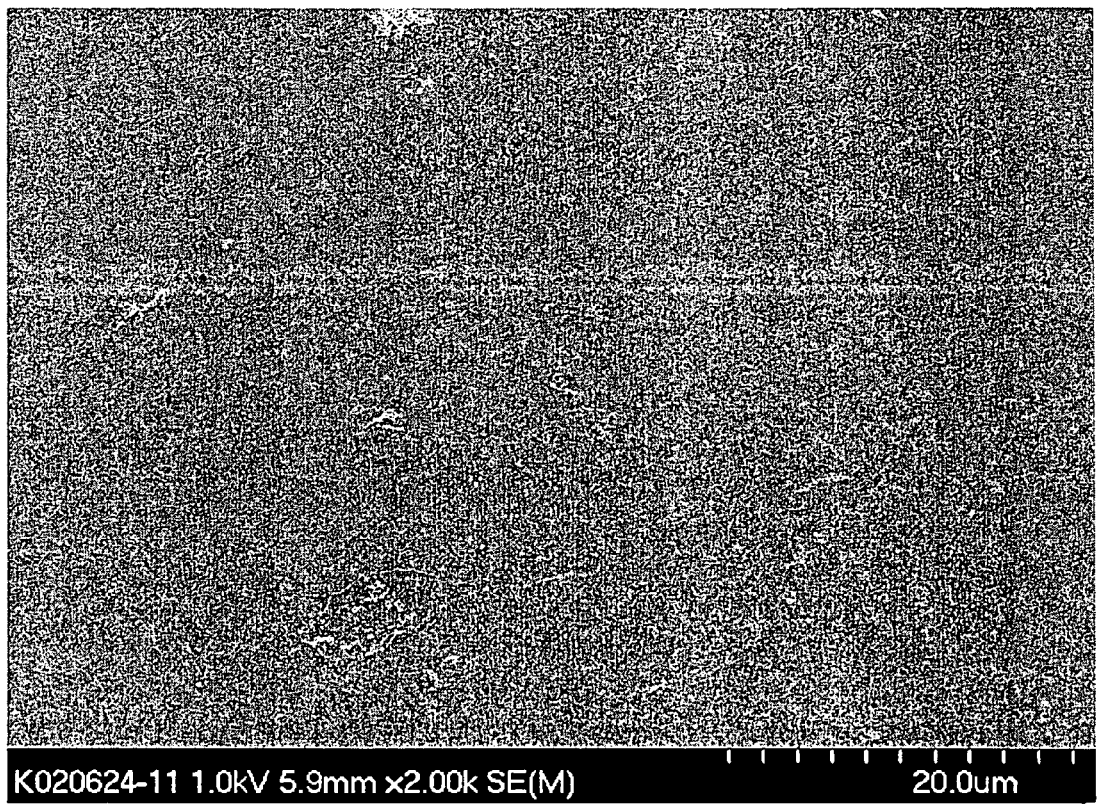
FIG. 10 is an electron photomicrograph of a PET film obtained in Example 68, which PET film is coated with resin (34) of the present invention and has been subjected to a test for evaluating platelet adhesion.
Figure 11:
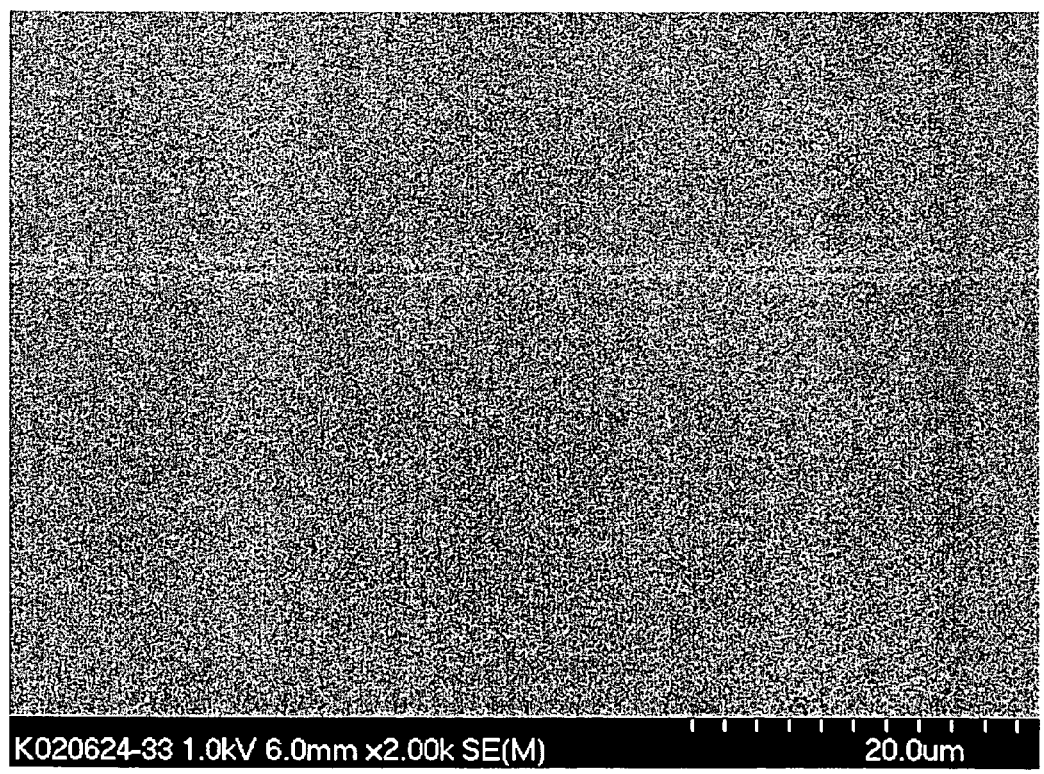
FIG. 11 is an electron photomicrograph of a PET film obtained in Example 68, which PET film is coated with resin (37) of the present invention and has been subjected to a test for evaluating platelet adhesion.
Figure 12:
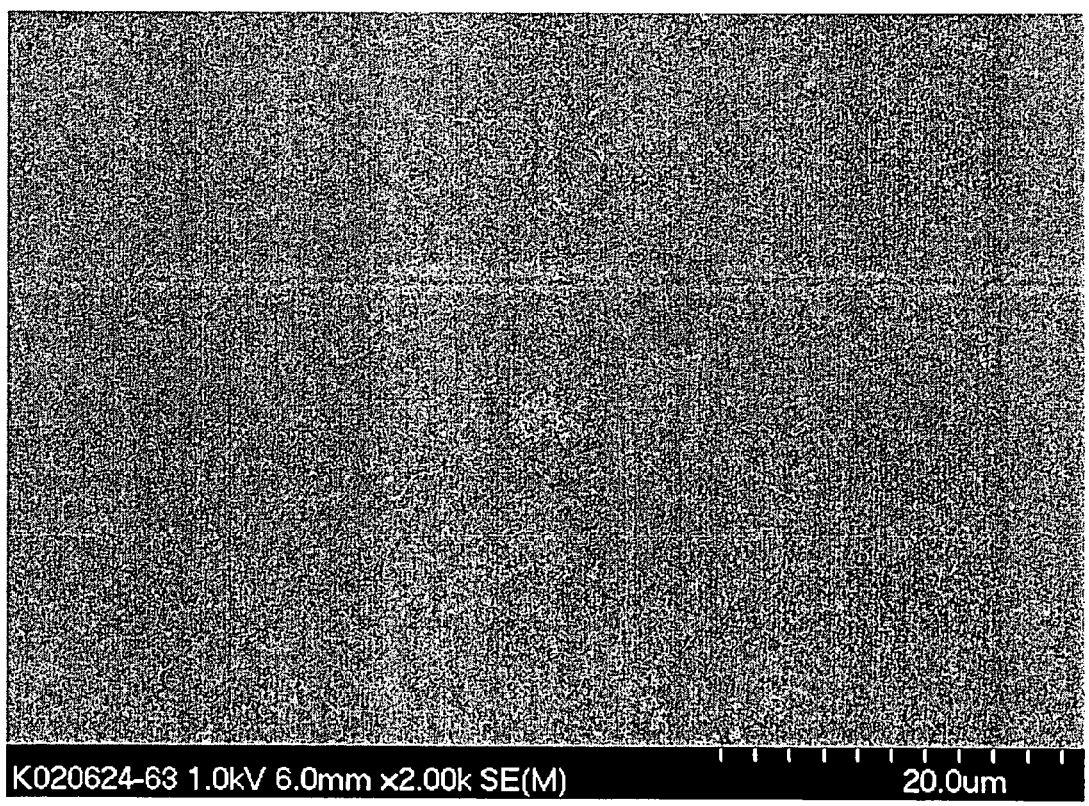
FIG. 12 is an electron photomicrograph of a PET film obtained in Example 68, which PET film is coated with resin (48) of the present invention and has been subjected to a test for evaluating platelet adhesion.

The weight average molecular weight of the polyether derivative (88) was determined by GPC under the same conditions as in Example 30, and the resultant GPC chart is shown in FIG. 5. The weight average molecular weight (Mw) of polyether derivative (88) was 90,000. The obtained polyether derivative was subjected to an instrumental analysis by $^1$H-NMR spectroscopy in the same manner as in Example 30 using heavy water as a solvent and DSS as a reference standard. The results are shown in FIG. 6. Further, the polyether derivative was also subjected to an analysis by $^{13}$C-NMR spectroscopy using heavy water as a solvent and DSS as a reference standard. The results are shown in FIG. 7.

Example 33

Synthesis of Polyether Derivative (89) Having a Methoxyethyl Group Introduced Therein To 250 mg of the polyether derivative DexT2000 (86) prepared in Example 30 were added 875 μl of water, 1 ml of dimethylsulfoxide (DMSO) and 465 μl (3.72 mmol) of 8 N aqueous sodium hydroxide to obtain a mixture. Then, a solution obtained by dissolving 340 μl (3.72 mmol) of methoxyethylchloride in 500 μl of DMSO was added to the obtained mixture, followed by a reaction at 50° C. for 16 hours. After completion of the reaction, the resultant reaction mixture was dialyzed for 4 days against purified water using dialysis membrane No. 2 (molecular weight cut-off: 12,000 to 14,000, manufactured and sold by Spectrum Laboratories Inc., U.S.A.).

The resultant dialyzate was lyophilized to thereby obtain 226 mg of a white amorphous product which was polyether derivative (89) having a methoxyethyl group introduced therein. The obtained product was subjected to a $^1$H-NMR analysis using heavy water as a solvent and DSS (sodium 2,2-dimethyl-2-silapentane-5-sulfonate) as a reference standard. The resultant NMR spectrum showed that a single peak ascribed to a pendant methoxyethyl group appeared at δ 3.38 ppm. Further, the amount of pendant methoxyethyl group introduced into the resin was determined by $^1$H-NMR analysis. The amount of the introduced pendant methoxyethyl group was 0.18 mol per mol of the recurring units, i.e., sugar residues derived from the raw material dextran T2000. The weight average molecular weight (Mw) of resin (89) was 90,000.

Example 34

Synthesis of Polyether Derivative (90) Having a Methoxyethyl Group Introduced Therein Substantially the same procedure as in the production of polyether derivative (89) in Example 33 was repeated, except that 250 mg of polyether derivative DexT500 (87) produced in Example 31 was used instead of 250 mg of polyether derivative DexT2000 (86), thereby obtaining 134 mg of polyether derivative (90) having a methoxyethyl group introduced therein. The obtained polyether derivative (90) was a white amorphous product.

Polyether derivative (90) was subjected to a $^1$H-NMR analysis using heavy water as a solvent and DSS as a reference standard. The resultant NMR spectrum showed that a single peak ascribed to a pendant methoxyethyl group appeared at δ 3.39 ppm. Further, the amount of pendant methoxyethyl group introduced into the resin was determined by $^1$H-NMR analysis. The amount of the introduced pendant methoxyethyl group was 0.24 mol per mol of the recurring unit in formula (1). The weight average molecular weight (Mw) of polyether derivative (90) was 120,000.

Example 35

Synthesis of Polyether Derivative (91) Having a Carboxymethyl Group Introduced Therein To 500 mg of polyether derivative DexT2000 (86) prepared in Example 30, step (1) were added 1,750 μl of water and 699 μl (5.60 mmol) of 8 N aqueous sodium hydroxide, thereby obtaining a mixture. Separately, a 5.7 mmol/ml aqueous sodium chloroacetate solution was prepared by dissolving sodium chloroacetate in water at 50° C. 1,050 μl of the thus prepared aqueous sodium chloroacetate solution was added to the above-obtained mixture, followed by a reaction at 50° C. for 16 hours. After completion of the reaction, the resultant reaction mixture was poured into 30 ml of methanol, thereby obtaining a precipitate. The obtained precipitate was, dialyzed for 2 days against purified water using dialysis membrane No. 2 (molecular weight cut-off: 12,000 to 14,000, manufactured and sold by Spectrum Laboratories Inc., U.S.A.).

The resultant dialyzate was lyophilized to thereby obtain 445 mg of a white amorphous product which was polyether derivative (91) having a carboxymethyl group introduced therein (hereinafter frequently referred to simply as "resin (91)"). The amount of pendant carboxymethyl group introduced in resin (91) was determined as follows. The carboxymethyl groups of resin (91) were converted into carboxylic acid groups by using an ion exchange resin (AG 50W-X2 Resin, manufactured and sold by Bio-Rad Laboratories, Inc., U.S.A.). The amount of pendant carboxylic acid group contained in the resultant resin was determined by back titration using 0.1 N sodium hydroxide and 0.1 N hydrochloric acid, and the obtained value was used as the amount of the pendant carboxymethyl group introduced in resin (91). The amount of the introduced pendant carboxymethyl group was 0.36 mol per mol of the recurring unit in formula (1). The weight average molecular weight (Mw) of resin (91) was 40,000.

Example 36

Synthesis of Polyether Derivative (92) Having a Carboxymethyl Group Introduced Therein Substantially the same procedure as in the production of polyether derivative (91) in Example 35 was repeated, except that 500 mg of polyether derivative DexT500 (87) prepared in Example 31 was used instead of 500 mg of polyether derivative DexT2000 (86), thereby obtaining 383 mg of polyether derivative (92) having a carboxymethyl group introduced therein. The obtained polyether derivative (92) was a white amorphous product.

The amount of the introduced pendant carboxymethyl group was 0.35 mol per mol of the recurring unit in formula (1). The weight average molecular weight (Mw) of polyether derivative (92) was 60,000.

Example 37

Synthesis of Polyether Derivative (93) Having a Methyl Group Introduced Therein

To 250 mg of polyether derivative DexT2000 (86) prepared in Example 30, step (1) were added 875 µl of water, 1 ml of dimethylsulfoxide (DMSO) and 465 µl (3.72 mmol) of 8 N aqueous sodium hydroxide to obtain a mixture. A solution obtained by dissolving 283 µl (1.86 mmol) of methyl iodide in 250 µl of DMSO was added to the obtained mixture and, then, 1 ml of water and 5 ml of DMSO were further added, followed by a reaction at 50° C. for 24 hours.

After completion of the reaction, the resultant reaction mixture was dialyzed for 4 days against purified water using dialysis membrane No. 2 (molecular weight cut-off: 12,000 to 14,000, manufactured and sold by Spectrum Laboratories Inc., U.S.A.). The resultant dialyzate was lyophilized to thereby obtain 191 mg of a white amorphous product which was polyether derivative (93) having a methyl group introduced therein.

The obtained product was subjected to a $^1$H-NMR analysis using heavy water as a solvent and DSS as a reference standard. The resultant NMR spectrum showed that a single peak ascribed to a pendant methyl group appeared at δ 3.41 ppm. Further, the amount of pendant methyl group introduced into the polyether derivative was determined by $^1$H-NMR analysis. The amount of the introduced pendant methyl group was 0.63 mol per mol of the recurring unit in formula (1). The weight average molecular weight (Mw) of polyether derivative (93) was 100,000.

Example 38

Synthesis of Polyether Derivative (94) Having a Methyl Group Introduced Therein

Substantially the same procedure as in the production of polyether derivative (93) in Example 37 was repeated, except that 250 mg of polyether derivative DexT500 (87) prepared in Example 31 was used instead of 250 mg of polyether derivative DexT2000 (86), thereby obtaining 125 mg of polyether derivative (94) having a methyl group introduced therein. The obtained polyether derivative (94) was a white amorphous product.

Polyether derivative (94) was subjected to a $^1$H-NMR analysis using heavy water as a solvent and DSS as a reference standard. The resultant NMR spectrum showed that a single peak ascribed to a pendant methyl group appeared at δ 3.42 ppm. Further, the amount of pendant methyl group introduced into the polyether derivative was determined by $^1$H-NMR analysis. The amount of the introduced pendant methyl group was 0.67 mol per mol of the recurring unit in formula (1). The weight average molecular weight (Mw) of polyether derivative (94) was 120,000.

Example 39

Synthesis of Polyether Derivative (95) Having a Propyl Group Introduced Therein

To 250 mg of polyether derivative DexT2000 (86) prepared in Example 30 were added 875 µl of water, 1 ml of dimethylsulfoxide (DMSO) and 465 µl (3.72 mmol) of 8 N aqueous sodium hydroxide to obtain a mixture. A solution obtained by dissolving 169 µl (1.86 mmol) of n-propyl bromide in 250 µl of DMSO was added to the obtained mixture and, then, 2 ml of water and 2 ml of DMSO were further added, followed by a reaction at 50° C. for 21 hours.

After completion of the reaction, the resultant reaction mixture was dialyzed for 4 days against purified water using dialysis membrane No. 2 (molecular weight cut-off: 12,000 to 14,000, manufactured and sold by Spectrum Laboratories Inc., U.S.A.). The resultant dialyzate was lyophilized to thereby obtain 201 mg of a white amorphous product which was polyether derivative (95) having a propyl group introduced therein.

The obtained product was subjected to a $^1$H-NMR analysis using heavy water as a solvent and DSS as a reference standard. The resultant NMR spectrum showed that a triplet peak ascribed to a methyl group appeared at δ 0.884-0.923 ppm, and that a quartet peak and a triplet peak both ascribed to a methylene group appeared at δ 1.568-1.621 ppm and δ 3.533 ppm, respectively. Further, the amount of pendant propyl group introduced into the resin was determined by $^1$H-NMR analysis. The amount of the introduced pendant propyl group was 0.28 mol per mol of the recurring unit in formula (1). The weight average molecular weight (Mw) of polyether derivative (95) was 90,000.

Example 40

Synthesis of Polyether Derivative (96) Having a Propyl Group Introduced Therein Substantially the same procedure as in the production of polyether derivative (95) in Example 39 was repeated, except that 250 mg of polyether derivative DexT500 (87) prepared in Example 31 was used instead of 250 mg of polyether derivative DexT2000 (86), thereby obtaining 102 mg of polyether derivative (96) having a propyl group introduced therein. The obtained polyether derivative (96) was a white amorphous product.

Polyether derivative (96) was subjected to a $^1$H-NMR analysis using heavy water as a solvent and DSS as a reference standard. The resultant NMR spectrum showed that a triplet peak ascribed to a methyl group appeared at δ 0.898-0.935 ppm, and that a sextet peak and a triplet peak both ascribed to a methylene group appeared at δ 1.564-1.653 ppm and δ 3.528-3.563 ppm, respectively. Further, the amount of pendant propyl group introduced into the resin was determined by $^1$H-NMR analysis. The amount of the introduced pendant propyl group was 0.21 mol per mol of the recurring unit in formula (1). The weight average molecular weight (Mw) of polyether derivative (96) was 120,000.

Example 41

Synthesis of Polyether Derivative (97) Having a Butyl Group Introduced Therein To 250 mg of polyether derivative DexT2000 (86) prepared in Example 30 were added 875 μl of water, 1 ml of dimethylsulfoxide (DMSO) and 465 μl (3.72 mmol) of 8 N aqueous sodium hydroxide to obtain a mixture. A solution obtained by dissolving 199 μl (1.86 mmol) of n-butyl bromide in 250 μl of DMSO was added to the obtained mixture and, then, 2 ml of water and 2 ml of DMSO were further added, followed by a reaction at 50° C. for 21 hours.

After completion of the reaction, the resultant reaction mixture was dialyzed for 4 days against purified water using dialysis membrane No. 2 (molecular weight cut-off: 12,000 to 14,000, manufactured and sold by Spectrum Laboratories Inc., U.S.A.). The resultant dialyzate was lyophilized to thereby obtain 217 mg of a white amorphous product which was polyether derivative (97) having a butyl group introduced therein.

The obtained product was subjected to a $^1$H-NMR analysis using heavy water as a solvent and DSS as a reference standard. The resultant NMR spectrum showed that a doublet peak ascribed to a methyl group appeared at δ 0.914-0.931 ppm, and that multiplet peaks ascribed to a methylene group appeared at δ 1.364 ppm, δ 1.571 ppm and δ 3.576 ppm. Further, the amount of pendant butyl group introduced into the resin was determined by $^1$H-NMR analysis. The amount of the introduced pendant butyl group was 0.33 mol per mol of the recurring unit in formula (1). The weight average molecular weight (Mw) of polyether derivative (97) was 100,000.

Example 42

Synthesis of Polyether Derivative (98) Having a Butyl Group Introduced Therein Substantially the same procedure as in the production of polyether derivative (97) in Example 41 was repeated, except that 250 mg of the polyether derivative DexT500 (87) prepared in Example 31 was used instead of 250 mg of polyether derivative DexT2000 (86), thereby obtaining 165 mg of polyether derivative (98) having a butyl group introduced therein. The obtained polyether derivative (98) was a white amorphous product.

Polyether derivative (98) was subjected to a $^1$H-NMR analysis using heavy water as a solvent and DSS as a reference standard. The resultant NMR spectrum showed that a multiplet peak ascribed to a methyl group appeared at δ 0.946 ppm, and that multiplet peaks ascribed to a methylene group appeared at δ 1.382 ppm, δ 1.586 ppm and δ 3.593 ppm. Further, the amount of pendant butyl group introduced into the resin was determined by $^1$H-NMR analysis. The amount of the introduced pendant butyl group was 0.33 mol per mol of the recurring unit in formula (1). The weight average molecular weight (Mw) of polyether derivative (98) was 120,000.

Example 43

Synthesis of Polyether Derivative (99) Having an Acetyl Group Introduced Therein To 250 mg of polyether derivative DexT2000 (86) prepared in Example 30 was added 2 ml of pyridine, followed by stirring at room temperature. To the resultant mixture was added 132 μl (1.86 mmol) of acetyl chloride and, then, 1 ml of pyridine was further added, followed by a reaction at 50° C. for 19 hours. After completion of the reaction, the resultant reaction mixture was dialyzed for 4 days against purified water using dialysis membrane No. 2 (molecular weight cut-off: 12,000 to 14,000, manufactured and sold by Spectrum Laboratories Inc., U.S.A.). The resultant dialyzate was lyophilized to thereby obtain 118 mg of a white amorphous product which was polyether derivative (99) having an acetyl group introduced therein.

The obtained product was subjected to a $^1$H-NMR analysis using heavy water as a solvent and DSS as a reference standard. The resultant NMR spectrum showed that a single peak ascribed to a pendant acetyl group appeared at δ 2.135 ppm. Further, the amount of pendant acetyl group introduced into the resin was determined by $^1$H-NMR analysis. The amount of the introduced pendant acetyl group was 0.56 mol per mol of the recurring unit in formula (1). The weight average molecular weight (Mw) of polyether derivative (99) was 90,000.

Example 44

Synthesis of Polyether Derivative (100) Having an Acetyl Group Introduced Therein Substantially the same procedure as in the production of polyether derivative (99) in Example 43 was repeated, except that 250 mg of polyether derivative DexT500 (87) prepared in Example 31 was used instead of 250 mg of polyether derivative DexT2000 (86), thereby obtaining 160 mg of polyether derivative (100) having an acetyl group introduced therein. The obtained polyether derivative (100) was a white amorphous product.

Polyether derivative (100) was subjected to a $^1$H-NMR analysis using heavy water as a solvent and DSS as a reference standard. The resultant NMR spectrum showed that a single peak ascribed to a pendant acetyl group appeared at δ 2.13 ppm. Further, the amount of pendant acetyl group introduced into the resin was determined by $^1$H-NMR analysis.

The amount of the introduced pendant acetyl group was 0.29 mol per mol of the recurring unit in formula (1). The weight average molecular weight (Mw) of polyether derivative (100) was 120,000.

Example 45

Synthesis of Polyether Derivative (101) Having an Acetyl Group Introduced Therein by Using Acetic Anhydride To 250 mg of polyether derivative DexT2000 (86) prepared in Example 30 was added 2 ml of pyridine, followed by stirring at room temperature. To the resultant mixture was added 176 μl (1.86 mmol) of acetic anhydride and, then, 1 ml of pyridine was further added, followed by a reaction at 50° C. for 19 hours. After completion of the reaction, the resultant reaction mixture was dialyzed for 4 days against purified water using dialysis membrane No. 2 (molecular weight cut-off: 12,000 to 14,000, manufactured and sold by Spectrum Laboratories Inc., U.S.A.). The resultant dialyzate was lyophilized to thereby obtain 287 mg of a white amorphous product which was polyether derivative (101) having an acetyl group introduced therein (hereinafter frequently referred to simply as "resin (101)").

The obtained product was subjected to a $^1$H-NMR analysis using heavy water as a solvent and DSS as a reference standard. The resultant NMR spectrum showed that a single peak ascribed to a pendant acetyl group appeared at δ 2.133 ppm. Further, the amount of pendant acetyl group introduced into the resin was determined by $^1$H-NMR analysis. The amount of the introduced pendant acetyl group was 0.74 mol per mol of the recurring unit in formula (1). The weight average molecular weight (Mw) of resin (101) was 90,000.

Example 46

Synthesis of Polyether Derivative (102) Having an Acetyl Group Introduced Therein by Using Acetic Anhydride Substantially the same procedure as in the production of polyether derivative (101) in Example 45 was repeated, except that 250 mg of polyether derivative DexT500 (87) was used instead of 250 mg of polyether derivative DexT2000 (86), thereby obtaining 330 mg of polyether derivative (102) having an acetyl group introduced therein. The obtained polyether derivative (102) was a white amorphous product.

Polyether derivative (102) was subjected to a $^1$H-NMR analysis using heavy water as a solvent and DSS as a reference standard. The resultant NMR spectrum showed that a single peak ascribed to a pendant acetyl group appeared at δ 2.132 ppm. Further, the amount of pendant acetyl group introduced into the resin was determined by $^1$H-NMR analysis. The amount of the introduced pendant acetyl group was 0.35 mol per mol of the recurring unit in formula (1). The weight average molecular weight (Mw) of polyether derivative (102) was 120,000.

Example 47

Synthesis of Polyether Derivative (103) Having a 3-methoxy-2-hydroxypropyl Group Introduced Therein To 250 mg of polyether derivative DexT2000 (86) prepared in Example 30, step (1) were added 875 μl of water, 1 ml of dimethylsulfoxide (DMSO) and 465 μl (3.72 mmol) of 8 N aqueous sodium hydroxide to obtain a mixture. A solution obtained by dissolving 166 μl (1.86 mmol) of glycidyl methyl ether in 250 μl of DMSO was added to the obtained mixture and, then, 3 ml of water and 3 ml of DMSO were further added, followed by a reaction at 50° C. for 22 hours. After completion of the reaction, the resultant reaction mixture was dialyzed for 4 days against purified water using dialysis membrane No. 2 (molecular weight cut-off: 12,000 to 14,000, manufactured and sold by Spectrum Laboratories Inc., U.S.A.). The resultant dialyzate was lyophilized to thereby obtain 184 mg of a white amorphous product which was polyether derivative (103) having a 3-methoxy-2-hydroxypropyl group introduced therein.

The obtained product was subjected to a $^1$H-NMR analysis using heavy water as a solvent and DSS as a reference standard. The resultant NMR spectrum showed that a single peak ascribed to a methoxy group of the pendant 3-methoxy-2-hydroxypropyl group appeared at δ 3.384 ppm. Further, the amount of pendant 3-methoxy-2-hydroxypropyl group introduced into the resin was determined by $^1$H-NMR analysis. The amount of the introduced pendant 3-methoxy-2-hydroxypropyl group was 0.21 mol per mol of the recurring unit in formula (1). The weight average molecular weight (Mw) of polyether derivative (103) was 100,000.

Example 48

Synthesis of Polyether Derivative (104) Having a 3-methoxy-2-hydroxypropyl Group Introduced Therein Substantially the same procedure as in the production of polyether derivative (103) in Example 47 was repeated, except that 250 mg of polyether derivative DexT500 (87) was used instead of 250 mg of polyether derivative DexT2000 (86), thereby obtaining 134 mg of polyether derivative (104) having a 3-methoxy-2-hydroxypropyl group introduced therein. The obtained polyether derivative (104) was a white amorphous product.

Polyether derivative (104) was subjected to a $^1$H-NMR analysis using heavy water as a solvent and DSS as a reference standard. The resultant NMR spectrum showed that a single peak ascribed to a methoxy group of the pendant 3-methoxy-2-hydroxypropyl group appeared at δ 3.384 ppm. Further, the amount of pendant 3-methoxy-2-hydroxypropyl group introduced into the resin was determined by $^1$H-NMR analysis. The amount of the introduced pendant 3-methoxy-2-hydroxypropyl group was 0.25 mol per mol of the recurring unit in formula (1). The weight average molecular weight (Mw) of polyether derivative (104) was 120,000.

Example 49

Synthesis of Polyether Derivative (105) Having a 3-t-butoxy-2-hydroxypropyl Group Introduced Therein To 250 mg of polyether derivative DexT2000 (86) prepared in Example 30, step (1) were added 875 μl of water, 1 ml of dimethylsulfoxide (DMSO) and 465 μl (3.72 mmol) of 8 N aqueous sodium hydroxide to obtain a mixture. A solution obtained by dissolving 264 μl (1.86 mmol) of t-butyl glycidyl ether in 250 μl of DMSO was added to the obtained mixture and, then, 3 ml of water and 3 ml of DMSO were further added, followed by a reaction at 50° C. for 22 hours. After completion of the reaction, the resultant reaction mixture was dialyzed for 4 days against purified water using dialysis membrane No. 2 (molecular weight cut-off: 12,000 to 14,000, manufactured and sold by Spectrum Laboratories Inc., U.S.A.). The resultant dialyzate was lyophilized to thereby obtain 187 mg of a white amorphous product which was polyether derivative (105) having a 3-t-butoxy-2-hydroxypropyl group introduced therein.

The obtained product was subjected to a $^1$H-NMR analysis using heavy water as a solvent and DSS as a reference standard. The resultant NMR spectrum showed that a single peak ascribed to a t-butyl group of the pendant 3-t-butoxy-2-hydroxypropyl group appeared at δ 1.224 ppm. Further, the amount of pendant 3-t-butoxy-2-hydroxypropyl group introduced into the resin was determined by $^1$H-NMR analysis. The amount of the introduced pendant 3-t-butoxy-2-hydroxypropyl group was 0.18 mol per mol of the recurring unit in formula (1). The weight average molecular weight (Mw) of polyether derivative (105) was 90,000.

Example 50

Synthesis of Polyether Derivative (106) Having a 3-t-butoxy-2-hydroxypropyl Group Introduced Therein Substantially the same procedure as in the production of polyether derivative (105) in Example 49 was repeated, except that 250 mg of polyether derivative DexT500 (87) prepared in Example 31 was used instead of 250 mg of polyether derivative DexT2000 (86), thereby obtaining 208 mg of polyether derivative (106) having a 3-t-butoxy-2-hydroxypropyl group introduced therein. The obtained polyether derivative (106) was a white amorphous product.

Polyether derivative (106) was subjected to a $^1$H-NMR analysis using heavy water as a solvent and DSS as a reference standard. The resultant NMR spectrum showed that a single peak ascribed to a t-butyl group of the pendant 3-t-butoxy-2-hydroxypropyl group appeared at δ 1.220 ppm. Further, the amount of pendant 3-t-butoxy-2-hydroxypropyl group introduced into the resin was determined by $^1$H-NMR analysis. The amount of the introduced pendant 3-t-butoxy-2-hydroxypropyl group was 0.18 mol per mol of the recurring unit in formula (1). The weight average molecular weight (Mw) of polyether derivative (106) was 120,000.

Example 51

Synthesis of Polyether Derivative (107) Having a 3-n-butoxy-2-hydroxypropyl Group Introduced Therein To 250 mg of the polyether derivative DexT2000 (86) prepared in Example 30 were added 875 µl of water, 1 ml of dimethylsulfoxide (DMSO) and 465 µl (3.72 mmol) of 8 N aqueous sodium hydroxide to obtain a mixture. A solution obtained by dissolving 266 µl (1.86 mmol) of n-butyl glycidyl ether in 250 µl of DMSO was added to the obtained mixture and, 3 ml of water and 3 ml of DMSO were further added, followed by a reaction at 50° C. for 22 hours. After completion of the reaction, the resultant reaction mixture was dialyzed for 4 days against purified water using dialysis membrane No. 2 (molecular weight cut-off: 12,000 to 14,000, manufactured and sold by Spectrum Laboratories Inc., U.S.A.). The resultant dialyzate was lyophilized to thereby obtain 213 mg of a white amorphous product which was polyether derivative (107) having a 3-n-butoxy-2-hydroxypropyl group introduced therein.

The obtained product was subjected to a $^1$H-NMR analysis using heavy water as a solvent and DSS as a reference standard. The resultant NMR spectrum showed peaks ascribed to a methyl group and a methylene group both present in an n-butyl group of the pendant 3-n-butoxy-2-hydroxypropyl group. Specifically, a triplet peak ascribed to the methyl group appeared at δ 0.888-0.926 ppm, and that multiplet peaks ascribed to the methylene group appeared at δ 1.301-1.395 ppm, δ 1.528-1.599 ppm and δ 3.555 ppm. Further, the amount of pendant 3-n-butoxy-2-hydroxypropyl group introduced into the resin was determined by $^1$H-NMR analysis. The amount of the introduced pendant 3-n-butoxy-2-hydroxypropyl group was 0.25 mol per mol of the recurring unit in formula (1). The weight average molecular weight (Mw) of polyether derivative (107) was 100,000.

Example 52

Synthesis of Polyether Derivative (108) Having a 3-n-butoxy-2-hydroxypropyl Group Introduced Therein Substantially the same procedure as in the production of polyether derivative (107) in Example 51 was repeated, except that 250 mg of polyether derivative DexT500 (87) prepared in Example 31 was used instead of 250 mg of polyether derivative DexT2000 (86), thereby obtaining 208 mg of polyether derivative (108) having a 3-n-butoxy-2-hydroxypropyl group introduced therein. The obtained polyether derivative (108) was a white amorphous product.

Polyether derivative (108) was subjected to a $^1$H-NMR analysis using heavy water as a solvent and DSS as a reference standard. The resultant NMR spectrum showed peaks ascribed to a methyl group and a methylene group both present in an n-butyl group of the pendant 3-n-butoxy-2-hydroxypropyl group. Specifically, a triplet peak ascribed to the methyl group appeared at δ 0.887-0.922 ppm, and multiplet peaks ascribed to the methylene group appeared at δ 1.300-1.393 ppm, δ 1.527-1.597 ppm and δ 3.495-3.510 ppm. Further, the amount of pendant 3-n-butoxy-2-hydroxypropyl group introduced into the resin was determined by $^1$H-NMR analysis. The amount of the introduced pendant 3-n-butoxy-2-hydroxypropyl group was 0.25 mol per mol of the recurring unit in formula (1). The weight average molecular weight (Mw) of polyether derivative (108) was 130,000.

Example 53

Synthesis of Polyether Derivative (109) Having a 3-phenoxy-2-hydroxypropyl group Introduced Therein To 250 mg of polyether derivative DexT2000 (86) prepared in Example 30 were added 875 µl of water, 1 ml of dimethylsulfoxide (DMSO) and 465 µl (3.72 mmol) of 8 N aqueous sodium hydroxide to obtain a mixture. A solution obtained by dissolving 125 µl (0.93 mmol) of glycidyl phenyl ether in 250 µl of DMSO was added to the obtained mixture and, then, 2 ml of water and 2 ml of DMSO were further added, followed by a reaction at 50° C. for 24 hours. After completion of the reaction, the resultant reaction mixture was dialyzed for 4 days against purified water using dialysis membrane No. 2 (molecular weight cut-off: 12,000 to 14,000, manufactured and sold by Spectrum Laboratories Inc., U.S.A.). The resultant dialyzate was lyophilized to thereby obtain 133 mg of a white amorphous product which was polyether derivative (109) having a 3-phenoxy-2-hydroxypropyl group introduced therein.

The obtained product was subjected to a $^1$H-NMR analysis using heavy water as a solvent and DSS as a reference standard. The resultant NMR spectrum showed that broad peaks ascribed to a phenyl group present in the pendant 3-phenoxy-2-hydroxypropyl group appeared at δ 7.033 ppm and δ 7.372 ppm. Further, the amount of pendant 3-phenoxy-2-hydroxypropyl group introduced into the resin was determined by $^1$H-NMR analysis. The amount of the introduced pendant 3-phenoxy-2-hydroxypropyl group was 0.22 mol per mol of the recurring unit in formula (1). The weight average molecular weight (Mw) of polyether derivative (109) was 100,000.

Example 54

Synthesis of Polyether Derivative (110) Having a 3-phenoxy-2-hydroxypropyl Group Introduced Therein Substantially the same procedure as in the production of polyether derivative (109) in Example 53 was repeated, except that 250 mg of polyether derivative DexT500 (87) prepared in Example 31 was used instead of 250 mg of polyether derivative DexT2000 (86), thereby obtaining 210 mg of polyether derivative (110) having a 3-phenoxy-2-hydroxypropyl group introduced therein. The obtained polyether derivative (110) was a white amorphous product.

Polyether derivative (110) was subjected to a $^1$H-NMR analysis using heavy water as a solvent and DSS as a reference standard. The resultant NMR spectrum showed that broad peaks ascribed to a phenyl group present in the pendant 3-phenoxy-2-hydroxypropyl group appeared at δ 7.032 ppm and δ 7.371 ppm. Further, the amount of pendant 3-phenoxy-2-hydroxypropyl group introduced into the resin was determined by $^1$H-NMR analysis. The amount of the introduced pendant 3-phenoxy-2-hydroxypropyl group was 0.23 mol per mol of the recurring unit in formula (1). The weight average molecular weight (Mw) of polyether derivative (110) was 130,000.

Example 55

Synthesis of Crosslinked Polyalkoxyalkyl Derivative (111) by Using 1,4-butanediol Diglycidyl Ether To 1,000 mg of polyether derivative DexT2000 (86) prepared in Example 30 were added 9 ml of water and 1 ml of 1 N aqueous sodium hydroxide to obtain a mixture. Then, 14.4 μl (0.0745 mmol) of 1,4-butanediol diglycidyl ether was added to the obtained mixture, followed by a reaction at room temperature for 28 hours, thereby obtaining a reaction mixture having an increased viscosity, as compared to that of the reaction system at the time of the start of the reaction. To the obtained reaction mixture were added 16 ml of ethylene glycol and 800 μl of 1 N hydrochloric acid, and the resultant mixture was dialyzed for 2 days against purified water using dialysis membrane No. 2 (molecular weight cut-off: 12,000 to 14,000, manufactured and sold by Spectrum Laboratories Inc., U.S.A.). The resultant dialyzate was lyophilized to thereby obtain 943 mg of a white amorphous product which was crosslinked polyalkoxyalkyl derivative (111).

Example 56

Synthesis of Crosslinked Polyalkoxyalkyl Derivative (112) by Using 1,4-butanediol Diglycidyl Ether A crosslinked polyalkoxyalkyl derivative was produced in substantially the same manner as in Example 55, except that 1,000 mg of polyether derivative DexT500 (87) prepared in Example 31 was used instead of 1,000 mg of polyether derivative DexT2000 (86), thereby obtaining crosslinked polyalkoxyalkyl derivative (112) in an amount of 732 mg. The obtained crosslinked polyalkoxyalkyl derivative (112) was a white amorphous product.

Example 57

Synthesis of Crosslinked Polyalkoxyalkyl Derivative (113) by Using Ethylene Glycol Diglycidyl Ether To 1,000 mg of polyether derivative DexT2000 (86) prepared in Example 30 were added 9 ml of water and 1 ml of 1 N aqueous sodium hydroxide to obtain a mixture. Then, 12 μl (0.074 mmol) of ethylene glycol diglycidyl ether was added to the obtained mixture, followed by a reaction at room temperature for 31.5 hours, thereby obtaining a reaction mixture having an increased viscosity, as compared to that of the reaction system at the time of the start of the reaction. To the obtained reaction mixture were added 16 ml of ethylene glycol and 800 μl of 1 N hydrochloric acid, and the resultant mixture was dialyzed for 2 days against purified water using dialysis membrane No. 2 (molecular weight cut-off: 12,000 to 14,000, manufactured and sold by Spectrum Laboratories Inc., U.S.A.). The resultant dialyzate was lyophilized to thereby obtain 853 mg of a white amorphous product which was crosslinked polyalkoxyalkyl derivative (113).

Example 58

Synthesis of Crosslinked Polyalkoxyalkyl Derivative (114) by Using Ethylene Glycol Diglycidyl Ether A crosslinked polyalkoxyalkyl derivative was produced in substantially the same manner as in Example 57, except that 1,000 mg of polyether derivative DexT500 (87) prepared in Example 31 was used instead of 1,000 mg of polyether derivative DexT2000 (86), thereby obtaining crosslinked polyalkoxyalkyl derivative (114) in an amount of 825 mg. The obtained crosslinked polyalkoxyalkyl derivative (114) was a white amorphous product.

Example 59

Synthesis of Crosslinked Polyalkoxyalkyl Derivative (115) Having A Carboxymethyl Group Introduced Therein To 250 mg of crosslinked polyalkoxyalkyl derivative (111) prepared in Example 55 were added 875 μl of water and 450 μl (3.6 mmol) of 8 N aqueous sodium hydroxide to obtain a mixture. Separately, a 5.6 mmol/ml aqueous sodium chloroacetate solution was prepared by dissolving sodium chloroacetate in water at 50° C. 1,050 μl of the thus prepared aqueous sodium chloroacetate solution was added to the above-obtained mixture, followed by a reaction for 16 hours. After completion of the reaction, the resultant reaction mixture was poured into 30 ml of methanol, thereby obtaining a precipitate. The obtained precipitate was dialyzed for 2 days against purified water using dialysis membrane No. 2 (molecular weight cut-off: 12,000 to 14,000, manufactured and sold by Spectrum Laboratories Inc., U.S.A.). The resultant dialyzate was lyophilized to thereby obtain 177 mg of a white amorphous product which was crosslinked polyalkoxyalkyl derivative (115) having a carboxymethyl group introduced therein (hereinafter frequently referred to simply as "resin (115)").

The amount of pendant carboxymethyl group introduced in resin (115) was determined as follows. The carboxymethyl groups of resin (115) were converted into carboxylic acid groups by using an ion exchange resin (AG 50W-X2 Resin, manufactured and sold by Bio-Rad Laboratories, Inc., U.S.A.). The amount of pendant carboxylic acid groups contained in the resultant resin was determined by back titration using 0.1 N sodium hydroxide and 0.1 N hydrochloric acid, and the obtained value was used as the amount of the pendant carboxymethyl group introduced in resin (115). The amount of the introduced pendant carboxymethyl group was 0.34 mol per mol of the recurring unit in formula (1).

Example 60

Synthesis of Crosslinked Polyalkoxyalkyl Derivative (116) Having a Carboxymethyl Group Introduced Therein Substantially the same procedure as in the production of resin (115) in Example 59 was repeated, except that 250 mg of crosslinked polyalkoxyalkyl derivative (112) prepared in Example 56 was used instead of 250 mg of crosslinked polyalkoxyalkyl derivative (111), thereby obtaining 201 mg of crosslinked polyalkoxyalkyl derivative (116) having a carboxymethyl group introduced therein. The obtained crosslinked polyalkoxyalkyl derivative (116) (hereinafter frequently referred to simply as "resin (116)") was a white amorphous product.

The amount of pendant carboxymethyl group introduced in resin (116) was determined as follows. The carboxymethyl groups of resin (116) were converted into carboxylic acid groups by using an ion exchange resin (AG 50W-X2 Resin, manufactured and sold by Bio-Rad Laboratories, Inc., U.S.A.). The amount of pendant carboxylic acid group contained in the resultant resin was determined by back titration using 0.1 N sodium hydroxide and 0.1 N hydrochloric acid, and the obtained value was used as the amount of the pendant carboxymethyl group introduced in resin (116). The amount of the introduced pendant carboxymethyl group was 0.44 mol per mol of the recurring unit in formula (1).

Example 61

Synthesis of Crosslinked Polyether Derivative (117) by Using 1,4-Diaminobutane

To 250 mg of polyether derivative DexT500 (92) having a carboxymethyl group introduced therein (which was prepared in Example 36) was added 1,750 µl of water and, then, 50 mg (0.57 mmol) of 1,4-diaminobutane and 109 mg (0.57 mmol) of water-soluble carbodiimide (WSC) hydrochloride were further added, followed by a reaction at room temperature for 24 hours. After completion of the reaction, the resultant reaction mixture was dialyzed for 2 days against purified water using dialysis membrane No. 2 (molecular weight cut-off: 12,000 to 14,000, manufactured and sold by Spectrum Laboratories Inc., U.S.A.). The resultant dialyzate was lyophilized to thereby obtain 193 mg of a white amorphous product which was crosslinked polyether derivative (117).

Example 62

Synthesis of Crosslinked Polyether Derivative (118) by Using 1,6-diaminohexane

To 250 mg of polyether derivative DexT500 (92) having a carboxymethyl group introduced therein (which was prepared in Example 36) was added 875 µl of water and, then, 33 mg (0.285 mmol) of 1,6-diaminohexane and 109 mg (0.285 mmol) of water-soluble carboduimide (WSC) hydrochloride were further added, followed by a reaction at room temperature for 24 hours. After completion of the reaction, the resultant reaction mixture was dialyzed for 2 days against purified water using dialysis membrane No. 2 (molecular weight cut-off: 12,000 to 14,000, manufactured and sold by Spectrum Laboratories Inc., U.S.A.). The resultant dialyzate was lyophilized to thereby obtain 171 mg of a white amorphous product which was crosslinked polyether derivative (118).

Example 63

Synthesis of Crosslinked Polyether Derivative (119) by Using 1,4-diaminobutane

To 250 mg of polyether derivative DexT500 (92) having a carboxymethyl group introduced therein (which was prepared in Example 36) were added 875 µl of water and 875 µl of dimethylformamide and, then, 25 mg (0.285 mmol) of 1,4-diaminobutane and 70.5 mg (0.285 mmol) of N-ethoxycarbonyl-2-ethoxy-1,2-dihydroquinoline (EEDQ) were further added, followed by a reaction at room temperature for 24 hours. After completion of the reaction, the resultant reaction mixture was dialyzed for 2 days against purified water using dialysis membrane No. 2 (molecular weight cut-off: 12,000 to 14,000, manufactured and sold by Spectrum Laboratories Inc., U.S.A.). The resultant dialyzate was lyophilized to thereby obtain 142 mg of a white amorphous product which was crosslinked polyether derivative (119).

Example 64

Synthesis of Crosslinked Polyether Derivative (120) by Using 1,6-diaminohexane

To 250 mg of polyether derivative DexT500 (92) having a carboxymethyl group introduced therein (which was prepared in Example 36) were added 875 µl of water and 875 µl of dimethylformamide and, then, 33 mg (0.285 mmol) of 1,6-diaminohexane and 70.5 mg (0.285 mmol) of EEDQ were further added, followed by a reaction at room temperature for 24 hours. After completion of the reaction, the resultant reaction mixture was dialyzed for 2 days against purified water using dialysis membrane No. 2 (molecular weight cut-off: 12,000 to 14,000, manufactured and sold by Spectrum Laboratories Inc., U.S.A.). The resultant dialyzate was lyophilized to thereby obtain 169 mg of a white amorphous product which was crosslinked polyether derivative (120).

Example 65

Preparation of a $^3$H-Labelled Polyether Derivative (121)

Polyether derivative DexT500 (87) produced in Example 31 was labeled with tritium (3H) in the following manner. 2 mg of polyether derivative DexT500 (87) was dissolved in 0.1 ml of 1 M sodium hydroxide, and 0.1 ml of DMF was added to the resultant solution to obtain a mixture. Subsequently, 0.1 ml (18.5 MBq) of a solution of [methyl-3H]dimethylsulfate in hexane was added to the obtained mixture, followed by stirring overnight to thereby obtain a reaction mixture. The obtained reaction mixture was added to 1 ml of ethanol to thereby form a precipitate. The precipitate was recovered and dissolved in 0.2 ml of 0.5 M sodium chloride solution. The resultant solution was added to 1 ml of ethanol to thereby form a precipitate, and the precipitate was recovered and dissolved in 1 ml of physiological saline, thereby obtaining a solution containing a $^3$H-labelled polyether derivative. Subsequently, the obtained solution was purified by gel filtration column chromatography using a gel filtration column (PD-10; manufactured and sold by Amersham Biosciences Corp., U.S.A.) and physiological saline as an eluant, thereby obtaining $^3$H-labelled polyether derivative (121).

Reference Example 1

Preparation of $^3$H-Labelled Dextran T110 (122)

Substantially the same procedure as in Example 65 above was repeated except that Dextran T110 (manufactured and sold by Amersham Biosciences Corp., U.S.A.) was used instead of polyether derivative DexT500 (87), thereby obtaining $^3$H-labelled Dextran T110 (122). The thus prepared $^3$H-labelled Dextran T110 (122) was used in Comparative Example 1 below.

Example 66

Preparation of Polyether Derivative Gel Sheet (123)

Polyether derivative DexT2000 (86) produced in Example 30 was used as a starting material. 1 ml of 1 N aqueous sodium hydroxide was added to 200 mg of polyether derivative DexT2000 (86) and, then, 0.15 ml (1 mmol) of ethylene glycol diglycidyl ether was also added thereto, followed by stirring to thereby obtain a reaction mixture. A part of the obtained reaction mixture was taken out and sandwiched between two glass plates, wherein the thickness of the space between the glass plates was adjusted using a vinyl tape. The resultant structure comprised of glass plates having the reaction mixture sandwiched therebetween was allowed to stand still at room temperature for 15 hours to cause crosslinking of the polyether derivative, to thereby obtain a gel in the form of a sheet (hereinafter referred to as "gel sheet (123)"). On the other hand, the remaining reaction mixture was stirred at room temperature for 15 hours to cause crosslinking of the polyether derivative, thereby obtaining a gel. The obtained gel sheet (123) was placed in a petri dish and neutralized with an equivalent amount of 1 N aqueous hydrochloric acid. Subsequently, the neutralized gel sheet (123) was shaken in 0.9% aqueous sodium chloride solution.

Example 67

Preparation of Polyether Derivative Gel Sheet (124)

Polyether derivative DexT500 (87) produced in Example 31 was used as a starting material. 1 ml of 1 N aqueous sodium hydroxide was added to 200 mg of polyether derivative DexT500 (87) and, then, 0.15 ml (1 mmol) of ethylene glycol diglycidyl ether was also added thereto, followed by stirring to thereby obtain a reaction mixture. A part of the obtained reaction mixture was taken out and sandwiched between two glass plates, wherein the thickness of the space between the glass plates was adjusted using a vinyl tape. The resultant structure comprised of glass plates having the reaction mixture sandwiched therebetween was allowed to stand still at room temperature for 15 hours to cause crosslinking of the polyether derivative, to thereby obtain a gel in the form of a sheet (hereinafter referred to as "gel sheet (124)"). On the other hand, the remaining reaction mixture was stirred at room temperature for 15 hours to cause crosslinking of the polyether derivative, thereby obtaining a gel. The obtained gel sheet (124) was placed in a petri dish and neutralized with an equivalent amount of 1 N aqueous hydrochloric acid. Subsequently, the neutralized gel sheet (124) was shaken in 0.9% aqueous sodium chloride solution.

Example 68

Evaluation of Human Platelet Adhesion: Experiment for Determining the Effect of a Resin to Inhibit the Adhesion of Platelets Resin (15) produced in Example 9, resins (33), (34) and (37) produced in Example 14 and resin (48) produced in Example 18 were individually evaluated in the following manner. A resin was dissolved in an aqueous 50% ethanol solution so as to obtain a resin solution having a resin concentration of 10 mg/ml. A polyethylene terephthalate (PET) film (thickness: 60 μm) was immersed in the obtained resin solution to cause the film to be coated with the resin, thereby obtaining a test sample. Human platelet adhesion to the obtained test sample was evaluated as follows.

The test sample was placed in a well of a 24-well cell culture plate, and fresh human platelet rich plasma (PRP) containing sodium citrate as an anticoagulant was added to the well containing the test sample, and the PRP was allowed to be in contact with the test sample at 37° C. for 2 hours. Then, the test sample was taken out from the well and the test sample was washed with physiological saline. The platelets attached to the test sample were fixed using glutaraldehyde, and the test sample was observed through a scanning electron microscope (SEM). Also, substantially the same procedure as in this evaluation of the test sample was repeated except that a non-coated PET film was used instead of the test sample.

Figure 13:
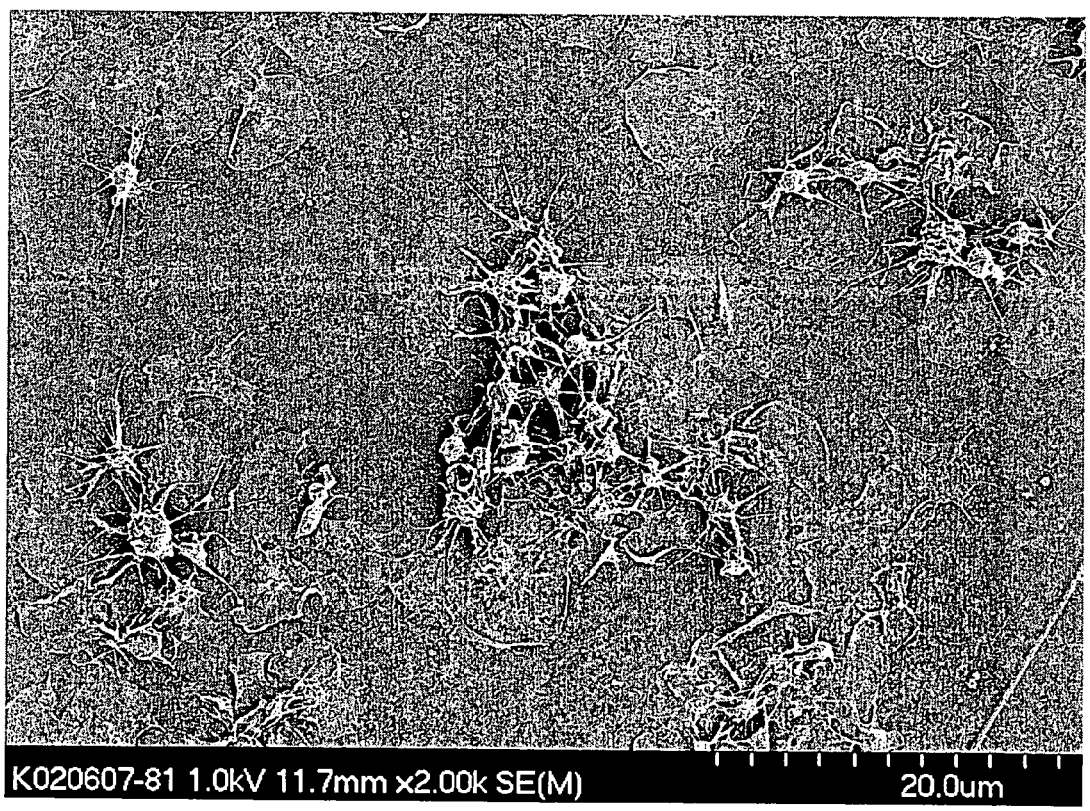
FIG. 13 is an electron photomicrograph showing a non-coated PET film which is used in Example 68, which PET film has been subjected to a test for evaluating platelet adhesion.

Scanning electron photomicrographs of the test samples of resin-coated PET films prepared using resins (15), (33), (34), (37) and (48) are shown in FIGS. 8, 9, 10, 11 and 12, respectively, and a scanning electron photomicrograph of the non-coated PET film is shown in FIG. 13. Platelets adhered to the non-coated PET film (see FIG. 13), but platelet adhesion was not observed on any of the resin-coated PET films (see FIGS. 8 to 12).

Example 69

Evaluation of Human Cell Adhesion: Experiment (1) for Determining the Effect of a Resin to Inhibit the Adhesion of Cells Resin (15) produced in Example 9, resins (33), (34) and (37) produced in Example 14 and resin (48) produced in Example 18 were individually evaluated in the following manner. Resin solutions respectively having resin concentrations of 10, 1, 0.1, 0.01 and 0.001 mg/ml were prepared by dissolving a resin in an aqueous 50% ethanol solution. Each of the obtained resin solutions was individually dispensed into a well of a 96-well microplate. On the other hand, an aqueous 50% ethanol solution was dispensed into another well of the microplate to thereby provide a well containing an aqueous 50% ethanol solution (wherein the well is intended to provide the below-mentioned "non-coated well" used as a control well). Then, the microplate was allowed to stand still at 4° C. overnight to thereby cause the wells (containing the resin solutions) to be coated with the resin. Subsequently, the resin solutions and aqueous 50% ethanol solution in the wells were removed by suction, followed by drying, to thereby obtain a microplate having resin-coated wells and a non-coated well (wherein the latter was intended for use as a control well). Adhesion of human cells to the resin-coated wells was evaluated as follows.

A suspension of HEK293 cells (human fetal renal cells) was dispensed into the resin-coated wells and non-coated well of the above-obtained microplate, and the cells were cultured for 2 days. Thereafter, the number of viable cells adhered to each of the resin-coated wells and non-coated well of the microplate was determined by means of CellTiter 96® AQ$_{ueous}$ Assay System (manufactured and sold by Promega Corporation, Madison, Wis., U.S.A.).

Figure 14:
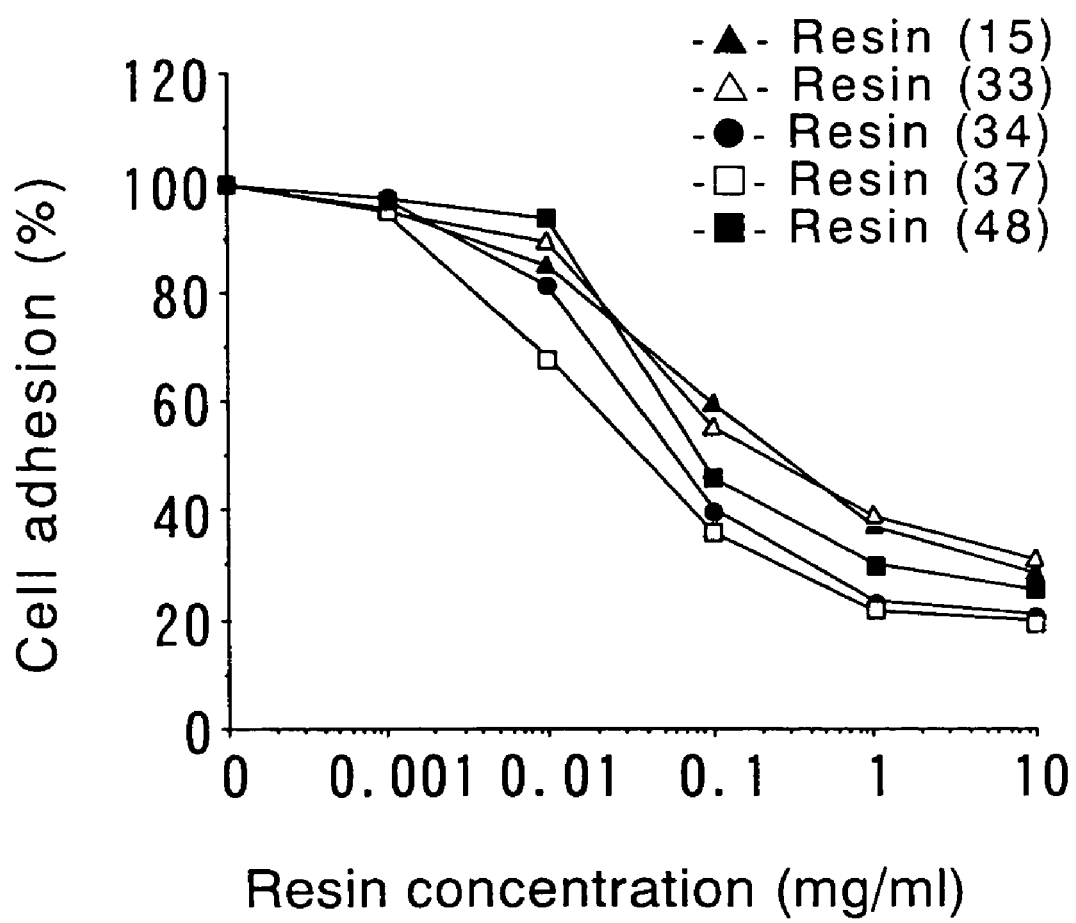
FIG. 14 is a graph showing the results of the evaluation of HEK293 cell (human fetal renal cell) adhesion to various resins, which evaluation is made in Example 69.

Results are shown in FIG. 14. In FIG. 14, the cell adhesion to each resin-coated well is expressed in terms of the percentage of the number of cells attached to the resin-coated well, based on the number of cells attached to the non-coated well. As shown in FIG. 14, resins (15), (33), (34), (37) and (48) inhibit cell adhesion, and the degree of inhibition is proportional to the resin concentration of the resin solution.

Example 70

Evaluation of Human Cell Adhesion: Experiment (2) for Determining the Effect of a Resin to Inhibit the Adhesion of Cells Resin (15) produced in Example 9, resins (33), (34) and (37) produced in Example 14 and resin (48) produced in Example 18 were individually evaluated in the following manner. A microplate having resin-coated wells and a non-coated well (wherein the latter was provided for use as a control well) was prepared in the same manner as in Example 69. Adhesion of human cells to the resin-coated wells was evaluated as follows.

A suspension of HeLa cells (human cervical cancer cells) was dispensed into the resin-coated wells and non-coated well of the above-obtained microplate, and the cells were cultured for 5 hours. After completion of the culture, the number of viable cells adhered to each of the resin-coated wells and non-coated well of the microplate was determined by means of CellTiter 96® AQ$_{ueous}$ Assay System (manufactured and sold by Promega Corporation, Madison, Wis., U.S.A.).

Figure 15:
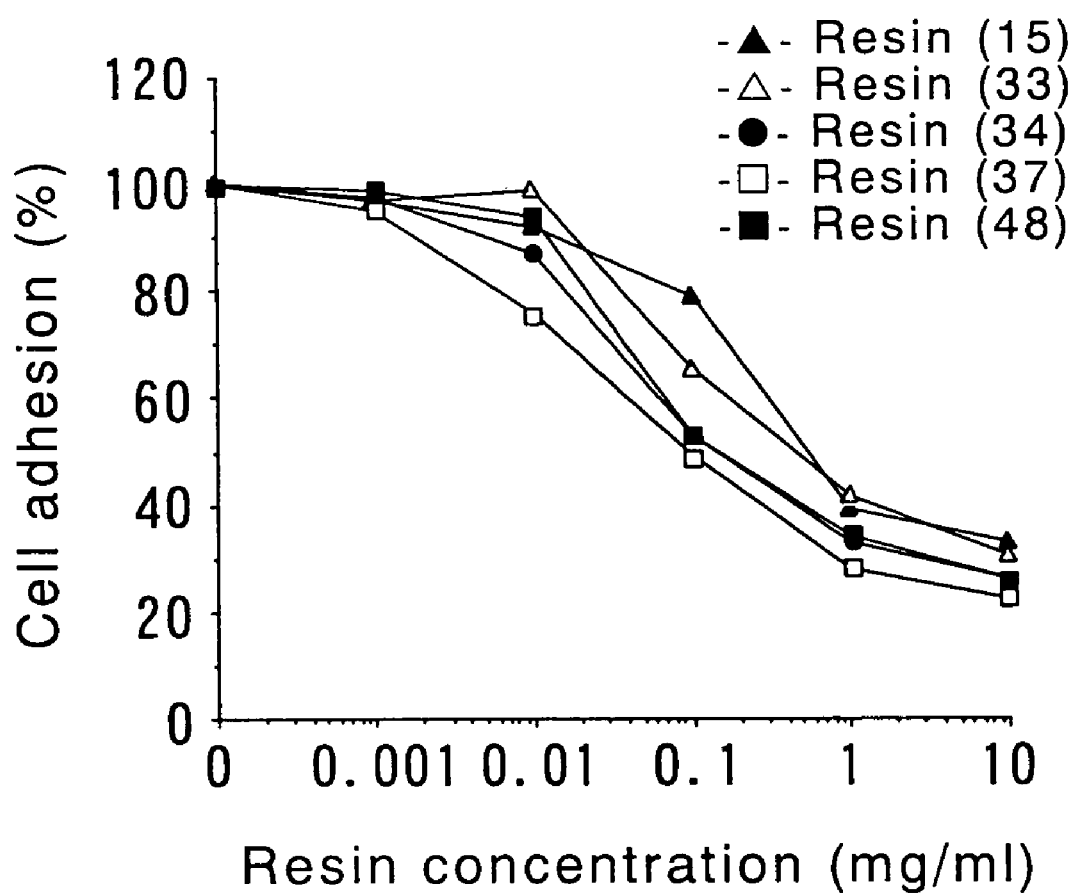
FIG. 15 is a graph showing the results of the evaluation of HeLa cell (human cervical cancer cell) adhesion to various resins, which evaluation is made in Example 70.

Results are shown in FIG. 15. In FIG. 15, the cell adhesion to each resin-coated well is expressed in terms of the percentage of the number of cells adhered to the resin-coated well, based on the number of cells adhered to the non-coated well. As shown in FIG. 15, resins (15), (33), (34), (37) and (48) inhibit cell adhesion, and the degree of inhibition is proportional to the resin concentration of the resin solution.

Example 71

Evaluation (1) of Plasma Protein Adsorption

Resin (15) produced in Example 9, resins (33), (34) and (37) produced in Example 14, resins (48) and (57) produced in Example 18 and resin (75) produced in Example 21 were individually evaluated in the following manner. Resin solutions respectively having resin concentrations of 10, 1, 0.1, 0.01 and 0.001 mg/ml were prepared by dissolving a resin in an aqueous 50% ethanol solution. 0.2 ml of each of the obtained resin solutions was individually dispensed into a well of Coaster 96-well EIA plate (Product No. 3590, manufactured and sold by Corning Incorporated, U.S.A.). On the other hand, an aqueous 50% ethanol solution was dispensed into another well of the EIA plate to thereby provide a well containing an aqueous 50% ethanol solution (wherein the well was intended to provide the below-mentioned "non-coated well" used as a control well). Then, the EIA plate was allowed to stand still at 4° C. overnight to thereby cause the wells (containing the resin solutions) to be coated with the resin. Subsequently, the resin solutions and aqueous 50% ethanol solution in the wells were removed by suction, followed by drying, to thereby obtain an EIA plate having resin-coated wells and a non-coated well (wherein the latter was intended for use as a control well). Adhesion of immunoglobulin G to the resin-coated wells was evaluated as follows.

0.1 ml of an immunoglobulin G solution containing 5 μg/ml of a purified human immunoglobulin G (IgG) (manufactured and sold by MP Biomedicals, U.S.A.) was dispensed into the resin-coated wells and non-coated well of the above-obtained EIA plate, and was allowed to remain in contact with the surfaces of the wells at 37° C. for 2 hours. Subsequently, the amounts of human IgG adsorbed on the surfaces of the wells were determined by enzyme-linked immunosorbent assay (ELISA) using a horseradish peroxidase (HRP)-conjugated goat IgG fraction to human IgG (whole molecule) (manufactured and sold by MP Biomedicals, U.S.A.).

Figure 16:
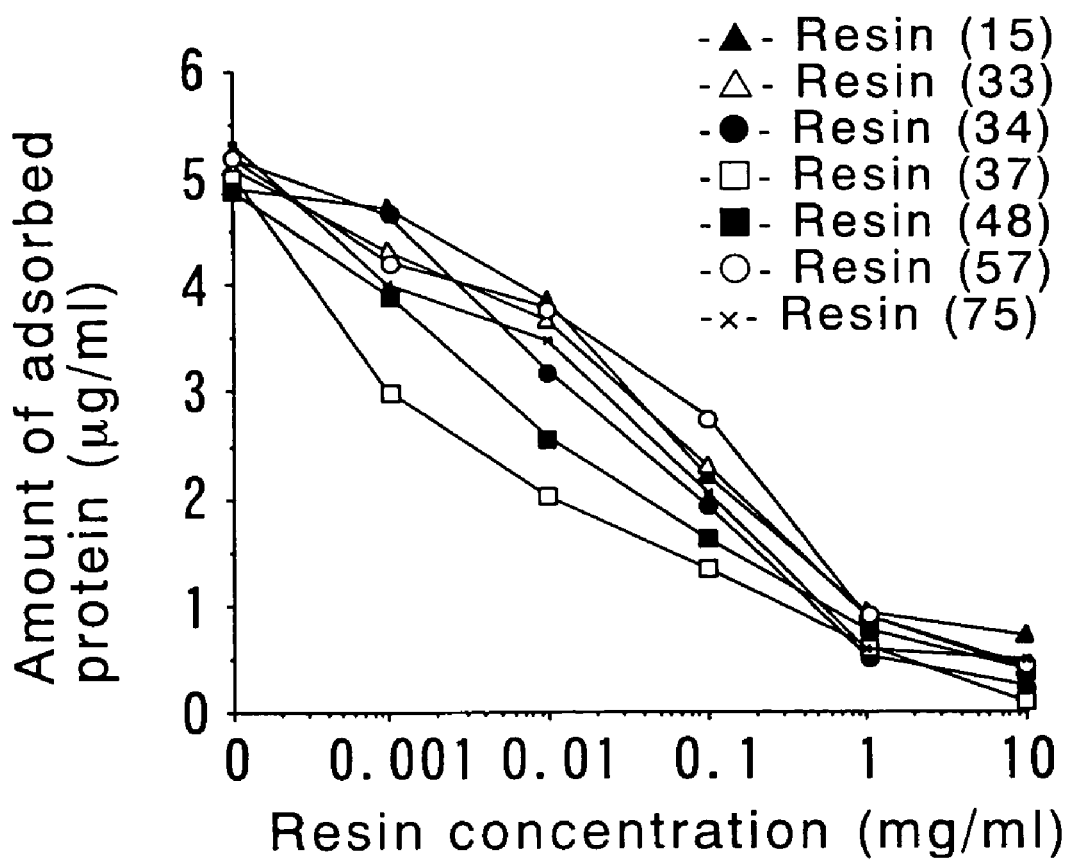
FIG. 16 is a graph showing the results of the evaluation of human immunoglobulin adhesion to various resins, which evaluation is made in Example 71.

The results are shown in FIG. 16. The determination of the amounts of IgG adsorbed on the wells of the EIA plate was performed using a calibration curve prepared by a method in which IgG standard solutions having known IgG concentrations are dispensed into wells of an EIA plate which is the same as used above, and the amounts of IgG adsorbed on the surfaces of the wells are measured.

As mentioned above, the resins evaluated were resin (15) produced in Example 9, resins (33), (34) and (37) produced in Example 14, resins (48) and (57) produced in Example 18 and resin (75) produced in Example 21. FIG. 16 shows that the amount of IgG adsorbed on the non-coated well was approximately 5 μg/ml. The evaluated resins inhibit IgG adsorption onto the wells of the EIA plate, and the degree of inhibition is proportional to the resin concentration of the resin solution.

Example 72

Evaluation (2) of Plasma Protein Adsorption

Resin (15) produced in Example 9, resins (33), (34) and (37) produced in Example 14, resins (48) and (57) produced in Example 18 and resin (75) produced in Example 21 were individually evaluated in the following manner. An EIA plate having resin-coated wells and a non-coated well (wherein the latter was intended for use as a control well) was prepared in the same manner as in Example 71. Adhesion of fibronectin to the resin-coated wells was evaluated as follows.

0.1 ml of a fibronectin solution containing 5 μg/ml of a human fibronectin (manufactured and sold by CHEMICON International, Inc., U.S.A.) was dispensed into the resin-coated wells and non-coated well of the above-obtained EIA plate, and was allowed to remain in contact with the surfaces of the wells at 37° C. for 2 hours. Subsequently, the amounts of human fibronectin adsorbed on the surfaces of the wells were determined by ELISA using a horseradish peroxidase (HRP)-conjugated goat IgG fraction to human fibronectin (manufactured and sold by MP Biomedicals, U.S.A.).

Figure 17:
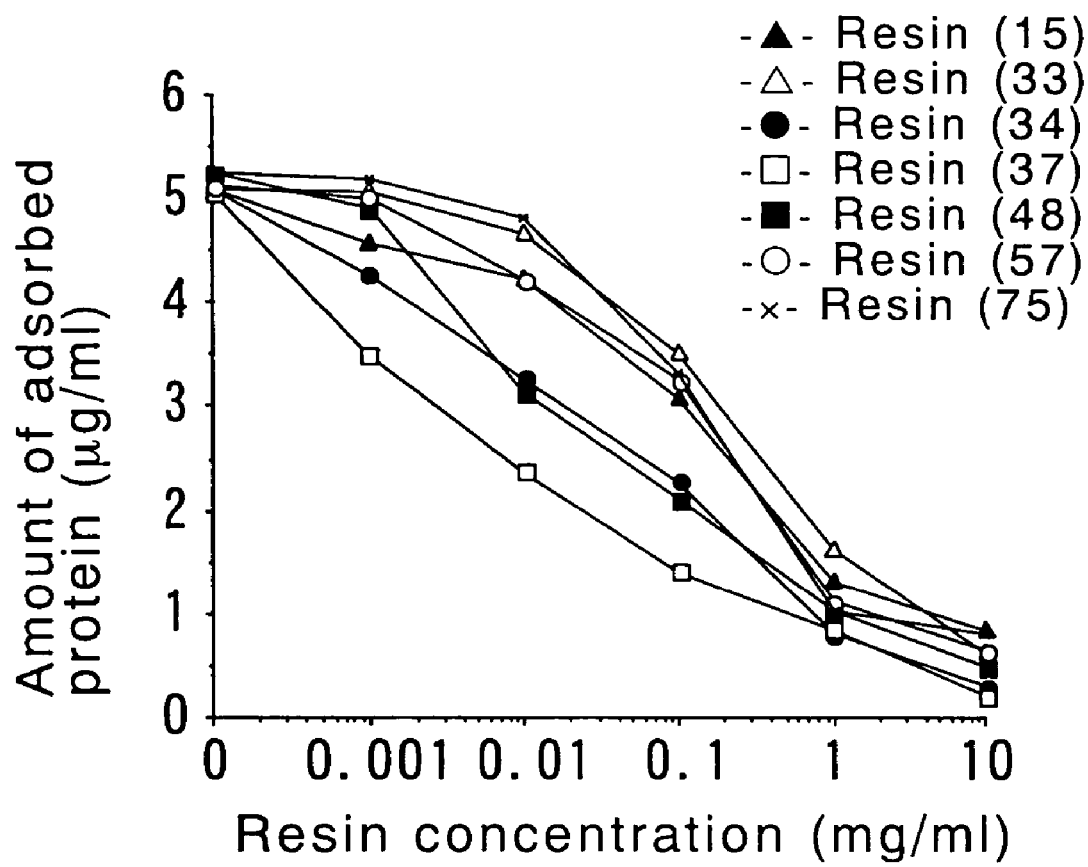
FIG. 17 is a graph showing the results of the evaluation of human fibronectin adhesion to various resins, which evaluation is made in Example 72.

The results are shown in FIG. 17. The determination of the amounts of fibronectin adsorbed on the wells of the EIA plate was performed using a calibration curve prepared by a method in which fibronectin standard solutions having known fibronectin concentrations are dispensed into wells of an EIA plate which is the same as used above, and the amounts of fibronectin adsorbed on the surfaces of the wells are measured.

As mentioned above, the resins evaluated were resin (15) produced in Example 9, resins (33), (34) and (37) produced in Example 14, resins (48) and (57) produced in Example 18 and resin (75) produced in Example 21. FIG. 17 shows that the amount of fibronectin adsorbed on the non-coated well was approximately 5 μg/ml. The evaluated resins inhibit fibronectin adsorption onto the wells of the EIA plate, and the degree of inhibition is proportional to the resin concentration of the resin solution.

Example 73

Evaluation (3) of Plasma Protein Adsorption

Resin (15) produced in Example 9, resins (33), (34) and (37) produced in Example 14, resins (48) and (57) produced in Example 18 and resin (75) produced in Example 21 were individually evaluated in the following manner. An EIA plate having resin-coated wells and a non-coated well (wherein the latter was intended for use as a control well) was prepared in the same manner as in Example 71. Adhesion of fibrinogen to the resin-coated wells was evaluated as follows.

0.1 ml of a fibrinogen solution containing 5 μg/ml of a human fibrinogen (manufactured and sold by Biogenesis Inc., U.S.A.) was dispensed into the resin-coated wells and non-coated well of the above-obtained EIA plate, and was allowed to remain in contact with the surfaces of the wells at 37° C. for 2 hours. Subsequently, the amounts of human fibrinogen adsorbed on the surfaces of the wells were determined by ELISA using a horseradish peroxidase (HRP)-conjugated goat IgG to human fibrinogen (manufactured and sold by EY Laboratories, Inc, U.S.A.).

Figure 18:
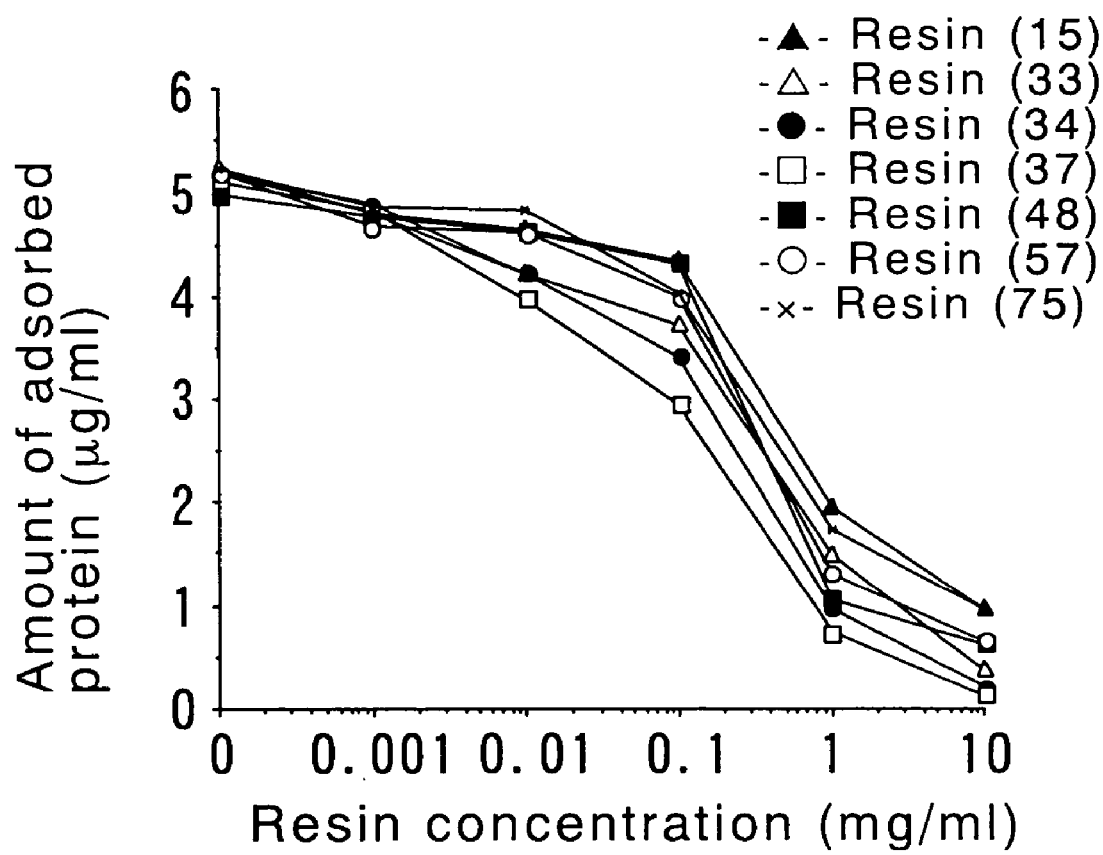
FIG. 18 is a graph showing the results of the evaluation of human fibrinogen adhesion to various resins, which evaluation is made in Example 73.

The results are shown in FIG. 18. The determination of the amounts of fibrinogen adsorbed on the wells of the EIA plate was performed using a calibration curve prepared by a method in which fibrinogen standard solutions having known fibrinogen concentrations are dispensed into wells of an EIA plate which is the same as used above, and the amounts of fibrinogen adsorbed on the surfaces of the wells are measured.

As mentioned above, the resins evaluated were resin (15) produced in Example 9, resins (33), (34) and (37) produced in Example 14, resins (48) and (57) produced in Example 18 and resin (75) produced in Example 21. FIG. 18 shows that the amount of fibrinogen adsorbed on the non-coated well was approximately 5 μg/ml. The evaluated resins inhibit fibrinogen adsorption onto the wells of the EIA plate, and the degree of inhibition is proportional to the resin concentration of the resin solution.

Example 74

Evaluation (4) of Plasma Protein Adsorption

Resin (15) produced in Example 9, resins (33), (34) and (37) produced in Example 14, resins (48) and (57) produced in Example 18 and resin (75) produced in Example 21 were individually evaluated in the following manner. An EIA plate having resin-coated wells and a non-coated well (wherein the latter was intended for use as a control well) was prepared in the same manner as in Example 71. Adhesion of albumin to the resin-coated wells was evaluated as follows.

0.1 ml of an albumin solution containing 2 μg/ml of a purified human albumin (manufactured and sold by MP Biomedicals, U.S.A.) was dispensed into the resin-coated wells and non-coated well of the above-obtained EIA plate, and was allowed to remain in contact with the surfaces of the wells at 37° C. for 2 hours. Subsequently, the amounts of human albumin adsorbed on the surfaces of the wells were determined by ELISA using a horseradish peroxidase (HRP)-conjugated goat IgG fraction to human albumin (manufactured and sold by MP Biomedicals, U.S.A.).

Figure 19:
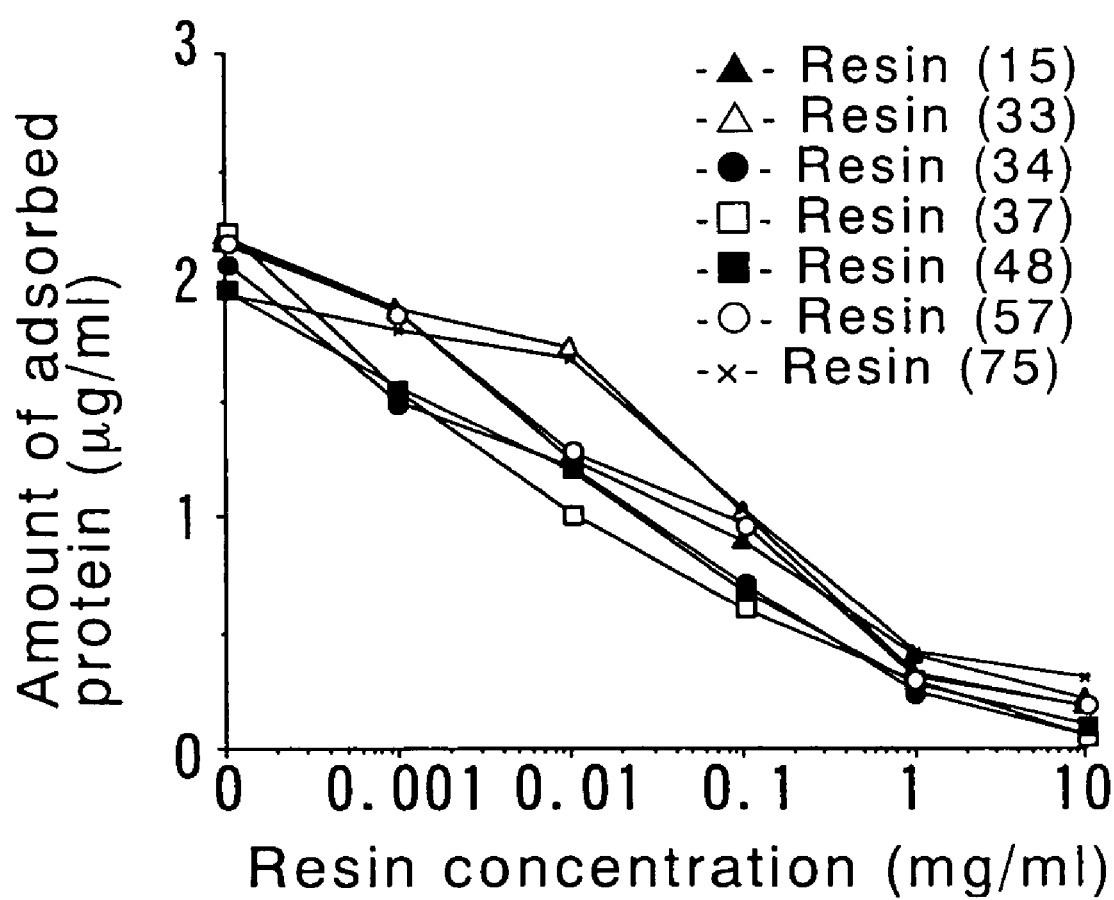
FIG. 19 is a graph showing the results of the evaluation of human albumin adhesion to various resins, which evaluation is made in Example 74.

The results are shown in FIG. 19. The determination of the amounts of albumin adsorbed on the wells of the EIA plate was performed using a calibration curve prepared by a method in which albumin standard solutions having known albumin concentrations are dispensed into wells of an EIA plate which is the same as used above, and the amounts of albumin adsorbed on the surfaces of the wells are measured.

As mentioned above, the resins evaluated were resin (15) produced in Example 9, resins (33), (34) and (37) produced in Example 14, resins (48) and (57) produced in Example 18 and resin (75) produced in Example 21. FIG. 19 shows that the amount of albumin adsorbed on the non-coated well was approximately 2 μg/ml. The evaluated resins inhibit albumin adsorption onto the wells of the EIA plate, and the degree of inhibition is proportional to the resin concentration of the resin solution.

Example 75

Evaluation (5) of Plasma Protein Adsorption

Resin (15) produced in Example 9, resins (33), (34) and (37) produced in Example 14 and resin (48) produced in Example 18 were individually evaluated in the following manner. Resin solutions respectively having resin concentrations of 10, 1, 0.1 and 0.01 mg/ml were prepared by dissolving different amounts of a resin individually in an aqueous 50% ethanol solution. PET films (thickness: 60 μm) were respectively immersed in the obtained resin solutions to cause the films to be coated with the resin at different concentrations, thereby obtaining test samples. Plasma protein adsorption of the test samples was evaluated as follows.

Each of the test samples was individually placed in a well of a 24-well cell culture plate, followed by washing. An immunoglobulin G solution containing 5 μg/ml of a purified human immunoglobulin G (IgG) (manufactured and sold by MP Biomedicals, U.S.A.) was dispensed into each of the wells each containing a test sample, and was allowed to remain in contact with the test samples at 37° C. for 2 hours. Subsequently, the amounts of human IgG adsorbed on the surfaces of the test samples were determined by ELISA using a horseradish peroxidase (HRP)-conjugated goat IgG fraction to human IgG (whole molecule) (manufactured and sold by MP Biomedicals, U.S.A.).

Also, substantially the same procedure as in the above-described evaluation of the test samples was repeated except that a non-coated PET film was used instead of the test samples.

Figure 20:
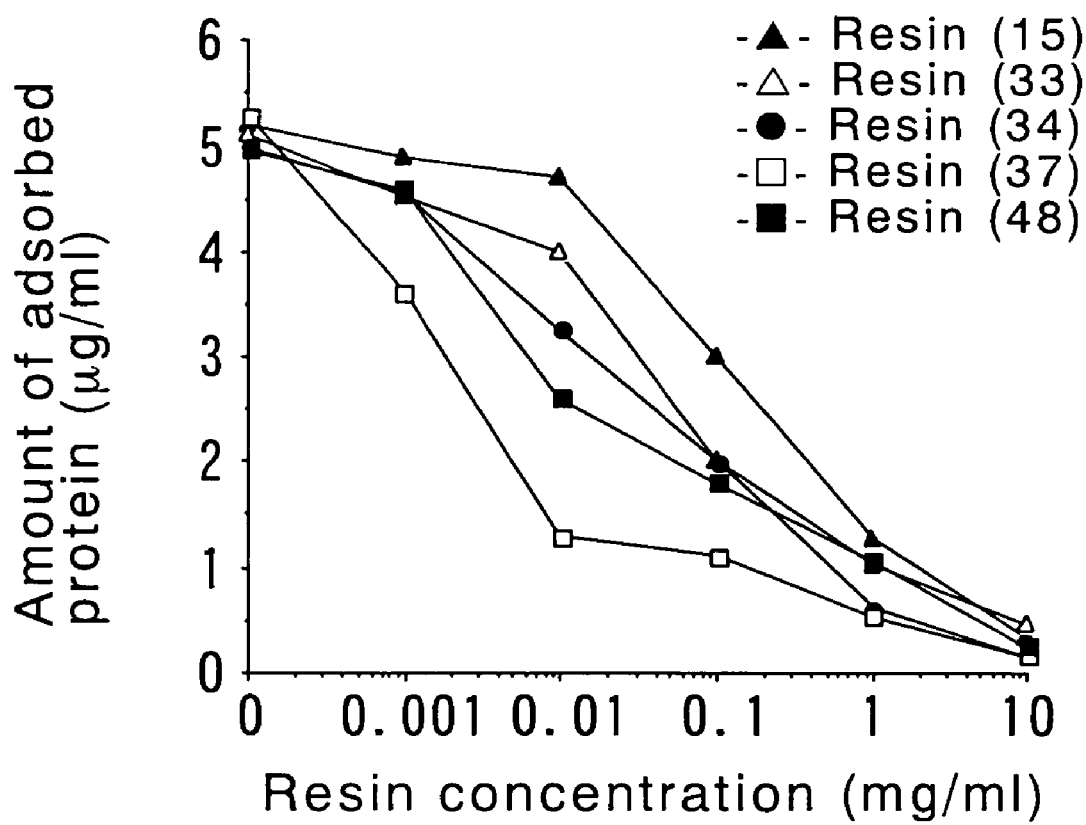
FIG. 20 is a graph showing the results of the evaluation of human immunoglobulin adhesion to PET films coated with various resins, which evaluation is made in Example 75.

Results are shown in FIG. 20. In FIG. 20, the amount of IgG adsorbed on each test sample is expressed in terms of the percentage of the amount of IgG adsorbed on the test sample, based on the amount of IgG adsorbed on the non-coated PET film. Resins (15), (33), (34), (37) and (48) inhibit IgG adsorption, and the degree of inhibition is proportional to the resin concentration of the resin solution.

Example 76

Evaluation of Toxicity: Experiment for Determining the Toxicity of a Resin by Intravenous Injection to Mouse Fifteen female BALB/c mice (purchased from Japan SLC Inc., Japan) were divided into five groups each consisting of three mice. Three groups of mice were, respectively, given administration of resins (54), (55) and (63) (each produced in Example 18). Specifically, each mouse of the three groups received administration of a resin solution (in physiological saline) by tail-vein injection under conditions wherein the dose of the resin was 2 g/kg and the volume of the resin solution administered was 25 ml/kg. The administration was performed intermittently once a week on days 2, 9 and 16 from the start of the experiment (i.e., 3 administrations in total). Each mouse of one group of the other two groups received the administration of only physiological saline wherein the physiological saline was administered in the same manner as in the above-mentioned administration of the resin solution, to thereby obtain a control group of mice. The other group of the two groups of mice did not receive any administration, to thereby obtain a normal group of mice.

Evaluation was made on the toxicity of each resin in terms of the loss in the average body weight, based on the average initial body weight (i.e., the average body weight of the mice on day 1). A resin was defined as being toxic when the loss in the average body weight was 10% or more of the average initial body weight.

Figure 21:
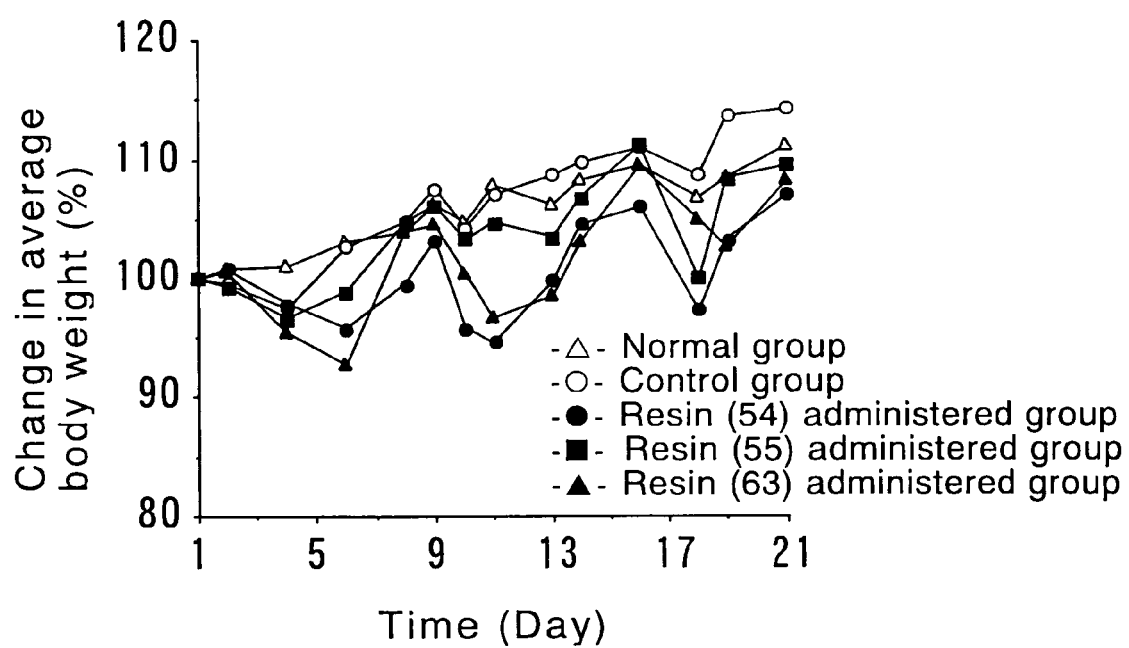
FIG. 21 is a graph showing the results of the evaluation of toxicity of the resin of the present invention, which evaluation is made in Example 76.

The results are shown in FIG. 21. With respect to the groups which received the administration of the resin solutions, some loss in the average body weight was observed after receiving the administration of the resin solutions, but this loss in the average body weight was not more than 10% of the initial average body weight. Further, few days after the administration of the resin solutions, the mice regained their weights to a level which was comparable to the average body weight of the control group which had received administration of only physiological saline and the average body weight of the normal group which had not received any administration. Thus, all of resins (54), (55) and (63) were found to have no toxicity.

Example 77

Pharmacokinetics (1) of a Resin

Six female BALB/c mice (purchased from Japan SLC Inc., Japan) were divided into two groups, each consisting of three mice, and mouse colon tumor cells (Colon 26 cells) were intradermally transplanted to the abdomen of each mouse of the two groups. Subsequently, one group of mice received the administration of a physiological saline solution of resin (82) (which was produced in Example 25 and which had paclitaxel bonded thereto through a peptide linker), wherein the dose of resin (82) was 50 mg/kg in terms of paclitaxel. The other group of mice received the administration of a solution of paclitaxel as such, wherein the dose of paclitaxel was 50 mg/kg, and the solution of paclitaxel was obtained by dissolving paclitaxel in a mixed solvent comprised of Cremophor EL (trade name) (manufactured and sold by Sigma-Aldrich Inc., U.S.A.) and ethanol (Cremophor EL: ethanol=1:1), followed by dilution of the resultant solution with physiological saline. At the points in time of 24 and 48 hours after the administration to the mice of the solution of the resin (82) and the solution of paclitaxel, evaluation was made of the paclitaxel concentration of each of the tumors of the mice in the two groups. Specifically, the paclitaxel concentration was determined by HPLC in accordance with a method described in S. Sugahara, M. Kajiki, H. Kuriyama and T. Kobayashi, Biol. Pharm. Bull., 25, 632-641 (2002).

Figure 22:
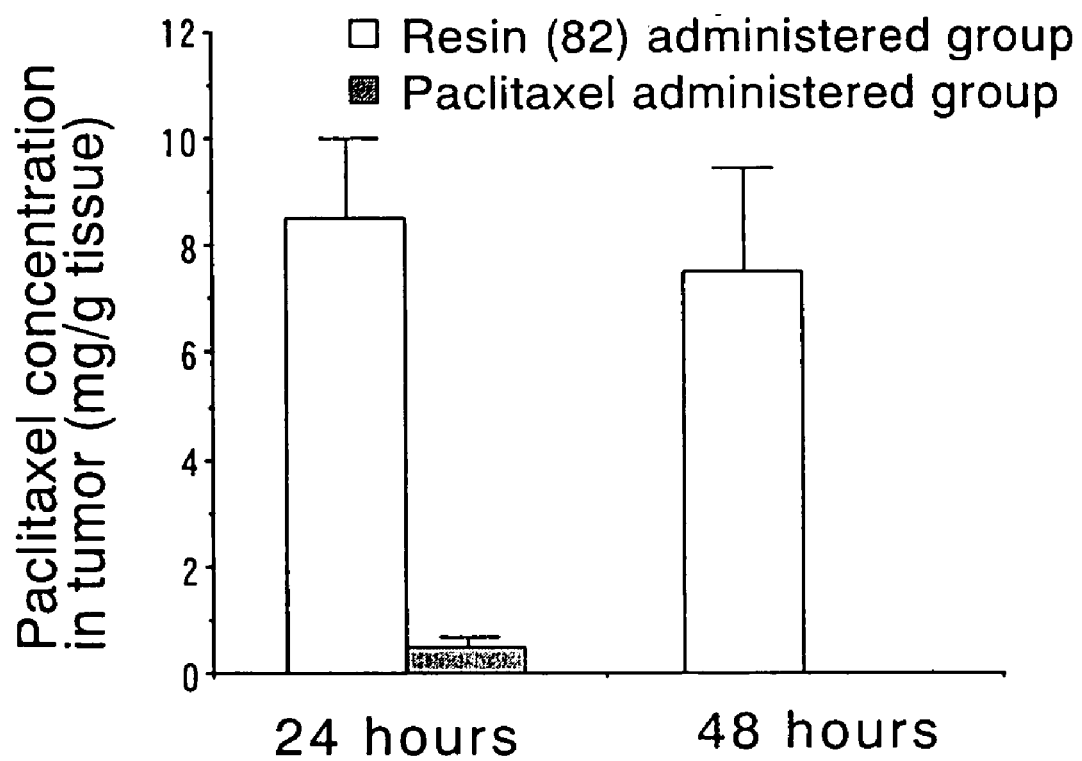
FIG. 22 is a graph showing the results of the paclitaxel concentration test performed in Example 77 in which the paclitaxel concentration is measured with respect to tumor cells of mice to which resin (82) of the present invention and paclitaxel had been administered, respectively.

The results are shown in FIG. 22. FIG. 22 shows that the paclitaxel concentration in the tumor was significantly high in the group of mice which had received the administration of the solution of resin (82) having paclitaxel bonded thereto, as compared to the case of the group of mice which had received the administration of the solution of paclitaxel as such.

Example 78

Pharmacokinetics (2) of a Resin

Pharmacokinetics of resin (83) produced in Example 26 and resin (85) produced in Example 29, each having paclitaxel bonded thereto, was evaluated in the same manner as in Example 77. Specifically, nine female BALB/c mice were divided into three groups, each consisting of three mice, and mouse colon tumor cells were intradermally transplanted to the abdomen of each mouse of the three groups. Subsequently, two groups of mice respectively received the administration of a physiological saline solution of resin (83) and the administration of a physiological saline solution of resin (85), under the same conditions as employed in the administration of resin (82) in Example 77, specifically, the dose of each of resin (83) and resin (85) was 50 mg/kg in terms of paclitaxel. The other group of mice received the administration of a solution of paclitaxel as such under the same conditions as employed in the administration of a solution of paclitaxel as such in Example 77, specifically, the dose of paclitaxel was 50 mg/kg, and the solution of paclitaxel was obtained by dissolving paclitaxel in a mixed solvent comprised of Cremophor EL (trade name) (manufactured and sold by Sigma-Aldrich Inc., U.S.A.) and ethanol (Cremophor EL ethanol=1:1), followed by dilution of the resultant solution with physiological saline. At the points in time of 24 and 48 hours after the administration to the mice of the solution of the resin (83), the solution of resin (85) and the solution of paclitaxel, evaluation was made of the paclitaxel concentration of each of the tumors of the mice in the three groups. Specifically, HPLC was performed in the same manner as in Example 77 to thereby determine the paclitaxel concentration.

Figure 23:
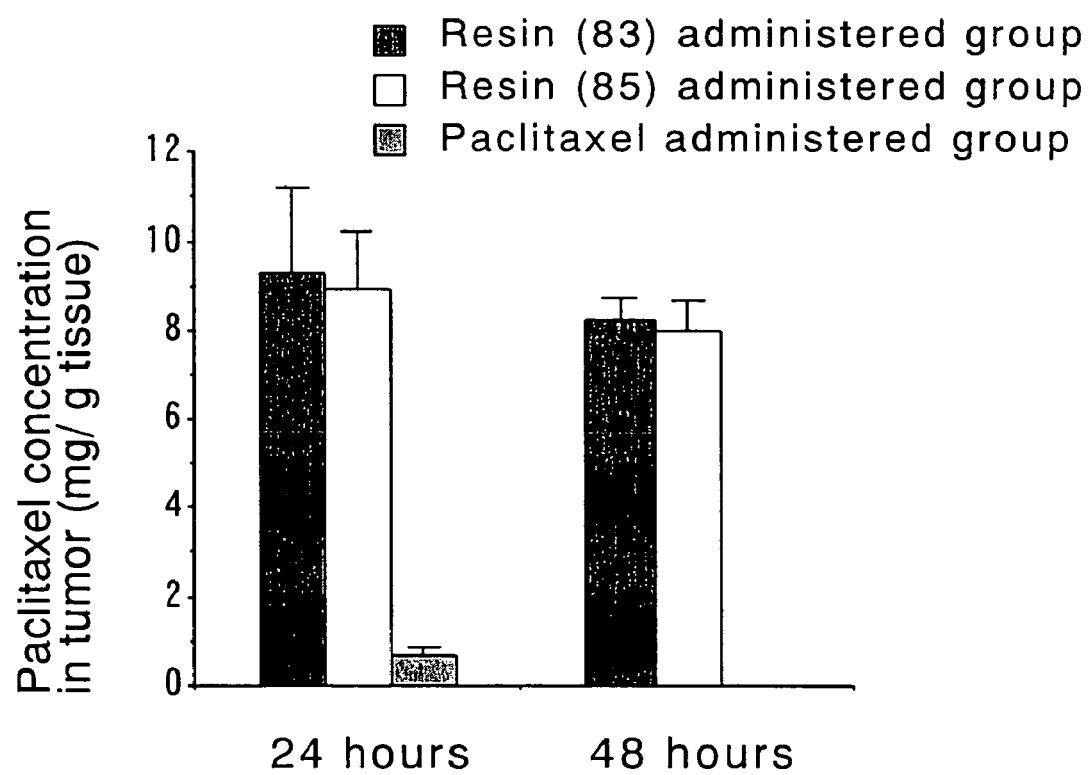
FIG. 23 is a graph showing the results of the paclitaxel concentration test performed in Example 78 in which the paclitaxel concentration is measured with respect to tumor cells of mice to which resin (83) of the present invention, resin (85) of the present invention and paclitaxel had been administered, respectively.

The results are shown in FIG. 23. FIG. 23 shows that the paclitaxel concentration in the tumor was significantly high in each of the groups of mice which had received the administration of the solutions of resins (83) and (85) having paclitaxel bonded thereto, as compared to the case of the group of mice which ha d received the administration of the solution of paclitaxel as such.

Example 79

Evaluation of Anti-Tissue Adhesion Property of a Resin

The anti-tissue adhesion property of gel sheets (78), (79) and (80), each prepared in Example 22, was evaluated in the following manner.

Twenty-eight female rats (Crj-CD(SD), 8 weeks old, purchased from Charles River Japan Inc., Japan) were divided into four groups, each consisting of seven rats. Each of three groups of rats was subjected to pentobarbital anesthesia, and an incision was made along the median line of the abdomen, whereupon the cecum was taken out from the abdominal cavity of the rat. The surface of the cecum was scratched with a gauze to remove about half of the serous membrane from the cecum, thus injuring the cecum. A gel sheet (size: 2×2 cm) was applied to the serous membrane-removed, injured portion of the cecum to cover the injury, and the thus treated, injured cecum was returned to the abdominal cavity of the rat, followed by suturing of the incision. By such procedure, the three groups of rats were caused to have injured ceca and, respectively, treated using the gel sheets (78), (79) and (80), thereby obtaining polymer-treated groups of rats. Separately, with respect to the other group of 7 rats, the same procedure as described above was repeated except that the application of a gel sheet was not performed and the injured cecum as such was returned to the abdominal cavity of each rat, to thereby obtain a non-treated group of rats as a control group. After a period of five days from the surgical operation, the rats of the four groups were subjected to surgical anatomy to determine whether or not tissue adhesion was present. The tissue adhesion was defined as an interfacial, fibrous adhesion which has a certain thickness and which binds together adjacent surfaces with such a strength that they cannot be easily separated from each other even when they are pulled in opposite directions using a forceps. The results are shown in Table 11 below.

TABLE 11

|  | Resin (78) | Resin (79) | Resin (80) | Control (no treatment) |
| --- | --- | --- | --- | --- |
| Tissue condition | No disorder | No disorder | No disorder | Slight inflammation |
| Ratio of mice having tissue adhesion | 3/7 | 2/7 | 2/7 | 6/7 |

As shown in Table 11, the ratio of mice having tissue adhesion was low in the 3 groups of rats which were, respectively, treated with the gel sheets (78), (79) and (80), as compared to the case of the group of non-treated rats.

Example 80

Evaluation of Wound Healing Promoting Effect of a Resin

The wound healing promoting effect of the gel sheets (79) and (80), each prepared in Example 22, was evaluated in the following manner.

Fifteen female rats (Crj-CD(SD), 7 weeks old, purchased from Charles River Japan Inc., Japan) were divided into three groups, each consisting of five rats. The fur of the dorsal region of each rat of the three groups was shaved, and the rats were subjected to pentobarbital anesthesia. A part of the dorsal skin of each rat was removed so as to form a circular wound (diameter: 2 cm) with complete skin loss. Gel sheets (79) and (80) were, respectively, used to treat two groups of wounded rats, thereby obtaining two groups of polymer-treated rats. Specifically, the wound of each rat of two groups was covered with a gel sheet and, then, the gel sheet was covered with a medical gauze of a non-woven fabric. The medical gauze was secured in place using an adhesive bandage, followed by taping. Separately, with respect to the other group of five rats, the same procedure as described above was repeated except that a gel sheet was not used (i.e., the wound was covered only with a medical gauze, which was secured in place using an adhesive bandage, followed by taping), to thereby obtain a non-treated group of rats. On days 0, 3, 5 and 7 from the surgical operation, measurement was made of the size (area) of the wounds of the mice of the three groups, and the level of wound healing was determined in terms of the average wound area remaining ratio (%), namely the ratio of the average wound area on a day on which the size of the wound was measured to the average wound area on day 0. Specifically, the wound area remaining ratio (%) was obtained according to the following formula:

Wound area remaining ratio (%)={(product of the major and minor diameters of the wound on a day on which the size of the wound was measured)/(product of the major and minor diameters of the wound on day 0)}×100.

The results are shown in Table 12 below.

TABLE 12

| Experimental Group | Average wound area remaining ratio (%) | | | |
| --- | --- | --- | --- | --- |
| | Day 0 | Day 3 | Day 5 | Day 7 |
| Resin (79) | 100 | 87 | 72 | 65 |
| Resin (80) | 100 | 88 | 70 | 61 |
| No treatment with resin | 100 | 91 | 86 | 78 |

Table 12 shows that the resins of the present invention in the form of gel sheets were able to promote the wound healing of rats.

Example 81

Evaluation of Wound Healing Promoting Effect of a Resin

The wound healing promoting effect of the gel sheets (79) and (80), each prepared in Example 22, was evaluated in the following manner.

Fifteen female rats (Crj-CD(SD), 7 weeks old, purchased from Charles River Japan Inc., Japan) were divided into three groups, each consisting of five rats. The fur of the dorsal region of each rat of the three groups was shaved, and the rats were subjected to pentobarbital anesthesia. A copper rod (diameter: 1.5 cm) was chilled in liquid nitrogen and the chilled copper rod was pressed against the shaved dorsal region of each rat to thereby form a frostbite wound. Gel sheets (79) and (80) were, respectively, used to treat two groups of wounded rats, thereby obtaining two groups of polymer-treated rats. Specifically, the frostbite wound of each rat of two groups was covered with a gel sheet and, then, the gel sheet was covered with a medical gauze of a non-woven fabric. The medical gauze was secured in place using an adhesive bandage, followed by taping. Separately, with respect to the other group of five rats, the same procedure as described above was repeated except that a gel sheet was not used (i.e., the frostbite wound was covered only with a medical gauze, which was secured in place using an adhesive bandage, followed by taping), to thereby obtain a non-treated group of rats. On days 0, 3, 5 and 7 from the surgical operation, measurement was made of the size (area) of the frostbite wounds of the mice of the three groups, and the level of wound healing was determined in terms of the average wound area remaining ratio (%), namely the ratio of the average wound area on a day on which the size of the frostbite wound was measured to the average wound area on day 0. Specifically, the wound area remaining ratio (%) was obtained according to the following formula:

Wound area remaining ratio (%)={(product of the major and minor diameters of the frostbite wound on a day on which the size of the frostbite wound was measured)/(product of the major and minor diameters of the frostbite wound on day 0)}×100.

The results are shown in Table 13 below.

TABLE 13

| Experimental Group | Average wound area remaining ratio (%) | | | |
|---|---|---|---|---|
| | Day 0 | Day 3 | Day 5 | Day 7 |
| Resin (79) | 100 | 84 | 73 | 62 |
| Resin (80) | 100 | 85 | 68 | 60 |
| No treatment with resin | 100 | 93 | 90 | 82 |

Table 13 shows that the resins of the present invention in the form of gel sheets were able to promote the wound healing of rats.

Example 82

Pharmacokinetics of $^3$H-Labeled Polyether Derivative DexT500 (121)

Three female Wister rats (6 weeks old, body weight: 100 to 120 g) received the administration of a resin solution by tail-vein injection, wherein the resin solution was prepared by dissolving, in physiological saline, $^3$H-labeled polyether derivative DexT500 (121) prepared in Example 65 and non-labeled polyether derivative DexT500 (0.87) prepared in Example 31, and the polyether derivatives were used in amounts such that the dose of the resin became 10 mg/kg and 1×10$^6$ dpm, which are, respectively, in terms of the total weight of $^3$H-labeled polyether derivative DexT500 (121) and non-labeled polyether derivative DexT500 (87) and in terms of radioactivity. The administration was performed only once. Six hours after the administration, the radioactivity in each of the spleen, kidney, muscles, bone marrow and liver of each of the mice was determined. The radioactivity concentration of each organ was expressed in terms of the radioactivity ratio per g of tissue, wherein the radioactivity ratio is defined as the percentage of the radioactivity in an organ, based on the dose of the resin in terms of radioactivity.

Figure 24:
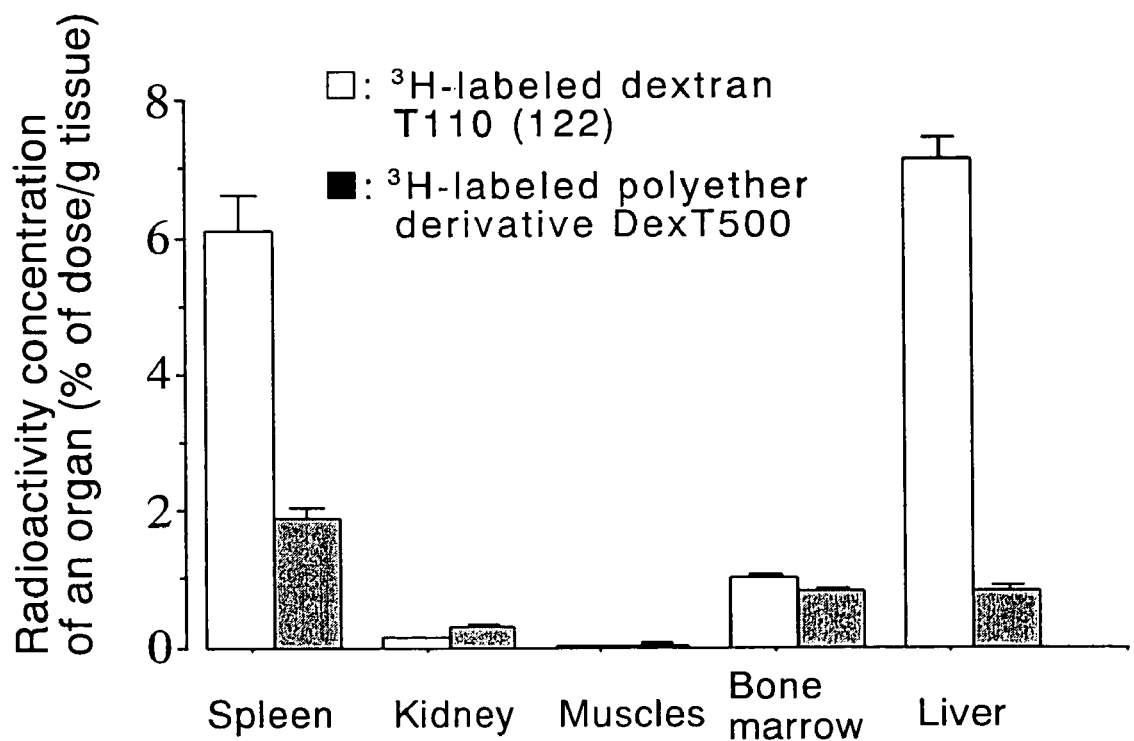
FIG. 24 is a graph showing the results of the evaluation of pharmacokinetics of resin (121) and resin (122), which evaluation is made in Example 82 and Comparative Example 1.

The results are shown in FIG. 24. FIG. 24 shows that the distribution of the $^3$H-labeled polyether derivative DexT500 (121) in the spleen and liver was significantly low, as compared to that in the case of $^3$H-labeled dextran T110 (122) evaluated in Comparative Example 1 below.

Comparative Example 1

Pharmacokinetics of $^3$H-Labeled Dextran T116 (122)

Three female Wister rats (6 weeks old, body weight: 100 to 120 g) received the administration of a dextran solution by tail-vein injection, wherein the dextran solution was prepared by dissolving, in physiological saline, $^3$H-labeled dextran T110 (122) prepared in Reference Example 1 and non-labeled dextran T110 (manufactured and sold by Amersham Biosciences Corp., U.S.A.), and the dextrans were used in amounts such that the dose of dextran became 10 mg/kg and 1×10$^6$ dpm, which are, respectively, in terms of the total weight of $^3$H-labeled dextran T110 (122) and non-labeled dextran T110 and in terms of radioactivity. The administration was performed only once.

Six hours after the administration, the radioactivity in each of the spleen, kidney, muscles, bone marrow and liver of each of the mice was determined. The radioactivity concentration of each organ was determined in the same manner as in Example 82. Specifically, the radioactivity concentration was expressed in terms of the radioactivity ratio per g of tissue, wherein the radioactivity ratio is defined as the percentage of the radioactivity in an organ, based on the dose of dextran in terms of radioactivity.

The results are shown in FIG. 24. FIG. 24 shows that the distribution of the $^3$H-labeled dextran T110 (122) in the spleen and liver was significantly high, as compared to that in the case of $^3$H-labeled polyether derivative DexT500 (121) evaluated in Example 82 above.

Example 83

Evaluation of Blood Compatibility (Anti-Platelet Adhesion Property) of a Resin: Experiment for Determining the Effect of a Resin to Inhibit the Adhesion of Platelets Polyether derivative DexT500 (87) produced in Example 31, polyether derivative DexT500 (108) produced in Example 52 and crosslinked polyalkoxyalkyl derivative (112) produced (using polyether derivative DexT500 (87)) in Example 56 were individually evaluated in the following manner. A resin was dissolved in an aqueous 50% ethanol solution so as to obtain a resin solution having a resin concentration of 10 mg/ml. A polyethylene terephthalate (PET) film (thickness: 60 μm) was immersed in the obtained resin solution to cause the film to be coated with the resin, thereby obtaining a test sample. Human platelet adhesion to the obtained test sample was evaluated as follows.

The test sample was placed in a well of a 24-well cell culture plate, and fresh human platelet rich plasma (PRP) containing sodium citrate as an anticoagulant was added to the well containing the test sample, and the PRP was allowed to be in contact with the test sample at 37° C. for 2 hours. Then, the test sample was taken out from the well and the test sample was washed with physiological saline. The platelets attached to the test sample were fixed using glutaraldehyde, and the test sample was observed through a scanning electron microscope (SEM). Also, substantially the same procedure as in this evaluation of the test sample was repeated except that a non-coated PET film was used instead of the test sample.

Figure 25:
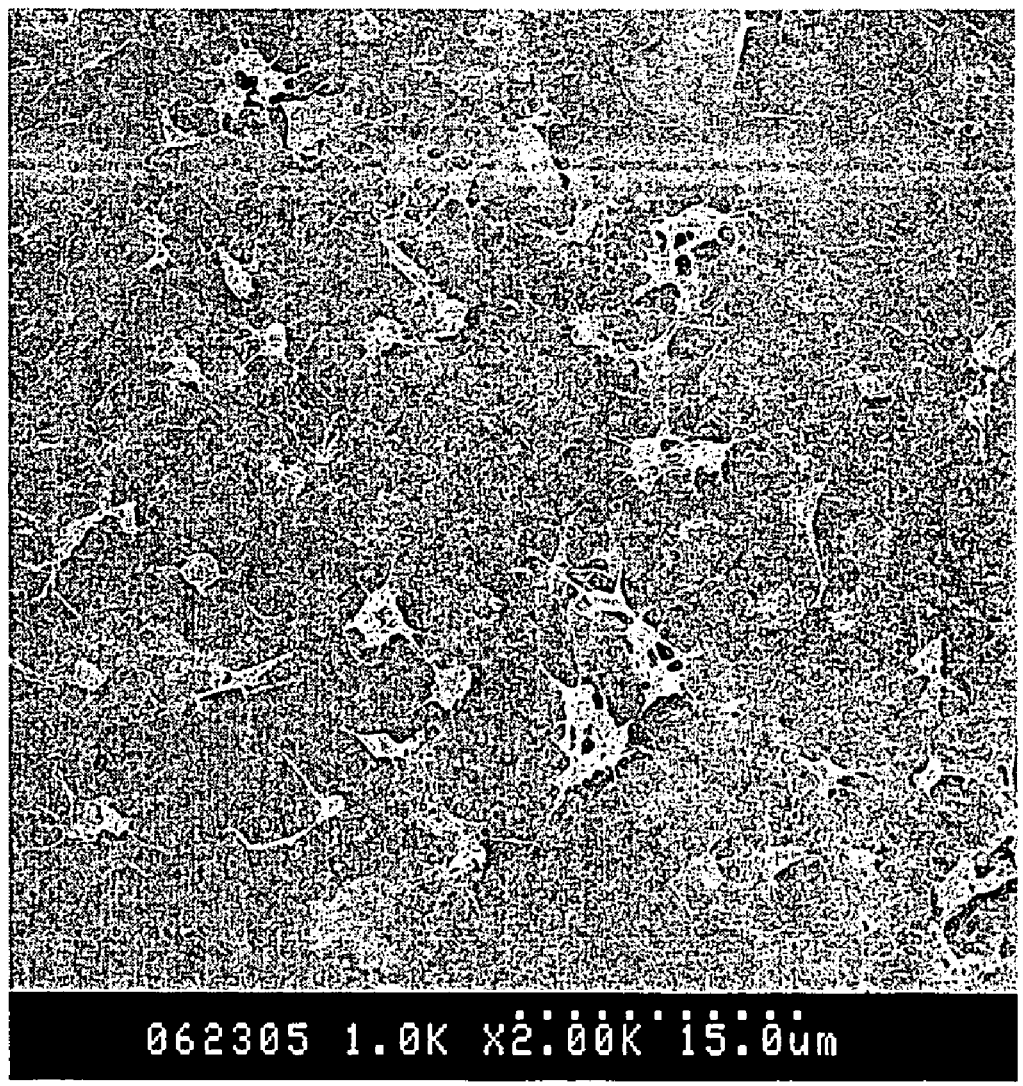
FIG. 25 is an electron photomicrograph of a non-coated PET film used in Example 83.
Figure 26:
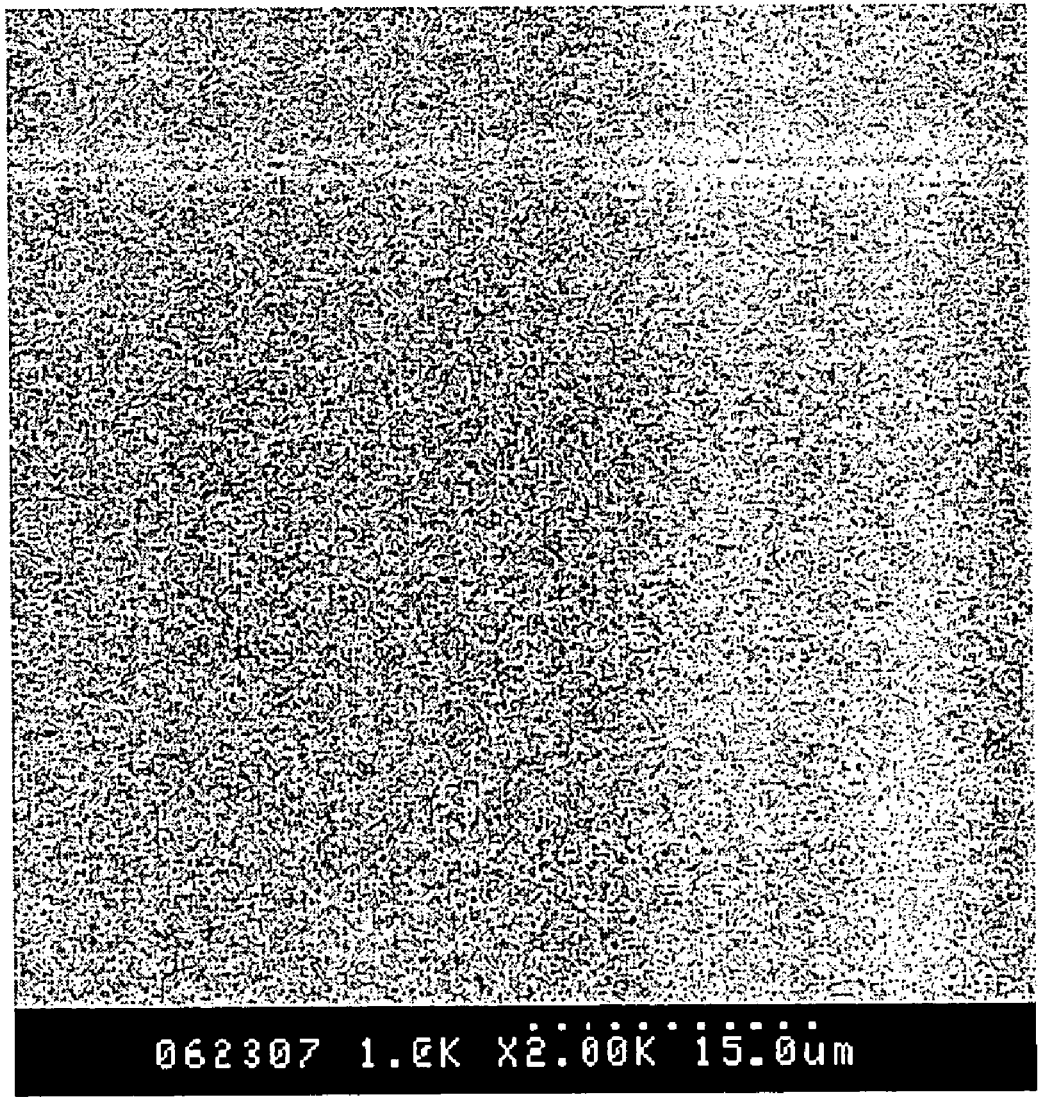
FIG. 26 is an electron photomicrograph of a PET film coated with resin (87) of the present invention, which PET film is obtained in Example 83.
Figure 27:
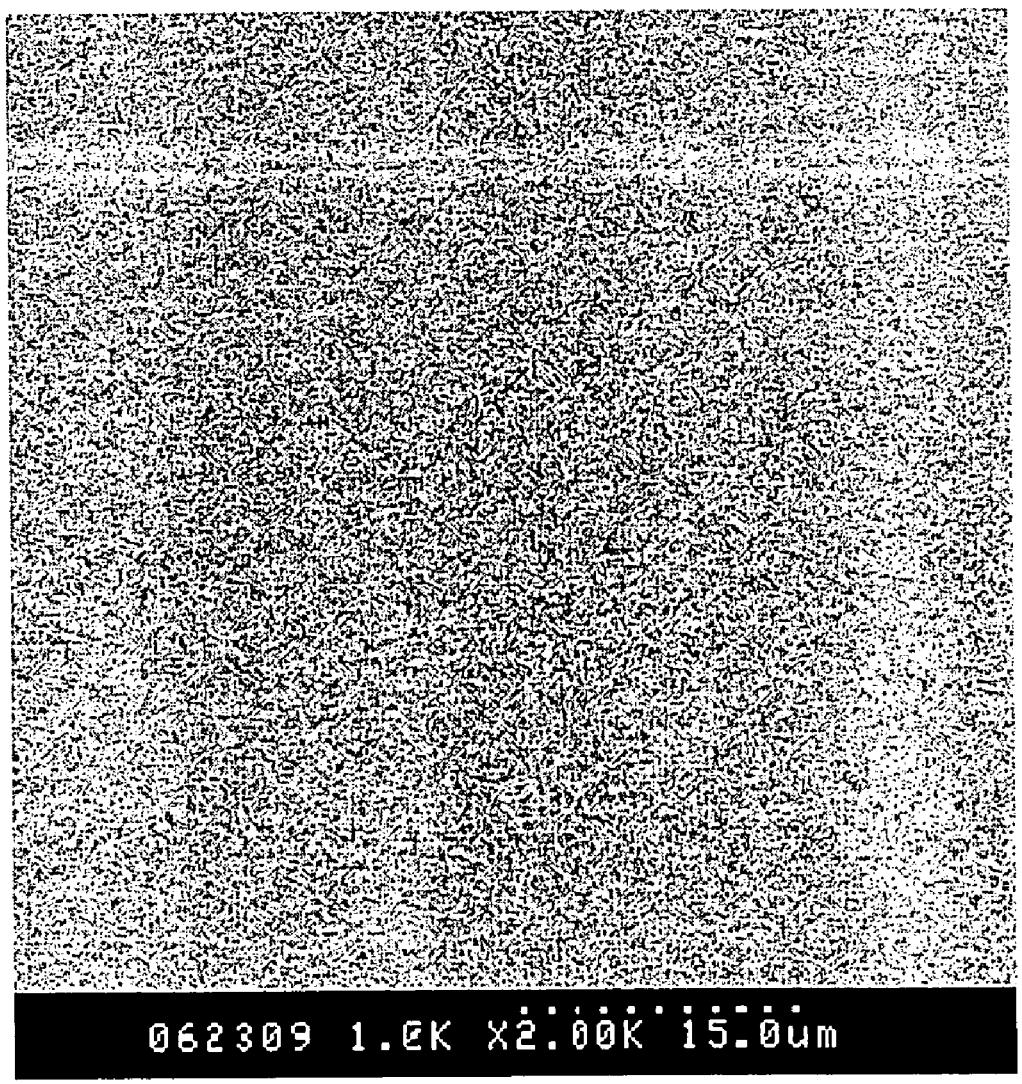
FIG. 27 is an electron photomicrograph of a PET film coated with resin (108) of the present invention, which PET film is obtained in Example 83.
Figure 28:
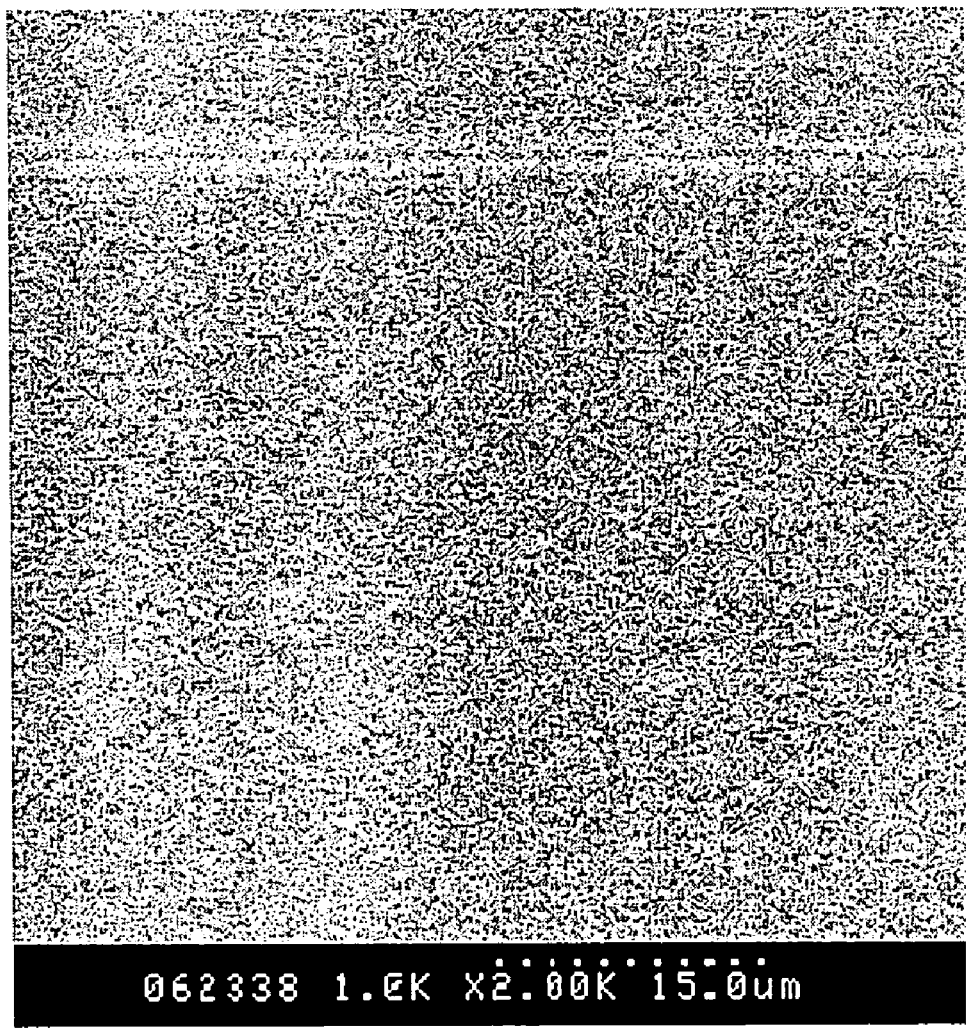
FIG. 28 is an electron photomicrograph of a PET film coated with resin (112) of the present invention, which PET film is obtained in Example 83.

Scanning electron photomicrographs of the test samples of resin-coated PET films (prepared using polyether derivatives (87) and (108) and crosslinked polyalkoxyalkyl derivative (112)) are shown in FIGS. 26, 27 and 28, respectively, and a scanning electron photomicrograph of the non-coated PET film is shown in FIG. 25. Platelets adhered to the non-coated PET film (see FIG. 25), but platelet adhesion was not observed on any of the resin-coated PET films (see FIGS. 26 to 28).

Example 84

Evaluation of Blood Compatibility (Anti-Cell Adhesion Property) of a Resin: Experiment for Determining the Effect of a Resin to Inhibit the Adhesion of Cells Polyether derivative DexT2000 (86) produced in Example 30, polyether derivative DexT500 (87) produced in Example 31, polyether derivative DexT500 (96) produced in Example 40, polyether derivative DexT500 (108) produced in Example 52, polyether derivative DexT500 (110) produced in Example 54 and crosslinked polyalkoxyalkyl derivative (112) produced (using polyether derivative DexT500 (87)) in Example 56 were individually evaluated in the following manner. Resin solutions respectively having resin concentrations of 10, 1, 0.1, 0.01 and 0.001 mg/ml were prepared by dissolving different amounts of a resin individually in an aqueous 50% ethanol solution. Each of the obtained resin solutions was individually dispensed into a well of a 24-well cell culture plate. On the other hand, an aqueous 50% ethanol solution was dispensed into another well of the cell culture plate to thereby provide a well containing an aqueous 50% ethanol solution (wherein the well was intended to provide the below-mentioned "non-coated well" used as a control well). Then, the cell culture plate was allowed to stand still at 4° C. overnight to thereby cause the wells (containing the resin solutions) to be coated with the resin. Subsequently, the resin solutions and aqueous 50% ethanol solution in the wells were removed by suction, followed by drying, to thereby obtain a culture plate having resin-coated wells and a non-coated well (wherein the latter was intended for use as a control well). Adhesion of human cells to the resin-coated wells was evaluated as follows.

A suspension of HEK293 cells (human fetal renal cells) was dispensed into the resin-coated wells and non-coated well of the above-obtained culture plate, and the cells were cultured for 2 days. Thereafter, the number of viable cells adhered to each of the resin-coated wells and non-coated well of the culture plate was determined by means of CellTiter 96® AQ$_{ueous}$ Assay System (manufactured and sold by Promega Corporation, U.S.A.).

Figure 29:
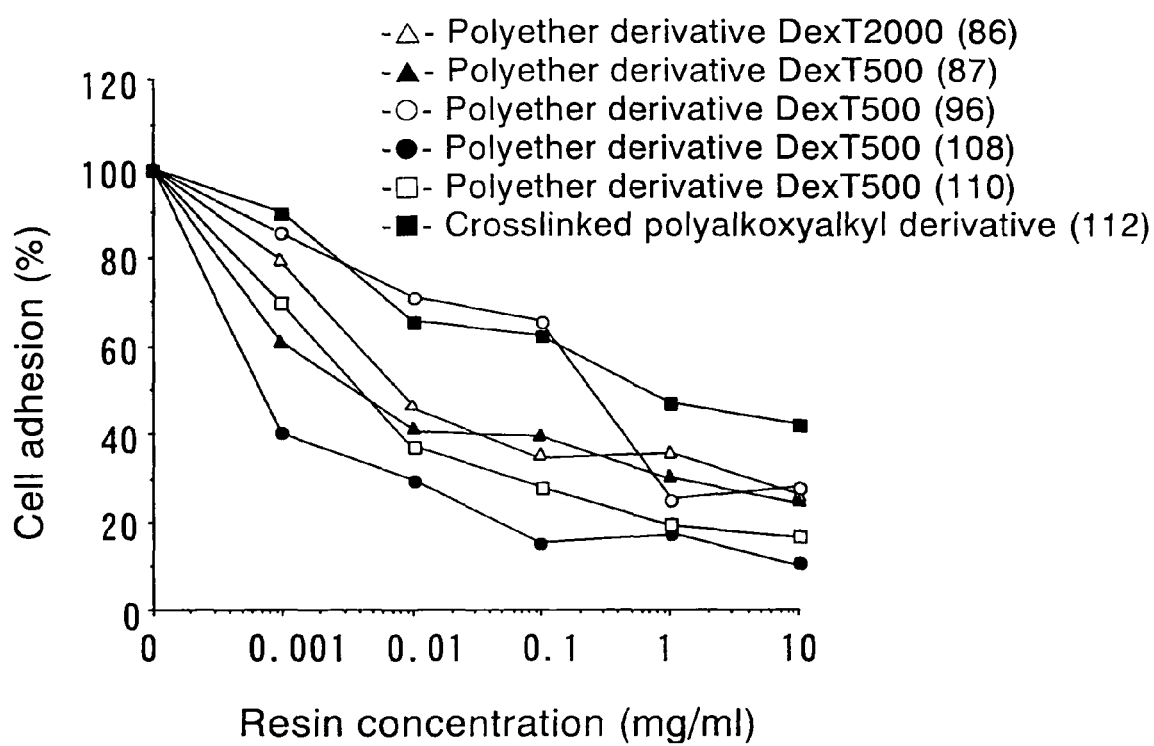
FIG. 29 is a graph showing the results of the evaluation of HEK293 cell (human fetal renal cell) adhesion to various resins, which evaluation is made in Example 84.

The results are shown in FIG. 29. In FIG. 29, the cell adhesion to each resin-coated well is expressed in terms of the percentage of the number of cells adhered to the resin-coated well, based on the number of cells adhered to the non-coated well. As shown in FIG. 29, polyether derivatives (86), (87), (96), (108) and (110) and crosslinked polyalkoxyalkyl derivative (112) inhibit the adhesion of HEK293 cells, and the degree of inhibition is proportional to the resin concentration of the resin solution. Among the resins evaluated, polyether derivative (108) was most effective for inhibiting cell adhesion, and polyether derivative (110) was the second effective resin. Polyether derivatives (86) and (87) were the third effective resins.

Example 85

Evaluation (1) of Blood Compatibility (Anti-Protein Adhesion Property) of a Resin Polyether derivative DexT500 (87) produced in Example 31, polyether derivative DexT500 (96) produced in Example 40, polyether derivative DexT500 (108) produced in Example 52 and polyether derivative DexT500 (110) produced in Example 54 and crosslinked polyalkoxyalkyl derivative (112) produced (using polyether derivative DexT500 (87)) in Example 56 were individually evaluated in the following manner. Resin solutions respectively having resin concentrations of 10, 1, 0.1, 0.01 and 0.001 mg/ml were prepared by dissolving different amounts of a resin individually in an aqueous 50% ethanol solution. 0.1 ml of each of the obtained resin solutions was individually dispensed into a well of Coaster 96-well EIA plate (Product No. 3590, manufactured and sold by Corning Incorporated, U.S.A.). On the other hand, an aqueous 50% ethanol solution was dispensed into another well of the EIA plate to thereby provide a well containing an aqueous 50% ethanol solution (wherein the well was intended to provide the below-mentioned "non-coated well" used as a control well). Then, the EIA plate was allowed to stand still at 4° C. overnight to thereby cause the wells (containing the resin solutions) to be coated with the resin. Subsequently, the resin solutions and aqueous 50% ethanol solution in the wells were removed, followed by washing, to thereby obtain an EIA plate having resin-coated wells and a non-coated well (wherein the latter was intended for use as a control well). Adhesion of immunoglobulin G to the resin-coated wells was evaluated as follows.

0.1 ml of an immunoglobulin G solution containing 5 µg/ml of a purified human immunoglobulin G (IgG) (manufactured and sold by MP Biomedicals, U.S.A.) was dispensed into the resin-coated wells and non-coated well of the above-obtained EIA plate, and was allowed to remain in contact with the surfaces of the wells at 37° C. for 2 hours. Subsequently, the amounts of human IgG adhered to the surfaces of the wells were determined by enzyme-linked immunosorbent assay (ELISA) using a horseradish peroxidase (HRP)-conjugated goat IgG fraction to human IgG (whole molecule) (manufactured and sold by MP Biomedicals, U.S.A.).

Figure 30:
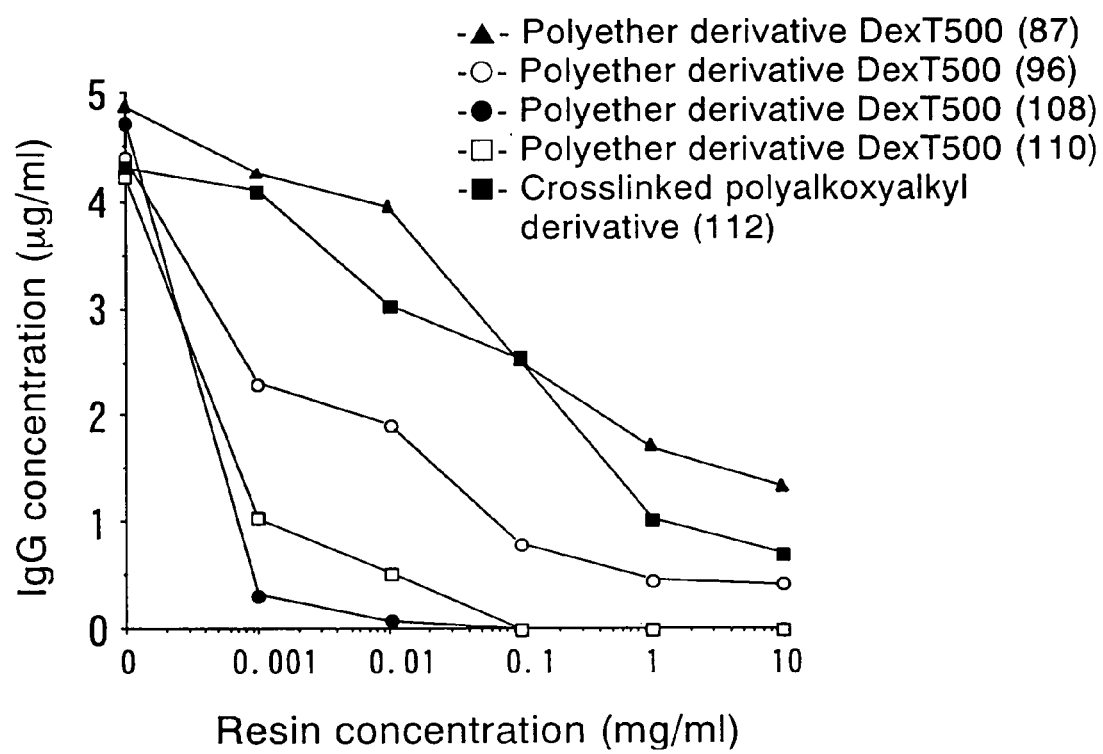
FIG. 30 is a graph showing the results of the evaluation of human immunoglobulin adhesion to various resins, which evaluation is made in Example 85.

The results are shown in FIG. 30. The determination of the amounts of IgG adhered to the wells of the EIA plate was performed using a calibration curve prepared by a method in which IgG standard solutions having known IgG concentrations are dispensed into wells of an EIA plate which is the same as used above, and the amounts of IgG adhered to the surfaces of the wells are measured.

As mentioned above, the resins evaluated were polyether derivative DexT500 (87) produced in Example 31, polyether derivative DexT500 (96) produced in Example 40, polyether derivative DexT500 (108) produced in Example 52 and polyether derivative DexT500 (110) produced in Example 54 and crosslinked polyalkoxyalkyl derivative (112) produced in Example 56. FIG. 30 shows that the amount of IgG adhered to the non-coated well was approximately 5 µg/ml. The evaluated resins inhibit IgG adhesion to the wells of the EIA plate, and the degree of inhibition is proportional to the resin concentration of the resin solution. Among the resins evaluated, polyether derivative DexT500 (108) was most effective for inhibiting IgG adhesion, and polyether derivative DexT500 (110) was second effective. Polyether derivative DexT500 (96) was third effective, and polyether derivative DexT500 (87) was least effective.

Example 86

Evaluation (2) of Blood Compatibility (Anti-Protein Adhesion Property) of a Resin Polyether derivative DexT500 (87) produced in Example 31, polyether derivative DexT500 (98) produced in Example 42, polyether derivative DexT500 (108) produced in Example 52, polyether derivative DexT2000 (109) produced in Example 53 and crosslinked polyalkoxyalkyl derivative (112) produced (using polyether derivative DexT500 (87)) in Example 56 were individually evaluated in the following manner. Resin solutions respectively having resin concentrations of 10, 1, 0.1, 0.01 and 0.001 mg/ml were prepared by dissolving different amounts of a resin individually in an aqueous 50% ethanol solution. 0.1 ml of each of the obtained resin solutions was individually dispensed into a well of Coaster 96-well EIA plate (Product No. 3590, manufactured and sold by Corning Incorporated, U.S.A.). On the other hand, an aqueous 50% ethanol solution was dispensed into another well of the EIA plate to thereby provide a well containing an aqueous 50% ethanol solution (wherein the well was intended to provide the below-mentioned "non-coated well" used as a control well). Then, the EIA plate was allowed to stand still at 4° C. overnight to thereby cause the wells (containing the resin solutions) to be coated with the resin. Subsequently, the resin solutions and aqueous 50% ethanol solution in the wells were removed, followed by washing, to thereby obtain an EIA plate having resin-coated wells and a non-coated well (wherein the latter was intended for use as a control well). Adhesion of fibronectin to the resin-coated wells was evaluated as follows.

0.1 ml of a fibronectin solution containing 5 µg/ml of a human fibronectin (manufactured and sold by CHEMICON International, Inc., U.S.A.) was dispensed into the resin-coated wells and non-coated well of the above-obtained EIA plate, and was allowed to remain in contact with the surfaces of the wells at 37° C. for 2 hours. Subsequently, the amounts of human fibronectin adhered to the surfaces of the wells were determined by ELISA using a horseradish peroxidase (HRP)-conjugated goat IgG fraction to human fibronectin (manufactured and sold by MP Biomedicals, U.S.A.).

Figure 31:
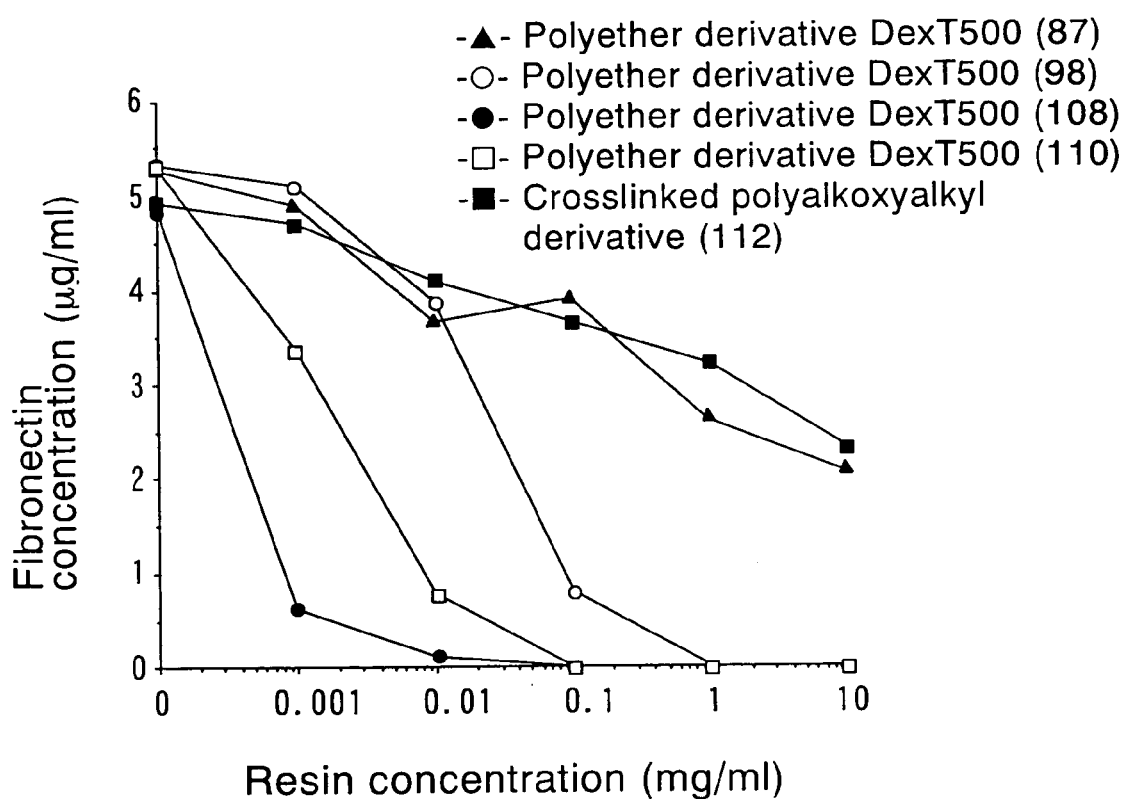
FIG. 31 is a graph showing the results of the evaluation of human fibronectin adhesion to various resins, which evaluation is made in Example 86.

The results are shown in FIG. 31. The determination of the amounts of fibronectin adhered to the wells of the EIA plate was performed using a calibration curve prepared by a method in which fibronectin standard solutions having known fibronectin concentrations are dispensed into wells of an EIA plate which is the same as used above, and the amounts of fibronectin adhered to the surfaces of the wells are measured.

As mentioned above, the resins evaluated were polyether derivative DexT500 (87) produced in Example 31, polyether derivative DexT500 (98) produced in Example 42, polyether derivative DexT500 (108) produced in Example 52, polyether derivative DexT2000 (109) produced in Example 53 and crosslinked polyalkoxyalkyl derivative (112) produced in Example 56. FIG. 31 shows that the amount of fibronectin adhered to the non-coated well was approximately 5 µg/ml. The evaluated resins inhibit fibronectin adhesion to the wells of the EIA plate, and the degree of inhibition is proportional to the resin concentration of the resin solution. Among the resins evaluated, polyether derivative DexT500 (108) was most effective for inhibiting fibronectin adhesion, and polyether derivative DexT2000 (109) was second effective. Polyether derivative DexT500 (98) was third effective and polyether derivative DexT500 (87) was least effective.

Example 87

Evaluation (3) of Blood Compatibility (Anti-Protein Adhesion Property) of a Resin Polyether derivative DexT500 (87) produced in Example 31, polyether derivative DexT500 (108) produced in Example 52, polyether derivative DexT500 (110) produced in Example 54 and crosslinked polyalkoxyalkyl derivative (112) produced (using polyether derivative DexT500 (87)) in Example 56 were individually evaluated in the following manner. Resin solutions respectively having resin concentrations of 10, 1, 0.1, 0.01 and 0.001 mg/ml were prepared by dissolving different amounts of a resin individually in an aqueous 50% ethanol solution. 0.1 ml of each of the obtained resin solutions was individually dispensed into a well of Coaster 96-well EIA plate (Product No. 3590, manufactured and sold by Corning Incorporated, U.S.A.). On the other hand, an aqueous 50% ethanol solution was dispensed into another well of the EIA plate to thereby provide a well containing an aqueous 50% ethanol solution (wherein the well was intended to provide the below-mentioned "non-coated well" used as a control well). Then, the EIA plate was allowed to stand still at 4° C. overnight to thereby cause the wells (containing the resin solutions) to be coated with the resin. Subsequently, the resin solutions and aqueous 50% ethanol solution in the wells were removed, followed by washing, to thereby obtain an EIA plate having resin-coated wells and a non-coated well (wherein the latter was intended for use as a control well). Adhesion of fibrinogen to the resin-coated wells was evaluated as follows.

0.1 ml of a fibrinogen solution containing 5 µg/ml of a purified human fibrinogen (manufactured and sold by Biogenesis Inc., U.S.A.) was dispensed into the resin-coated wells and non-coated well of the above-obtained EIA plate, and was allowed to remain in contact with the surfaces of the wells at 37° C. for 2 hours. Subsequently, the amounts of human fibrinogen adhered to the surfaces of the wells were determined by ELISA using a horseradish peroxidase (HRP)-conjugated goat IgG to human fibrinogen (manufactured and sold by EY Laboratories, Inc., U.S.A.).

Figure 32:
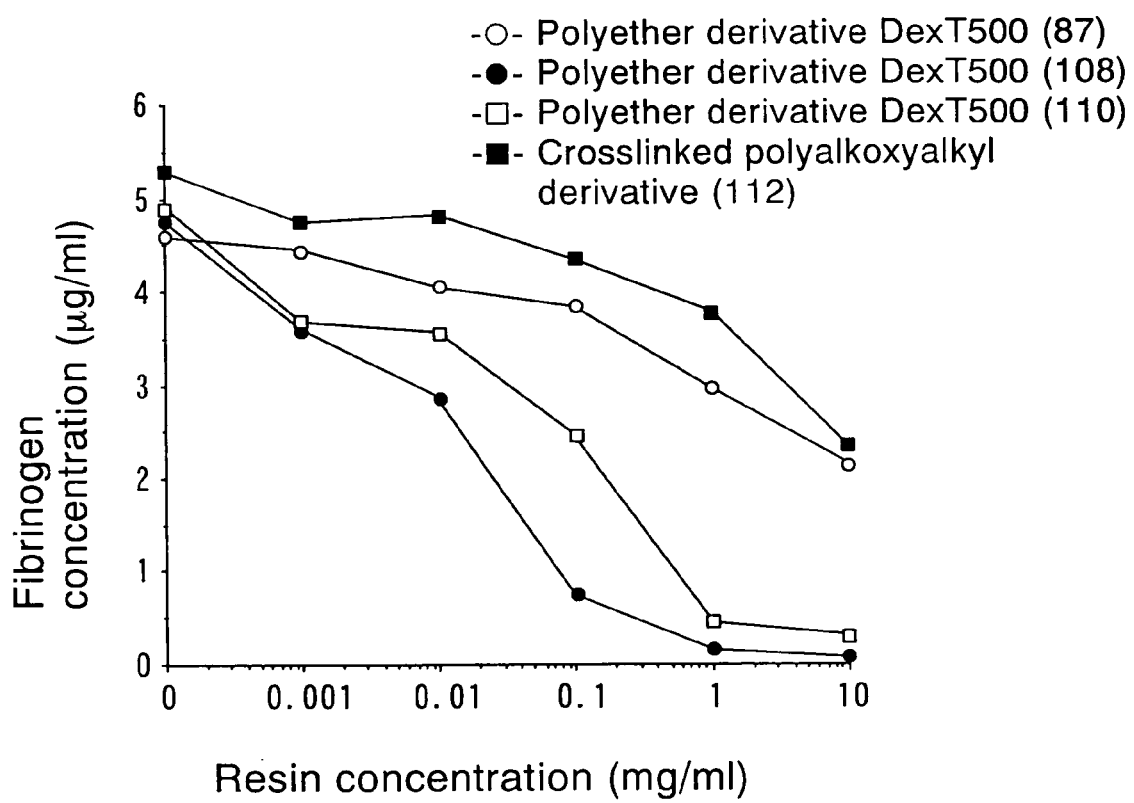
FIG. 32 is a graph showing the results of the evaluation of human fibrinogen adhesion to various resins, which evaluation is made in Example 87.

The results are shown in FIG. 32. The determination of the amounts of fibrinogen adhered to the wells of the EIA plate was performed using a calibration curve prepared by a method in which fibrinogen standard solutions having known fibrinogen concentrations are dispensed into wells of an EIA plate which is the same as used above, and the amounts of fibrinogen adhered to the surfaces of the wells are measured.

As mentioned above, the resins evaluated were polyether derivative DexT500 (87) produced in Example 31, polyether derivative DexT500 (108) produced in Example 52, polyether derivative DexT500 (110) produced in Example 54 and crosslinked polyalkoxyalkyl derivative (112) produced in Example 56. FIG. 32 shows that the amount of fibrinogen adhered to the non-coated well was approximately 5 µg/ml. The evaluated resins inhibit fibrinogen adhesion to the wells of the EIA plate, and the degree of inhibition is proportional to the resin concentration of the resin solution. Among the resins evaluated, polyether derivative DexT500 (108) was most effective for inhibiting fibrinogen adhesion, and polyether derivative DexT500 (110) was second effective. Polyether derivative DexT500 (87) was least effective.

Example 88

Evaluation of Blood Compatibility (Anti-Protein Adhesion Property) of a Resin

Polyether derivative DexT500 (87) produced in Example 31, polyether derivative DexT500 (96) produced in Example 40, polyether derivative DexT500 (108) produced in Example 52, polyether derivative DexT500 (110) produced in Example 54 and crosslinked polyalkoxyalkyl derivative (112) produced (using polyether derivative DexT500 (87)) in Example 56 were individually evaluated in the following manner. Resin solutions respectively having resin concentrations of 10, 1, 0.1 and 0.01 mg/ml were prepared by dissolving different amounts of a resin individually in an aqueous 50% ethanol solution. A polyethylene terephthalate (PET) film (thickness: 60 µm) was immersed in the obtained resin solution to cause the film to be coated with the resin, thereby obtaining a test sample. Adhesion of immunoglobulin G to the thus obtained test samples was evaluated as follows.

The test sample was placed in a well of a 24-well cell culture plate and washed, then, an immunoglobulin G solution containing 5 μg/ml of a purified human immunoglobulin G (IgG) (manufactured and sold by MP Biomedicals, U.S.A.) was added to the well containing the test sample, and was allowed to remain in contact with the test sample at 37° C. for 2 hours.

Subsequently, the amounts of human IgG adhered to the surfaces of the test sample were determined by ELISA using a horseradish peroxidase (HRP)-conjugated goat IgG fraction to human IgG (whole molecule) (manufactured and sold by MP Biomedicals, U.S.A.).

Figure 33:
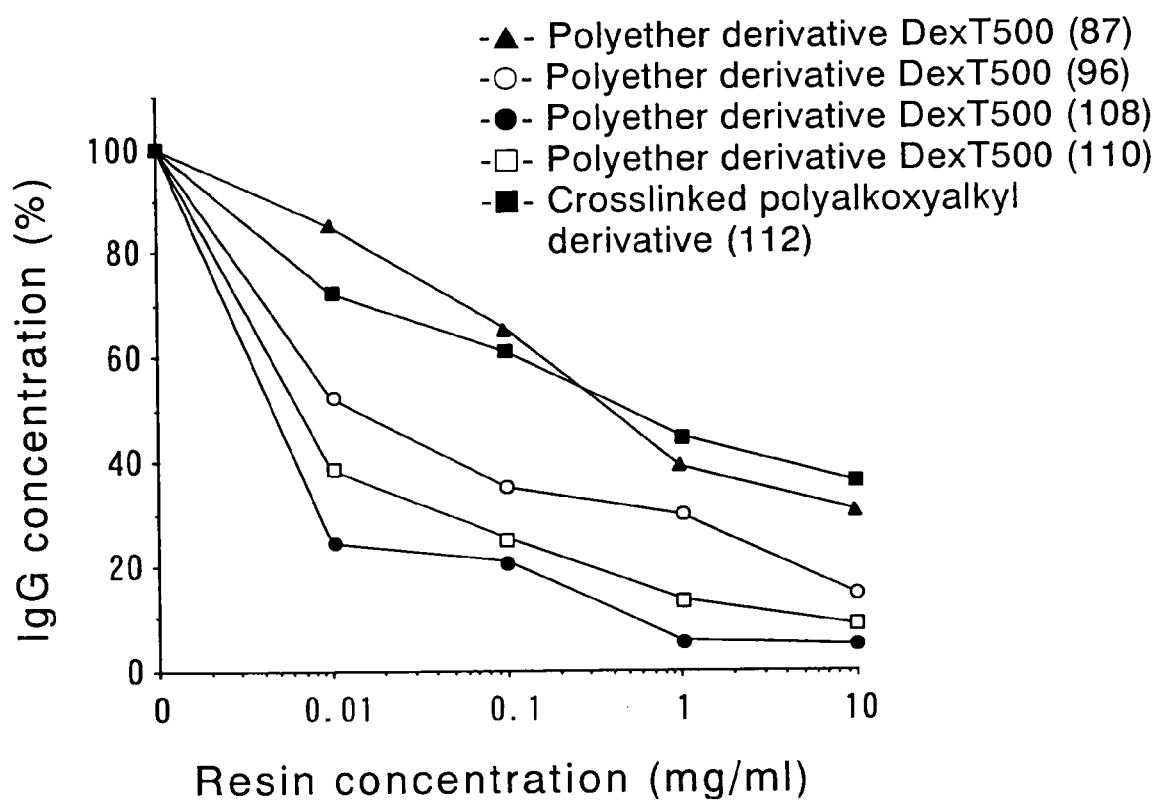
FIG. 33 is a graph showing the results of the evaluation of human immunoglobulin adhesion to PET films, which evaluation is made in Example 88.

The results are shown in FIG. 33. As mentioned above, the resins evaluated were polyether derivative DexT500 (87) produced in Example 31, polyether derivative DexT500 (96) produced in Example 40, polyether derivative DexT500 (108) produced in Example 52, polyether derivative DexT500 (110) produced in Example 54 and crosslinked polyalkoxyalkyl derivative (112). The evaluated resins inhibit IgG adhesion to the PET film, and the degree of inhibition is proportional to the resin concentration of the resin solution. As apparent from FIG. 33, among the resins evaluated, polyether derivative DexT500 (108) was most effective for inhibiting IgG adhesion, and polyether derivative DexT500 (110) was second effective. Polyether derivative DexT500 (96) was third effective, crosslinked polyalkoxyalkyl derivative (112) was fourth effective, and polyether derivative DexT500 (87) was least effective.

Example 89

Evaluation of Toxicity: Experiment for Determining the Toxicity of a Polyether Derivative by Intravenous Injection to Mouse Five groups of female BALB/c mice, each consisting of five mice, were, respectively, given administration of polyether derivative DexT2000 (86) produced in Example 30, polyether derivative DexT500 (87) produced in Example 31, polyether derivative Pullulan T1600 (88) produced in Example 32, polyether derivative DexT500 (108) produced in Example 52 and polyether derivative DexT500 (110) produced in Example 54. Specifically, each mouse received administration of a polyether derivative solution (in physiological saline) by tail-vein injection under conditions wherein the dose of the polyether derivative was 2 g/kg and the volume of the polyether derivative solution administered was 25 ml/kg. The administration was performed intermittently once a week on days 2, 9 and 16 from the start of the experiment (i.e., 3 administrations in total). Separately, two groups of female BALB/c mice, each consisting of five mice, were provided. Each mouse of one group of the two groups received the administration of dextran T110 solution (in physiological saline) wherein dextran T110 solution was administered under the same conditions as in the above-mentioned administration of the polyether derivative solution, to thereby obtain a control group of mice. The other group of the two groups of mice received the administration of only physiological saline wherein the physiological saline was administered in the same manner as in the above-mentioned administration of the polyether derivative solution.

Evaluation was made on the toxicity of each polyether derivative in terms of the loss in the average body weight, based on the average initial body weight (i.e., the average body weight of the mice on day 1). A polyether derivative was defined as being toxic when the loss in the average body weight was 10% or more of the average initial body weight.

Figure 34:
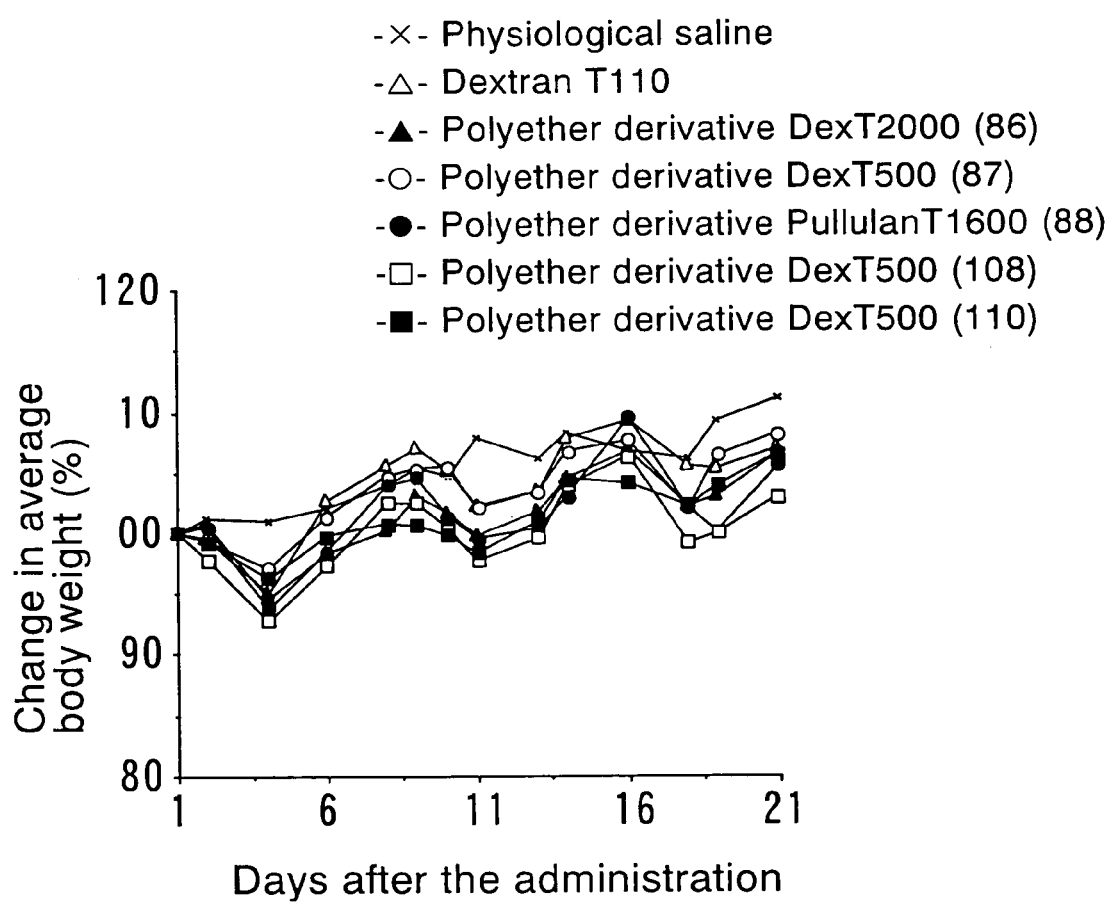
FIG. 34 is a graph showing the results of the evaluation of toxicity of the resin of the present invention, which evaluation is made in Example 89.

The results are shown in FIG. 34. With respect to the groups which received the administration of the polyether derivative solutions, some loss in the average body weight was observed after receiving the administration of the polyether derivative solutions, but this loss in the average body weight was not more than 10% of the initial average body weight. Further, few days after the administration of the polyether derivative solutions, the mice regained their weights to a level which was comparable to the average body weight of the group which had received administration of only physiological saline. Accordingly, all of polyether derivative DexT2000 (86), polyether derivative DexT500 (87), polyether derivative Pullulan T1600 (88), polyether derivative DexT500 (108) and polyether derivative DexT500 (110) were found to have no toxicity.

Example 90

Evaluation of Anti-Tissue Adhesion Property of a Resin

The anti-tissue adhesion property of gel sheet (123) prepared in Example 66 and gel sheet (124) prepared in Example 67, was evaluated in the following manner.

Twenty-one female rats (Crj-CD(SD), 8 weeks old, purchased from Charles River Japan Inc., Japan) were divided into three groups, each consisting of seven rats. Each of two groups of rats was subjected to pentobarbital anesthesia, and an incision was made along the median line of the abdomen, whereupon the cecum was taken out from the abdominal cavity of the rat. The surface of the cecum was scratched with a gauze to remove about half of the serous membrane from the cecum, thus injuring the cecum. A gel sheet (size: 2×2 cm) was applied to the serous membrane-removed, injured portion of the cecum to cover the injury, and the thus treated, injured cecum was returned to the abdominal cavity of the rat, followed by suturing of the incision. By such procedure, the two groups of rats were caused to have injured ceca and, respectively, treated using the gel sheets (123) and (124), thereby obtaining polymer-treated groups of rats. Separately, with respect to the other group of 7 rats, the same procedure as described above was repeated except that the application of a gel sheet was not performed and the injured cecum as such was returned to the abdominal cavity of each rat, to thereby obtain a non-treated group of rats as a control group. After a period of five days from the surgical operation, the rats of the three groups were subjected to surgical anatomy to determine whether or not tissue adhesion was present. The tissue adhesion was defined as an interfacial, fibrous adhesion which has a certain thickness and which binds together adjacent surfaces with such a strength that they cannot be easily separated from each other even when they are pulled in opposite directions using a forceps. The results are shown in Table 14 below.

TABLE 14

| | Resin (123) | Resin (124) | Control (no treatment) |
|---|---|---|---|
| Tissue condition | No disorder | No disorder | Slight inflammation |

TABLE 14-continued

|  | Resin (123) | Resin (124) | Control (no treatment) |
|---|---|---|---|
| Ratio of mice having tissue adhesion | 2/7 | 1/7 | 6/7 |

As shown in Table 14, the ratio of mice having tissue adhesion was low in the 2 groups of rats which were, respectively, treated with the gel sheets (123) and (124), as compared to the case of the group of non-treated rats.

Example 91

Evaluation of Wound Healing Promoting Effect of a Resin

The wound healing promoting effect of gel sheet (123) prepared in Example 66 and gel sheet (124) prepared in Example 67, was evaluated in the following manner.

Fifteen female rats (Crj-CD(SD), 7 weeks old, purchased from Charles River Japan Inc., Japan) were divided into three groups, each consisting of five rats. The fur of the dorsal region of each rat of the three groups was shaved, and the rats were subjected to pentobarbital anesthesia. A part of the dorsal skin of each rat was removed so as to form a circular wound (diameter: 2 cm) with complete skin loss. Gel sheets (123) and (124) were, respectively, used to treat two groups of wounded rats, thereby obtaining two groups of polymer-treated rats. Specifically, the wound of each rat of two groups was covered with a gel sheet (size: 2 cm×2 cm) and, then, the gel sheet was covered with a medical gauze of a non-woven fabric. The medical gauze was secured in place using an adhesive bandage, followed by taping. Separately, with respect to the other group of five rats, the same procedure as described above was repeated except that a gel sheet was not used (i.e., the wound was covered only with a medical gauze, which was secured in place using an adhesive bandage, followed by taping), to thereby obtain a non-treated group of rats. On days 0, 3, 5 and 7 from the surgical operation, measurement was made of the size (area) of the wounds of the mice of the three groups, and the level of wound healing was determined in terms of the average wound area remaining ratio (%), namely the ratio of the average wound area on a day on which the size of the wound was measured to the average wound area on day 0. Specifically, the wound area remaining ratio (%) was obtained according to the following formula:

Wound area remaining ratio (%)={(product of the major and minor diameters of the wound on a day on which the size of the wound was measured)/(product of the major and minor diameters of the wound on day 0)}×100.

The results are shown in Table 15 below.

TABLE 15

| Experimental Group | Average wound area remaining ratio (%) | | | |
|---|---|---|---|---|
| | Day 0 | Day 3 | Day 5 | Day 7 |
| Resin (123) | 100 | 82 | 71 | 62 |
| Resin (124) | 100 | 85 | 69 | 64 |

TABLE 15-continued

| Experimental Group | Average wound area remaining ratio (%) | | | |
|---|---|---|---|---|
| | Day 0 | Day 3 | Day 5 | Day 7 |
| No treatment with resin | 100 | 93 | 89 | 80 |

Table 15 shows that the resins of the present invention in the form of gel sheets were able to promote the wound healing of rats.

Example 92

Evaluation of Wound Healing Promoting Effect of a Resin

The wound healing promoting effect of gel sheet (123) prepared in Example 66 and gel sheet (124) prepared in Example 67, was evaluated in the following manner.

Fifteen female rats (Crj-CD(SD), 7 weeks old, purchased from Charles River Japan Inc., Japan) were divided into three groups, each consisting of five rats. The fur of the dorsal region of each rat of the three groups was shaved, and the rats were subjected to pentobarbital anesthesia. A copper rod (diameter: 1.5 cm) was chilled in liquid nitrogen and the chilled copper rod was pressed against the shaved dorsal region of each rat to thereby form a frostbite wound. Gel sheets (123) and (124) were, respectively, used to treat two groups of wounded rats, thereby obtaining two groups of polymer-treated rats. Specifically, the frostbite wound of each rat of two groups was covered with a gel sheet (2 cm×2 cm) and, then, the gel sheet was covered with a medical gauze of a non-woven fabric. The medical gauze was secured in place using an adhesive bandage, followed by taping. Separately, with respect to the other group of five rats, the same procedure as described above was repeated except that a gel sheet was not used (i.e., the frostbite wound was covered only with a medical gauze, which was secured in place using an adhesive bandage, followed by taping), to thereby obtain a non-treated group of rats. On days 0, 3, 5 and 7 from the surgical operation, measurement was made of the size (area) of the frostbite wounds of the mice of the three groups, and the level of wound healing was determined in terms of the average wound area remaining ratio (%), namely the ratio of the average wound area on a day on which the size of the frostbite wound was measured to the average wound area on day 0. Specifically, the wound area remaining ratio (%) was obtained according to the following formula:

Wound area remaining ratio (%)={(product of the major and minor diameters of the frostbite wound on a day on which the size of the frostbite wound was measured)/(product of the major and minor diameters of the frostbite wound on day 0)}×100.

The results are shown in Table 16 below.

TABLE 16

| Experimental Group | Average wound area remaining ratio (%) | | | |
|---|---|---|---|---|
| | Day 0 | Day 3 | Day 5 | Day 7 |
| Resin (123) | 100 | 75 | 71 | 58 |
| Resin (124) | 100 | 79 | 66 | 57 |

TABLE 16-continued

| Experimental Group | Average wound area remaining ratio (%) | | | |
|---|---|---|---|---|
| | Day 0 | Day 3 | Day 5 | Day 7 |
| No treatment with resin | 100 | 93 | 83 | 75 |

Table 16 shows that the resins of the present invention in the form of gel sheets were able to promote the wound healing of rats.

Example 93

14.2 ml of n-butyl glycidyl ether, 41.3 ml of ethylene oxide, 4.6 ml of 1 M triisobutyl aluminum in hexane, 0.5 ml of 1 M potassium 2-methyl-2-butoxide in tetrahydrofuran (THF) and 150 ml of hexane as a solvent were charged into a pressure reaction vessel under an argon atmosphere, followed by a reaction at 25° C. for 24 hours. After completion of the reaction, the solvents were removed from the reaction mixture, thereby obtaining 39 g of the desired copolymer (125) which was a white solid. The weight average molecular weight of the obtained copolymer was 41,000 as determined by GPC.

Copolymer (125) was subjected to a $^1$H-NMR analysis using tetramethylsilane (TMS) as a reference standard and deuterated methanol (CD$_3$OD) as a solvent. The resultant NMR spectrum showed that multiplet peaks ascribed to an n-butyl group appeared at δ 0.94 ppm, δ 1.39 ppm and δ 1.54 ppm, and that a peak ascribed mainly to polyethylene glycol appeared at δ 3.40-3.90 ppm. Further, the amount of n-butyl group introduced into the copolymer was determined by $^1$H-NMR analysis. The amount of the introduced n-butyl group was 4.5 mol %, based on the total molar amount of recurring units.

Example 94

14.2 ml of n-butyl glycidyl ether, 41.3 ml of ethylene oxide, 4.5 ml of 1 M triisobutyl aluminum in hexane, 0.5 ml of 1 M potassium t-butoxide in tetrahydrofuran (THF) and 200 ml of hexane as a solvent were charged into a pressure reaction vessel under an argon atmosphere, followed by a reaction at 25° C. for 20 hours. After completion of the reaction, the solvents were removed from the reaction mixture, thereby obtaining 46 g of the desired copolymer (126) which was a white solid. The weight average molecular weight of the obtained copolymer was 67,000 as determined by GPC.

Copolymer (126) was subjected to a $^1$H-NMR analysis using tetramethylsilane (TMS) as a reference standard and deuterated methanol (CD$_3$OD) as a solvent. The resultant NMR spectrum showed that multiplet peaks ascribed to an n-butyl group appeared at δ 0.94 ppm, δ 1.39 ppm and δ 1.54 ppm, and that a peak ascribed mainly to polyethylene glycol appeared at δ 3.39-3.90 ppm. Further, the amount of n-butyl group introduced into the copolymer was determined by $^1$H-NMR analysis. The amount of the introduced n-butyl group was 2.8 mol %, based on the total molar amount of recurring units (the above-mentioned amount of n-butyl group introduced into the copolymer is hereinafter referred to simply as "n-butyl group introduction ratio").

Substantially the same procedure as in the production of copolymer (126) above was repeated except that the amounts of n-butyl glycidyl ether and ethylene oxide were changed as shown in Table 17 below, thereby obtaining copolymers (127) and (128). The n-butyl group introduction ratio of each of copolymers (127) and (128) was determined by $^1$H-NMR analysis. The results are also shown in Table 17 below.

TABLE 17

| | Copolymer (127) | Copolymer (128) |
|---|---|---|
| n-butyl glycidyl ether (ml) | 14.5 | 14.5 |
| Ethylene oxide (ml) | 37.5 | 34.0 |
| 1 M triisobutyl aluminum in hexane (ml) | 4.2 | 3.5 |
| 1 M potassium t-butoxide in THF (ml) | 0.4 | 0.4 |
| Amount of product (g) | 36.0 | 32.0 |
| n-butyl group introduction ratio (mol %) | 9.4 | 4.8 |
| Mw as determined by GPC | 17,000 | 20,000 |

Example 95

14.2 ml of n-butyl glycidyl ether, 41.3 ml of ethylene oxide, 5.0 ml of 1 M triisobutyl aluminum in hexane, and 500 ml of hexane as a solvent were charged into a pressure reaction vessel under an argon atmosphere, followed by a reaction at 25° C. for 20 hours. After completion of the reaction, the solvents were distilled off from the reaction mixture under reduced pressure, thereby obtaining 41 g of the desired copolymer (129) which was a white solid. The weight average molecular weight of the obtained copolymer was 34,000 as determined by GPC.

Copolymer (129) was subjected to a $^1$H-NMR analysis using tetramethylsilane (TMS) as a reference standard and deuterated methanol (CD$_3$OD) as a solvent. The resultant NMR spectrum showed that multiplet peaks ascribed to an n-butyl group appeared at δ 0.94 ppm, δ 1.40 ppm and δ 1.55 ppm, and that a peak ascribed mainly to polyethylene glycol appeared at δ 3.44-3.89 ppm. Further, the amount of n-butyl group introduced into the copolymer was determined by $^1$H-NMR analysis. The amount of the introduced n-butyl group was 6.3 mol %, based on the total molar amount of recurring units (the above-mentioned amount of n-butyl group introduced into the copolymer is hereinafter referred to simply as "n-butyl group introduction ratio").

Substantially the same procedure as in the production of copolymer (129) above was repeated except that the amounts of n-butyl glycidyl ether and ethylene oxide were changed as shown in Table 18 below, thereby obtaining copolymers (130) and (131). The n-butyl group introduction ratio of each of copolymers (130) and (131) was determined by $^1$H-NMR analysis. The results are also shown in Table 18 below.

TABLE 18

| | Copolymer (130) | Copolymer (131) |
|---|---|---|
| n-butyl glycidyl ether (ml) | 14.5 | 14.5 |
| Ethylene oxide (ml) | 82.4 | 61.7 |
| 1 M triisobutyl aluminum in hexane (ml) | 5.0 | 5.0 |
| Amount of product (g) | 48.0 | 47.0 |
| n-butyl group introduction ratio (mol %) | 4.6 | 5.1 |
| Mw as determined by GPC | 21,000 | 24,000 |

Example 96

15 ml of n-butyl glycidyl ether, 90 ml of ethylene oxide, 0.7 ml of 1 M potassium t-butoxide in tetrahydrofuran (THF) and 200 ml of diethylene glycol diethyl ether as a solvent were charged into a pressure reaction vessel under an argon atmosphere, followed by a reaction at 80° C. for 24 hours. After completion of the reaction, the solvents were distilled off from the reaction mixture under reduced pressure, thereby obtaining 50.3 g of the desired copolymer (132) which was a white solid. The weight average molecular weight of the obtained copolymer was 47,000 as determined by GPC.

Copolymer (132) was subjected to a $^1$H-NMR analysis using tetramethylsilane (TMS) as a reference standard and deuterated methanol (CD$_3$OD) as a solvent. The resultant NMR spectrum showed that multiplet peaks ascribed to an n-butyl group appeared at δ 0.94 ppm, δ 1.40 ppm and δ 1.55 ppm, and that a peak ascribed mainly to polyethylene glycol appeared at δ 3.40-3.82 ppm. Further, the amount of n-butyl group introduced into the copolymer was determined by $^1$H-NMR analysis. The amount of the introduced n-butyl group was 5.7 mol %, based on the total molar amount of recurring units (the above-mentioned amount of n-butyl group introduced into the copolymer is hereinafter referred to simply as "n-butyl group introduction ratio").

Substantially the same procedure as in the production of copolymer (132) above was repeated except that the amounts of n-butyl glycidyl ether and ethylene oxide were changed as shown in Table 19 below, thereby obtaining copolymers (133) and (134). The n-butyl group introduction ratio of each of copolymers (133) and (134) was determined by $^1$H-NMR analysis. The results are also shown in Table 19 below.

TABLE 19

|  | Copolymer (133) | Copolymer (134) |
|---|---|---|
| n-butyl glycidyl ether (ml) | 16 | 16 |
| Ethylene oxide (ml) | 14.4 | 45 |
| 1 M potassium t-butoxide in THF (ml) | 0.7 | 0.7 |
| Amount of product (g) | 22.0 | 46.7 |
| n-butyl group introduction ratio (mol %) | 33.3 | 10.5 |
| Mw as determined by GPC | 35,000 | 40,000 |

Example 97

15 ml of glycidyl phenyl ether, 90 ml of ethylene oxide, 0.7 ml of 1 M potassium t-butoxide in tetrahydrofuran (THF) and 200 ml of ethylene glycol dimethyl ether as a solvent were charged into a pressure reaction vessel under an argon atmosphere, followed by a reaction at 90° C. for 24 hours. After completion of the reaction, the solvents were distilled off from the reaction mixture under reduced pressure, thereby obtaining 86.2 g of the desired copolymer (135) which was a white solid. The weight average molecular weight of the obtained copolymer was 120,000 as determined by GPC.

Copolymer (135) was subjected to a $^1$H-NMR analysis using tetramethylsilane (TMS) as a reference standard and deuterated methanol (CD$_3$OD) as a solvent. The resultant NMR spectrum showed that multiplet peaks ascribed to a phenyl group appeared at δ 6.78-6.96 ppm and δ 7.12-7.29 ppm, and that a peak ascribed mainly to polyethylene glycol appeared at δ 3.40-4.15 ppm. Further, the amount of phenyl group introduced into the copolymer was determined by $^1$H-NMR analysis. The amount of the introduced phenyl group was 6.4 mol %, based on the total molar amount of recurring units (the above-mentioned amount of phenyl group introduced into the copolymer is hereinafter referred to simply as "phenyl group introduction ratio").

Substantially the same procedure as in the production of copolymer (135) above was repeated except that the amounts of glycidyl phenyl ether and ethylene oxide were changed as shown in Table 20 below, thereby obtaining copolymers (136) and (137). The phenyl group introduction ratio of each of copolymers (136) and (137) was determined by $^1$H-NMR analysis. The results are also shown in Table 20 below.

TABLE 20

|  | Copolymer (136) | Copolymer (137) |
|---|---|---|
| Glycidyl phenyl ether (ml) | 15 | 15 |
| Ethylene oxide (ml) | 40 | 60 |
| 1 M potassium t-butoxide in THF (ml) | 0.7 | 0.7 |
| Amount of product (g) | 46.7 | 59.0 |
| Phenyl group introduction ratio (mol %) | 10.9 | 7.6 |
| Mw as determined by GPC | 90,000 | 100,000 |

Example 98

11.4 ml of n-butyl glycidyl ether, 1.8 ml of glycidyl methyl ether, 41.3 ml of ethylene oxide, 4.6 ml of 1 M triisobutyl aluminum in hexane, 0.5 ml of 1 M potassium 2-methyl-2-butoxide in tetrahydrofuran (THF) and 150 ml of hexane as a solvent were charged into a pressure reaction vessel under an argon atmosphere, followed by a reaction at 25° C. for 20 hours. After completion of the reaction, the solvents were distilled off from the reaction mixture under reduced pressure, thereby obtaining 31 g of the desired copolymer (138) which was a white solid. The weight average molecular weight of the obtained copolymer was 33,000 as determined by GPC.

Copolymer (138) was subjected to a $^1$H-NMR analysis using tetramethylsilane (TMS) as a reference standard and deuterated methanol (CD$_3$OD) as a solvent. The resultant NMR spectrum showed that multiplet peaks ascribed to an n-butyl group appeared at δ 0.94 ppm, δ 1.39 ppm and δ 1.54 ppm, and that a peak ascribed to a methoxy group and a peak ascribed mainly to polyethylene glycol respectively appeared at δ 3.30 ppm and δ 3.40-3.90 ppm. Further, the amounts of n-butyl group and methoxy group introduced into the copolymer were determined by $^1$H-NMR analysis. The amount of the introduced n-butyl group was 3.3 mol % and the amount of the introduced methoxy group was 0.8 mol %, both based on the total molar amount of recurring units.

Example 99

14.2 ml (100 mmol) of n-butyl glycidyl ether, 41.3 ml (826 mmol) of ethylene oxide, 4.5 ml (4.5 mmol) of 1 M triisobutyl aluminum in hexane, 56 mg (0.5 mmol) of potassium t-butoxide and 500 ml of hexane as a solvent were charged into a pressure reaction vessel under an argon atmosphere, followed by a reaction at 25° C. for 20 hours. After completion of the reaction, the solvents were distilled off from the reaction mixture under reduced pressure, thereby obtaining 36 g of the desired copolymer (139) which was a white solid. The weight average molecular weight of the obtained copolymer was 67,000 as determined by GPC.

Copolymer (139) was subjected to a $^1$H-NMR analysis using tetramethylsilane (TMS) as a reference standard and deuterated methanol (CD$_3$OD) as a solvent. The resultant NMR spectrum showed that multiplet peaks ascribed to an n-butyl group appeared at δ 0.94 ppm, δ 1.39 ppm and δ 1.54 ppm, and that a peak ascribed mainly to polyethylene glycol appeared at δ 3.39-3.90 ppm. Further, the amount of n-butyl group introduced into the copolymer was determined by $^1$H-NMR analysis. The amount of the introduced n-butyl group was 2.84 mol %, based on the total molar amount of recurring units (the above-mentioned amount of n-butyl group introduced into the copolymer is hereinafter referred to simply as "n-butyl group introduction ratio").

Substantially the same procedure as in the production of copolymer (139) above was repeated except that the amounts of n-butyl glycidyl ether and ethylene oxide were changed as shown in Table 21 below, thereby obtaining copolymers (140) and (141). The n-butyl group introduction ratio of each of copolymers (140) and (141) was determined by $^1$H-NMR analysis. The results are also shown in Table 21 below.

TABLE 21

|  | Copolymer (140) | Copolymer (141) |
| --- | --- | --- |
| n-butyl glycidyl ether (mmol) | 100 | 100 |
| Ethylene oxide (mmol) | 750 | 685 |
| Triisobutyl aluminum (mmol) | 4.5 | 3.5 |
| Potassium t-butoxide (mmol) | 0.5 | 0.5 |
| Amount of product (g) | 32.2 | 30.1 |
| n-butyl group introduction ratio (mol %) | 9.38 | 4.79 |
| Mw as determined by GPC | 17,000 | 20,000 |

Example 100

14.2 ml (100 mmol) of n-butyl glycidyl ether, 41.3 ml (826 mmol) of ethylene oxide, 5.0 ml (5.0 mmol) of 1 M triisobutyl aluminum in hexane and 500 ml of hexane as a solvent were charged into a pressure reaction vessel under an argon atmosphere, followed by a reaction at 25° C. for 20 hours. After completion of the reaction, the solvents were distilled off from the reaction mixture under reduced pressure, thereby obtaining 31 g of the desired copolymer (142) which was a white solid. The weight average molecular weight of the obtained copolymer was 34,000 as determined by GPC.

Copolymer (142) was subjected to a $^1$H-NMR analysis using tetramethylsilane (TMS) as a reference standard and deuterated methanol (CD$_3$OD) as a solvent. The resultant NMR spectrum showed that multiplet peaks ascribed to an n-butyl group appeared at δ 0.94 ppm, δ 1.40 ppm and δ 1.55 ppm, and that a peak ascribed mainly to polyethylene glycol appeared at δ 3.44-3.89 ppm. Further, the amount of n-butyl group introduced into the copolymer was determined by $^1$H-NMR analysis. The amount of the introduced n-butyl group was 6.29 mol %, based on the total molar amount of recurring units (the above-mentioned amount of n-butyl group introduced into the copolymer is hereinafter referred to simply as "n-butyl group introduction ratio").

Substantially the same procedure as in the production of copolymer (142) above was repeated except that the amounts of n-butyl glycidyl ether and ethylene oxide were changed as shown in Table 22 below, thereby obtaining copolymers (143) and (144). The n-butyl group introduction ratio of each of copolymers (143) and (144) was determined by $^1$H-NMR analysis. The results are also shown in Table 22 below.

TABLE 22

|  | Copolymer (143) | Copolymer (144) |
| --- | --- | --- |
| n-butyl glycidyl ether (mmol) | 100 | 100 |
| Ethylene oxide (mmol) | 1650 | 1235 |
| Triisobutyl aluminum (mmol) | 5.0 | 5.0 |
| Amount of product (g) | 48.0 | 47.0 |
| n-butyl group introduction ratio (mol %) | 4.59 | 5.14 |
| Mw as determined by GPC | 21,000 | 24,000 |

Example 101

15 ml (106 mmol) of n-butyl glycidyl ether, 90 ml (1,802 mmol) of ethylene oxide, 76 mg (0.68 mmol) of potassium t-butoxide and 200 ml of diethylene glycol diethyl ether as a solvent were charged into a pressure reaction vessel under an argon atmosphere, followed by a reaction at 80° C. for 24 hours. After completion of the reaction, the solvents were distilled off from the reaction mixture under reduced pressure, thereby obtaining 50.3 g of the desired copolymer (145) which was a white solid. The weight average molecular weight of the obtained copolymer was 47,000 as determined by GPC.

Copolymer (145) was subjected to a $^1$H-NMR analysis using tetramethylsilane (TMS) as a reference standard and deuterated methanol (CD$_3$OD) as a solvent. The resultant NMR spectrum showed that multiplet peaks ascribed to an n-butyl group appeared at δ 0.94 ppm, δ 1.40 ppm and δ 1.55 ppm, and that a peak ascribed mainly to polyethylene glycol appeared at δ 3.40-3.82 ppm. Further, the amount of n-butyl group introduced into the copolymer was determined by $^1$H-NMR analysis. The amount of the introduced n-butyl group was 5.70 mol %, based on the total molar amount of recurring units (the above-mentioned amount of n-butyl group introduced into the copolymer is hereinafter referred to simply as "n-butyl group introduction ratio").

Substantially the same procedure as in the production of copolymer (145) above was repeated except that the amounts of n-butyl glycidyl ether and ethylene oxide were changed as shown in Table 23 below, thereby obtaining copolymers (146) and (147). The n-butyl group introduction ratio of each of copolymers (146) and (147) was determined by $^1$H-NMR analysis. The results are also shown in Table 23 below.

TABLE 23

|  | Copolymer (146) | Copolymer (147) |
| --- | --- | --- |
| n-butyl glycidyl ether (mmol) | 112 | 100 |
| Ethylene oxide (mmol) | 288 | 900 |
| Potassium t-butoxide (mmol) | 0.7 | 0.7 |
| Amount of product (g) | 18.5 | 36.7 |
| n-butyl group introduction ratio (mol %) | 33.34 | 10.48 |
| Mw as determined by GPC | 35,000 | 40,000 |

Example 102

15 ml (111 mmol) of glycidyl phenyl ether, 90 ml (1,802 mmol) of ethylene oxide, 78 mg (0.70 mmol) of potassium t-butoxide and 200 ml of ethylene glycol dimethyl ether as a solvent were charged into a pressure reaction vessel under an argon atmosphere, followed by a reaction at 90° C. for 24 hours. After completion of the reaction, the solvents were distilled off from the reaction mixture under reduced pressure, thereby obtaining 55.9 g of the desired copolymer (148) which was a white solid. The weight average molecular weight of the obtained copolymer was 140,000 as determined by GPC.

Copolymer (148) was subjected to a $^1$H-NMR analysis using tetramethylsilane (TMS) as a reference standard and deuterated methanol (CD$_3$OD) as a solvent. The resultant NMR spectrum showed that multiplet peaks ascribed to a phenyl group appeared at δ 6.78-6.96 ppm and δ 7.12-7.29 ppm, and that a peak ascribed mainly to polyethylene glycol appeared at δ 3.40-4.15 ppm. Further, the amount of phenyl group introduced into the copolymer was determined by $^1$H-NMR analysis. The amount of the introduced phenyl group was 6.44 mol %, based on the total molar amount of recurring units (the above-mentioned amount of phenyl group introduced into the copolymer is hereinafter referred to simply as "phenyl group introduction ratio").

Substantially the same procedure as in the production of copolymer (148) above was repeated except that the amounts of glycidyl phenyl ether and ethylene oxide were changed as shown in Table 24 below, thereby obtaining copolymers (149) and (150). The phenyl group introduction ratio of each of copolymers (149) and (150) was determined by $^1$H-NMR analysis. The results are also shown in Table 24 below.

2TABLE 24

|  | Copolymer (149) | Copolymer (150) |
|---|---|---|
| Glycidyl phenyl ether (mmol) | 111 | 111 |
| Ethylene oxide (mmol) | 801 | 1201 |
| Potassium t-butoxide (mmol) | 0.7 | 0.7 |
| Amount of product (g) | 36.7 | 48.0 |
| Phenyl group introduction ratio (mol %) | 10.92 | 7.58 |
| Mw as determined by GPC | 90,000 | 120,000 |

Example 103

10 ml (64 mmol) of ethylene glycol diglycidyl ether, 90 ml (1,820 mmol) of ethylene oxide, 76 mg (0.68 mmol) of potassium t-butoxide and 400 ml of ethylene glycol dimethyl ether as a solvent were charged into a pressure reaction vessel under an argon atmosphere, followed by a reaction at 40° C. for 24 hours. After completion of the reaction, the solvents were distilled off from the reaction mixture under reduced pressure, thereby obtaining 25.5 g of the desired copolymer (151) which was a white solid.

Substantially the same procedure as in the production of copolymer (151) above was repeated except that the amounts of ethylene glycol diglycidyl ether and ethylene oxide were changed as shown in Table 25 below, thereby obtaining copolymers (152) and (153). The amounts of the products obtained are also shown in Table 25 below.

TABLE 25

|  | Copolymer (152) | Copolymer (153) |
|---|---|---|
| Ethyleneglycol diglycidyl ether (mmol) | 56 | 42 |
| Ethylene oxide (mmol) | 1,620 | 1,650 |
| Potassium t-butoxide (mmol) | 0.7 | 0.7 |
| Amount of product (g) | 36.5 | 28.3 |

Example 104

50 ml (42 mmol) of allyl glycidyl ether, 21.1 ml (424 mmol) of ethylene oxide, 4.5 ml (4.5 mmol) of 1 M triisobutyl aluminum in hexane, 56 mg (0.5 mmol) of potassium t-butoxide and 250 ml of hexane as a solvent were charged into a pressure reaction vessel under an argon atmosphere, followed by a reaction at 25° C. for 20 hours. After completion of the reaction, the solvents were distilled off from the reaction mixture under reduced pressure, thereby obtaining 13.7 g of the desired copolymer (154) which was a white solid. The weight average molecular weight of the obtained copolymer was 45,000 as determined by GPC.

Copolymer (154) was subjected to a $^1$H-NMR analysis using tetramethylsilane (TMS) as a reference standard and deuterated methanol (CD$_3$OD) as a solvent. The resultant NMR spectrum showed that multiplet peaks ascribed to an allyl group appeared at δ 3.95 ppm, δ 5.10-5.30 ppm and δ 5.80-5.90 ppm, and that a peak ascribed mainly to polyethylene glycol appeared at δ 3.40-4.15 ppm. Further, the amount of allyl group introduced into the copolymer was determined by $^1$H-NMR analysis. The amount of the introduced allyl group was 4.52 mol %, based on the total molar amount of recurring units (the above-mentioned amount of allyl group introduced into the copolymer is hereinafter referred to simply as "allyl group introduction ratio").

Substantially the same procedure as in the production of copolymer (154) above was repeated except that the amounts of allyl glycidyl ether and ethylene oxide were changed as shown in Table 26 below, thereby obtaining copolymers (155) and (156). The allyl group introduction ratio of each of copolymers (155) and (156) was determined by $^1$H-NMR analysis. The results are also shown in Table 26 below.

TABLE 26

|  | Copolymer (155) | Copolymer (156) |
|---|---|---|
| Allyl glycidyl ether (mmol) | 42 | 42 |
| Ethylene oxide (mmol) | 409 | 180 |
| Triisobutyl aluminum (mmol) | 2.3 | 4.5 |
| Potassium t-butoxide (mmol) | 0.5 | 0.7 |
| Amount of product (g) | 16.0 | 9.5 |
| Allyl group introduction ratio (mol %) | 3.92 | 11.00 |
| Mw as determined by GPC | 64,000 | 23,000 |

Example 105

25 ml (176 mmol) of t-butyl glycidyl ether, 152 ml (3,043 mmol) of ethylene oxide, 107 mg (0.95 mmol) of potassium t-butoxide and 200 ml of ethylene glycol dimethyl ether as a solvent were charged into a pressure reaction vessel under an argon atmosphere, followed by a reaction at 80° C. for 25 hours. After completion of the reaction, the solvents were distilled off from the reaction mixture under reduced pressure, thereby obtaining 94.0 g of a t-butyl group-containing copolymer which was a white solid. The weight average molecular weight of the obtained t-butyl group-containing copolymer was 81,000 as determined by GPC.

The above-obtained copolymer was subjected to a ¹H-NMR analysis using tetramethylsilane (TMS) as a reference standard and deuterated dimethylsulfoxide (DMSO) as a solvent. The resultant NMR spectrum showed that a single peak ascribed to a t-butyl group appeared at δ 1.11 ppm, and that a peak ascribed mainly to polyethylene glycol appeared at δ 3.40-3.82 ppm. Further, the amount of t-butyl group introduced into the copolymer was determined by ¹H-NMR analysis. The amount of the introduced t-butyl group was 5.10 mol %, based on the total molar amount of recurring units.

To 20.84 g of the above-obtained copolymer cooled with ice was added 200 ml of 4 N hydrogen chloride in 1,4-dioxane, and the resultant mixture was reacted at room temperature for 30 hours. After completion of the reaction, the reaction solvent (1,4-dioxane) was distilled off from the reaction mixture under reduced pressure. The resultant residue was dialyzed for 2 days against purified water using a dialysis membrane (trade name: Spectra/Por 2, molecular weight cut-off: 12,000 to 14,000) manufactured and sold by Spectrum Laboratories Inc., U.S.A. The resultant dialyzate was filtered through a membrane filter (trade name: DURAPORE, pore size: 0.22 μm) manufactured and sold by Millipore Corporation, Japan, and the resultant filtrate was lyophilized, thereby obtaining 14.61 g of desired copolymer (157) which was a white amorphous product.

Copolymer (157) was subjected to a ¹H-NMR analysis using tetramethylsilane as a reference standard and deuterated DMSO as a solvent. The peak ascribed to a t-butyl group of the above-obtained t-butyl group-containing copolymer (which appeared at δ 1.11 ppm) disappeared from the resultant NMR spectrum of copolymer (157) and, thus, it was confirmed that the pendant t-butyl groups were eliminated from the t-butyl group-containing copolymer obtained above by the reaction with 4 N HCl. The weight average molecular weight of copolymer (157) was 71,000 as determined by GPC.

Subsequently, 1.0 ml of 1 N aqueous sodium hydroxide was added to 200 mg of copolymer (157) and, then, 0.15 ml of ethylene glycol diglycidyl ether was also added thereto, followed by stirring to thereby obtain a reaction mixture. A part of the obtained reaction mixture was taken out and sandwiched between two glass plates, wherein the thickness of the space between the glass plates was adjusted to about 0.5 mm using a vinyl tape. The resultant structure comprised of glass plates having the reaction mixture sandwiched therebetween was allowed to stand still at 37° C. for 15 hours to cause crosslinking of the copolymer, to thereby obtain a gel in the form of a sheet. On the other hand, the remaining reaction mixture was stirred at room temperature for 15 hours to cause crosslinking of the copolymer, thereby obtaining a gel.

The obtained gel in the form of a sheet (hereinafter referred to simply as a "gel sheet") was placed in a petri dish and neutralized with 1 N aqueous hydrochloric acid. Subsequently, the neutralized gel sheet was shaken in physiological saline (sodium chloride concentration: 0.9%), thereby obtaining gel sheet (158) (thickness: about 0.5 mm). The obtained gel sheet (158) was used in Examples 125 and 126 below.

Substantially the same procedure as in the production of gel sheet (158) above was repeated except that the thickness of the space between the glass plates was adjusted to about 1.0 mm, thereby obtaining gel sheet (159) (thickness: about 1.0 cm).

Example 106

33 ml of t-butyl glycidyl ether, 85 ml of ethylene oxide, 1 ml of 1 M potassium t-butoxide in tetrahydrofuran, 10 ml of 1 M triisobutyl aluminum in hexane and 300 ml of hexane as a solvent were charged into a pressure reaction vessel under an argon atmosphere, followed by a reaction at 25° C. for 24 hours. After completion of the reaction, the solvents were distilled off from the reaction mixture under reduced pressure, thereby obtaining 62 g of the desired copolymer (160) which was a white solid.

Figure 35:
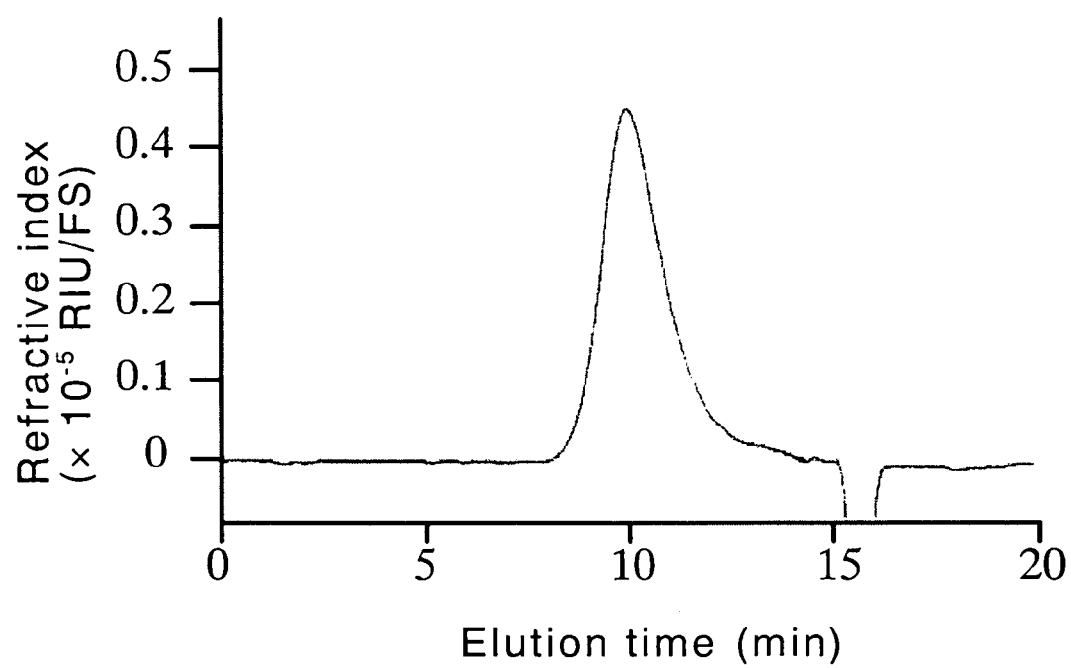
FIG. 35 is a GPC chart of copolymer (160) obtained in Example 106.

The weight average molecular weight of the obtained copolymer was 53,000 as determined by GPC using a calibration curve obtained with respect to standard polyethylene glycol (PEG) samples, each having a narrow molecular weight distribution (hereinafter, this GPC is referred to as "GPC using a PEG calibration curve"). The resultant GPC chart is shown in FIG. 35. Further, copolymer (160) was subjected to a ¹H-NMR analysis using tetramethylsilane as a reference standard and deuterated methanol as a solvent. The resultant NMR spectrum showed that a single peak ascribed to a t-butyl group appeared at δ 1.20 ppm, and that a peak ascribed mainly to polyethylene glycol appeared at δ 3.40-3.82 ppm. Further, the amount of t-butyl group introduced into the copolymer was determined by ¹H-NMR analysis. The amount of the introduced t-butyl group was 3.9 mol %, based on the total molar amount of recurring units.

To 20 g of copolymer (160) obtained above was added 200 ml of 4 N hydrogen chloride in 1,4-dioxane at room temperature, and the resultant mixture was reacted at room temperature for 24 hours. After completion of the reaction, the reaction solvent (1,4-dioxane) was distilled off from the reaction mixture under reduced pressure. The resultant residue was dialyzed for 2 days against purified water, using a dialysis membrane (trade name: Spectra/Por 2, molecular weight cut-off: 12,000 to 14,000) manufactured and sold by Spectrum Laboratories Inc., U.S.A. The resultant dialyzate was filtered through a membrane filter (trade name: DURAPORE, pore size: 0.22 μm) manufactured and sold by Millipore Corporation, Japan, and the resultant filtrate was lyophilized, thereby obtaining 16.6 g of desired copolymer (161) which was a white amorphous product.

Figure 36:
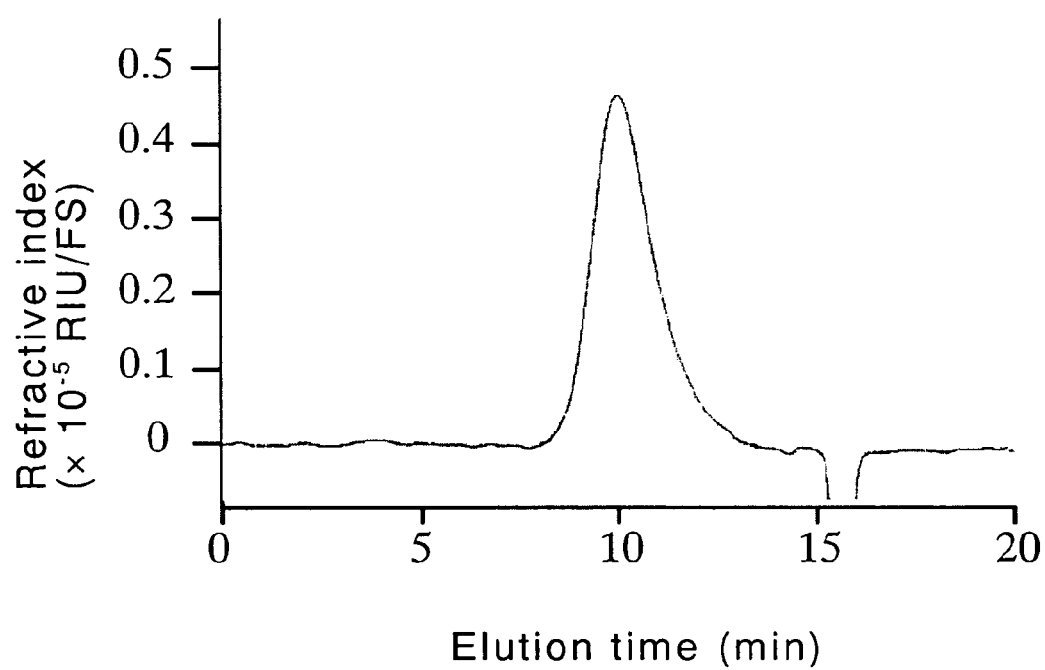
FIG. 36 is a GPC chart of copolymer (161) obtained in Example 106.

Copolymer (161) was subjected to a ¹H-NMR analysis using tetramethylsilane as a reference standard and deuterated methanol as a solvent. The peak ascribed to a t-butyl group of copolymer (160) (which appeared at δ 1.20 ppm) disappeared from the resultant NMR spectrum of copolymer (161) and, thus, it was confirmed that the pendant t-butyl groups were eliminated from copolymer (160) by the reaction with 4 N hydrogen chloride. The weight average molecular weight of the obtained copolymer (161) was 61,000 and Mw/Mn was 1.54, as determined by GPC using a PEG calibration curve. The GPC chart is shown in FIG. 36.

The solubility of copolymer (161) in each of water, N-methylpyrrolidone, N,N-dimethylformamide, toluene, tetrahydrofuran, ethyl acetate, ethanol and hexane was evaluated. It was found that the solubility of copolymer (161) in each of water, N-methylpyrrolidone, N,N-dimethylformamide, toluene, tetrahydrofuran, ethyl acetate and ethanol was 100 mg/ml or more and that copolymer (161) was insoluble in hexane.

Example 107

42 ml of t-butyl glycidyl ether, 85 ml of ethylene oxide, 1.1 ml of 1 M potassium 2-methyl-2-butoxide in tetrahydrofuran, 11.1 ml of 1 M triisobutyl aluminum in hexane and 300 ml of hexane as a solvent were charged into a pressure reaction vessel under an argon atmosphere, followed by a reaction at 25° C. for 24 hours. After completion of the reaction, the solvents were distilled off from the reaction mixture under reduced pressure, thereby obtaining 55 g of the desired copolymer (162) which was a white solid.

Figure 37:
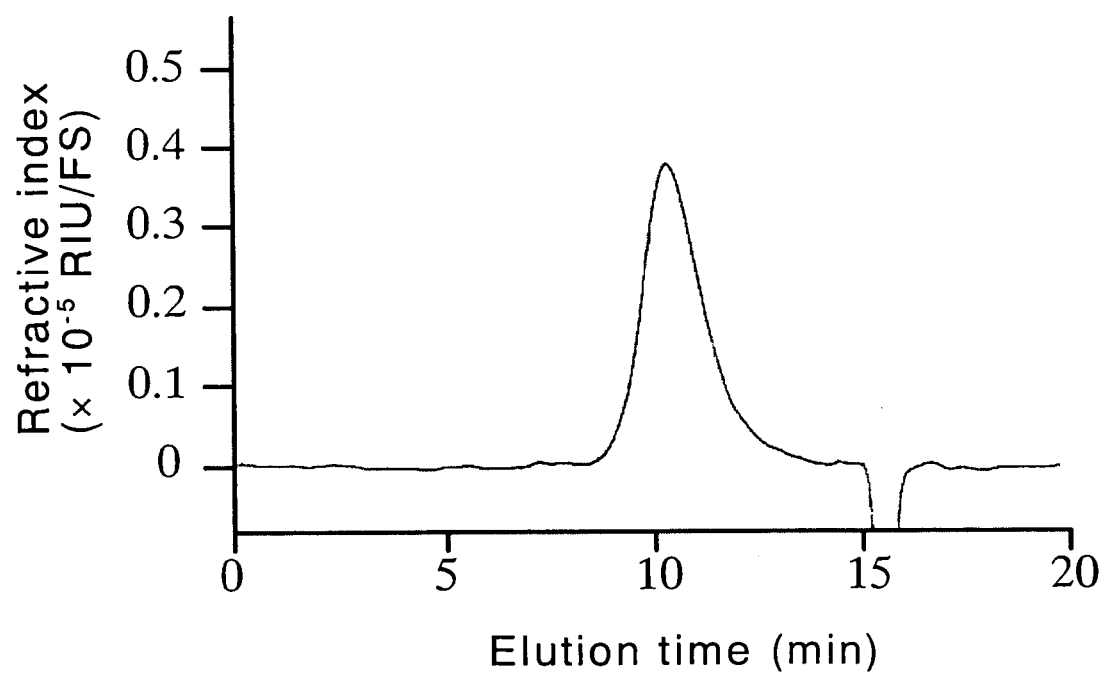
FIG. 37 is a GPC chart of copolymer (162) obtained in Example 107.

The weight average molecular weight of the obtained copolymer was 40,000 as determined by GPC using a PEG calibration curve. The resultant GPC chart is shown in FIG. 37. Further, copolymer (162) was subjected to a $^1$H-NMR analysis using tetramethylsilane as a reference standard and deuterated methanol as a solvent. The resultant NMR spectrum showed that a single peak ascribed to a t-butyl group appeared at δ 1.22 ppm, and that a peak ascribed mainly to polyethylene glycol appeared at δ 3.42-3.82 ppm. Further, the amount of t-butyl group introduced into the copolymer was determined by $^1$H-NMR analysis. The amount of the introduced t-butyl group was 5.7 mol %, based on the total molar amount of recurring units.

To 20.8 g of copolymer (162) obtained above was added 200 ml of 4 N hydrogen chloride in 1,4-dioxane at room temperature, and the resultant mixture was reacted at room temperature for 24 hours. After completion of the reaction, the reaction solvent (1,4-dioxane) was distilled off from the resultant reaction mixture under reduced pressure. The resultant residue was dialyzed for 2 days against purified water using a dialysis membrane (trade name: Spectra/Por 2, molecular weight cut-off: 12,000 to 14,000) manufactured and sold by Spectrum Laboratories Inc., U.S.A. The resultant dialyzate was filtered through a membrane filter (trade name: DURAPORE, pore size: 0.22 μm) manufactured and sold by Millipore Corporation, Japan, and the resultant filtrate was lyophilized, thereby obtaining 15.1 g of desired copolymer (163) which was a white amorphous product.

Figure 38:
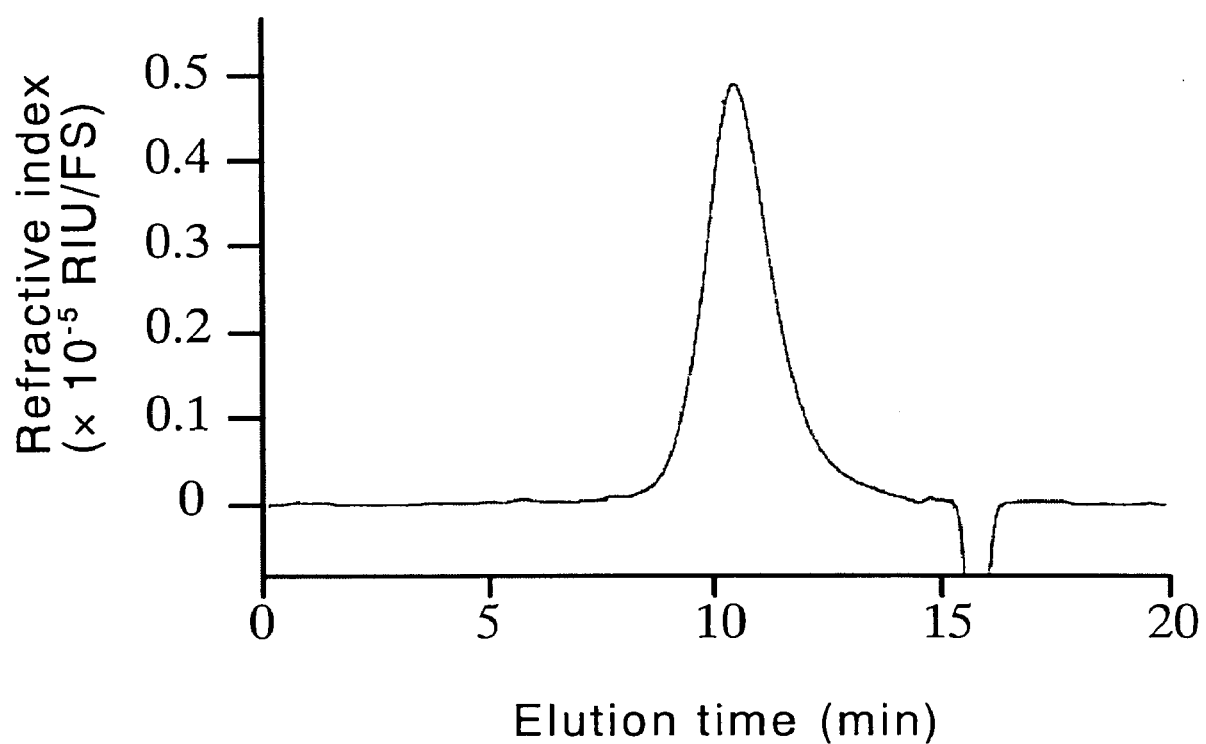
FIG. 38 is a GPC chart of copolymer (163) obtained in Example 107.

Copolymer (163) was subjected to a $^1$H-NMR analysis using tetramethylsilane as a reference standard and deuterated methanol as a solvent. The peak ascribed to a t-butyl group of copolymer (162) (which appeared at δ 1.22 ppm) disappeared from the resultant NMR spectrum of copolymer (163) and, thus, it was confirmed that the pendant t-butyl groups were eliminated from copolymer (162) by the reaction with 4 N hydrogen chloride. The weight average molecular weight of the obtained copolymer (163) was 44,000 and Mw/Mn was 1.70, as determined by GPC using a PEG calibration curve. The GPC chart is shown in FIG. 38.

Example 108

30 ml of t-butyl glycidyl ether, 86 ml of ethylene oxide, 2 ml of 1 M potassium t-butoxide in tetrahydrofuran, 18 ml of 1 M triisobutyl aluminum in hexane and 300 ml of hexane as a solvent were charged into a pressure reaction vessel under an argon atmosphere, followed by a reaction at 25° C. for 24 hours. After completion of the reaction, the solvents were distilled off from the resultant reaction mixture under reduced pressure, thereby obtaining 61 g of the desired copolymer (164) which was a white solid.

The weight average molecular weight of the obtained copolymer was 28,000 as determined by GPC using a PEG calibration curve. Further, copolymer (164) was subjected to a $^1$H-NMR analysis using tetramethylsilane as a reference standard and deuterated methanol as a solvent. The resultant NMR spectrum showed that a single peak ascribed to a t-butyl group appeared at δ 1.20 ppm, and that a peak ascribed mainly to polyethylene glycol appeared at δ 3.40-3.82 ppm. Further, the amount of t-butyl group introduced into the copolymer was determined by $^1$H-NMR analysis. The amount of the introduced t-butyl group was 5.2 mol %, based on the total molar amount of recurring units.

To 20 g of copolymer (164) obtained above was added 200 ml of 5 N hydrochloric acid at room temperature, and the resultant mixture was reacted at room temperature for 10 hours. After completion of the reaction, the reaction solvent was distilled off from the resultant reaction mixture under reduced pressure. The resultant residue was dialyzed for 2 days against purified water using a dialysis membrane (trade name: Spectra/Por 2, molecular weight cut-off: 12,000 to 14,000) manufactured and sold by Spectrum Laboratories Inc., U.S.A. The resultant dialyzate was filtered through a membrane filter (trade name: DURAPORE, pore size: 0.22 μm) manufactured and sold by Millipore Corporation, Japan, and the resultant filtrate was lyophilized, thereby obtaining 15.8 g of desired copolymer (165) which was a white amorphous product.

Copolymer (165) was subjected to a $^1$H-NMR analysis using tetramethylsilane as a reference standard and deuterated methanol as a solvent. The peak ascribed to a t-butyl group of copolymer (164) (which appeared at δ 1.20 ppm) disappeared from the resultant NMR spectrum of copolymer (165) and, thus, it was confirmed that the pendant t-butyl groups were eliminated from copolymer (164) by the reaction with 5 N hydrochloric acid. The weight average molecular weight of the obtained copolymer (165) was 27,000 and Mw/Mn was 1.79, as determined by GPC using a PEG calibration curve.

Example 109

Substantially the same procedure as in the production of copolymer (164) in Example 108 was repeated except that the amounts of t-butyl glycidyl ether (tBGE) and ethylene oxide were changed as shown in Table 27 below, thereby obtaining copolymers (166) to (168) (which are random copolymers). The yield and weight average molecular weight of each of copolymers (166) to (168) were determined by GPC using a PEG calibration curve. In addition, the molar amount of the introduced pendant t-butyl group, based on the total molar amount of the recurring units of the copolymer, was determined by $^1$H-NMR analysis. The results are also shown in Table 27 below.

Further, the pendant t-butyl groups were eliminated from each of copolymers (166) to (168) under the same conditions as in Example 108. The elimination of the pendant t-butyl groups from each of copolymers (166) to (168) was confirmed by $^1$H-NMR analysis in the same manner as in Example 108. Thus, copolymers (169) to (171) were obtained.

The weight average molecular weight and molecular weight distribution (Mw/Mn) of each of copolymers (169) to (171) were determined by GPC using a PEG calibration curve. The results are also shown in Table 27 below.

As shown in Table 27 below, the amounts of introduced pendant t-butyl group (i.e., the amounts of t-butyl glycidyl ether units) of the copolymers (166), (167) and (168) were respectively 1.84 mol %, 2.28 mol % and 3.81 mol %, based on the total molar amount of the recurring units.

TABLE 27

| | Copolymer (166) | Copolymer (167) | Copolymer (168) |
|---|---|---|---|
| tBGE (ml) | 6.1 | 11.9 | 13.6 |
| Ethylene oxide (ml) | 100 | 100 | 100 |
| 1 M potassium t-butoxide solution in hexane (ml) | 1.3 | 1.3 | 1.4 |
| 1 M triisobutyl aluminum in THF (ml) | 12.6 | 12.5 | 13.5 |

TABLE 27-continued

|  | Copolymer (166) | Copolymer (167) | Copolymer (168) |
|---|---|---|---|
| Yield of the reaction product (g) | 51 | 57 | 55 |
| Weight average molecular weight as determined by GPC using a PEG calibration curve | 54,000 | 55,000 | 42,000 |
| t-butyl group introduction ratio (mol %) | 1.84 | 2.28 | 3.81 |
| Copolymer obtained by eliminating the t-butyl groups (protecting groups) | Copolymer (169) | Copolymer (170) | Copolymer (171) |
| Weight average molecular weight as determined by GPC using a PEG calibration curve | 51,000 | 51,000 | 41,000 |
| Molecular weight distribution (Mw/Mn) | 1.38 | 1.34 | 1.34 |

Example 110

15 ml of t-butyl glycidyl ether, 91 ml of ethylene oxide, 0.6 ml of 1 M potassium t-butoxide in tetrahydrofuran and 200 ml of ethylene glycol dimethyl ether as a solvent were charged into a pressure reaction vessel under an argon atmosphere, followed by a reaction at 80° C. for 19 hours. After completion of the reaction, the solvents were distilled off from the resultant reaction mixture under reduced pressure, thereby obtaining 56 g of the desired copolymer (172) which was a white solid.

The weight average molecular weight of the obtained copolymer was 54,000 as determined by GPC using a PEG calibration curve. Further, copolymer (172) was subjected to a $^1$H-NMR analysis using tetramethylsilane as a reference standard and deuterated dimethylsulfoxide (DMSO) as a solvent. The resultant NMR spectrum showed that a single peak ascribed to a t-butyl group appeared at δ 1.11 ppm, and that a peak ascribed mainly to polyethylene glycol appeared at δ 3.40-3.82 ppm. Further, the amount of t-butyl group introduced into the copolymer was determined by $^1$H-NMR analysis. The amount of the introduced t-butyl group was 5.6 mol %, based on the total molar amount of recurring units.

To 20.35 g of copolymer (172) obtained above was added 200 ml of 4 N hydrogen chloride in 1,4-dioxane while cooling with ice, and the resultant mixture was reacted at room temperature for 30 hours. After completion of the reaction, the reaction solvent (1,4-dioxane) was distilled off from the resultant reaction mixture under reduced pressure. The resultant residue was dialyzed for 2 days against purified water using a dialysis membrane (trade name: Spectra/Por 2, molecular weight cut-off: 12,000 to 14,000) manufactured and sold by Spectrum Laboratories Inc., U.S.A. The resultant dialyzate was filtered through a membrane filter (trade name: DURAPORE, pore size: 0.22 μm) manufactured and sold by Millipore Corporation, Japan, and the resultant filtrate was lyophilized, thereby obtaining 15.7 g of desired copolymer (173) which was a white amorphous product.

Copolymer (173) was subjected to a $^1$H-NMR analysis using tetramethylsilane as a reference standard and deuterated DMSO as a solvent. The peak ascribed to a t-butyl group of copolymer (172) (which appeared at δ 1.11 ppm) disappeared from the resultant NMR spectrum of copolymer (173) and, thus, it was confirmed that the pendant t-butyl groups were eliminated from copolymer (172) by the reaction with 4 N hydrogen chloride. The weight average molecular weight of the obtained copolymer (173) was 58,000 and Mw/Mn was 1.54, as determined by GPC using a PEG calibration curve.

Example 111

Copolymer (161) produced in Example 106 was used as a starting material. 200 mg of copolymer (161) was dissolved in 1 ml of 1 N aqueous sodium hydroxide and, then, 0.15 ml of ethylene glycol diglycidyl ether was added thereto, followed by stirring to thereby obtain a reaction mixture. A part of the obtained reaction mixture was taken out and sandwiched between two glass plates, wherein the thickness of the space between the glass plates was adjusted using a vinyl tape. The resultant structure comprised of glass plates having the reaction mixture sandwiched therebetween was allowed to stand still at 50° C. for 15 hours to cause crosslinking of the copolymer, to thereby obtain a gel in the form of a sheet. On the other hand, the remaining reaction mixture was stirred at room temperature for 15 hours to cause crosslinking of the copolymer, thereby obtaining a gel. The obtained gel in the form of a sheet (hereinafter referred to simply as a "gel sheet") was placed in a petri dish and neutralized with 1 ml of 1 N hydrochloric acid. Subsequently, the neutralized gel sheet was shaken in physiological saline (0.9% sodium chloride). The resultant gel sheet was about 0.2 mm thick.

Example 112

Substantially the same procedure as in the production of a gel sheet in Example 111 was repeated, except that copolymers (169), (170) and (171) produced in Example 109 were individually used as a starting material, and the amounts of sodium hydroxide and ethylene glycol diglycidyl ether were changed so that the molar amounts of sodium hydroxide and ethylene glycol diglycidyl ether were respectively equivalent to and 4 times the molar amount of OH group present in the copolymer (the amounts of the materials used are shown in Table 28 below).

Copolymer (171) formed a gel sheet. The gel sheet produced using copolymer (171) was placed in a petri dish and neutralized with 1 N hydrochloric acid. Subsequently, the neutralized gel sheet was shaken in physiological saline (0.9% sodium chloride). The gel sheet was about 0.2 mm thick.

TABLE 28

|  | Copolymer (169) | Copolymer (170) | Copolymer (171) |
|---|---|---|---|
| Amount of starting material (mg) | 100 | 100 | 100 |
| t-butyl group introduction ratio (OH group introduction ratio) (mol %) | 1.84 | 2.28 | 3.81 |
| Amount of 8 N aqueous sodium hydroxide (μl) | 5.2 | 6.4 | 10.5 |
| Amount of distilled water (μl) | 157 | 150 | 125 |
| Amount of ethylene glycol diglycidyl ether (μl) | 24 | 30 | 49 |

Example 113

1 g of polysulfone was dissolved in 3 ml of N-methylpyrrolidone (NMP), and then 100 mg of copolymer (125) (i.e., polyether) produced in Example 93 was dissolved therein to thereby obtain a resin solution in the form of a viscous transparent liquid. The obtained resin solution was placed between two glass plates having spacers (0.1 mm thick) positioned between the glass plates at the both end portions of the glass plates, and the resultant structure comprised of glass plates having the resin solution sandwiched therebetween was immediately placed in a water bath to thereby obtain polysulfone-copolymer membrane (a) which was a white membrane having a uniform thickness.

Substantially the same procedure as in the production of membrane (a) above was repeated except that the type and amount of the copolymer were changed as shown in Table 29 below, thereby obtaining polysulfone-copolymer membranes (b) to (f). As shown in Table 29, during the production of each of membranes (b) to (f), the copolymer of the present invention and the polysulfone were able to be easily dissolved in NMP, thereby forming a resin solution in the form of a viscous transparent liquid. Also, a membrane was able to be formed from the viscous transparent resin solution.

Separately, 1 g of polysulfone was dissolved in 3 ml of NMP to thereby obtain a polysulfone solution. Substantially the same procedure as in the production of membrane (a) above was repeated except that the obtained polysulfone solution was used instead of the resin solution containing both polysulfone and copolymer (125), thereby obtaining a polysulfone membrane.

Each of polysulfone-copolymer membranes (a) to (f) and the polysulfone membrane obtained above was washed by keeping the membrane in boiling purified water for 4 hours. This washing was performed three times in total to remove NMP contained in the membrane. Test specimens (circular shape; diameter: about 15 mm) for evaluating the plasma protein adsorption were stamped out from the resultant membranes and used in Example 117 below.

Example 114

1 g of polyether sulfone was dissolved in 3 ml of N-methylpyrrolidone (NMP), and then 100 mg of copolymer (125) (i.e., polyether) produced in Example 93 was dissolved therein to thereby obtain a resin solution in the form of a viscous transparent liquid. The obtained resin solution was placed between two glass plates having spacers (0.1 mm thick) positioned between the glass plates at the both end portions of the glass plates, and the resultant structure comprised of glass plates having the resin solution sandwiched therebetween was immediately placed in a water bath to thereby obtain polyether sulfone-copolymer membrane (g) which was a white membrane having a uniform thickness.

Substantially the same procedure as in the production of membrane (g) above was repeated except that the type and amount of the copolymer were changed as shown in Table 30 below, thereby obtaining polyether sulfone-copolymer membranes (h) to (1). As shown in Table 30, during the production of each of membranes (h) to (1), the copolymer of the present invention and the polyether sulfone were able to be easily dissolved in NMP, thereby forming a resin solution in the form of a viscous transparent liquid. Also, a membrane was able to be formed from the viscous transparent resin solution.

Separately, 1 g of polyether sulfone was dissolved in 3 ml of NMP to thereby obtain a polyether sulfone solution. Substantially the same procedure as in the production of membrane (g) above was repeated except that the obtained polyether sulfone solution was used instead of the resin solution containing both polyether sulfone and copolymer (125), thereby obtaining a polyether sulfone membrane.

Each of polyether sulfone-copolymer membranes (g) to (1) and the polyether sulfone membrane obtained above was washed by keeping the membrane in boiling purified water

TABLE 29

|  | Membrane (b) | Membrane (c) | Membrane (d) | Membrane (e) | Membrane (f) |
| --- | --- | --- | --- | --- | --- |
| Resin of the present invention | Copolymer (126) | Copolymer (129) | Copolymer (132) | Copolymer (135) | Copolymer (138) |
| Amount (g) of the resin of the present invention | 0.05 | 0.5 | 0.1 | 0.25 | 0.1 |
| Amount (g) of polysulfone | 1.0 | 1.0 | 1.0 | 1.0 | 1.0 |
| Amount (ml) of NMP | 3.0 | 3.0 | 3.0 | 3.0 | 3.0 |
| Solubility (miscibility) of the copolymer and polysulfone in NMP | can be dissolved uniformly | can be dissolved uniformly | can be dissolved uniformly | can be dissolved uniformly | can be dissolved uniformly |
| Membrane production | Possible | Possible | Possible | Possible | Possible |
| Color of the membrane | White | White | White | White | White | for 4 hours. This washing was performed three times in total to remove NMP contained in the membrane. Test specimens (circular shape; diameter: about 15 mm) for evaluating the plasma protein adsorption were stamped out from the resultant membranes and used in Example 118 below.

TABLE 30

|  | Membrane (h) | Membrane (i) | Membrane (j) | Membrane (k) | Membrane (l) |
|---|---|---|---|---|---|
| Resin of the present invention | Copolymer (126) | Copolymer (129) | Copolymer (132) | Copolymer (135) | Copolymer (138) |
| Amount (g) of the resin of the present invention | 0.05 | 0.5 | 0.1 | 0.25 | 0.1 |
| Amount (g) of polyether sulfone | 1.0 | 1.0 | 1.0 | 1.0 | 1.0 |
| Amount (ml) of NMP | 3.0 | 3.0 | 3.0 | 3.0 | 3.0 |
| Solubility (miscibility) of the copolymer and polysulfone in NMP | can be dissolved uniformly | can be dissolved uniformly | can be dissolved uniformly | can be dissolved uniformly | can be dissolved uniformly |
| Membrane production | Possible | Possible | Possible | Possible | Possible |
| Color of the membrane | White | White | White | White | White |

Example 115

Evaluation of Human Cell Adhesion: Experiment for Determining the Effect of a Copolymer to Inhibit the Adhesion of Cells and Experiment for Determining the Cell Toxicity of a Copolymer Copolymer (125) produced in Example 93, copolymer (126) produced in Example 94 and copolymer (135) produced in Example 97 were individually evaluated in the following manner. Copolymer solutions respectively having copolymer concentrations of 5, 2.5, 1, 0.5 and 0.1 mg/ml were prepared by dissolving different amounts of a copolymer individually in an aqueous 70% ethanol solution. Each of the obtained copolymer solutions was individually dispensed into a well of a 96-well microplate. On the other hand, an aqueous 70% ethanol solution was dispensed into another well of the microplate to thereby provide a well containing an aqueous 70% ethanol solution (wherein the well was intended to provide the below-mentioned "non-coated well" used as a control well). Then, the microplate was allowed to stand still at 4° C. overnight to thereby cause the wells (containing the copolymer solutions) to be coated with the copolymer. Subsequently, the copolymer solutions and aqueous 70% ethanol solution in the wells were removed by suction, followed by drying, to thereby obtain a microplate having copolymer-coated wells and a non-coated well (wherein the latter was intend for use as a control well). Adhesion of human cells to the copolymer-coated wells was evaluated as follows.

0.1 ml of a suspension of HEL cells (human lung cells) containing $3 \times 10^5$ HEL cells/ml was dispensed into the copolymer-coated wells and non-coated well of the above-obtained microplate, and the cells were cultured for 2 hours. Thereafter, the number of viable cells adhered to each of the copolymer-coated wells and non-coated well of the microplate was determined by means of CellTiter 96® $AQ_{ueous}$ Assay System (manufactured and sold by Promega Corporation, Madison, Wis., U.S.A.).

In addition, the toxicity of each of the above-mentioned copolymers (125), (126) and (135) was evaluated in the following manner. A microplate having copolymer-coated wells and a non-coated well (wherein the latter was intended for use as a control well) was prepared in the same manner as mentioned above, and HEL cells were cultured in the copolymer-coated wells and non-coated well of the prepared microplate in the same manner as mentioned above. Then, with respect to each of the copolymer-coated wells and non-coated well of the microplate, the number of viable cells adhered to the well, and the total number of viable cells adhered to the well and viable cells which were not adhered to the well but contained in the cell suspension, were determined by means of CellTiter 96® $AQ_{ueous}$ Assay System (manufactured and sold by Promega Corporation, U.S.A.).

Figure 39:
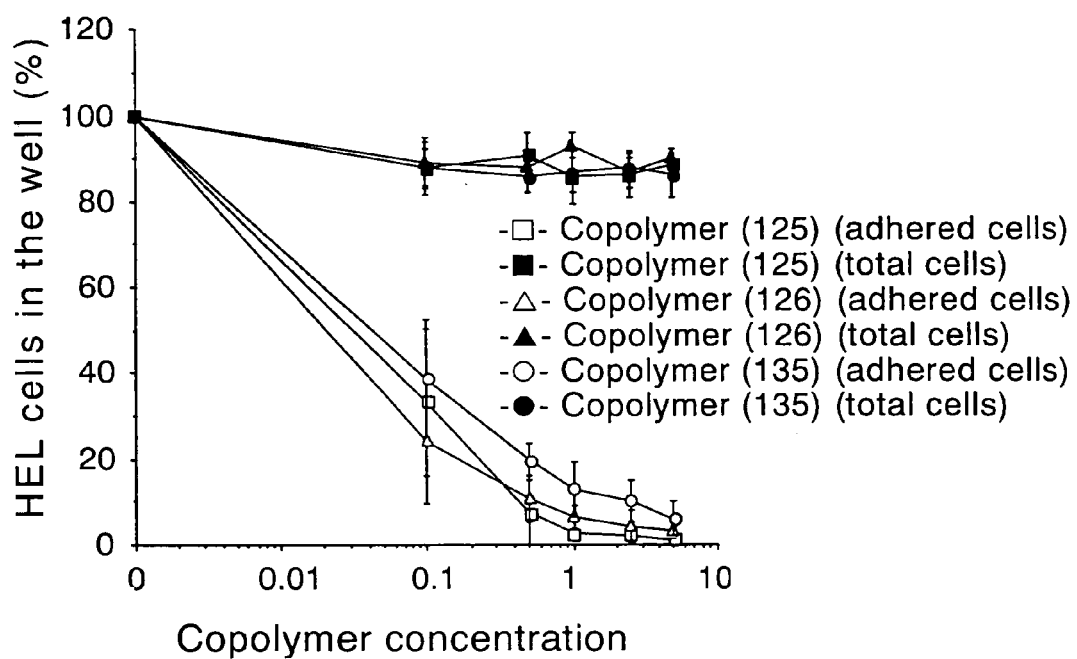
FIG. 39 is a graph showing the results of the evaluation of HEL cell (human lung cell) adhesion to various resins, which evaluation is made in Example 115.

The results of the above-mentioned evaluations are shown in FIG. 39. In FIG. 39, the cell adhesion to each copolymer-coated well is expressed in terms of the percentage of the number of cells adhered to the copolymer-coated well, based on the number of cells adhered to the non-coated well. As shown in FIG. 39, copolymers (125), (126) and (135) inhibit cell adhesion, and the degree of inhibition is proportional to the copolymer concentration of the copolymer solution. (In FIG. 39, the cell adhesion inhibitory activities of copolymers (125), (126) and (135) are indicated by the marks □, Δ and ○, respectively.)

Further, the number of viable cells in each copolymer-coated well is expressed in terms of the percentage of the number of viable cells (i.e., the total number of viable cells adhered to the well and viable cells contained in the cell suspension) in the copolymer-coated well, based on the number of viable cells in the non-coated well. As shown in FIG. 39, the number of viable cells in each copolymer-coated well was at least 70%, based on the number of viable cells in the non-coated well. That is, with respect to all of the concentrations at which the copolymers were evaluated, each of copolymers (125), (126) and (135) was found to have no toxicity to human cells. (In FIG. 39, the non-toxic properties of copolymers (125), (126) and (135) are indicated by ■, ▲ and ●, respectively.)

Example 116

Evaluation (1) of plasma Protein Adsorption

Copolymer (125) produced in Example 93, copolymer (126) produced in Example 94 and copolymer (135) produced in Example 97 were individually evaluated in the following manner. Copolymer solutions respectively having copolymer concentrations of 10, 1, 0.1, 0.01 and 0.001 mg/ml were prepared by dissolving different amounts of a copolymer individually in an aqueous 70% ethanol solution. 0.2 ml of each of the obtained copolymer solutions was individually dispensed into a well of Coaster 96-well EIA plate (Product No. 3590, manufactured and sold by Corning Incorporated, U.S.A.). On the other hand, an aqueous 70% ethanol solution was dispensed into another well of the EIA plate to thereby provide a well containing an aqueous 70% ethanol solution (wherein the well was intended to provide the below-mentioned "non-coated well" used as a control well). Then, the EIA plate was allowed to stand still at 4° C. overnight to thereby cause the wells (containing the copolymer solutions) to be coated with the copolymer. Subsequently, the copolymer solutions and aqueous 70% ethanol solution in the wells were removed by suction, followed by drying, to thereby obtain an EIA plate having copolymer-coated wells and a non-coated well (wherein the latter was intended for use as a control well). Adhesion of immunoglobulin G to the copolymer-coated wells was evaluated as follows.

0.1 ml of an immunoglobulin G solution containing 5 μg/ml of a purified human immunoglobulin G (IgG) (manufactured and sold by MP Biomedicals, U.S.A.) was dispensed into the copolymer-coated wells and non-coated well of the above-obtained EIA plate, and was allowed to remain in contact with the surfaces of the wells at 37° C. for 2 hours. Subsequently, the amounts of human IgG adsorbed on the surfaces of the wells were determined by enzyme-linked immunosorbent assay (ELISA) using a horseradish peroxidase (HRP)-conjugated goat IgG fraction to human IgG (whole molecule) (manufactured and sold by MP Biomedicals, U.S.A.).

Figure 40:
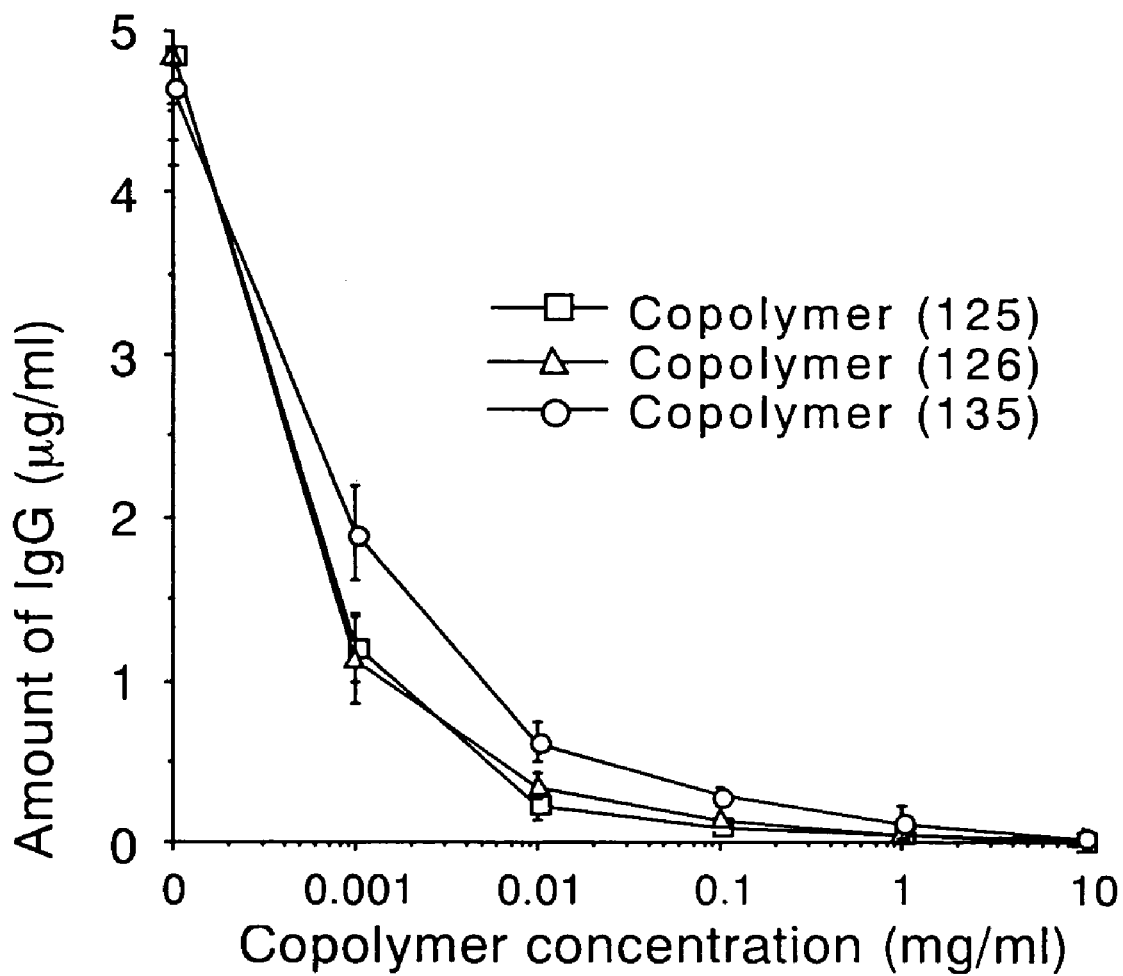
FIG. 40 is a graph showing the results of the evaluation of human immunoglobulin adhesion, which evaluation is made in Example 116.

The results are shown in FIG. 40. The determination of the amounts of IgG adsorbed on the wells of the EIA plate was performed using a calibration curve prepared by a method in which IgG standard solutions having known IgG concentrations are dispensed into wells of an EIA plate which is the same as used above, and the amounts of IgG adsorbed on the surfaces of the wells are measured.

As mentioned above, the copolymers evaluated were copolymer (125) produced in Example 93, copolymer (126) produced in Example 94 and copolymer (135) produced in Example 97. FIG. 40 shows that the amount of IgG adsorbed on the non-coated well was approximately 5 μg/ml. The evaluated copolymers inhibit IgG adsorption onto the wells of the EIA plate, and the degree of inhibition is proportional to the copolymer concentration of the copolymer solution.

Example 117

Evaluation (2) of Plasma Protein Adsorption

Polysulfone-copolymer membranes (a) and (b), each produced in Example 113, were individually evaluated in the following manner. A polysulfone-copolymer membrane was secured to the bottom of a well of a 24-well plate by using a silicon ring, to obtain a well containing a polysulfone-copolymer membrane. On the other hand, a polysulfone membrane (as a control membrane) was secured to the bottom of another well of the 24-well plate to obtain a well containing a polysulfone membrane.

0.8 ml of an albumin solution containing 2 μg/ml of a purified human albumin (manufactured and sold by MP Biomedicals, U.S.A.) was dispensed into the wells containing a polysulfone-copolymer membrane and a polysulfone membrane obtained above, and was allowed to remain in contact with the membranes at 37° C. for 2 hours. Subsequently, the amounts of human albumin adsorbed on the membranes were determined by enzyme-linked immunosorbent assay (ELISA) using a horseradish peroxidase (HRP)-conjugated goat IgG fraction to human albumin (manufactured and sold by MP Biomedicals, U.S.A.).

The results are shown in Table 31 below. The determination of the amounts of albumin adsorbed on the membranes was performed using a calibration curve prepared by a method in which albumin standard solutions having known albumin concentrations are applied to the polysulfone membranes (which are the same as that used as a control membrane), and the amounts of albumin adsorbed on the polysulfone membranes are measured. The albumin adsorption of each polysulfone-copolymer membrane is expressed in terms of the percentage of the amount of albumin adsorbed on the polysulfone-copolymer membrane, based on the amount of albumin adsorbed on the polysulfone membrane.

As a result, both of the evaluated polysulfone-copolymer membranes (a) and (b) were found to be highly effective for inhibiting albumin adsorption.

TABLE 31

|  | Membrane (a) | Membrane (b) | polysulfone membrane |
|---|---|---|---|
| Copolymer of the present invention | Copolymer (125) | Copolymer (126) | — |
| Additional polymer used | Polysulfone | Polysulfone | Polysulfone |
| Human albumin adsorption (%) | 9% | 7% | 100% |

Example 118

Evaluation (3) of Plasma Protein Adsorption

Polysulfone-copolymer membranes (g) and (h), each produced in Example 114, were individually evaluated in the same manner as in Example 117.

The results are shown in Table 32 below. The determination of the amounts of albumin adsorbed on the membranes was performed using a calibration curve prepared by a method in which albumin standard solutions having known albumin concentrations are applied to the polysulfone membranes (which are the same as that used as a control membrane), and the amounts of albumin adsorbed on the polysulfone membranes are measured. The albumin adsorption of each polysulfone-copolymer membrane is expressed in terms of the percentage of the amount of albumin adsorbed on the polysulfone-copolymer membrane, based on the amount of albumin adsorbed on the polysulfone membrane.

As a result, both of the evaluated polysulfone-copolymer membranes (g) and (h) were found to be highly effective for inhibiting albumin adsorption.

TABLE 32

|  | Membrane (g) | Membrane (h) | polysulfone membrane |
|---|---|---|---|
| Copolymer of the present invention | Copolymer (125) | Copolymer (126) | — |
| Additional polymer used | Polysulfone | Polysulfone | Polysulfone |
| Human albumin adsorption (%) | 11% | 9% | 100% |

Example 119

Evaluation of Toxicity: Experiment for Determining the Toxicity of a Copolymer by Intravenous Injection to Mouse Two groups of female BALB/c mice (purchased from Japan SLC Inc., Japan), each consisting of three mice, were, respectively, given administration of copolymer (125) produced in Example 93 and copolymer (138) produced in Example 98. Specifically, each mouse received administration of a copolymer solution (in physiological saline) by tail-vein injection under conditions wherein the dose of the copolymer was 500 mg/kg and the volume of the copolymer solution administered was 25 ml/kg. The administration was performed only once. Separately, a group of three female BALB/c mice (purchased from Japan SLC Inc., Japan) was provided. Each mouse of the group received the administration of only physiological saline wherein the physiological saline was administered in the same manner as in the above-mentioned administration of the copolymer solution, to thereby obtain a control group of mice.

Evaluation was made on the toxicity of each copolymer in terms of the loss in the average body weight, based on the average initial body weight (i.e., the average body weight of the mice on day 1). A copolymer was defined as being toxic when the loss in the average body weight was 10% or more, based on the average initial body weight.

Figure 41:
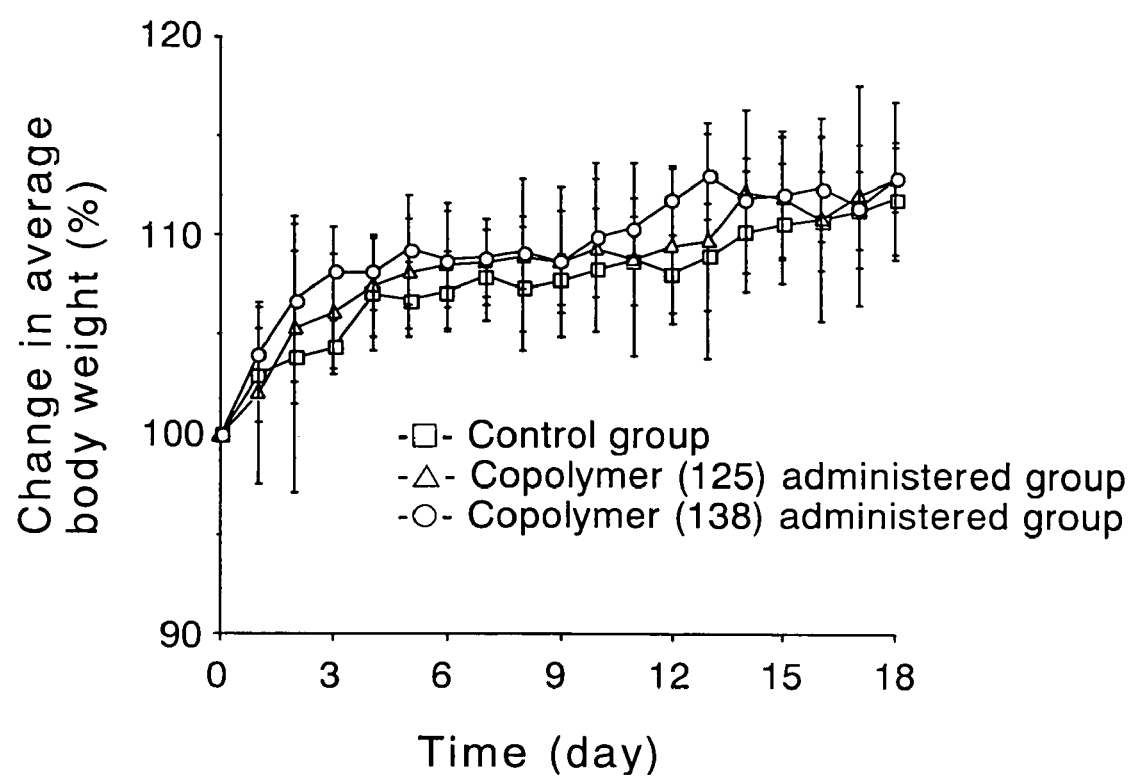
FIG. 41 is a graph showing the results of the evaluation of toxicity of copolymer (125) and copolymer (138) of the present invention, which evaluation is made in Example 119.
Figure 42:
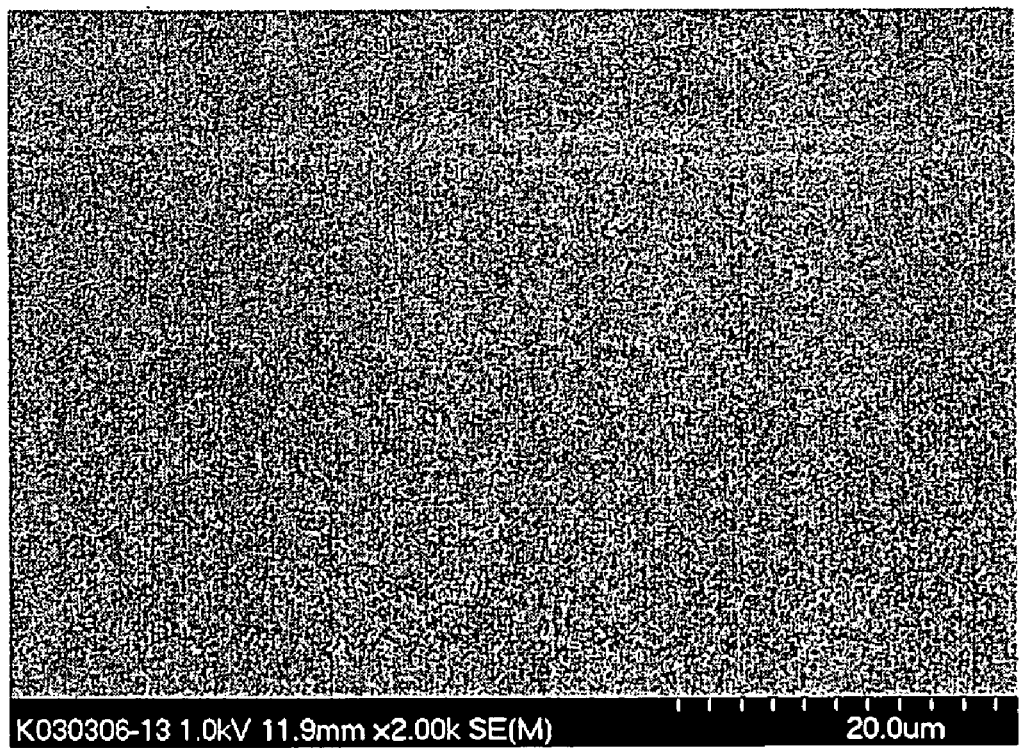
FIG. 42 is an SEM photograph of a PET film coated with copolymer (139), which PET film is obtained in Example 120.
Figure 43:
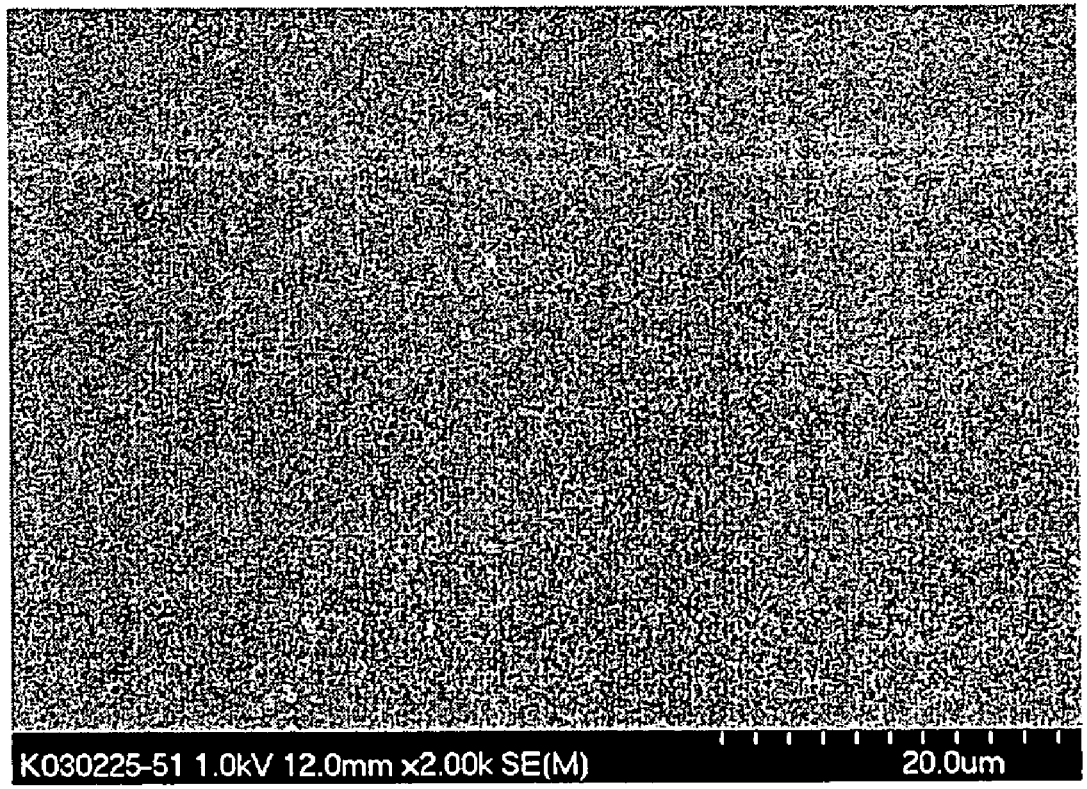
FIG. 43 is an SEM photograph of a PET film coated with copolymer (142), which PET film is obtained in Example 120.
Figure 44:
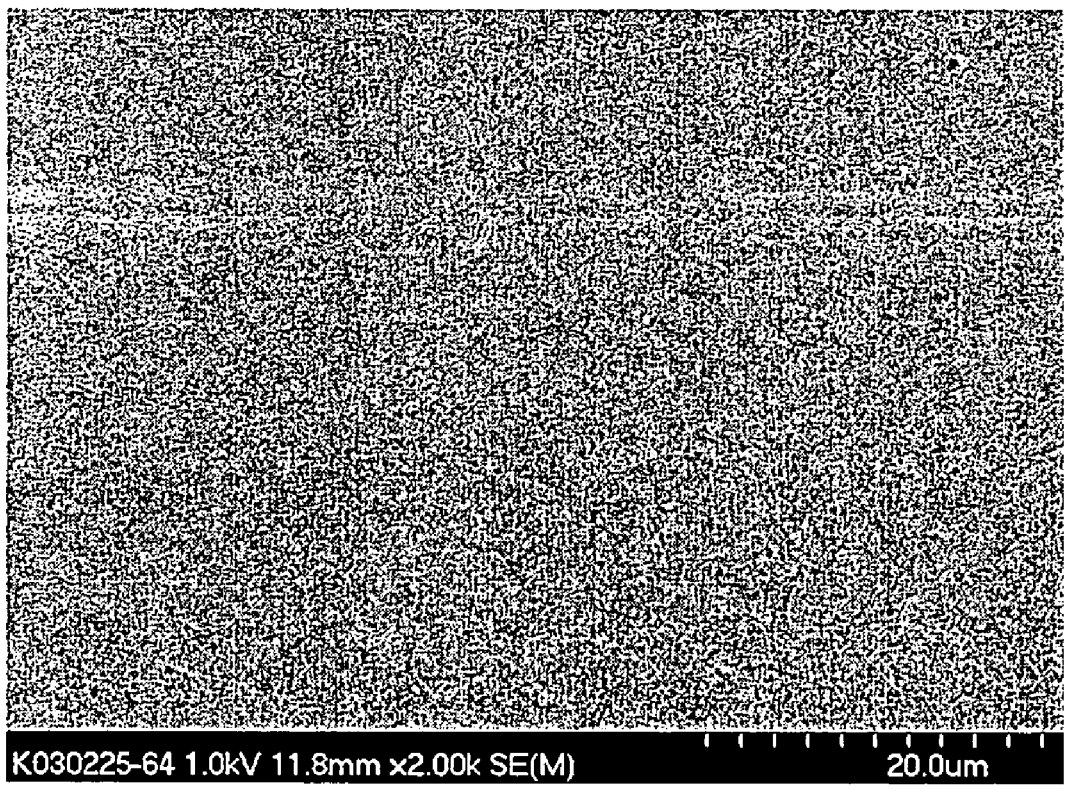
FIG. 44 is an SEM photograph of a PET film coated with copolymer (145), which PET film is obtained in Example 120.
Figure 45:
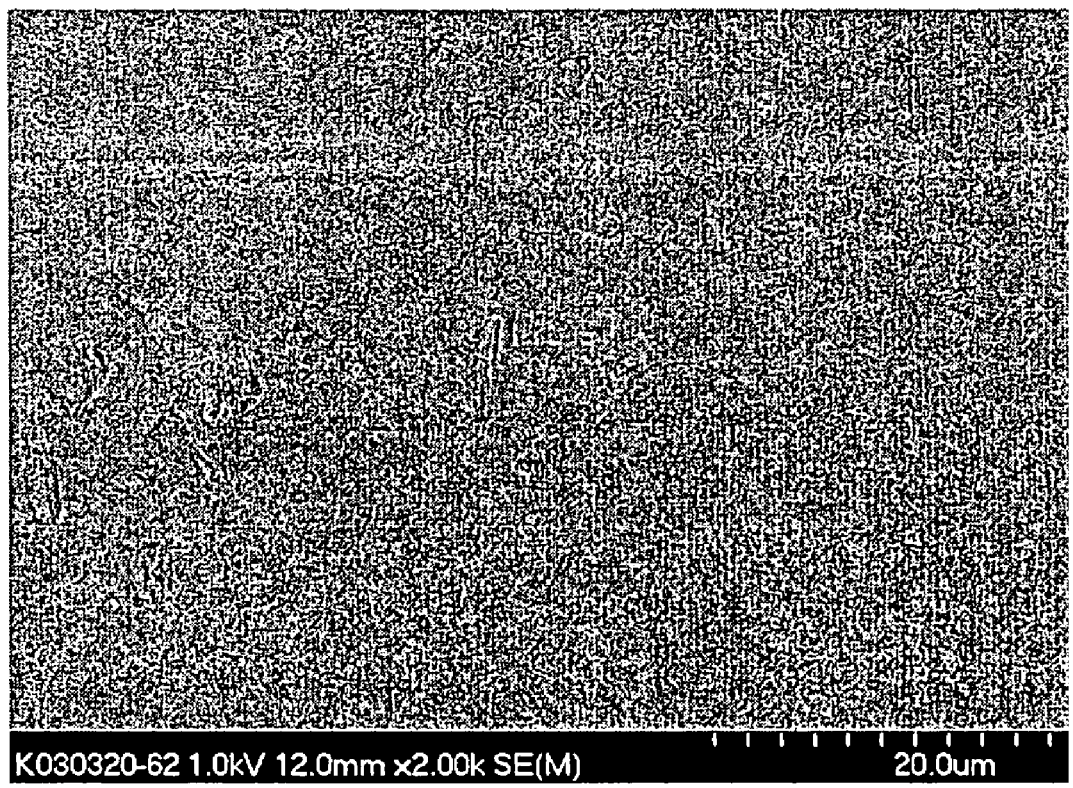
FIG. 45 is an SEM photograph of a PET film coated with copolymer (148), which PET film is obtained in Example 120.

The results are shown in FIG. 41. With respect to the groups which received the administration of the copolymer solutions, substantially no loss in the average body weight was observed after receiving the administration of the copolymer solution, namely, the loss observed in the average body weight was not more than 10% of the initial average body weight. Further, on each day on which the average body weight was determined, there was no significant difference in the average body weight as between the groups which had received the administration of the copolymer solution and the control group which had received the administration of physiological saline. Thus, both of copolymers (125) and (138) were found to have no toxicity.

Example 120

Evaluation of Human Platelet Adhesion: Experiment for Determining the Effect of a Resin to Inhibit the Adhesion of Platelets Copolymer (139) produced in Example 99, copolymer (142) produced in Example 100, copolymer (145) produced in Example 101 and copolymer (148) produced in Example 102 were individually evaluated in the following manner. A copolymer was dissolved in an aqueous 70% ethanol solution so as to obtain a copolymer solution having a copolymer concentration of 10 mg/ml. A polyethylene terephthalate (PET) film (thickness: 60 μm) was immersed in the obtained copolymer solution to cause the film to be coated with the copolymer, thereby obtaining a test sample. Human platelet adhesion to the obtained test sample was evaluated as follows.

Fresh human plasma containing sodium citrate as an anticoagulant was subjected to centrifugation at 1,000 rpm for 10 minutes, to thereby recover fresh human plasma (I) containing platelets. Remainder of the centrifuged fresh human plasma (after recovering fresh human plasma (I)) was subjected to further centrifugation at 2,500 rpm for 10 minutes, thereby obtaining fresh human plasma (II) containing platelets. Fresh human plasmas (I) and (II) were mixed together, thereby obtaining fresh human platelet rich plasma (PRP) having a platelet concentration of $300 \times 10^5$ cells/ml.

The test sample obtained above was placed in a well of a 24-well cell culture plate. The fresh human PRP obtained above was added to the well containing the test sample, and the PRP was allowed to be in contact with the test sample at 37° C. for 1 hour. Then, the test sample was taken out from the well and the test sample was washed with physiological saline. The platelets attached to the test sample were fixed using glutaraldehyde, and the test sample was observed through a scanning electron microscope (SEM). Also, substantially the same procedure as in this evaluation of the test sample was repeated except that a non-coated PET film was used instead of the test sample.

Figure 46:
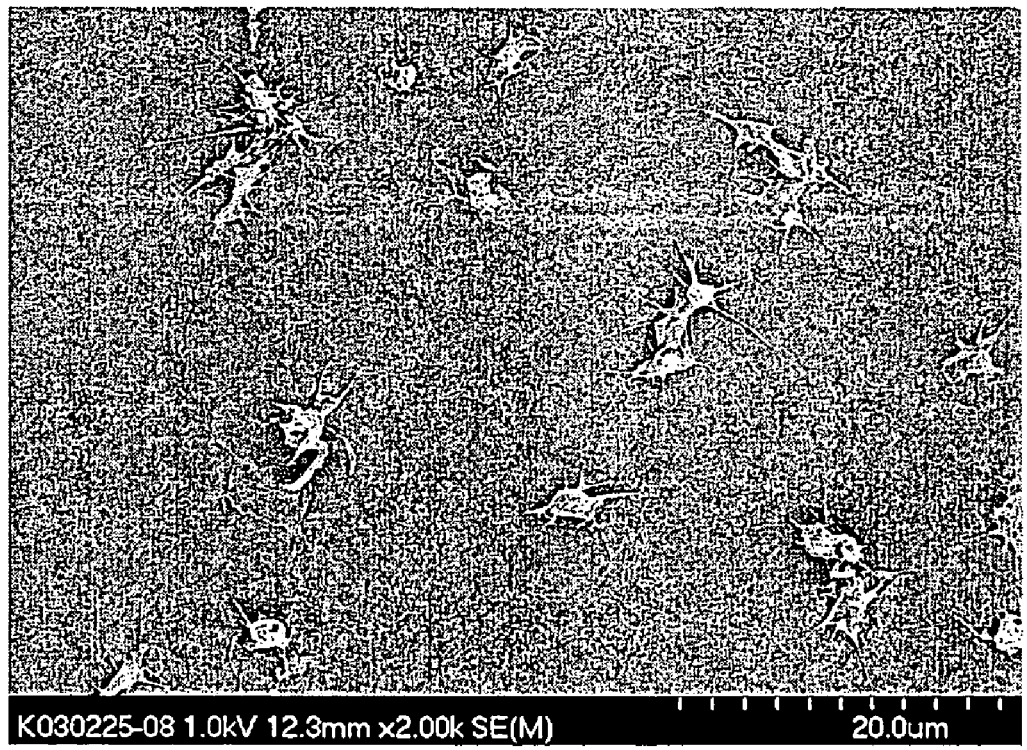
FIG. 46 is an SEM photograph of a non-coated PET film used in Example 120.
Figure 47A:
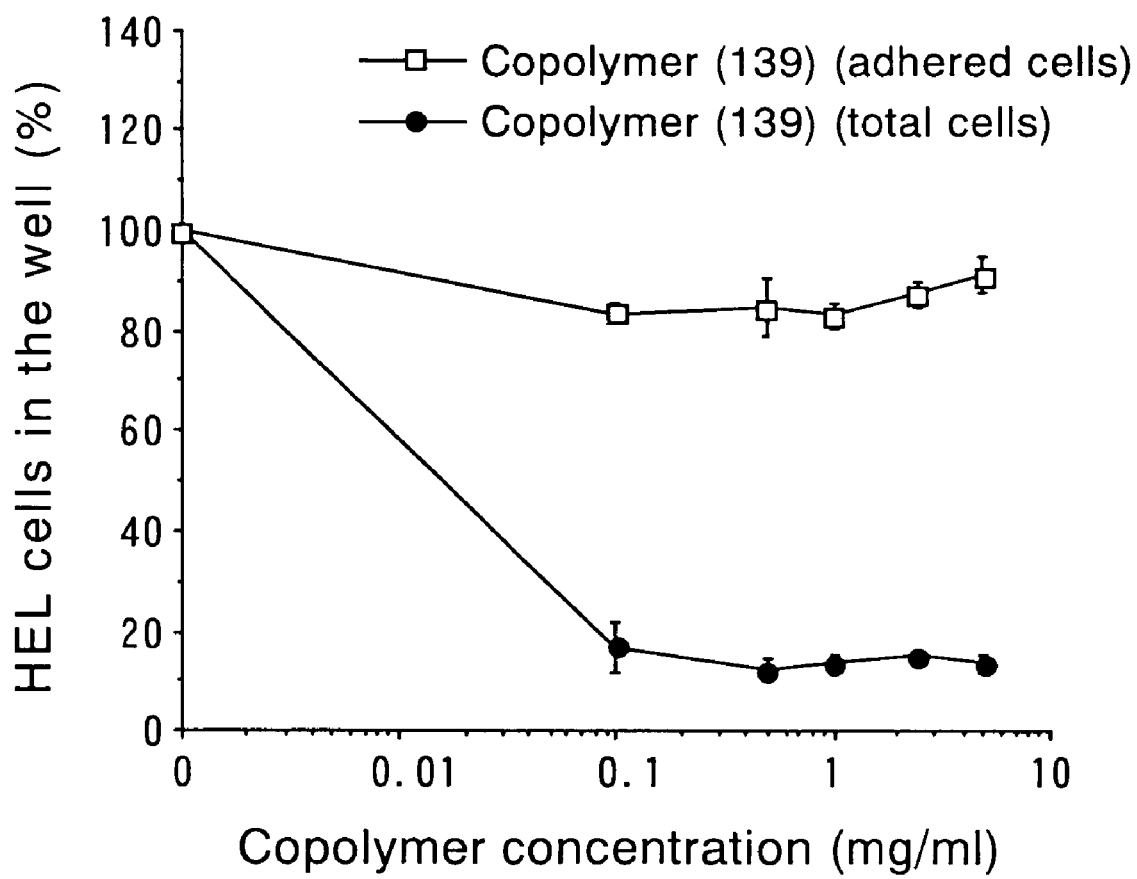
FIG. 47(a) is a graph showing the results of the evaluation of HEL cell (human lung cell) adhesion to copolymer (139), which evaluation is made in Example 121.
Figure 47B:
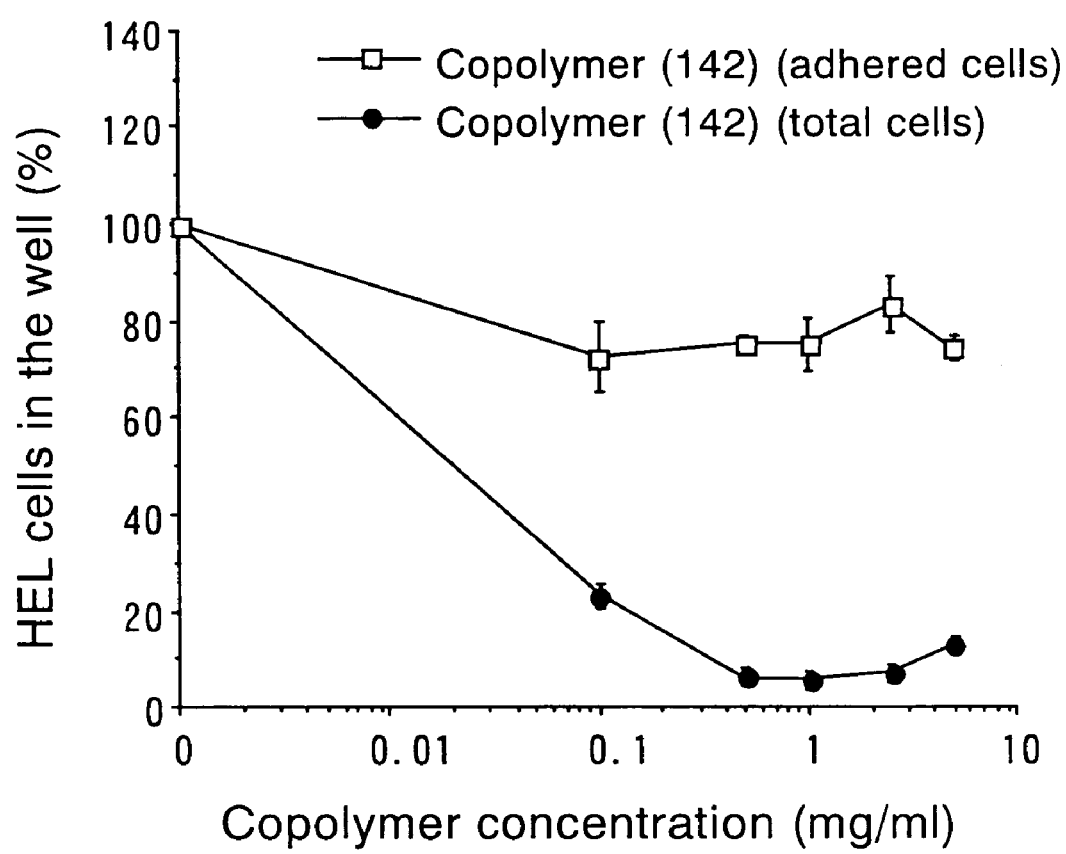
FIG. 47(b) is a graph showing the results of the evaluation of HEL cell (human lung cell) adhesion to copolymer (142), which evaluation is made in Example 121.
Figure 47C:
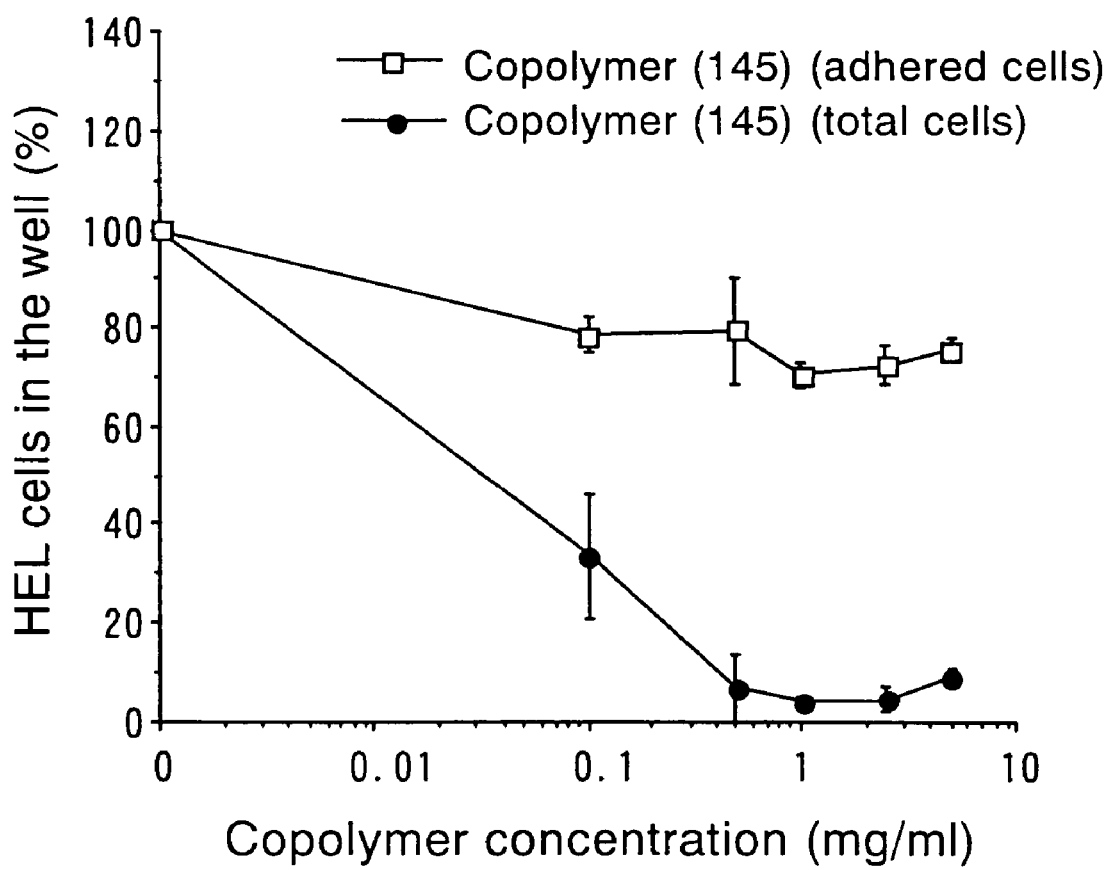
FIG. 47(c) is a graph showing the results of the evaluation of HEL cell (human lung cell) adhesion to copolymer (145), which evaluation is made in Example 121.
Figure 47D:
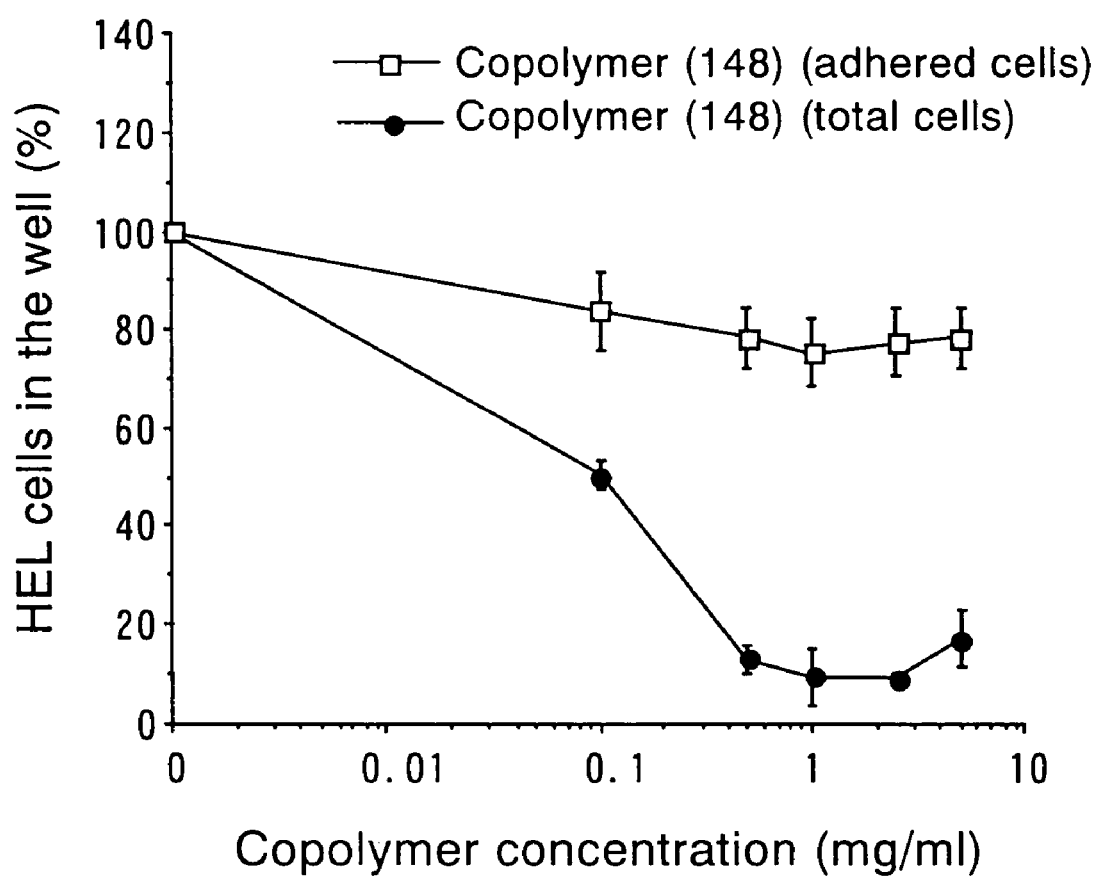
FIG. 47(d) is a graph showing the results of the evaluation of HEL cell (human lung cell) adhesion to copolymer (148), which evaluation is made in Example 121.

Scanning electron photomicrographs of the test samples of copolymer-coated PET films (prepared using copolymers (139), (142), (145) and (148)) are shown in FIGS. 42, 43, 44 and 45, respectively, and a scanning electron photomicrograph of the non-coated PET film is shown in FIG. 46. Platelets adhered to the non-coated PET film (see FIG. 46), but platelet adhesion was not observed on any of the copolymer-coated PET films (see FIGS. 42 to 45).

Example 121

Evaluation of Human Cell Adhesion: Experiment for Determining the Effect of a Copolymer to Inhibit the Adhesion of Cells and Experiment for Determining the Cell Toxicity of a Copolymer Copolymer (139) produced in Example 99, copolymer (142) produced in Example 100, copolymer (145) produced in Example 101 and copolymer (148) produced in Example 102 were individually evaluated in the following manner. Copolymer solutions respectively having copolymer concentrations of 5, 2.5, 1, 0.5 and 0.1 mg/ml were prepared by dissolving different amounts of a copolymer individually in an aqueous 70% ethanol solution. 0.2 ml of each of the obtained copolymer solutions was individually dispensed into a well of a 96-well microplate. On the other hand, an aqueous 70% ethanol solution was dispensed into another well of the microplate to thereby provide a well containing an aqueous 70% ethanol solution (wherein the well was intended to provide the below-mentioned "non-coated well" used as a control well). Then, the microplate was allowed to stand still at 4° C. overnight to thereby cause the wells (containing the copolymer solutions) to be coated with the copolymer. Subsequently, the copolymer solutions and aqueous 70% ethanol solution in the wells were removed by suction, followed by drying, to thereby obtain a microplate having copolymer-coated wells and a non-coated well (wherein the latter was intended for use as a control well). Adhesion of human cells to the copolymer-coated wells was evaluated as follows.

0.1 ml of a suspension of HEL cells (human lung cells) containing 3×10$^5$ HEL cells/ml was dispensed into the copolymer-coated wells and non-coated well of the above-obtained microplate, and the cells were cultured for 2 hours. Thereafter, the number of viable cells adhered to each of the copolymer-coated wells and non-coated well of the microplate was determined by means of CellTiter 96® AQ$_{ueous}$ Assay System (manufactured and sold by Promega Corporation, U.S.A.).

In addition, the toxicity of each of the above-mentioned copolymers (139), (142), (145) and (148) was evaluated in the following manner. A microplate having copolymer-coated wells and a non-coated well (wherein the latter was intended for use as a control well) was prepared in the same manner as mentioned above, and HEL cells were cultured in the copolymer-coated wells and non-coated well of the prepared microplate in the same manner as mentioned above. Then, with respect to each of the copolymer-coated wells and non-coated well of the microplate, the number of viable cells adhered to the well, and the total number of viable cells adhered to the well and viable cells which were not adhered to the well but contained in the cell suspension, were determined by means of CellTiter 96® AQ$_{ueous}$ Assay System (manufactured and sold by Promega Corporation, U.S.A.).

The results of the above-mentioned evaluations of copolymers (139), (142), (145) and (148) are shown in FIGS. 47(a), 47(b), 47(c) and 47(d), respectively. In each of FIGS. 47(a), 47(b), 47(c) and 47(d), the cell adhesion to each copolymer-coated well is expressed in terms of the percentage of the number of cells adhered to the copolymer-coated well, based on the number of cells adhered to the non-coated well. As shown in FIGS. 47(a), 47(b), 47(c) and 47(d), copolymers (139), (142), (145) and (148) inhibit cell adhesion, and the degree of inhibition is proportional to the copolymer concentration of the copolymer solution. (In each of FIGS. 47(a), 47(b), 47(c) and 47(d), the cell adhesion inhibitory activity of the copolymer is indicated by ●.)

Further, the number of viable cells in each copolymer-coated well is expressed in terms of the percentage of the number of viable cells (i.e., the total number of viable cells adhered to the well and viable cells contained in the cell suspension) in the copolymer-coated well, based on the number of viable cells in the non-coated well. As shown in each of FIGS. 47(a), 47(b), 47(c) and 47(d), the number of viable cells in each copolymer-coated well was at least 70%, based on the number of viable cells in the non-coated well. That is, with respect to all of the concentrations at which the copolymers were evaluated, each of copolymers (139), (142), (145) and (148) was found to have no toxicity to human cells. (In each of FIGS. 47(a), 47(b), 47(c) and 47(d), the non-toxic property of the copolymer is indicated by D.)

Example 122

Evaluation (1) of Plasma Protein Adsorption

Copolymer (139) produced in Example 99, copolymer (142) produced in Example 100, copolymer (145) produced in Example 101 and copolymer (148) produced in Example 102 were individually evaluated in the following manner. Copolymer solutions respectively having copolymer concentrations of 10, 1, 0.1, 0.01 and 0.001 mg/ml were prepared by dissolving different amounts of a copolymer individually in an aqueous 70% ethanol solution. 0.2 ml of each of the obtained copolymer solutions was individually dispensed into a well of Coaster 96-well EIA plate (Product No. 3590, manufactured and sold by Corning Incorporated, U.S.A.). On the other hand, an aqueous 70% ethanol solution was dispensed into another well of the EIA plate to thereby provide a well containing an aqueous 70% ethanol solution (wherein the well was intended to provide the below-mentioned "non-coated well" used as a control well). Then, the EIA plate was allowed to stand still at 4° C. overnight to thereby cause the wells (containing the copolymer solutions) to be coated with the copolymer. Subsequently, the copolymer solutions and aqueous 70% ethanol solution in the wells were removed by suction, followed by drying, to thereby obtain an EIA plate having copolymer-coated wells and a non-coated well (wherein the latter was intended for use as a control well). Adhesion of immunoglobulin G to the copolymer-coated wells was evaluated as follows.

0.1 ml of an immunoglobulin G solution containing 5 μg/ml of a purified human immunoglobulin G (IgG) (manufactured and sold by MP Biomedicals, U.S.A.) was dispensed into the copolymer-coated wells and non-coated well of the above-obtained EIA plate, and was allowed to remain in contact with the surfaces of the wells at 37° C. for 2 hours. Subsequently, the amounts of human IgG adsorbed on the surfaces of the wells were determined by enzyme-linked immunosorbent assay (ELISA) using a horseradish peroxidase (HRP)-conjugated goat IgG fraction to human IgG (whole molecule) (manufactured and sold by MP Biomedicals, U.S.A.).

Figure 48:
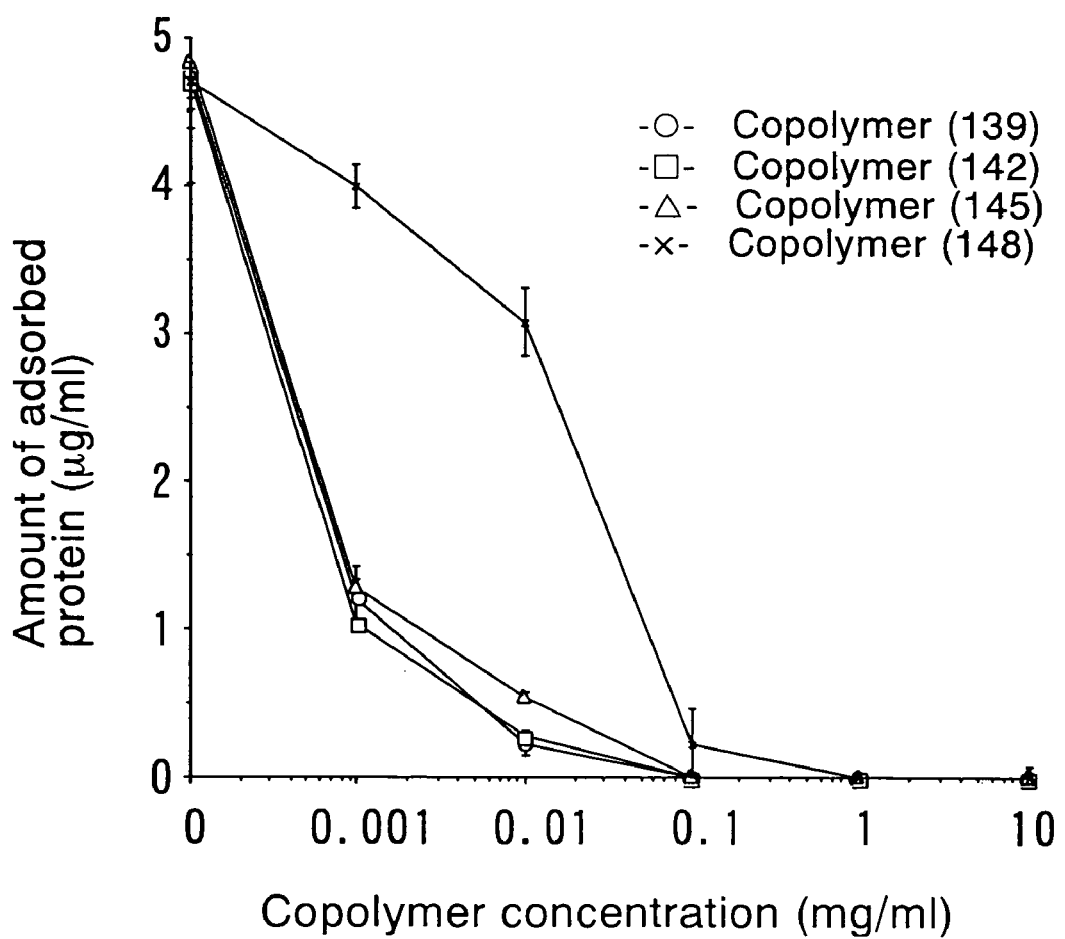
FIG. 48 is a graph showing the results of the evaluation of human immunoglobulin adhesion, which evaluation is made in Example 122.

The results are shown in FIG. 48. The determination of the amounts of IgG adsorbed on the wells of the EIA plate was performed using a calibration curve prepared by a method in which IgG standard solutions having known IgG concentrations are dispensed into wells of an EIA plate which is the same as used above, and the amounts of IgG adsorbed on the surfaces of the wells are measured.

As mentioned above, the copolymers evaluated were copolymer (139) produced in Example 99, copolymer (142) produced in Example 100, copolymer (145) produced in Example 101 and copolymer (148) produced in Example 102. FIG. 48 shows that the amount of IgG adsorbed on the non-coated well was approximately 5 μg/ml. The evaluated copolymers inhibit IgG adsorption onto the wells of the EIA plate, and the degree of inhibition is proportional to the copolymer concentration of the copolymer solution.

Example 123

Evaluation (2) of Plasma Protein Adsorption

Copolymer (139) produced in Example 99, copolymer (142) produced in Example 100, copolymer (145) produced in Example 101 and copolymer (148) produced in Example 102 were individually evaluated in the following manner. An EIA plate having copolymer-coated wells and a non-coated well (wherein the latter was intended for use as a control well) was prepared in the same manner as in Example 122. Adhesion of fibrinogen to the copolymer-coated wells was evaluated as follows.

0.1 ml of a fibrinogen solution containing 5 μg/ml of a purified human fibrinogen (manufactured and sold by Biogenesis Inc., U.S.A.) was dispensed into the copolymer-coated wells and non-coated well of the above-obtained EIA plate, and was allowed to remain in contact with the surfaces of the wells at 37° C. for 2 hours. Subsequently, the amounts of human fibrinogen adsorbed on the surfaces of the wells were determined by ELISA using a horseradish peroxidase (HRP)-conjugated goat IgG to human fibrinogen (manufactured and sold by EYlaboratories, Inc, U.S.A.).

Figure 49:
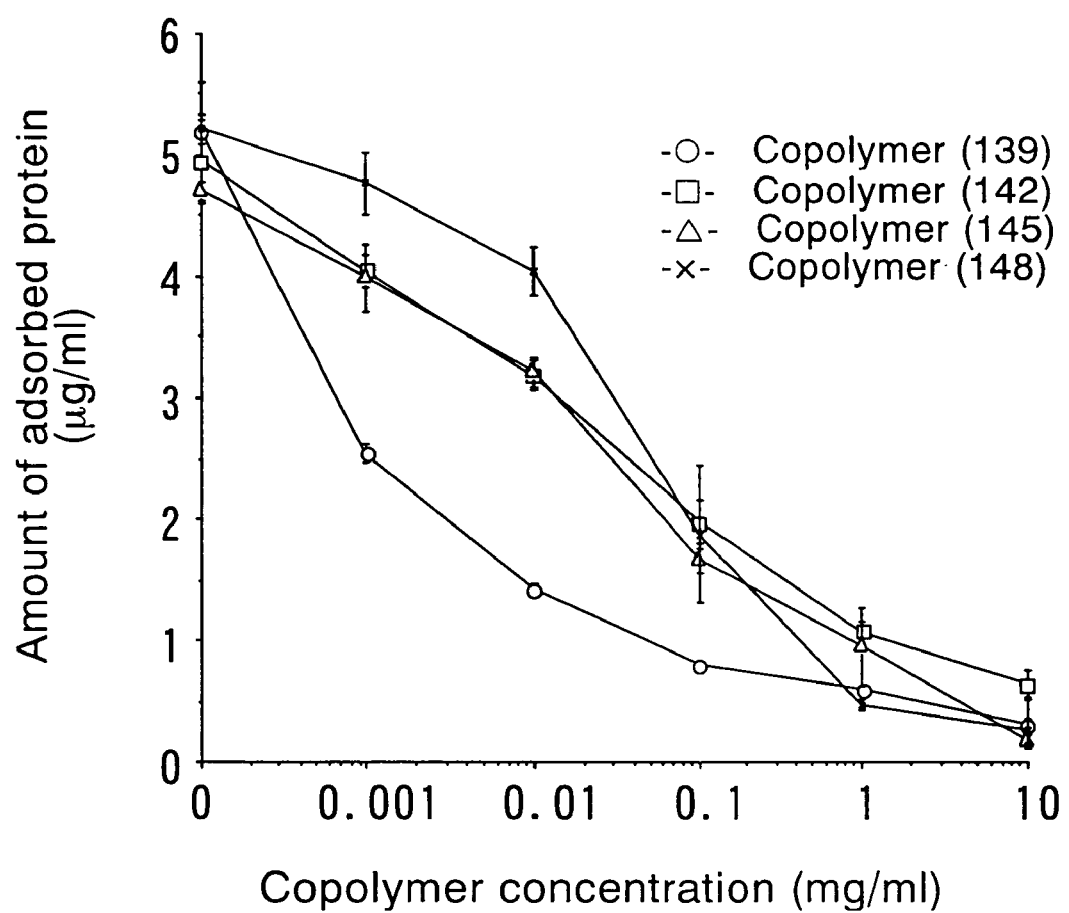
FIG. 49 is a graph showing the results of the evaluation of human fibrinogen adhesion, which evaluation is made in Example 123.

The results are shown in FIG. 49. The determination of the amounts of fibrinogen adsorbed on the wells of the EIA plate was performed using a calibration curve prepared by a method in which fibrinogen standard solutions having known fibrinogen concentrations are dispensed into wells of an EIA plate which is the same as used above, and the amounts of fibrinogen adsorbed on the surfaces of the wells are measured.

As mentioned above, the copolymers evaluated were copolymer (139) produced in Example 99, copolymer (142) produced in Example 100, copolymer (145) produced in Example 101 and copolymer (148) produced in Example 102. FIG. 49 shows that the amount of fibrinogen adsorbed on the non-coated well was approximately 5 μg/ml. The evaluated copolymers inhibit fibrinogen adsorption onto the wells of the EIA plate, and the degree of inhibition is proportional to the copolymer concentration of the copolymer solution.

Example 124

Evaluation of Toxicity: Experiment for Determining the Toxicity of a Copolymer by Intravenous Injection to Mouse Two groups of female BALB/c mice (purchased from Japan SLC Inc., Japan), each group consisting of three mice, were, respectively, given administration of copolymer (139) produced in Example 99 and copolymer (157) produced in Example 105. Specifically, each mouse received administration of a copolymer solution (in physiological saline) by tail-vein injection under conditions wherein the dose of the copolymer was 1 g/kg and the volume of the copolymer solution administered was 25 ml/kg. The administration was performed intermittently once a week on days 2, 9 and 16 from the start of the experiment (i.e., 3 administrations in total). Separately, two groups of female BALB/c mice (purchased from Japan SLC Inc., Japan), each group consisting of three mice, were provided. Each mouse of one group of the two groups received the administration of only physiological saline wherein the physiological saline was administered in the same manner as in the above-mentioned administration of the copolymer solution, to thereby obtain a control group of mice. The other group of the two groups of mice did not receive any administration, to thereby obtain a normal group of mice.

Evaluation was made on the toxicity of each copolymer in terms of the loss in the average body weight, based on the average initial body weight (i.e., the average body weight of the mice on day 1). A copolymer was defined as being toxic when the loss in the average body weight was 10% or more, base on the average initial body weight.

Figure 50:
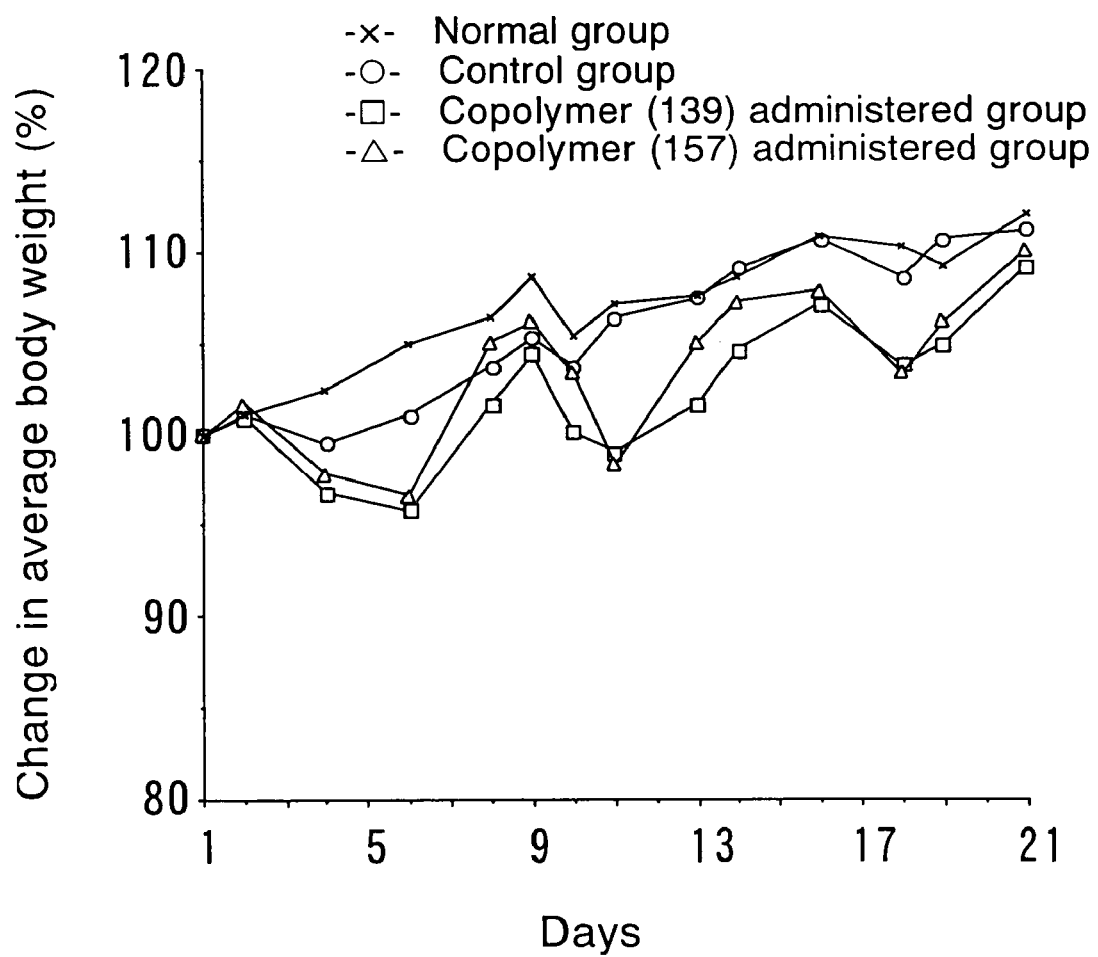
FIG. 50 is a graph showing the results of the evaluation of toxicity of copolymers of the present invention, which evaluation is made in Example 124.

The results are shown in FIG. 50. With respect to the groups which received the administration of the copolymer solutions, some loss in the average body weight was observed after receiving the administration of the copolymer solutions, but this loss in the average body weight was not more than 10%, based on the initial average body weight. Further, few days after the administration of the copolymer solutions, the mice regained their weights to a level which was comparable to the average body weight of the control group which had received administration of only physiological saline and the normal group of mouse which had not received any administration. Thus, both of copolymers (139) and (157) were found to have no toxicity.

Example 125

The anti-tissue adhesion property of gel sheet (158) (which is a copolymer gel in the form of a sheet) prepared in Example 105, was evaluated in the following manner.

Fourteen female rats (Crj-CD(SD), 7 weeks old, purchased from Charles River Japan Inc., Japan) were divided into two groups, each consisting of seven rats. One of the two groups of rats was subjected to pentobarbital anesthesia, and an incision was made along the median line of the abdomen, whereupon the cecum was taken out from the abdominal cavity of the rat. The surface of the cecum was scratched with a gauze to remove about half of the serous membrane from the cecum, thus injuring the cecum. A gel sheet (size: 4×4 cm) was applied to the serous membrane-removed, injured portion of the cecum to cover the injury, and the thus treated, injured cecum was returned to the abdominal cavity of the rat, followed by suturing of the incision. By such procedure, a group of rats was caused to have injured ceca and treated using gel sheet (158), thereby obtaining a copolymer-treated group of rats. Separately, with respect to the other group of 7 rats, the same procedure as described above was repeated except that the application of a gel sheet was not performed and the injured cecum as such was returned to the abdominal cavity of each rat, to thereby obtain a non-treated group of rats as a control group. After a period of five days from the surgical operation, the rats of the two groups were subjected to surgical anatomy to determine whether or not tissue adhesion was present. The tissue adhesion was defined as an interfacial, fibrous adhesion which has a certain thickness and which binds together adjacent surfaces with such a strength that they cannot be easily separated from each other even when they are pulled in opposite directions using a forceps. The results are shown in Table 33 below.

TABLE 33

|  | Gel sheet (158) | Control (no treatment) |
| --- | --- | --- |
| Tissue condition | No disorder | Slight inflammation |
| Ratio of mice having tissue adhesion | 2/7 | 5/7 |

As shown in Table 33, the ratio of mice having tissue adhesion was low in the group of rats which was treated with the gel sheet (158), as compared to the case of the group of non-treated rats.

Example 126

The wound healing promoting effect of the gel sheet (158) prepared in Example 105, was evaluated in the following manner.

Ten female rats (Crj-CD(SD), 7 weeks old, purchased from Charles River Japan Inc., Japan) were divided into two groups, each consisting of five rats. The fur of the dorsal region of each rat of the two groups was shaved, and the rats were subjected to pentobarbital anesthesia. A part of the dorsal skin of each rat was removed so as to form a square wound (size: 2×2 cm) with complete skin loss. Gel sheet (158) was used to treat one group of wounded rats, thereby obtaining one group of polymer-treated rats. Specifically, the wound of each rat of one group was covered with a gel sheet (size: 2×2 cm) and, then, the gel sheet was covered with a medical gauze of a non-woven fabric. The medical gauze was secured in place by suturing the gauze to the epithelium which was exposed at the wound. Separately, with respect to the other group of five rats, the same procedure as described above was repeated except that a gel sheet was not used (i.e., the wound was covered only with a medical gauze, which was secured in place by suturing the gauze to the epithelium which was exposed at the wound), to thereby obtain a non-treated group of rats. On days 0, 5 and 7 from the surgical operation, measurement was made of the size (area) of the wounds of the mice of the two groups, and the level of wound healing was determined in terms of the average wound area remaining ratio (%), namely the ratio of the average wound area on a day on which the size of the wound was measured to the average wound area on day 0. Specifically, the wound area remaining ratio (%) was obtained according to the following formula:

Wound area remaining ratio (%)={(product of the length and width of the wound on a day on which the size of the wound was measured)/(product of the length and width of the wound on day 0)}× 100.

The results are shown in Table 34 below.

TABLE 34

| Experimental Group | Average wound area remaining ratio (%) | | |
|---|---|---|---|
| | Day 0 | Day 5 | Day 7 |
| Copolymer (158) | 100 | 70 | 50 |
| No treatment with copolymer | 100 | 90 | 80 |

Table 34 shows that the copolymer of the present invention in the form of a gel sheet was able to promote the wound healing of rats.

Example 127

Each of three female rats (Crj-CD(SD), 7 weeks old, purchased from Charles River Japan Inc., Japan) was subjected to pentobarbital anesthesia, and an incision was made along the median line of the abdomen, whereupon the cecum was taken out from the abdominal cavity of the rat. The surface of the cecum was scratched with a gauze to remove about half of the serous membrane from the cecum, thus injuring the cecum. Gel sheet (174) (size: 4×4 cm) produced in Example 111 was applied to the serous membrane-removed, injured portion of the cecum to cover the injury, and the thus treated, injured cecum was returned to the abdominal cavity of the rat, followed by suturing of the incision. By such procedure, the group of rats was caused to have injured ceca and treated using gel sheet (174), thereby obtaining a polymer-treated group of rats.

After a period of five days from the surgical operation, the rats were subjected to surgical anatomy to determine whether or not tissue adhesion was present. The tissue adhesion was defined as an interfacial, fibrous adhesion which has a certain thickness and which binds together the gel sheet and an adjacent tissue with such a strength that they cannot be easily separated from each other even when they are pulled in opposite directions using a forceps. As a result, no tissue adhesion was observed in the polymer-treated group of rats, and the gel sheet remained transparent without any adsorption of proteins.

Example 128

Evaluation of Toxicity

Two groups of female BALB/c mice (purchased from Japan SLC Inc., Japan), each group consisting of five mice, were given administration of copolymer (161) produced in Example 106. Specifically, each mouse of the two groups of mice received administration of a copolymer solution (in physiological saline) by tail-vein injection, wherein the dose of the copolymer was 1,000 mg/kg for one group of mice and was 300 mg/kg for the other group of mice. The volume of the copolymer solution administered was 25 ml/kg for both groups of mice. The administration was performed intermittently on days 0, 3 and 6 from the start of the experiment (i.e., 3 administrations in total). Separately, a group of five female BALB/c mice (purchased from Japan SLC Inc., Japan) was provided. Each mouse of the group received the administration of only physiological saline wherein the physiological saline was administered in the same manner as in the above-mentioned administration of the copolymer solution, to thereby obtain a control group of mice.

Evaluation was made on the toxicity of the copolymer in terms of the loss in the average body weight, based on the average initial body weight (i.e., the average body weight of the mice on day 0). The copolymer was defined as being toxic when the loss in the average body weight was 10% or more, based on the average initial body weight.

Figure 51:
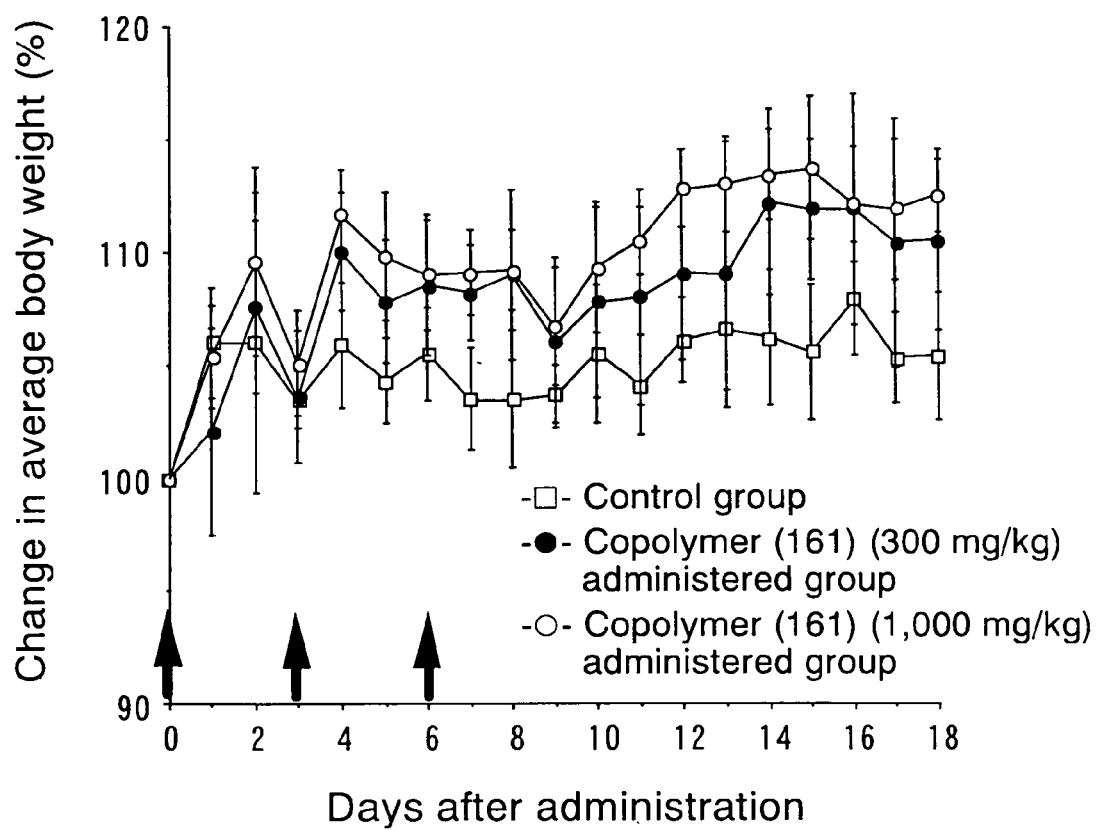
FIG. 51 is a graph showing the results of the evaluation of toxicity of copolymers of the present invention, which evaluation is made in Example 128.

The results are shown in FIG. 51. With respect to the groups of mice which received the administration of the copolymer solutions, the loss observed in the average body weight was not more than 10%, based on the initial average body weight. Further, on each day on which the average body weight was determined, there was no significant difference in the average body weight as between the group of mice which had received the administration of the copolymer at the dose of 1,000 mg/kg, the group which had received the administration of the copolymer at the dose of 300 mg/kg, and the control group which had received the administration of physiological saline. Thus, copolymer (161) was found to have no toxicity. In FIG. 51, an average body weight±standard deviation (SD) is plotted, and the up arrows indicate the days on which the copolymer solution or physiological saline was administered.

Example 129 and Comparative Example 2

Copolymer (125) produced in Example 93 was dissolved in purified water so as to obtain a 1% by weight aqueous solution of copolymer (125). Separately, 10 g of a commercially available monoalkyl quaternary ammonium salt was dissolved in purified water so as to obtain a 1% by weight aqueous solution of monoalkyl quaternary ammonium salt. Each of the obtained solution of copolymer (125) and the obtained solution of monoalkyl quaternary ammonium salt was individually evaluated with respect to the antistatic effects and the sensory properties, as follows.

Twenty Japanese women (age: 22 to 40 years old) who were irritable by static electricity were randomly divided into two groups to thereby obtain group A and group B each consisting of 10 women. The women of group A were asked to continue to apply the solution of copolymer (125) to their skins for 1 month (Example 129), and the women of group B were asked to continue to apply the solution of monoalkyl quaternary ammonium salt to their skins for 1 month (Comparative Example 2). After the 1-month period during which group A and group B respectively continued to use the solution of copolymer (125) and the solution of monoalkyl quaternary ammonium salt, the anti-static effects of these solutions on the skin and the sensory properties of these solutions were evaluated.

The results are shown in Table 35 below. As shown in Table 35, the solution of the copolymer of the present invention (i.e., copolymer (125)) exhibited excellent properties with respect to the sensory properties and the antistatic effects on the skin, as compared to those properties of the solution of monoalkyl quaternary ammonium salt.

TABLE 35

| Evaluation of performance | | Example 129 Copolymer (125) Group A | Comparative Example 2 Monoalkyl quaternary ammonium salt Group B |
|---|---|---|---|
| Antistatic effects | Static electricity can be prevented from accumulating on the clothes | 9/10 | 2/10 |
|  | Dirt can be prevented from attaching to the skin | 8/10 | 1/10 |
| Sensory Properties | Surface of the skin becomes tacky | 0/10 | 0/10 |
|  | Solution spreads well over the skin | 8/10 | 3/10 |
|  | Skin becomes smooth | 9/10 | 2/10 |
|  | Surface of the skin becomes greasy | 0/10 | 0/10 |
|  | Solution is well compatible with the skin | 9/10 | 4/10 |

Example 130

Stimulation inhibitory properties of each of copolymers (126) and (128) produced in Example 94 were evaluated in the following manner. Using copolymers (126) and (128) individually, copolymer solutions respectively having copolymer concentrations of 0.1, 0.05 and 0.01% by weight were prepared by dissolving a copolymer in purified water. To each of the prepared copolymer solutions was added a piece of a 100% cotton fabric so as to impregnate the fabric with the copolymer solution. The fabrics were taken out from the solutions, wringed lightly and dried in air to thereby obtain copolymer-impregnated fabrics. Discs (diameter: 6 mm) were stamped out from each of the obtained fabrics.

A mother liquor of Allergen Scratch Extract for Diagnosis "Cedar Pollen" was diluted 10-fold with a mixture of purified water and glycerol (water:glycerol ratio=1:1) to thereby obtain a solution of an allergenic substance. 10 µl of the obtained solution of an allergenic substance was dropped on each of the above-prepared discs of fabric to thereby obtain test specimens each containing an allergenic substance and a copolymer (as a stimulation inhibitory substance).

Separately, discs (diameter: 6 mm) were stamped out from a 100% cotton fabric (which is same as used above), and 10 µl of the obtained allergen solution was dropped on each of the above-prepared discs, to thereby obtain control specimens containing only an allergenic substance.

The stimulation inhibitory properties of each of the above-prepared test specimens each containing an allergenic substance and a copolymer and the above-prepared control specimens containing only an allergenic substance, were evaluated as follows. Each of the test specimens and the control specimens was individually pressed lightly onto the skin of the antebrachial region of each of five subjects having allergy to cedar pollen and the test specimens and the control specimens were held on the skin for 20 minutes. Subsequently, the test specimens and the control specimens were removed from the skin. Twenty minutes after the removal of the test specimens and the control specimens, each of the portions of the skin where the test specimens and control specimens had been held was visually examined to detect any skin allergic reaction. The severity of the skin allergic reaction was evaluated in accordance with the criteria for allergy which are shown in Table 36 below. The allergenic property of each of the test specimens and the control specimens was evaluated using an allergy index score which is calculated in accordance with the following formula: (average of the scores obtained from 5 subjects)×100. The results are shown in Table 37.

From the results shown in Table 37 below, it was found that the copolymer of the present invention has a stimulation inhibitory property. Since the copolymer was found to be able to decrease the experimental allergenic stimulation when the copolymer was coated onto fibers, it is expected that the copolymer of the present invention can be used as a coating not only for fibers but also for various materials other than fibers.

TABLE 36

| Skin Allergic Reaction | Criteria | Score |
|---|---|---|
| No reaction | − | 0.0 |
| Slight local redness | ± | 0.5 |
| Evident swelling (size: less than 5 mm) | + | 1.0 |
| Evident swelling (size: 5 mm or more) | ++ | 2.0 |

TABLE 37

| No. | Copolymer | Concentration (% by weight) | Allergy index score |
|---|---|---|---|
| 1 | (126) | 0.1 | 30 |
| 2 | (126) | 0.05 | 20 |
| 3 | (126) | 0.01 | 20 |
| 4 | (128) | 0.1 | 20 |
| 5 | (128) | 0.05 | 30 |
| 6 | (128) | 0.01 | 20 |
| 7 | None | — | 110 |

Example 131 and Comparative Example 3

Detergencies of Copolymer (141), Copolymer (144) and a Pluronic Surfactant, for Removing Proteins from Contact Lenses In accordance with the formulations shown in Table 38, all of the components were dissolved in purified water, thereby obtaining three contact lens cleansing solutions respectively containing, as detergents, copolymer (141) produced in Example 99, copolymer (144) produced in Example 100 and a conventional Pluronic surfactant. Each of the obtained contact lens cleansing solutions was evaluated in the following manner.

An artificial tear containing an albumin, γ-globulin and a lysozyme was prepared in accordance with the FDA formulation and used as a protein solution for forming protein dirt on the contact lenses. Commercially available hard contact lenses were provided and the surface of each lens was washed to thereby remove the preservation solution (used for shipping the lenses) from the lenses. Each of the washed contact lenses was individually placed in 5 ml of the artificial tear at 70° C. for 3 hours to form protein dirt adhered to the contact lenses, thereby obtaining dirt-carrying contact lenses.

The thus obtained dirt-carrying contact lenses were individually immersed in 5 ml of the above-prepared contact lens cleansing solution at room temperature for 4 hours to cleanse the contact lenses. Subsequently, the contact lenses were individually rinsed three times with 500 ml of physiological saline and then immersed in an aqueous sodium carbonate containing 1% SDS at 37° C. overnight to extract the protein dirt remaining on the contact lens, thereby obtaining a protein extract.

Separately, a dirt-carrying contact lens was prepared in the same manner as mentioned above. The dirt-carrying contact lens was immersed in an aqueous sodium carbonate containing 1% SDS at 37° C. overnight to extract the protein dirt adhered to the contact lens, thereby obtaining a control protein extract.

The protein concentrations of the above-obtained protein extracts were individually determined using Micro BCA kit (manufactured and sold by Pierce Biotechnology, Inc., U.S.A.), to thereby determine the amounts of protein dirt remaining on the contact lenses after immersing in the contact lens cleansing solutions. Further, the protein concentration of the control protein extract was also determined in the same manner as mentioned above, to thereby determine the amount of protein dirt present on the contact lens before immersing in a contact lens cleansing solution. Detergency of each of the contact lens cleansing solutions, for removing the protein dirt from the contact lense, was evaluated in terms of a protein dirt removal ratio (%) which is calculated in accordance with the following formula:

Protein dirt removal ratio (%)={(Amount of protein dirt present on the contact lens before immersing in the cleansing solution−Amount of protein dirt remaining on the contact lens after immersing in the cleansing solution)/Amount of protein dirt present on the contact lens before immersing in the cleansing solution}×100.

The results are also shown in Table 38 below. As shown in Table 38, the copolymers (141) and (144) of the present invention exhibited high detergency for removing protein dirt from a contact lens, as compared to that of a Pluronic surfactant used in conventional contact lens cleansing solutions.

TABLE 38

| | | Components | Example 131 Concentration (% by weight) | | Comparative Example 3 Concentration (% by weight) |
|---|---|---|---|---|---|
| Formulation | A | Detergent | Copolymer (141): 0.1 | Copolymer (144): 0.1 | Pluronic surfactant: 0.1 |
| | B | Antibacterial agent: PHMB | 0.0001 | 0.0001 | 0.0001 |
| | C | Inorganic salt compound: Boric acid | 0.02 | 0.02 | 0.02 |
| | D | Buffer: NaOH | 0.025 | 0.025 | 0.025 |

TABLE 38-continued

| | Components | Example 131 Concentration (% by weight) | | Comparative Example 3 Concentration (% by weight) |
|---|---|---|---|---|
| E | Salt: NaCl | 0.58 | 0.58 | 0.58 |
| F | Chelating agent: EDTA-2Na | 0.1 | 0.1 | 0.1 |
| Detergency in terms of a protein dirt removal ratio (%) | | 78 | 73 | 42 |

In the following Examples, the following abbreviations are used.
DMF: N,N-dimethylformamide
Trt: triphenylmethyl group (trityl group)
Z: benzyloxycarbonyl group
Fmoc: 9-fluorenylmethyloxycarbonyl group
DMAP: N,N-dimethyl aminopyridine
WSCD.HCl: water-soluble carbodiimide hydrochloride
DIPC: N,N'-diisopropyl carbodiimide
tBuOK: Potassium t-butoxide
DMSO-d6: deuterated dimethylsulfoxide Example 132

(Step 1) Production of Carboxymethylated Polyether (175)

3 g of copolymer (157) obtained in Example 105 was dissolved in 50 ml of toluene to obtain a copolymer solution, and to the obtained copolymer solution were added a solution obtained by dissolving 1.8 g of potassium t-butoxide in 10 ml of t-butyl alcohol, 50 mg of 18-crown-6-ether and 1.8 ml of brominated ethyl acetate in this order, followed by a reaction at 70° C. for 7 hours, thereby obtaining a first reaction mixture. After completion of the reaction, the solvents were distilled off from the first reaction mixture under reduced pressure. To the resultant residue was added 20 ml of 1 N aqueous sodium hydroxide, followed by a reaction at room temperature for 5 hours, thereby obtaining a second reaction mixture. The obtained second reaction mixture was dialyzed for 2 days against purified water at 4° C. using a dialysis membrane (molecular weight cut-off: 12,000 to 14,000, manufactured and sold by Spectrum Laboratories Inc., U.S.A.). The resultant dialyzate was filtered through a membrane filter (pore size: 0.22 μm), and the resultant filtrate was lyophilized, thereby obtaining 3.0 g of carboxymethylated polyether (175) (hereinafter referred to simply as "compound (175)"). The amount of carboxyl group introduced into copolymer (157) was determined by $^1$H-NMR analysis. The amount of the introduced carboxyl group was 3.5 mol %, based on the total molar amount of recurring units. The weight average molecular weight of compound (175) was 70,000 as determined by GPC.

(Step 2) Production of 2'-gly-paclitaxel (176)

2'-Gly-paclitaxel (176) was produced in the same manner as in Example 28.

(Step 3) Production of Carboxymethylated polyether-2'-Gly-paclitaxel (177)

100 mg of compound (175) obtained in step 1 above was dissolved in 2 ml of water. To the resultant solution was added 2 ml of DMF while cooling over ice. To the resultant mixture were added 0.5 ml of a solution obtained by dissolving 30 mg of 2'-Gly-paclitaxel (176) obtained in step 2 above in an aqueous DMF (water:DMF ratio=1:1), and 0.5 ml of a solution obtained by dissolving 100 mg of WSC HCl in DMF, followed by stirring at room temperature for two hours, thereby obtaining a reaction mixture. The obtained reaction mixture was dialyzed for 2 days against purified water at 4° C. using a dialysis membrane (molecular weight cut-off: 12,000 to 14,000, manufactured and sold by Spectrum Laboratories Inc., U.S.A.). The resultant dialyzate was filtered through a membrane filter (pore size: 0.22 μm), and the resultant filtrate was lyophilized, thereby obtaining 85 mg of carboxymethylated polyether-2'-Gly-paclitaxel (177) (hereinafter referred to simply as "compound (177)"). The amount of paclitaxel introduced in compound (177) was calculated from the absorbance of compound (177) at 254 nm and the weight of compound (177). The amount of the introduced paclitaxel was 3.9% by weight, based on the weight of compound (177).

Example 133

(Step 1) Production of 2'-Ala-paclitaxel (178)

145 mg (0.65 mmol) of Z-Ala, 79 mg (0.65 mmol) of DMAP and 427 mg (0.5 mmol) of paclitaxel were dissolved in 20 ml of methylene chloride to obtain a solution. To the obtained solution was added 82 mg (0.65 mmol) of DIPC and stirred overnight at room temperature to effect a reaction. After completion of the reaction, the solvents were distilled off from the resultant reaction mixture under reduced pressure. The resultant residue was purified by silica gel column chromatography (silica gel: Art No. 9385, Silica gel 60, 200-400 mesh, manufactured and sold by Merck KGaA, Germany; column: 4.0×30 cm; eluent: methylene chloride/acetonitrile ratio=70/30), to thereby obtain 431 mg of 2'-Z-Ala-paclitaxel. 400 mg of the obtained 2'-Z-Ala-paclitaxel was dissolved in 20 ml of dioxane to obtain a solution, and to the obtained solution was added 200 mg of a palladium-carbon catalyst, followed by a reaction for 4 hours under an atmosphere of hydrogen while stirring, to thereby obtain a reaction mixture. The obtained reaction mixture was subjected to filtration to remove the catalyst, and the solvents were distilled off from the reaction mixture under reduced pressure. Then, the resultant residue was purified by silica gel column chromatography (silica gel: Art No. 9385, Silica gel 60, 200-400 mesh, manufactured and sold by Merck KGaA, Germany; column: 2.0×30 cm; eluent: methylene chloride/methanol/acetonitrile ratio=95/5/5), to thereby obtain 230 mg of 2'-Ala-paclitaxel (178).

$^1$H-NMR (solvent: DMSO-d6; reference standard: TMS): δ1.01 (s, 3H, Me-17), 1.03 (s, 3H, Me-16), 1.14 (s, 3H, Me-Ala), 1.51 (s, 3H, Me-19), 1.61 (dd, 1H, J=15.6, 9.2 Hz, H-14b), 1.64 (t, 1H, J=12.8 Hz, H-6b), 1.81 (s, 3H, Me-18), 1.88 (dd, 1H, J=15.3, 9.5 Hz, H-14a), 2.11 (s, 3H, Ac-10), 2.27 (s, 3H, Ac-4), 2.33 (m, 1H, H-6a), 3.52 (q, 1H, J=7.0 Hz, H-Ala), 3.60 (d, 1H, J=7.3 Hz, H-3), 4.02 (d, 1H, J=15.0 Hz, H-20), 4.03 (d, 1H, J=15.0 Hz, H-20), 4.12 (ddd, 1H, J=6.6, 6.6, 17.4 Hz, H-7), 4.66 (s, 1H, OH-1), 4.91 (d, 1H, J=6.6, OH-7), 4.92 (dd, 1H, J=9.8 Hz, H-5), 5.35 (d, 1H, J=8.6, H-2'), 5.43 (d, 1H, J=7.0 Hz, H-2), 5.64 (t, 1H, J=8.6 Hz, H-3'), 5.87 (t, 1H, J=9.2 Hz, H-13), 6.30 (s, 1H, H-10), 7.20 to 8.00 (aromatic, 15 H), 9.17 (d, 1H, J=8.9 Hz, CONH-3')

HRMS: m/z 925.3797 (M+H)$^+$: the molecular weight calculated for $C_{50}H_{57}O_{15}N_2$ was 925.3759

(Step 2) Production of Carboxymethylated polyether-2'-Ala-paclitaxel (179)

Substantially the same procedure as in step 3 of Example 132 was repeated, except that 30 mg of 2'-Ala-paclitaxel (178) produced in step 1 above was used instead of 30 mg of 2'-Gly-paclitaxel (176), thereby obtaining 95 mg of carboxymethylated polyether-2'-Ala-paclitaxel (179) (hereinafter referred to simply as "compound (179)"). The amount of paclitaxel introduced in compound (179) was calculated from the absorbance of compound (179) at 254 nm and the weight of compound (179). The amount of the introduced paclitaxel was 2.1% by weight, based on the weight of compound (179).

Example 134

(Step 1) Production of 2'-Leu-paclitaxel (180)

Substantially the same procedure as in step 1 of Example 133 was repeated, except that 172 mg (0.65 mmol) of Z-Leu was used instead of Z-Ala, thereby obtaining 450 mg of 2'-Z-Leu-paclitaxel. 400 mg of the obtained 2'-Z-Leu-paclitaxel was dissolved in 20 ml of dioxane to obtain a solution, and to the obtained solution was added 200 mg of a palladium-carbon catalyst, followed by a reaction for 4 hours under an atmosphere of hydrogen while stirring, to thereby obtain a reaction mixture. The obtained reaction mixture was subjected to filtration to remove the catalyst, and the solvents were distilled off from the reaction mixture under reduced pressure. Then, the resultant residue was purified by silica gel column chromatography (silica gel: Art No. 9385, Silica gel 60, 200-400 mesh, manufactured and sold by Merck KGaA, Germany; column: 4.0×30 cm; eluent: methylene chloride/methanolacetonitrile ratio=95/5/5), to thereby obtain 280 mg of 2'-Leu-paclitaxel (180).

$^1$H-NMR (solvent: DMSO-d6; reference standard: TMS): δ0.66 (d, 3H, Me-Leu) 0.70 (d, 3H, Me-Leu) 1.01 (s, 3H, Me-17) 1.03 (s, 3H, Me-16) 1.26 (ddd, 1H, J=6.4, 8.5, 13.4 Hz, H-Leu) 1.36 (ddd, 1H, J=5.8, 7.6, 13.4 Hz, H-Leu) 1.51 (s, 3H, Me-19) 1.56 (dd, 1H, J=15.3, 9.0 Hz, H-14b) 1.64 (m, 1H, H-6b) 1.67 (m, 1H, H-Leu) 1.79 (s, 3H, Me-18) 1.84 (dd, 1H, J=15.3, 9.5 Hz, H-14a) 2.10 (s, 3H, Ac-10) 2.25 (s, 3H, Ac-4) 2.33 (ddd, 1H, J=14.7, 9.5, 6.4 Hz, H-6a) 3.38 (dd, 1H, J=8.6, 5.8 Hz, H-Leu) 3.59 (d, 1H, J=7.0 Hz, H-3) 4.01 (d, 1H, J=16.8 Hz, H-20) 4.03 (d, 1H, J=16.8 Hz, H-20) 4.12 (ddd, 1H, J=6.9, 6.9, 11.0 Hz, H-7) 4.64 (s, 1H, OH-1) 4.90 (d, 1H, J=7.0, OH-7) 4.92 (d, 1H, J=10.1 Hz, H-5) 5.34 (d, 1H, J=9.2, H-2') 5.42 (d, 1H, J=7.0 Hz, H-2) 5.62 (t, 1H, J=9.0 Hz, H-3') 5.86 (t, 1H, J=9.2 Hz, H-13) 6.30 (s, 1H, H-10) 7.20 to 8.00 (aromatic, 15H) 9.16 (d, 1H, J=8.9 Hz, CONH-3')

HRMS: m/z 967.4321 (M+H)$^+$: the molecular weight calculated for $C_{53}H_{63}O_{15}N_2$ was 967.4228

(Step 2) Production of Carboxymethylated polyether-2'-Leu-paclitaxel (181)

Substantially the same procedure as in step 3 of Example 132 was repeated, except that 30 mg of 2'-Leu-paclitaxel (180) produced in step 1 above was used instead of 30 mg of 2'-Gly-paclitaxel (176), thereby obtaining 90 mg of carboxymethylated polyether-2'-Leu-paclitaxel (181) (hereinafter referred to simply as "compound (181)"). The amount of paclitaxel introduced in compound (181) was calculated from the absorbance of compound (181) at 254 nm and the weight of compound (181). The amount of the introduced paclitaxel was 2.0% by weight, based on the weight of compound (181).

Example 135

(Step 1) Production of 2'-Ile-paclitaxel (182)

212 mg (0.6 mmol) of Fmoc-Ile, 73 mg (0.6 mmol) of DMAP and 427 mg (0.5 mmol) of paclitaxel were dissolved in 20 ml of methylene chloride to obtain a solution. To the obtained solution was added 76 mg (0.6 mmol) of DIPC and stirred overnight at room temperature to effect a reaction. After completion of the reaction, the solvents were distilled off from the resultant reaction mixture under reduced pressure. The resultant residue was purified by silica gel column chromatography (silica gel: Art No. 9385, Silica gel 60, 200-400 mesh, manufactured and sold by Merck KGaA, Germany; column: 2.0×30 cm; eluent: methylene chloride/acetonitrile ratio=70/30), to thereby obtain 550 mg of 2'-Fmoc-Ile-paclitaxel. 470 mg of the obtained 2'-Fmoc-Ile-paclitaxel was dissolved in 10 ml of DMF, followed by addition thereto of 2 ml of piperidine at room temperature, to obtain a mixture. The obtained mixture was stirred for 5 minutes to thereby remove the Fmoc group. The solvents were distilled off from the mixture under reduced pressure. The resultant residue was purified by silica gel column chromatography (silica gel: Art No. 9385, Silica gel 60, 200-400 mesh, manufactured and sold by Merck KGaA, Germany; column: 4.0×30 cm; eluent: methylene chloride/methanol/acetonitrile ratio=95/5/5), thereby obtaining 350 mg of 2'-Ile-paclitaxel (182).

$^1$H-NMR (solvent: DMSO-d6; reference standard: TMS): δ0.62 (t, 3H, J=7.5 Hz, Me-Ile) 0.81 (d, 3H, J=6.7 Hz, Me-Ile) 1.01 (s, 3H, Me-17) 1.03 (s, 3H, Me-16) 1.07 (ddd, 1H, J=14.4, 7.3, 4.9 Hz, H-Ile) 1.32 (ddd, 1H, J=13.4, 7.6, 4.6 Hz, H-Ile) 1.51 (s, 3H, Me-19) 1.56 (dd, 1H, J=15.3, 9.2 Hz, H-14b) 1.56 to 1.61 (m, 1H, H-Ile) 1.64 (dd, 1H, J=13.7, 3.1 Hz, H-6b) 1.79 (s, 3H, Me-18) 1.87 (dd, 1H, J=15.3, 9.8 Hz, H-14a) 2.10 (s, 3H, Ac-10) 2.29 (s, 3H, Ac-4) 2.33 (ddd, 1H, J=14.4, 9.6, 6.4 Hz, H-6a) 3.60 (d, 1H, J=7.3 Hz, H-3) 3.60 to 3.67 (m, 1H, H-Ile) 4.02 (d, 1H, J=16.6 Hz, H-20) 4.03 (d, 1H, J=16.6 Hz, H-20) 4.12 (ddd, 1H, J=10.8, 6.7, 6.7 Hz, H-7) 4.64 (s, 1H, OH-1) 4.90 (d, 1H, J=7.0, OH-7) 4.92 (d, 1H, J=9.8 Hz, H-5) 5.37 (d, 1H, J=8.9 Hz, H-2') 5.43 (d, 1H, J=7.3 Hz, H-2) 5.64 (t, 1H, J=8.7 Hz, H-3') 5.85 (dt, 1H, J=0.9, 9.2 Hz, H-13) 6.30 (s, 1H, H-10) 7.20 to 8.00 (aromatic, 15H) 9.15 (d, 1H, J=9.2 Hz, CONH-3')

HRMS: m/z 967.4234 (M+H)$^+$: the molecular weight calculated for $C_{53}H_{63}O_{15}N_2$ was 967.4228

(Step 2) Production of Carboxymethylated polyether-2'-Ile-paclitaxel (183)

Substantially the same procedure as in step 3 of Example 132 was repeated, except that 30 mg of 2'-Ile-paclitaxel (182) produced in step 1 above was used instead of 30 mg of 2'-Gly-paclitaxel (176), thereby obtaining 90 mg of carboxymethylated polyether-2'-Ile-paclitaxel (183) (hereinafter referred to simply as "compound (183)"). The amount of paclitaxel introduced in compound (183) was calculated from the absorbance of compound (183) at 254 nm and the weight of compound (183). The amount of the introduced paclitaxel was 1.7% by weight, based on the weight of compound (183).

Example 136

(Step 1) Production of 2'-Phe-paclitaxel (184)

194 mg (0.65 mmol) of Z-Phe, 79 mg (0.65 mmol) of DMAP and 427 mg (0.5 mmol) of paclitaxel were dissolved in 20 ml of methylene chloride to obtain a solution. To the obtained solution was added 82 mg (0.65 mmol) of DIPC and stirred overnight at room temperature to effect a reaction. After completion of the reaction, the solvents were distilled off from the resultant reaction mixture under reduced pressure. The resultant residue was purified by silica gel column chromatography (silica gel: Art No. 9385, Silica gel 60, 200-400 mesh, manufactured and sold by Merck KGaA, Germany; column: 4.0×30 cm; eluent: methylene chloride/acetonitrile ratio=70/30), to thereby obtain 420 mg of 2'-Z-Phe-paclitaxel. 400 mg of the obtained 2'-Z-Phe-paclitaxel was dissolved in 20 ml of dioxane to obtain a solution, and to the obtained solution was added 200 mg of a palladium-carbon catalyst, followed by a reaction for 4 hours under an atmosphere of hydrogen while stirring, to thereby obtain a reaction mixture. The obtained reaction mixture was subjected to filtration to remove the catalyst, and the solvents were distilled off from the reaction mixture under reduced pressure. Then, the resultant residue was purified by silica gel column chromatography (silica gel: Art No. 9385, Silica gel 60, 200-400 mesh, manufactured and sold by Merck KGaA, Germany; column: 4.0×30 cm; eluent: methylene chloride/methanol/acetonitrile ratio=95/5/5), to thereby obtain 260 mg of 2'-Phe-paclitaxel (184).

$^1$H-NMR (solvent: DMSO-d6; reference standard: TMS): δ1.02 (s, 3H, Me-17) 1.05 (s, 3H, Me-16) 1.52 (s, 3H, Me-19) 1.64 (dd, 1H, J=15.6, 9.2 Hz, H-14b) 1.66 (dd, 1H, J=14.4, 11.3 Hz, H-6b) 1.85 (s, 3H, Me-18) 1.93 (dd, 1H, J=15.3, 9.5 Hz, H-14a) 2.11 (s, 3H, Ac-10) 2.30 (s, 3H, Ac-4) 2.32 (ddd, 1H, J=14.7, 9.6, 6.6 Hz, H-6a) 2.99 (dd, 1H, 14.5, 6.9 Hz, PheCH2) 3.13 (dd, 1H, 14.4, 5.2 Hz, PheCH2) 3.61 (d, 1H, J=7.3 Hz, H-3) 4.10 (dd, 1H, J=11.0, 6.7 Hz, H-7) 4.52 (t, 1H, J=5.8 Hz, PheCH) 4.68 (s, 1H, OH-1) 4.89 (d, 1H, J=7.0, OH-7) 4.92 (d, 1H, J=9.8 Hz, H-5) 5.47 (d, 1H, J=7.3 Hz, H-2') 5.50 (d, 1H, J=7.3 Hz, H-2) 5.78 (t, 1H, J=8.2 Hz, H-3') 5.94 (t, 1H, J=8.9 Hz, H-13) 6.30 (s, 1H, H-10) 7.00 to 8.10 (m, 20H, aromatic) 8.49 (brs, 2H, NH2) 9.26 (d, 1H, J=8.9 Hz, CONH-3')

HRMS: m/z 1001.4076 (M+H)$^+$: the molecular weight calculated for $C_{56}H_{61}O_{15}N_2$ was 1001.4072

(Step 2) Production of Carboxymethylated polyether-2'-Phe-paclitaxel (185)

Substantially the same procedure as in step 3 of Example 132 was repeated, except that 30 mg of 2'-Phe-paclitaxel (185) produced in step 1 above was used instead of 30 mg of 2'-Gly-paclitaxel (176), thereby obtaining 95 mg of carboxymethylated polyether-2'-Phe-paclitaxel (185) (hereinafter referred to simply as "compound (185)"). The amount of paclitaxel introduced in compound (185) was calculated from the absorbance of compound (185) at 254 nm and the weight of compound (185). The amount of the introduced paclitaxel was 4.5% by weight, based on the weight of compound (185).

Example 137

(Step 1) Production of 2'-Phe-Gly-paclitaxel Hydrochloride (186)

1.1 g (5 mmol) of Phe-Gly (manufactured and sold by PEPTIDE INSTITUTE INC., Japan) was dissolved in a mixture of 2 ml of water, 2 ml of 2-propanol and 1.5 ml of diethylamine to obtain a solution. To the obtained solution was gradually added 1.8 g (6.5 mmol) of trityl chloride, followed by stirring for one hour. To the resultant reaction mixture was added water, to thereby generate a precipitate. The generated precipitate was collected, washed with water and then dissolved in 5 ml of acetic acid, to thereby obtain an acidic solution. The solvents were distilled off from the obtained acidic solution under reduced pressure, to thereby obtain 1.5 g of Trt-Phe-Gly. 604 mg (1.3 mmol) of the obtained Trt-Phe-Gly, 158 mg (1.3 mmol) of DMAP and 853 mg (1.0 mmol) of paclitaxel were dissolved in 20 ml of methylene chloride to obtain a solution. To the obtained solution was added 164 mg (1.3 mmol) of DIPC and stirred overnight at room temperature to effect a reaction. After completion of the reaction, the solvents were distilled off from the resultant reaction mixture under reduced pressure. The resultant residue was purified by silica gel column chromatography (silica gel: Art No. 9385, Silica gel 60, 200-400 mesh, manufactured and sold by Merck KGaA, Germany; column: 4.0×30 cm; eluent: methylene chloride/acetonitrile ratio=80/20), to thereby obtain 980 mg of 2'-Trt-Phe-Gly-paclitaxel. 800 mg of the obtained 2'-Trt-Phe-Gly-paclitaxel was treated with 10 ml of 90% acetic acid to effect a reaction for removing an N-trityl group. The resultant product was purified by silica gel column chromatography (silica gel Art No. 9385, Silica gel 60, 200-400 mesh, manufactured and sold by Merck KGaA, Germany; column 4.0×30 cm; eluent: methylene chloride/methanol/acetonitrile ratio=95/5/5), and subsequently converted from an acetate to a corresponding hydrochloride with an ion exchange resin, to thereby obtain 450 mg of 2'-Phe-Gly-paclitaxel hydrochloride (186).

$^1$H-NMR (solvent: DMSO-d6; reference standard: TMS): δ1.01 (s, 3H, Me-17) 1.03 (s, 3H, Me-16) 1.42 (dd, 1H, J=15.5, 9.1 Hz, H-14b) 1.50 (s, 3H, Me-19) 1.63 (t, 1H, J=12.2 Hz, H-6b) 1.75 (dd, 1H, J=12.3, 9.5 Hz, H-14a) 1.81 (s, 3H, Me-18) 2.12 (s, 3H, Ac-10) 2.23 (s, 3H, Ac-4) 2.29 (ddd, 1H, J-=14.4, 9.2, 7.0 Hz, H-6a) 2.90 (dd, 1H, 14.2, 7.8 Hz, PheCH2) 3.08 (dd, 1H, 14.4, 5.2 Hz, PheCH2) 3.56 (d, 1H, J=7.0 Hz, H-3) 4.05 to 4.10 (m, 2H, H-7, PheCH) 4.15 (dd, 1H, J=18.0, 5.8 Hz, Gly) 4.61 (brs, 1H, OH-1) 4.90 (brs, 1H, OH-7) 4.90 (d, 1H, J=5.3 Hz, H-5) 5.38 (d, 1H, J=8.9 Hz, H-2') 5.41 (d, 1H, J=7.0 Hz, H-2) 5.53 (t, 1H, J=8.6 Hz, H-3') 5.83 (t, 1H, J=8.8 Hz, H-13) 6.29 (s, 1H, H-10) 7.16 to 8.00 (m, 20H, aromatic) 8.15 (brs, 2H, NH2) 9.02 (t, 1H, J=5.8 Hz, Gly-NH) 9.29 (d, 1H, J=8.9 Hz, CONH-3')

HRMS: m/z 1058.4241 (M+H)$^+$: the molecular weight calculated for $C_{58}H_{64}O_{16}N_3$ was 1058.4287

(Step 2) Production of Carboxymethylated polyether-2'-Phe-Gly-paclitaxel (187)

100 mg of compound (175) obtained in step 1 of Example 132 was dissolved in 2 ml of water. To the resultant solution was added 2 ml of DMF while cooling over ice. To the resultant mixture were added 0.5 ml of a solution obtained by dissolving 22 mg of 2'-Phe-Gly-paclitaxel (186) obtained in step 1 above in an aqueous DMF (water:DMF ratio=1:1), and 0.5 ml of a solution obtained by dissolving 100 mg of WSC.HCl in DMF, followed by stirring at room temperature for two hours, thereby obtaining a reaction mixture. The obtained reaction mixture was dialyzed for 2 days against purified water at 4° C. using a dialysis membrane (molecular weight cut-off: 12,000 to 14,000, manufactured and sold by Spectrum Laboratories Inc., U.S.A.). The resultant dialyzate was filtered through a membrane filter (pore size: 0.22 μm), and the resultant filtrate was lyophilized, thereby obtaining 80 mg of carboxymethylated polyether-2'-Phe-Gly-paclitaxel (187) (hereinafter referred to simply as "compound (187)"). The amount of paclitaxel introduced in compound (187) was calculated from the absorbance of compound (187) at 254 nm and the weight of compound (187). The amount of the introduced paclitaxel was 3.0% by weight, based on the weight of compound (187).

Example 138

(Step 1) Production of 2'-Gly-Phe-paclitaxel Hydrochloride (188) Drochloride (188)

Substantially the same procedure as in step 1 of Example 137 was repeated except that 1.1 g (5 mmol) of Gly-Phe (manufactured and sold by PEPTIDE INSTITUTE INC., Japan) was used instead of Phe-Gly, thereby obtaining 1.5 g of Trt-Gly-Phe. 604 mg (1.3 mmol) of the produced Trt-Gly-Phe, 158 mg (1.3 mmol) of DMAP and 853 mg (1.0 mmol) of paclitaxel (manufactured and sold by Dabur India Ltd., India) were dissolved in 20 ml of methylene chloride to obtain a solution. To the obtained solution was added 164 mg (1.3 mmol) of DIPC and stirred overnight at room temperature to effect a reaction. After completion of the reaction, the solvents were distilled off from the resultant reaction mixture under reduced pressure. The resultant residue was purified by silica gel column chromatography (silica gel: Art No. 9385, Silica gel 60, 200-400 mesh, manufactured and sold by Merck KGaA, Germany; column: 4.0×30 cm; eluent: methylene chloride/acetonitrile ratio=80/20), to thereby obtain 960 mg of 2'-Trt-Gly-Phe-paclitaxel. 800 mg of the obtained 2'-Trt-Gly-Phe-paclitaxel was treated with 10 ml of 90% acetic acid to effect a reaction for removing an N-trityl group. The resultant product was purified by silica gel column chromatography (silica gel Art No. 9385, Silica gel 60, 200-400 mesh, manufactured and sold by Merck KGaA, Germany; column 4.0×30 cm; eluent: methylene chloride/methanol/acetonitrile ratio=95/5/5), and subsequently converted from an acetate to a corresponding hydrochloride with an ion exchange resin, to thereby obtain 500 mg of 2'-Gly-Phe-paclitaxel hydrochloride (188).

$^1$H-NMR (solvent: DMSO-d6; reference standard: TMS): δ1.02 (s, 3H, Me-17) 1.05 (s, 3H, Me-16) 1.52 (s, 3H, Me-19) 1.66 (dd, 1H, J=15.0, 9.5 Hz, H-14b) 1.66 (t, 1H, J=10.7 Hz, H-6b) 1.82 (s, 3H, Me-18) 1.94 (dd, 1H, J=15.2, 9.7 Hz, H-14a) 2.11 (s, 3H, Ac-10) 2.30 (br, 1H, H-6a) 2.33 (s, 3H, Ac-4) 2.76 (dd, 1H, 14.1, 9.5 Hz, PheCH2) 2.97 (dd, 1H, 14.0, 3.6 Hz, PheCH2) 3.46 (d, 1H, J=16.2, Gly) 3.51 (d, 1H, J=16.5, Gly) 3.61 (d, 1H, J=7.3 Hz, H-3) 4.03 (d, 1H, J=8.9 Hz, H-20) 4.05 (d, 1H, J=8.9 Hz, H-20) 4.10 (dd, 1H, J=10.5, 6.9 Hz, H-7) 4.71 (brs, 1H, OH-1) 4.79 (ddd, 1H, J=9.0, 9.0, 3.7 Hz, PheCH) 4.92 (brs, 1H, OH-7) 4.93 (d, 1H, J=10.4 Hz, H-5) 5.40 (d, 1H, J=7.6 Hz, H-2') 5.44 (d, 1H, J=7.3 Hz, H-2) 5.79 (dd, 1H, J=8.6, 7.9 Hz, H-3') 5.93 (t, 1H, J=8.9 Hz, H-13) 6.29 (s, 1H, H-10) 6.97 to 8.02 (m, 20H, aromatic) 7.97 (brs, 2H, GlyNH2) 8.88 (d, 1H, J=8.2 Hz, Phe-NH) 9.30 (d, 1H, J=9.2 Hz, CONH-3')

HRMS: m/z 1058.4333 (M+H)$^+$: the molecular weight calculated for $C_{58}H_{64}O_{16}N_3$ was 1058.4287

(Step 2) Production of Carboxymethylated polyether-2'-Gly-Phe-paclitaxel (189)

100 mg of compound (175) obtained in step 1 of Example 132 was dissolved in 2 ml of water. To the resultant solution was added 2 ml of DMF while cooling over ice. To the resultant mixture were added 0.5 ml of a solution obtained by dissolving 15 mg of 2'-Gly-Phe-paclitaxel (188) obtained in step 1 above in an aqueous DMF (water:DMF ratio=1:1), and 0.5 ml of a solution obtained by dissolving 100 mg of WSC.HCL in DMF, followed by stirring at room temperature for two hours, thereby obtaining a reaction mixture. The obtained reaction mixture was dialyzed for 2 days against purified water at 4° C. using a dialysis membrane (molecular weight cut-off: 12,000 to 14,000, manufactured and sold by Spectrum Laboratories Inc., U.S.A.). The resultant dialyzate was filtered through a membrane filter (pore size: 0.22 µm), and the resultant filtrate was lyophilized, thereby obtaining 85 mg of carboxymethylated polyether-2'-Gly-Phe-paclitaxel (189) (hereinafter referred to simply as "compound (189)"). The amount of paclitaxel introduced in compound (189) was calculated from the absorbance of compound (189) at 254 nm and the weight of compound (189). The amount of the introduced paclitaxel was 4.0% by weight, based on the weight of compound (189).

Example 139

Production of Trt-Gly-Gly-Phe-Gly (190)

(1) Synthesis of Phe-Gly-OBn para-toluenesulfonate (191)

25 g (104 mmol) of Phe-Gly.H$_2$O (manufactured and sold by Kokusan Chemical Works Ltd., Japan) was dissolved in a mixed solvent comprised of 19.8 g (104 mmol) of para-toluenesulfonic acid monohydrate, 25 ml of benzyl alcohol and 200 ml of toluene to obtain a mixture. The obtained mixture was refluxed for 5 hours by means of a Dean-Stark apparatus, to thereby obtain a reaction mixture. After completion of the reaction, the solvents were distilled off from the obtained reaction mixture under reduced pressure. To the resultant residue was added diethylether, to thereby obtain 35 g of Phe-Gly-OBn para-toluenesulfonate (191).

(2) Synthesis of Trt-Gly-Gly (192)

6.6 g (50 mmol) of Gly-Gly (manufactured and sold by PEPTIDE INSTITUTE INC., Japan) was dissolved in a mixed solvent comprised of 20 ml of H$_2$O, 40 ml of 2-propanol and 15 ml of diethylamine to obtain a solution. To the obtained solution was gradually added 18.1 g (65 mmol) of trityl chloride, followed by stirring for 1 hour. To the resultant reaction mixture was added H$_2$O, to thereby generate a precipitate. The generated precipitate was recovered, washed with water and, then, dissolved in 5 ml of acetic acid, to thereby obtain an acidic solution. The solvents were distilled off from the obtained acidic solution under reduced pressure, to thereby obtain 13.1 g of Trt-Gly-Gly (192).

(3) Synthesis of Trt-Gly-Gly-Phe-Gly-OBn (193)

To 10 ml of dry DMF were added 1.54 g of Trt-Gly-Gly (192), 0.52 g of N-hydroxysuccinimide and 0.93 g of DCC, followed by a reaction at 4° C. for 3 hours, to thereby obtain a reaction mixture. To the obtained reaction mixture was added a solution obtained by dissolving 2.0 g of Phe-Gly-OBn para-toluenesulfonate (191) synthesized in item (1) above and 0.41 g of N-methylmorpholine in 10 ml of DMF, followed by a reaction at 4° C. for 15 hours, to thereby obtain a reaction mixture. A precipitate contained in the obtained reaction mixture was removed and the solvents were distilled off from the reaction mixture under reduced pressure. The resultant residue was purified by silica gel column chromatography (silica gel: Art No. 9365, Silica gel 60, 200-400 mesh, manufactured and sold by Merck KGaA, Germany; eluent: chloroform/methanol ratio=20/1), thereby obtaining 1.5 g of Trt-Gly-Gly-Phe-Gly-OBn (193).

(4) Synthesis of Trt-Gly-Gly-Phe-Gly (190)

1.3 g of Trt-Gly-Gly-Phe-Gly-OBn (193) obtained in item (3) above was dissolved in 20 ml of DMF to obtain a solution. To the obtained solution were added 0.5 g of a 10% palladium-carbon catalyst and 0.4 g of 1,4-cyclohexadiene, followed by a reaction at room temperature for 30 minutes, to thereby obtain a reaction mixture. The obtained reaction mixture was subjected to filtration to remove the catalyst, thereby obtaining a solution. The solvents were distilled off from the obtained solution under reduced pressure. The resultant residue was purified by silica gel column chromatography (silica gel: Art No. 9365, Silica gel 60, 200-400 mesh, manufactured and sold by Merck KGaA, Germany; eluent: chloroform/methanol ratio=7/1), thereby obtaining 1.0 g of Trt-Gly-Gly-Phe-Gly (190).

Anal. Calcd for C$_{34}$H$_{34}$N$_4$O$_5$: C, 70.57; H, 5.92; N, 9.68. Found: C, 70.03; H, 6.07; N, 9.67.

Analysis of amino acids: Phe (1) 1.00, Gly (3) 2.91.

Conditions for hydrolysis: 6N HCl, 110° C., 22 hrs.

Example 140

Production of Z-Gly-Gly-Phe (194)

10.6 g of BOC-Phe (manufactured and sold by PEPTIDE INSTITUTE INC., Japan) was dissolved in 100 ml of ethyl acetate to obtain a solution. To the obtained solution were added 10.0 g of phenacyl bromide and 5.1 g of triethylamine while cooling over ice, followed by stirring. The reaction temperature was elevated to room temperature, followed by stirring overnight to effect a reaction, thereby obtaining a reaction mixture. The solvents were distilled off from the obtained reaction mixture under reduced pressure. The resultant residue was dissolved in 50 ml of ethyl acetate to obtain a solution and the obtained solution was washed with a saturated aqueous sodium hydrogencarbonate and, then, with saturated saline. The washed solution was dried with magnesium sulfate and concentrated under reduced pressure, to thereby obtain 13.4 g of BOC-Phe phenacyl ester. Further, to 1.9 g of the obtained BOC-Phe phenacyl ester was added 5 ml of trifluoroacetic acid (TFA), followed by stirring for 10 minutes. TFA was distilled off from the resultant mixture under reduced pressure. To the resultant residue were added 20 ml of DMF, 0.61 g of N-methylmorpholine, 1.24 g of DCC, 0.81 g of HOBT and 1.05 g of BOC-Gly (manufactured and sold by PEPTIDE INSTITUTE INC., Japan), followed by stirring overnight at room temperature, to thereby obtain a reaction mixture. The obtained reaction mixture was concentrated under reduced pressure. The resultant residue was dissolved in 50 ml of ethyl acetate to obtain a solution, and the obtained solution was washed with 0.1 N aqueous hydrochloric acid cooled with ice, saturated saline, a saturated aqueous sodium hydrogencarbonate and again saturated saline successively. The washed solution was dried with magnesium sulfate and concentrated under reduced pressure, to thereby obtain 1.5 g of BOC-Gly-Phe phenacyl ester. Further, to 1.6 g of the obtained BOC-Gly-Phe phenacyl ester was added 5 ml of trifluoroacetic acid (TFA), followed by stirring for 10 minutes, to thereby obtain a reaction mixture. TFA was distilled off from the obtained reaction mixture under reduced pressure. To the resultant residue were added 20 ml of DMF, 0.40 g of N-methylmorpholine, 0.83 g of DCC, 0.54 g of HOBT and 0.84 g of Z-Gly (manufactured and sold by Kokusan Chemical Works Ltd., Japan), followed by stirring at room temperature overnight, to thereby obtain a reaction mixture. The obtained reaction mixture was concentrated under reduced pressure. The resultant residue was dissolved in 50 ml of ethyl acetate to obtain a solution and the obtained solution was washed with 0.1 N aqueous hydrochloric acid cooled with ice, saturated saline, a saturated aqueous sodium hydrogencarbonate and again saturated saline successively. The washed solution was dried with magnesium sulfate and concentrated under reduced pressure, to thereby obtain 1.1 g of Z-Gly-Gly-Phe phepacyl ester. 1.1 g of the obtained Z-Gly-Gly-Phe phenacyl ester was dissolved in 30 ml of 90% acetic acid, to obtain a mixture. To the obtained mixture was added 4 g of zinc powder, followed by stirring at room temperature for 5 hours, to thereby obtain a reaction mixture. The obtained reaction mixture was subjected to filtration and the solvents were distilled off from the filtered reaction mixture under reduced pressure. The resultant residue was dissolved in 30 ml of ethyl acetate and the resultant solution was washed with 10% citric acid and, then, with saturated saline successively. The washed solution was dried with magnesium sulfate and concentrated under reduced pressure, to thereby obtain 0.62 g of Z-Gly-Gly-Phe (194).

Example 141

Production of 2'-Gly-Gly-Phe-Gly-paclitaxel Hydrochloride (195)

739 mg (1.3 mmol) of Trt-Gly-Gly-Phe-Gly (190) obtained in Example 139, 158 mg (1.3 mmol) of DMAP and 853 mg (1.0 mmol) of paclitaxel were dissolved in 20 ml of methylene chloride to obtain a solution. To the obtained solution was added 164 mg (1.3 mmol) of DIPC, followed by stirring at room temperature for 4 hours, to thereby obtain a reaction mixture. The solvents were distilled off from the obtained reaction mixture under reduced pressure. The resultant residue was purified by silica gel column chromatography (silica gel: Art No. 9385, Silica gel 60, 200-400 mesh, manufactured and sold by Merck KGaA, Germany; column: 4.0× 50 cm; eluent: methylene chloride/methanol/acetonitrile ratio=95/5/30), thereby obtaining 1,246 mg of 2'-Nα-Trt-Gly-Gly-Phe-Gly-paclitaxel (196).

HRMS: m/z 1414.5763 (M+H)$^+$: the molecular weight calculated for $C_{81}H_{84}O_{18}N_5$ was 1414.5811

1,100 mg of the above-obtained 2'-Nα-Trt-Gly-Gly-Phe-Gly-paclitaxel (196) was treated with 10 ml of 75% acetic acid to remove N-trityl group. The resultant product was purified by silica gel column chromatography (silica gel: Art No. 9385, Silica gel 60, 200-400 mesh, manufactured and sold by Merck KGaA, Germany; column: 4.0×50 cm; eluent: methylene chloride/methanol/acetonitrile ratio=85/15/5), and subsequently converted to a corresponding hydrochloride with an anion exchange resin, thereby obtaining 530 mg of 2'-Gly-Gly-Phe-Gly-paclitaxel hydrochloride (195).

$^1$H-NMR (solvent: DMSO-d6; reference standard: TMS): δ1.00 (s, 3H, Me-17) 1.03 (s, 3H, Me-16) 1.42 (dd, 1H, J=15.4, 9.2 Hz, H-14b) 1.49 (s, 3H, Me-19) 1.63 (brt, 1H, J=12.1 Hz, H-6b) 1.74 (dd, 1H, J=15.4, 9.2 Hz, H-14a) 1.80 (s, 3H, Me-18) 2.11 (s, 3H, Ac-10) 2.23 (s, 3H, Ac-4) 2.30 (m, 1H, H6a) 2.72 (dd, 1H, J=13.9, 10.2 Hz, PheCH2Hb) 3.02 (dd, 1H, J=13.9, 3.8 Hz, PheCH2CHa) 3.52 (brs, 2H, GlyCH2) 3.56 (d, 1H, J=7.2 Hz, H-3) 3.66 (dd, 1H, 16.9, 5.4 Hz, GlyCH2b) 3.84 (dd, 1H, 16.9, 5.4 Hz, GlyCH2a) 4.01 (dd, 2H, J=14.5, 8.4 Hz, H-20a, H-20b) 4.01 (2H, GlyCH2) 4.09 (m, 1H, H-7) 4.55 (ddd, 1H, J=10.2, 8.5, 3.8 Hz, PheCH2CH) 4.61 (s, 1H, OH-1) 4.89 (dd, 1H, J=8.9, 1.3 Hz, H-5) 4.92 (brs, 1H, OH-7) 5.41 (d, 1H, J=7.2, H-2) 5.43 (d, 1H, J=6.3 Hz, H-2') 5.51 (1H, J=8.5 Hz, H-3') 5.83 (t, 1H, J=9.2 Hz, H-13) 6.29 (s, 1H, H-10) 7.10 to 8.00 (aromatic, 20H) 8.33 (d, 1H, PheCONH) 8.51 (t, 1H, J=5.5 Hz, Gly-CONH) 8.69 (t, 1H, J=6.0 Hz, GlyCONH) 9.34 (d, 1H, J=8.5 Hz, CONH-3')

HRMS: m/z 1172.4711 (M+H)$^+$: the molecular weight calculated for $C_{62}H_{70}O_{18}N_5$ was 1172.4716

Anal. Calcd for: $C_{62}H_{69}O_{18}N_5$, HCl.2.5H$_2$O: C, 59.40; H, 6.03; N, 5.59.

Found: C, 59.55; H, 6.04; N, 5.60

Example 142

Production of Carboxymethylated polyether-2'-Gly-Gly-Phe-Gly-paclitaxel (197)

1.0 g of carboxymethylated polyether (175) obtained in step 1 of Example 132 was dissolved in 20 ml of water. To the resultant solution was added 20 ml of DMF while cooling over ice. To the resultant mixture were added 8 ml of a solution obtained by dissolving 200 mg of 2'-Gly-Gly-Phe-Gly-paclitaxel hydrochloride (195) obtained in Example 141 in an aqueous DMF (water:DMF ratio=1:1), and 5 ml of a solution obtained by dissolving 1.0 g of WSC.HCl in DMF, followed by stirring at room temperature for 6 hours, to thereby obtain a reaction mixture. The obtained reaction mixture was dialyzed for 2 days against purified water at 4° C. using a dialysis membrane (molecular weight cutoff: 12,000 to 14,000, manufactured and sold by Spectrum Laboratories Inc., U.S.A.). The resultant dialyzate was filtered through a membrane filter (pore size: 0.22 μm), and the resultant filtrate was lyophilized, thereby obtaining 950 mg of carboxymethylated polyether-2'-Gly-Gly-Phe-Gly-paclitaxel (197) (hereinafter referred to simply as "compound (197)"). The amount of paclitaxel introduced in compound (197) was calculated from the absorbance of compound (197) at 254 nm and the weight of compound (197). The amount of the introduced paclitaxel was 4.5% by weight, based on the weight of compound (197).

Example 143

Production of 7-Gly-Gly-Phe-Gly-paclitaxel (198)

427 mg (0.5 mmol) of paclitaxel was dissolved in methylene chloride to obtain a solution. To the obtained solution was added 129 mg (1.0 mmol) of diisopropylethylamine, to obtain a mixture. To the obtained mixture was added 170 mg (1.0 mmol) of benzyloxycarbonyl chloride while cooling over ice, followed by stirring overnight at room temperature, to thereby obtain a reaction mixture. The solvents were distilled off from the obtained reaction mixture under reduced pressure. The resultant residue was purified by silica gel column chromatography (silica gel: Art No. 9385, Silica gel 60, 200-400 mesh, manufactured and sold by Merck KGaA, Germany; column: 2.0×30 cm; eluent: methylene chloride/acetonitrile ratio=80/20), thereby obtaining 423 mg of 2'-Z-paclitaxel. 270 mg (0.27 mmol) of the obtained 2'-Z-paclitaxel was dissolved in methylene chloride to obtain a solution. To the obtained solution were added 85 mg (0.41 mmol) of Z-Gly, 84 mg (0.41 mmol) of N,N'-dicyclohexyl-carbodiimide and 50.1 mg (0.41 mmol) of DMAP, followed by stirring at room temperature for 3 days, to thereby obtain a reaction mixture. The solvents were distilled off from the obtained reaction mixture under reduced pressure. The resultant residue was purified by silica gel column chromatography (silica gel: Art No. 9385, Silica gel 60, 200-400 mesh, manufactured and sold by Merck KGaA, Germany; column: 4.0× 50 cm; eluent: methylene chloride/acetonitrile ratio=80/20), thereby obtaining 300 mg of 2'-Z-7-Z-Gly-paclitaxel. 200 mg (0.16 mmol) of the obtained 2'-Z-7-Z-Gly-paclitaxel was dissolved in 100 ml of ethyl acetate, to thereby obtain a solution. To the obtained solution was added a palladium-carbon catalyst, followed by introduction thereinto of hydrogen gas while stirring, to thereby effect a reaction. After completion of the reaction, the resultant reaction mixture was subjected to filtration to remove the catalyst, to thereby obtain a solution. The solvents were distilled off from the obtained solution under reduced pressure. The resultant residue was purified by silica gel column chromatography (silica gel Art No. 9385, Silica gel 60, 200-400 mesh, manufactured and sold by Merck KGaA, Germany; column: 4.0×50 cm; eluent: methylene chloride/acetonitrile ratio=50/50), thereby obtaining 87 mg of 7-Gly-paclitaxel.

70 mg (0.09 mmol) of the obtained 7-Gly-paclitaxel was dissolved in 20 ml of DMF to obtain a solution. To the obtained solution were added 58 mg (0.13 mmol) of Z-Gly-Gly-Phe (194) produced in Example 140, 26 mg (0.13 μmmol) of WSC.HCl and 18 mg (0.13 mmol) of 1-hydroxybenzotriazole, followed by stirring at room temperature for 3 days, to thereby obtain a reaction mixture. The solvents were distilled off from the obtained reaction mixture under reduced pressure. The resultant residue was purified by silica gel column chromatography (silica gel: Art No. 9385, Silica gel 60, 200-400 mesh, manufactured and sold by Merck KGaA, Germany; column: 4.0×50 cm; eluent: methylene chloride/methanol/acetonitrile ratio=85/15/5), thereby obtaining 94 mg of 7-Z-Gly-Gly-Phe-Gly-paclitaxel (199).

80 mg (0.06 mmol) of the obtained 7-Z-Gly-Gly-Phe-Gly-paclitaxel (199) was dissolved in 20 ml of methanol to obtain a solution. To the obtained solution was added a palladium-carbon catalyst, followed by introduction thereinto of hydrogen gas while stirring, to thereby effect a reaction. After completion of the reaction, the resultant reaction mixture was subjected to filtration to remove the catalyst, to thereby obtain a solution. The solvents were distilled off from the obtained solution under reduced pressure. The resultant residue was purified by silica gel column chromatography (silica gel: Art No. 9385, Silica gel 60, 200-400 mesh, manufactured and sold by Merck KGaA, Germany; column: 4.0×30 cm; eluent: methylene chloride/methanol/acetonitrile ratio=95/5/30), thereby obtaining 50 mg of 7-Gly-Gly-Phe-Gly-paclitaxel (198).

$^1$H-NMR (solvent: DMSO-d6; reference standard: TMS): δ0.99 (s, 3H, Me-17) 1.05 (s, 3H, Me-16) 1.67 (s, 3H, Me-19) 1.68 (m, 1H, H6b) 1.75 (s, 3H, Me-18) 1.79 (dd, 1H, J=15.3, 8.9 Hz, H-14b) 1.90 (dd, 1H, J=15.3, 8.9 Hz, H-14a) 2.15 (s, 3H, Ac-10) 2.26 (s, 3H, Ac-4) 2.42 (m, 1H, H6a) 2.74 (dd, 1H, J=13.9, 10.5 Hz, PheCH2CHb) 3.05 (dd, 1H, J=13.9, 3.8 Hz, PheCH2CHa) 3.54 (brs, 2H, GlyCH2) 3.66 (dd, 1H, J=16.8, 5.3 Hz, GlyCH2b) 3.69 (dd, 1H, J=16.8, 5.3 Hz, GlyCH2a) 3.72 (d, 1H, J=6.8 Hz, H-3) 3.80 (dd, 1H, J=16.8, 5.8 Hz, GlyCH2b) 3.85 (dd, 1H, J=16.8, 5.8 Hz, GlyCH2a) 4.06 (s, 2H, H-20) 4.57 (ddd, 1H, J=10.5, 8.9, 3.8 Hz, PheCH2CH) 4.62 (brt, 1H, J=7.0 Hz, H-2') 4.85 (s, 1H, OH-1) 4.99 (d, 1H, J=9.8 Hz, H-5) 5.42 (t, 1H, J=8.1 Hz, H-3') 5.43 (d, 1H, J=6.8 Hz, H-2) 5.47 (dd, 2H, J=10.4, 7.6 Hz, H-7) 5.91 (t, 1H, J=8.5 Hz, H-13) 6.23 (d, 1H, OH-2') 7.00 to 8.00 (aromatic, 20H) 8.05 (brs, 1H, NH2) 8.30 (d, 1H, J=8.9 Hz, PheCONH) 8.47 (t, 1H, J=5.6 Hz, GlyCONH) 8.56 (t, 1H, J=5.5 Hz, GlyCONH) 9.00 (d, 1H, J=8.5 Hz, CONH-3')

Example 144

Production of Carboxymethylated polyether-7-Gly-Gly-Phe-Gly-paclitaxel (200)

1.0 g of carboxymethylated polyether (175) obtained in step 1 of Example 132 was dissolved in 20 ml of water. To the resultant solution was added 20 ml of DMF while cooling over ice. To the resultant mixture were added 8 ml of a solution obtained by dissolving 180 mg of 7-Gly-Gly-Phe-Gly-paclitaxel (198) obtained in Example 143 in an aqueous DMF (water:DMF ratio=1:1), and 5 ml of a solution obtained by dissolving 1.0 g of WSC.HCl in DMF, followed by stirring at room temperature for 6 hours, to thereby obtain a reaction mixture. The obtained reaction mixture was dialyzed for 2 days against purified water at 4° C. using a dialysis membrane (molecular weight cut-off: 12,000 to 14,000, manufactured and sold by Spectrum Laboratories Inc., U.S.A.). The resultant dialyzate was filtered through a membrane filter (pore size: 0.22 μm), and the resultant filtrate was lyophilized, thereby obtaining 900 mg of carboxymethylated polyether-7-Gly-Gly-Phe-Gly-paclitaxel (200) (hereinafter referred to simply as "compound (200)"). The amount of paclitaxel introduced in compound (200) was calculated from the absorbance of compound (200) at 254 nm and the weight of compound (200). The amount of the introduced paclitaxel was 5.0% by weight, based on the weight of compound (200).

Example 145

Solubility of Compounds (177), (181), (189), (197) and (200) in Physiological Saline Compound (177) obtained in step 3 of Example 132, compound (181) obtained in step 2 of Example 134, compound (189) obtained in step 2 of Example 138, compound (197) obtained in Example 142 and compound (200) obtained Example 144, which are carboxymethylated polyethers having paclitaxel bonded thereto through a linker, were individually evaluated in the following manner.

10 mg of each of compounds (177), (181), (189), (197) and (200) was precisely weighed and individually added to 0.1 ml of physiological saline. As a result, each compound completely dissolved in physiological saline. This means that the dissolution ratios of compounds (177), (181), (189), (197) and (200) in terms of paclitaxel were 3.9 mg/ml (physiological saline), 2.0 mg/ml (physiological saline), 4.0 mg/ml (physiological saline), 4.5 mg/ml (physiological saline) and 5.0 mg/ml (physiological saline), respectively.

On the other hand, 1 mg of paclitaxel (manufactured and sold by Hauser Chemical Research, Inc., U.S.A.) was not able to be completely dissolved in 10 ml of physiological saline.

Example 146

Evaluation of the Release of Paclitaxel from Compounds (177), (179), (181) and (183) in Mouse Plasma and Human Plasma Compound (177) obtained in step 3 of Example 132, compound (179) obtained in step 2 of Example 133, compound (181) obtained in step 2 of Example 134 and compound (183) obtained in step 2 of Example 135, which are carboxymethylated polyethers having paclitaxel bonded thereto through a linker, were individually evaluated in the following manner.

Figure 52:
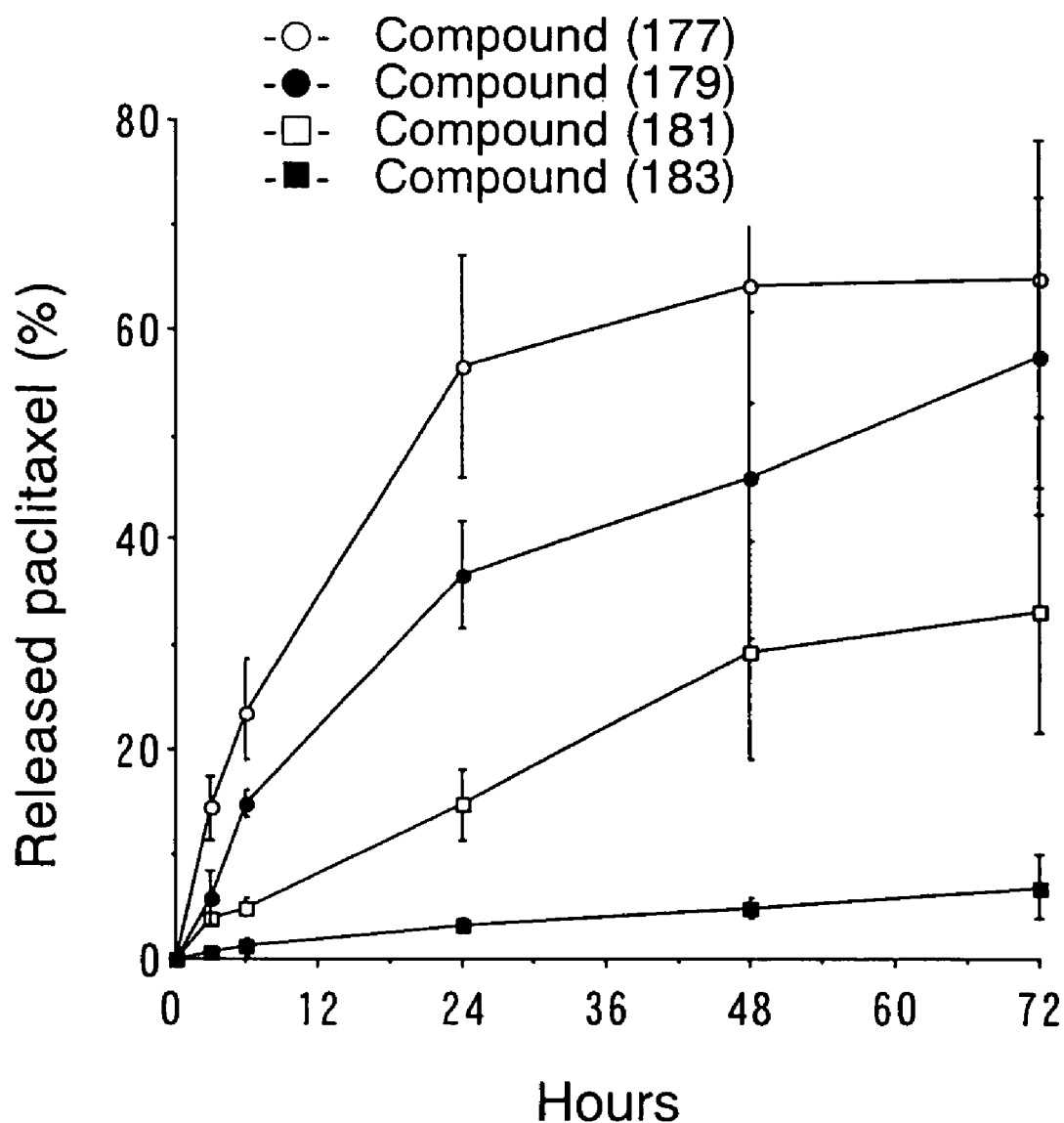
FIG. 52 is a graph showing the change with the lapse of time in the amount of the drug isolated from each of compound (177), compound (179), compound (181) and compound (183) in a mouse plasma having a temperature of 37° C., which change is evaluated in Example 146.
Figure 53:
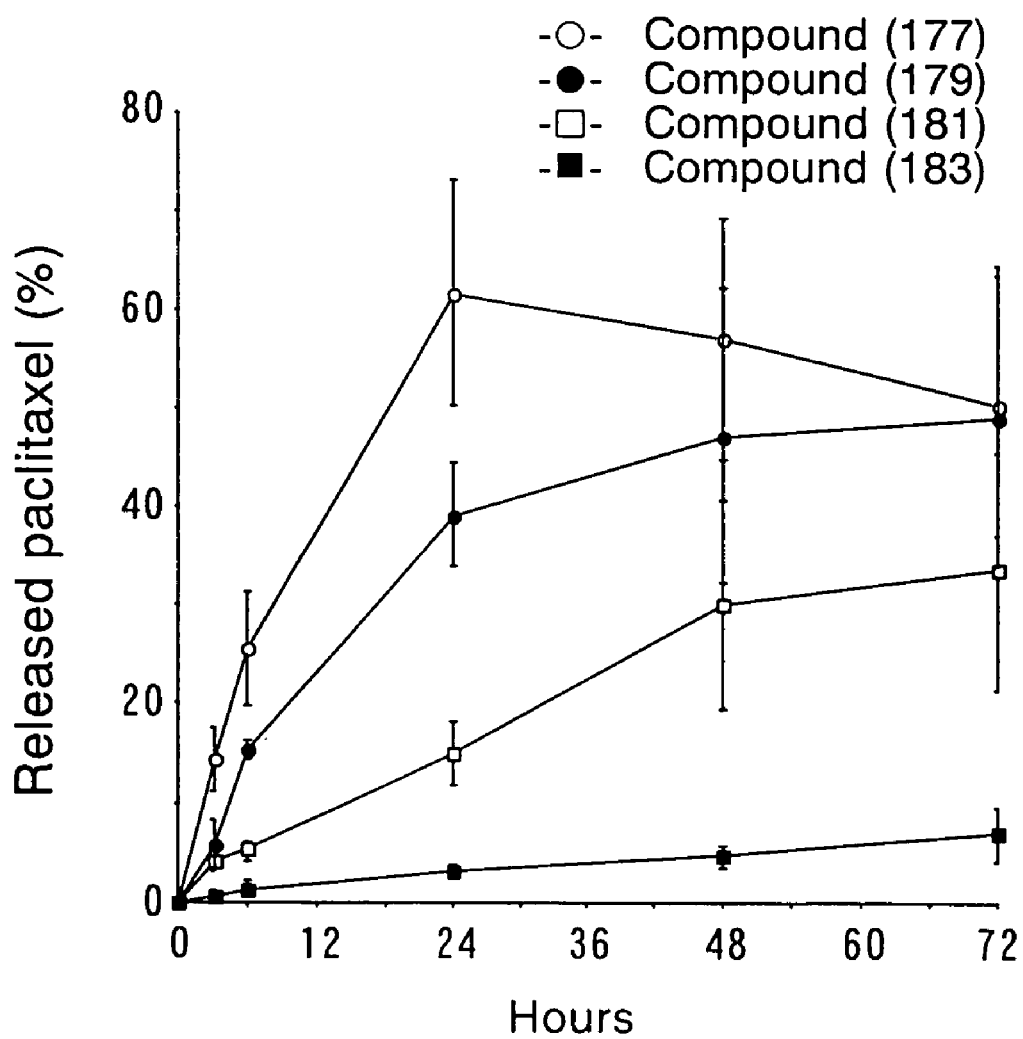
FIG. 53 is a graph showing the change with the lapse of time in the amount of the drug isolated from each of compound (177), compound (179), compound (181) and compound (183) in a human plasma having a temperature of 37° C., which change is evaluated in Example 146.

Each of compounds (177), (179), (181) and (183) was individually dissolved in physiological saline so that the final concentration of the compound in terms of paclitaxel was 125 µg/ml, thereby obtaining four solutions. 20 µl of each of the above-obtained four solutions was individually added to each of 200 µl of mouse plasma and 200 µl of human plasma, and the amounts of paclitaxel released from the compounds at 37° C. were determined as follows. Recovery of paclitaxel from the plasma by solid-phase extraction and subsequent determination of the amount of paclitaxel released from each of compounds (177), (179), (181) and (183) in plasma by HPLC were performed according to the methods described in Yakugaku Zasshi (Journal of the Pharmaceutical Society Japan), 114, p. 351-355 (1994). The changes (with the lapse of time) of the release of paclitaxel from the compounds in mouse plasma and human plasma are shown in FIGS. 52 and 53, respectively. With respect to the rates of the release of paclitaxel from the compounds, the same tendency was observed in both of mouse plasma and human plasma. The magnitudes of the rates of the release of paclitaxel from the respective compounds were in the order of (177)>(179)>(181)>(183). The rate of the release of paclitaxel had a correlation with the magnitude of the steric hindrance of the amino acid used as a linker in the compound.

Example 147

Evaluation of the Release of Paclitaxel from Compounds (177), (185), (187) and (189) in Mouse Plasma and Human Plasma Compounds (177) obtained in step 3 of Example 132, compound (185) obtained in step 2 of Example 136, compound (187) obtained in step 2 of Example 137 and compound (189) obtained in step 2 of Example 138, which are carboxymethylated polyethers having paclitaxel bonded thereto through a linker, were individually evaluated in the following manner.

Figure 54:
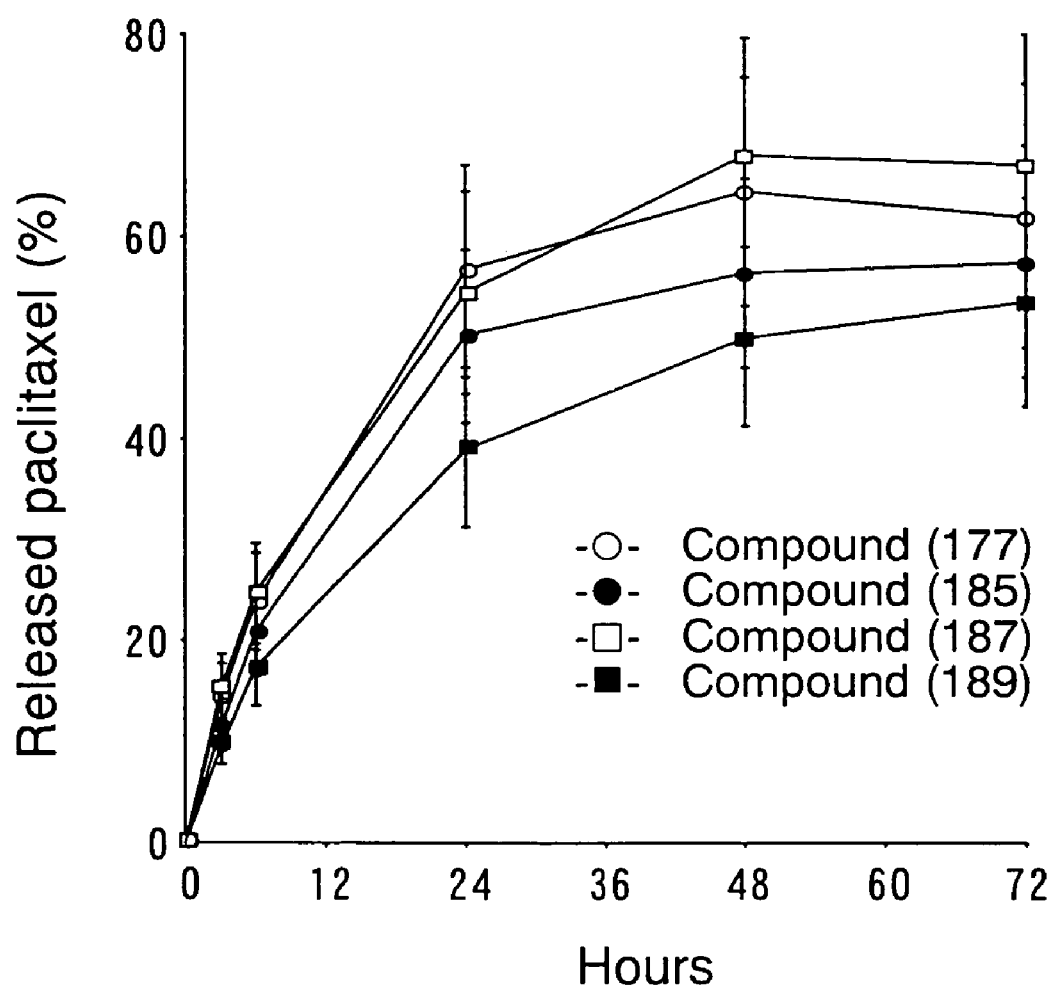
FIG. 54 is a graph showing the change with the lapse of time in the amount of the drug isolated from each of compound (177), compound (185), compound (187) and compound (189) in a mouse plasma having a temperature of 37° C., which change is evaluated in Example 147.
Figure 55:
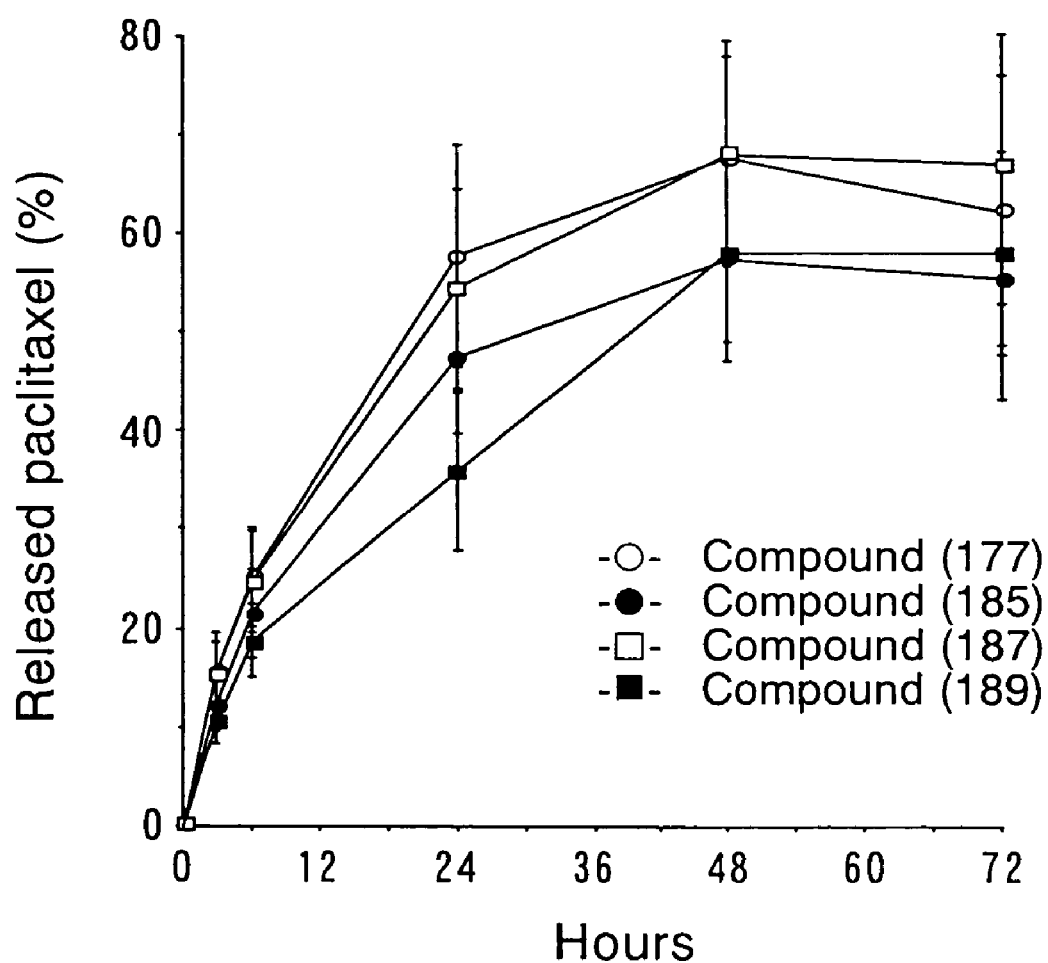
FIG. 55 is a graph showing the change with the lapse of time in the amount of the drug isolated from each of compound (177), compound (185), compound (187) and compound (189) in a human plasma having a temperature of 37° C., which change is evaluated in Example 147.

Each of compounds (177), (185), (187) and (189) was individually dissolved in physiological saline so that the final concentration of the compound in terms of paclitaxel was 125 µg/ml, thereby obtaining four solutions. 20 µl of each of the above-obtained four solutions was individually added to each of 200 µl of mouse plasma and 200 µl of human plasma, and the amounts of paclitaxel released from the respective compounds at 37° C. were determined as follows. Recovery of paclitaxel from the plasma by solid-phase extraction and subsequent determination of the amount of paclitaxel released from each of compounds (177), (185), (187) and (189) in plasma by HPLC were performed according to the methods described in Yakugaku Zasshi (Journal of the Pharmaceutical Society Japan), 114, p. 351-355 (1994). The changes (with the lapse of time) of the release of paclitaxel from the compounds in mouse plasma and human plasma are shown in FIGS. 54 and 55, respectively. In mouse plasma, the magnitudes of the rates of the release of paclitaxel from the compounds (177) and (185) were in the order of (177)>(185). The rate of the release of paclitaxel has a correlation with the magnitude of the steric hindrance of the amino acid used as a linker in the compound. In addition, the rate of the release of paclitaxel has a correlation with the magnitude of the steric hindrance of the peptide used as a linker in the compound. Specifically, in mouse plasma and human plasma, the magnitudes of the rates of the release of paclitaxel from compounds (187) and (189) were in the order of (187)>(189). Accordingly, the rate of the release of paclitaxel has a correlation with the magnitude of the steric hindrance of the amino acid which is directly bonded to the drug.

Example 148

Evaluation of the Release of Paclitaxel from Compounds (197) and (200) in Mouse Plasma and Human Plasma Compound (197) obtained in Example 142 and compound (200) obtained in Example 144, which are carboxymethylated polyethers having paclitaxel bonded thereto through a linker, were individually evaluated in the following manner.

Figure 56:
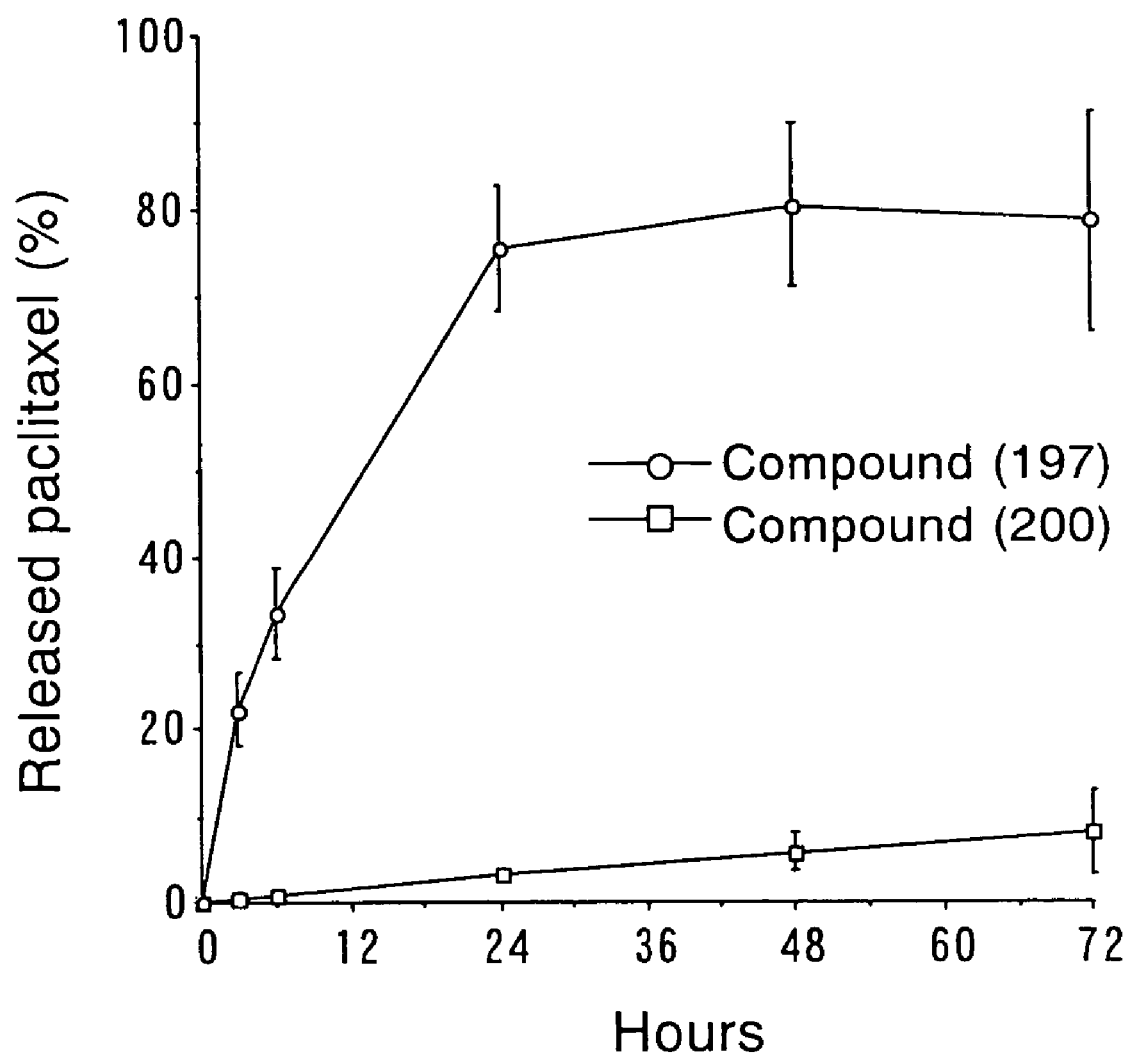
FIG. 56 is a graph showing the change with the lapse of time in the amount of the drug isolated from each of compound (197) and compound (200) in a mouse plasma having a temperature of 37° C., which change is evaluated in Example 148.
Figure 57:
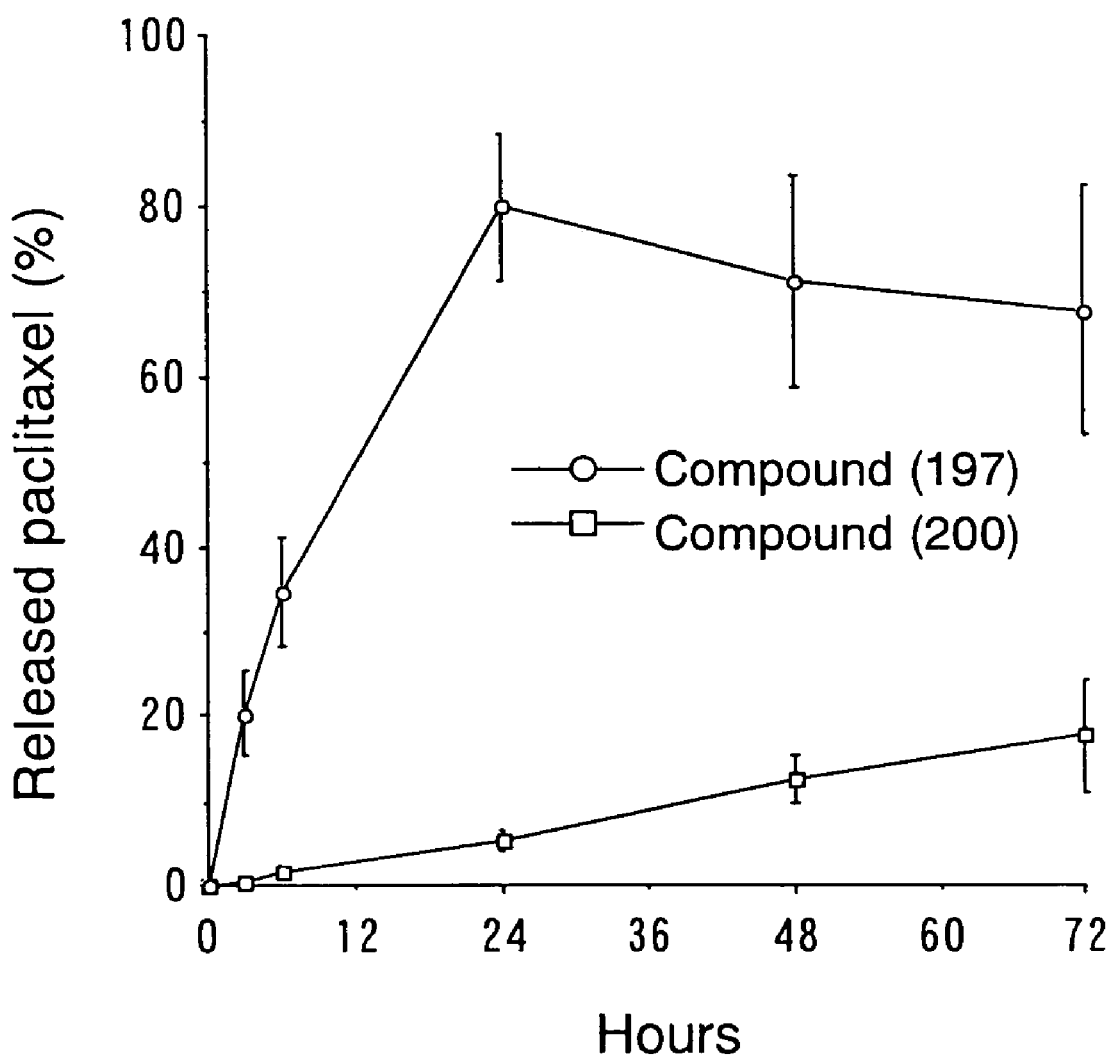
FIG. 57 is a graph showing the change with the lapse of time in the amount of the drug isolated from each of compound (197) and compound (200) in a human plasma having a temperature of 37° C., which change is evaluated in Example 148.

Each of compounds (197) and (200) was individually dissolved in physiological saline so that the final concentration of the compound in terms of paclitaxel was 250 µg/ml, to thereby obtain two solutions. 20 µl of each of the obtained two solutions was individually added to each of 200 µl of mouse plasma and 200 µl of human plasma, and the amounts of paclitaxel released from the respective compounds at 37° C. were determined as follows. Recovery of paclitaxel from the plasma by solid-phase extraction and subsequent determination of the amount of paclitaxel released from each of compounds (197) and (200) in plasma by HPLC were performed according to the methods described in Yakugaku Zasshi (Journal of the Pharmaceutical Society Japan), 114, p. 351-355 (1994). The changes (with the lapse of time) of the release of paclitaxel from the compounds in mouse plasma and human plasma are shown in FIGS. 56 and 57, respectively. The concentration of the paclitaxel released from the compound (197) became maximum after 8 to 24 hours from the addition of compound (197) to plasma. On the other hand, the release of paclitaxel from compound (200) was moderate and sustained, as compared to the case of compound (197).

Example 149

Antitumor Assays (1)

Compound (197) obtained in Example 142, which is a carboxymethylated polyether having paclitaxel bonded thereto through a linker, was evaluated in the following manner.

A test sample solution was prepared by dissolving compound (197) in physiological saline. Further, a control solution was prepared by dissolving paclitaxel as such in a mixture of ethanol, Cremophore EL (manufactured and sold by Sigma, U.S.A.) and physiological saline. Thus, two types of solutions, namely, a test sample solution and a control solution were obtained. Twenty-one female C57BL/6 mice (six weeks old) were divided into three groups, each consisting of seven mice, and subsequently, B16 melanoma cells were intradermally transplanted to the groin of each of the mice ($5 \times 10^6$ cells per mouse). After eight days from the transplantation, each mouse of two groups of the three groups received the administration of the test sample solution by tail-vein injection, wherein the dose of compound (197) in terms of paclitaxel was 50 mg/kg for one group and was 20 mg/kg for the other group. Each mouse of the other one group of the three groups received the administration of the control solution, wherein the control solution was administered in substantially the same manner as in the above-mentioned administration of the test sample solution, except that the dose of paclitaxel was 50 mg/kg, thereby obtaining a control group of mice. Separately, a group consisting of thirteen female C57BL/6 mice (six weeks old), which were transplanted with B16 melanoma cells in the same manner as mentioned above, was provided. Each of the mice of such group received the administration of physiological saline, to thereby obtain a non-treated group of mice. After six days from the administration of the test sample solution, control solution and physiological saline to the mice, evaluation was made of the antitumor activity of compound (197) in terms of the relative average tumor volume (%), namely the ratio of the average tumor volume of the mice of each of the three treated groups (i.e., two groups of mice administered with the test sample solution and one group of mice administered with the control solution), relative to the average tumor volume of the mice of the non-treated group (i.e., a group of mice administered with physiological saline).

The tumor volume was determined as follows. The major and minor diameters (a and b, respectively) (each in mm) of the tumor were externally measured, and the tumor volume (V) was obtained according to the following formula.

$$V = \frac{a \times b^2}{2} \ (mm)^3$$

Figure 58:
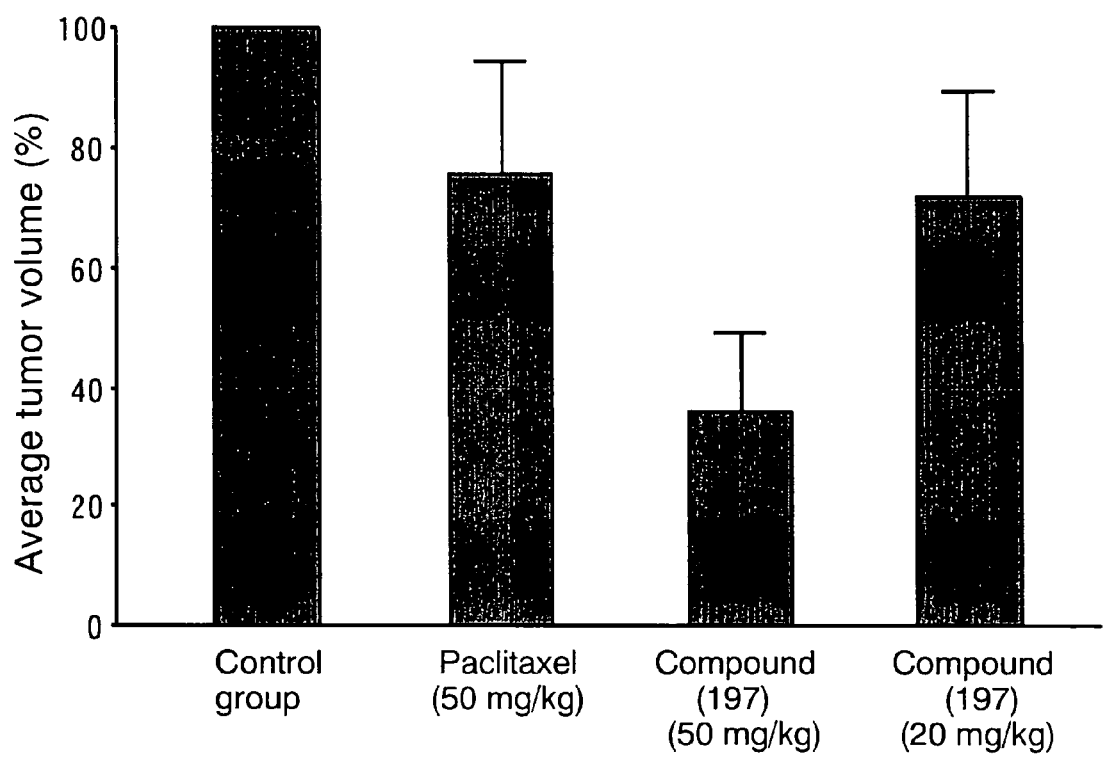
FIG. 58 is a graph showing the average tumor volume of each of a non-administered mouse group and test solution-administered mouse groups, which average tumor volume is evaluated in Example 149 after 6 days from the administration of the test solution.

The relationship between the dose of compound (197) and the relative average tumor volumes (%) is shown in FIG. 58. The antitumor activity of compound (197) (which employs the resin of the present invention), observed with respect to the group of mice which had received the administration of compound (197) at the dose of 50 mg/kg (in terms of paclitaxel), was significantly excellent, as compared to the antitumor activity of paclitaxel, observed with respect to the group of mice which had received the administration of paclitaxel as such.

Example 150

Antitumor Assays (2)

Compound (197) obtained in Example 142, which is a carboxymethylated polyether having paclitaxel bonded thereto through a linker, was evaluated in the following manner.

A test sample solution was prepared by dissolving compound (197) in physiological saline. Further, a control solution was prepared by dissolving paclitaxel as such in a mixture of ethanol, Cremophore EL (manufactured and sold by Sigma, U.S.A.) and physiological saline. Thus, two types of solutions, namely, a test sample solution and a control solution were obtained. Six female Balb/C mice (six weeks old) were divided into two groups, each consisting of three mice, and subsequently, a 4% suspension of Colon 26 tumor cells was intradermally transplanted to the flank of each of the mice. After two days from the transplantation, each mouse of one group of the two groups received the administration of the test sample solution by tail-vein injection, wherein the dose of compound (197) was 50 mg/kg in terms of paclitaxel. Each mouse of the other group of the two groups received administration of the control solution, wherein the control solution was administered in the same manner as in the case of the administration of the test sample solution (i.e., the dose of paclitaxel was 50 mg/kg), thereby obtaining a control group of mice. Separately, a group consisting of five female Balb/C mice (six weeks old), which were transplanted with Colon 26 tumor cells in the same manner as mentioned above, was provided. Each of the mice of such group received the administration of only physiological saline in the same manner as in the case of the administration of the test sample solution, to thereby obtain a non-treated group of mice. Each of the above-mentioned administration of the test sample solution, control solution and physiological saline was performed every 4 days, 7 times in total in the above-mentioned manner.

Evaluation was made of the antitumor activity in terms of the change (with the lapse of time) of the average tumor volume (%). The tumor volume was determined as follows. The major and minor diameters (a and b, respectively) (each in mm) of the tumor were externally measured, and the tumor volume (V) was obtained according to the following formula.

$$V = \frac{a \times b^2}{2} \ (mm)^3$$

Figure 59:
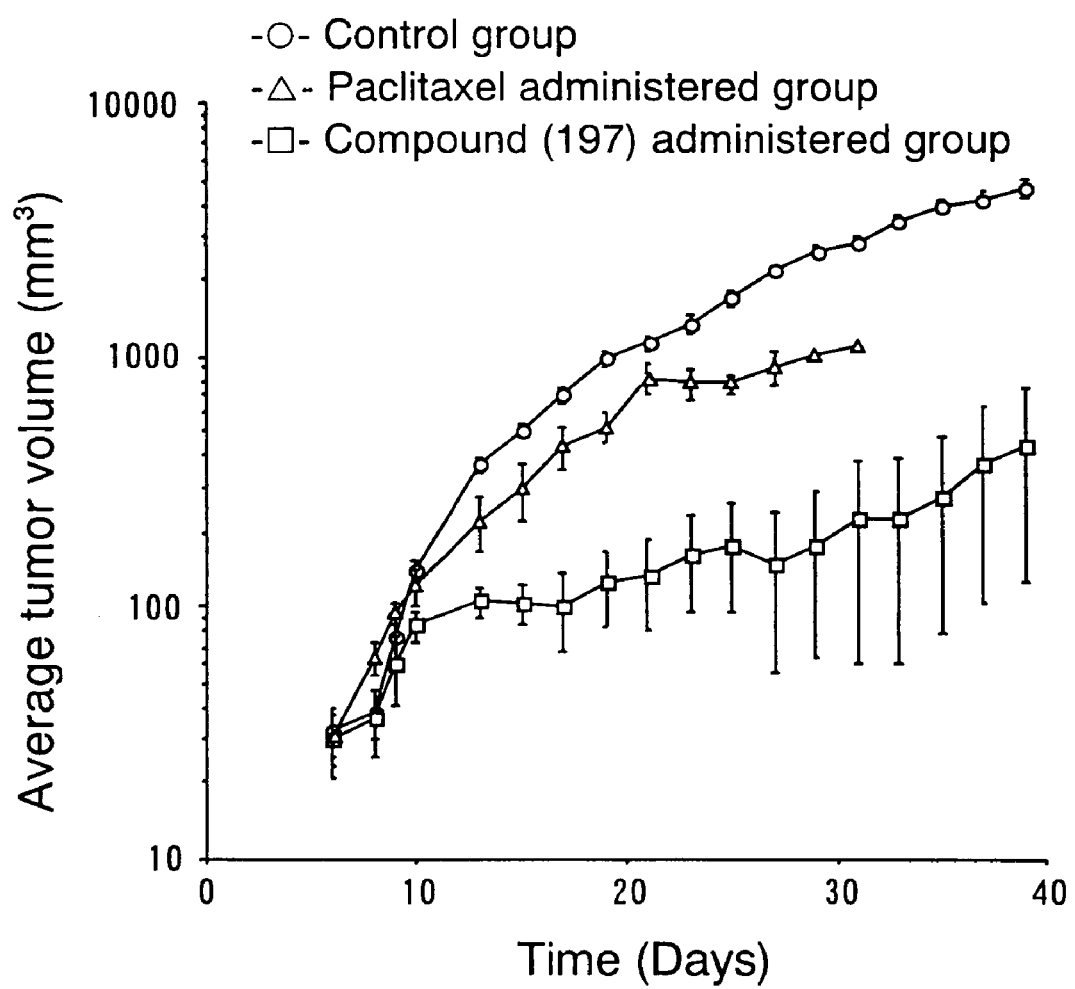
FIG. 59 is a graph showing the change with the lapse of time in the average tumor volume of each of a non-administered mouse group and test solution-administered mouse groups, which change is evaluated in Example 150.

The changes (with the lapse of time) in average tumor volume of the mice which had received the administration with respect to each of the test sample solution, control solution and physiological saline, are shown in FIG. 59. As is apparent from FIG. 59, the antitumor activity of compound (197), observed with respect to the group of mice which had received the administration of compound (197) at the dose of 50 mg/kg (in terms of paclitaxel), was significantly excellent, as compared to the antitumor activity of paclitaxel, observed with respect to the group of mice which had received the administration of paclitaxel as such.

Example 151

Antitumor Assays (3)

Compound (177) obtained in step 3 of Example 132, compound (179) obtained in step 2 of Example 133, compound (181) obtained in step 2 of Example 134 and compound (183) obtained in step 2 of Example 135, which are carboxymethylated polyethers having paclitaxel bonded thereto through a linker, were individually evaluated in the following manner.

Test sample solutions were prepared by dissolving each of compounds (177), (179), (181) and (183) individually in physiological saline. Further, a control solution was prepared by dissolving paclitaxel as such in a mixture of ethanol, Cremophore EL (manufactured and sold by Sigma, U.S.A.) and physiological saline. Thus, five types of solutions, namely, four types of test sample solutions and one control solution were obtained. Twenty-five female Balb/C mice (six weeks old) were divided into five groups, each consisting of five mice, and subsequently, a 4% suspension of Colon 26 tumor cells was intradermally transplanted to the flank of each of the mice. After two days from the transplantation, four groups of the five groups of mice respectively received the administration of the four test sample solutions obtained above, wherein the dose of the compound was 50 mg/kg in terms of paclitaxel. Each mouse of the other group of the five groups received administration of the control solution, wherein the control solution was administered in the same manner as in the case of the administration of the test sample solution (i.e., the dose of paclitaxel was 50 mg/kg), thereby obtaining a control group of mice. Separately, a group consisting of nine female Balb/C mice (six weeks old), which were transplanted with Colon 26 tumor cells in the same manner as mentioned above, was provided. Each of the mice of such group received the administration of only physiological saline in the same manner as in the case of the administration of the test sample solution, to thereby obtain a non-treated group of mice. Each of the above-mentioned administration of the test sample solution, control solution and physiological saline was performed every 7 days, 4 times in total in the above mentioned manner.

Evaluation was made of the antitumor activity in terms of the change (with the lapse of time) of the average tumor volume (%). The tumor volume was determined as follows. The major and minor diameters (a and b, respectively) (each in mm) of the tumor were externally measured, and the tumor volume was obtained according to the following formula.

$$V = \frac{a \times b^2}{2} \text{ (mm)}^3$$

Figure 60:
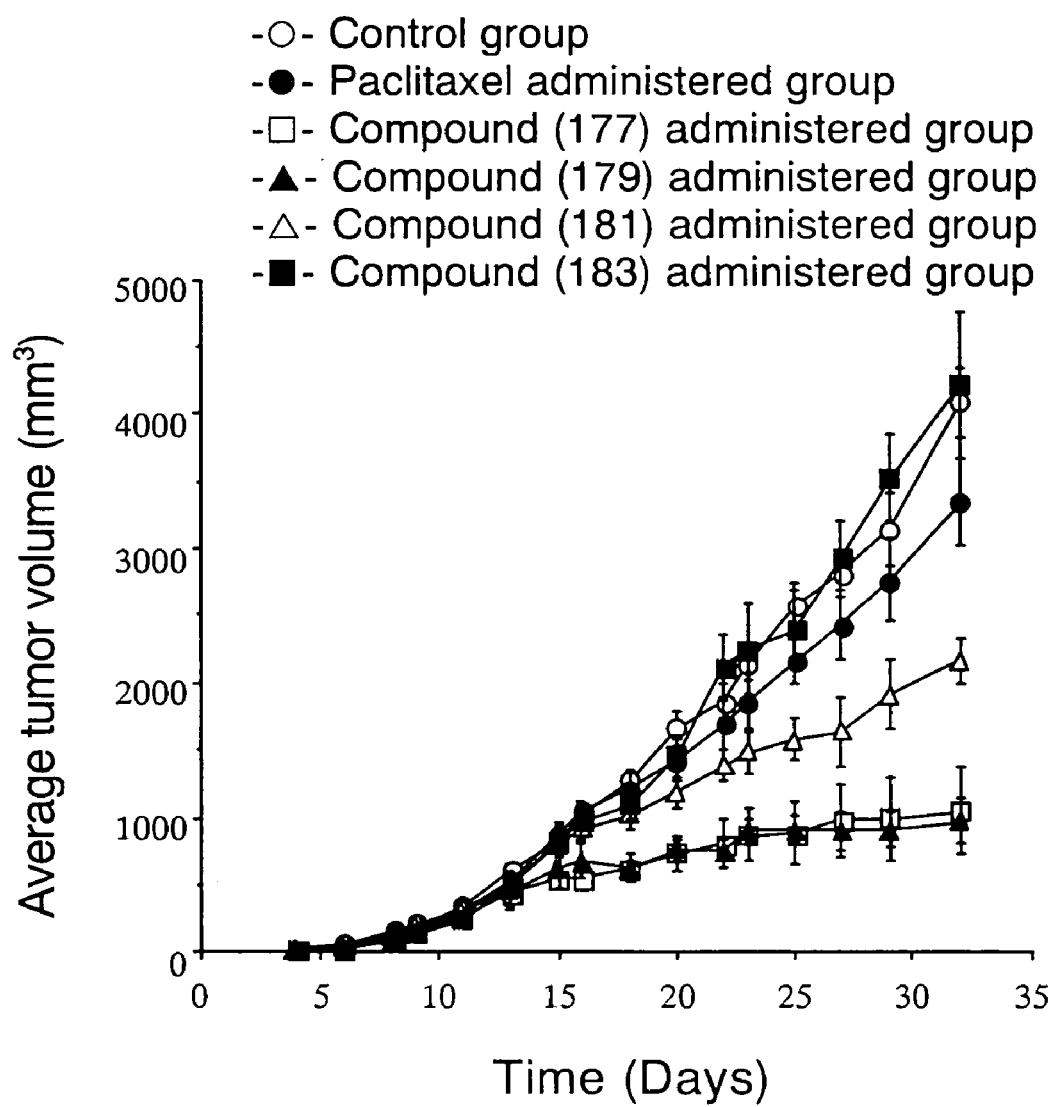
FIG. 60 is a graph showing the change with the lapse of time in the average tumor volume of each of a non-administered mouse group and test solution-administered mouse groups, which change is evaluated in Example 151.

The changes (with the lapse of time) in average tumor volume of the mice which had received the administrations with respect to each of the test sample solutions, control solution and physiological saline, are shown in FIG. 60. As is apparent from FIG. 60, the antitumor activity of compounds (177) and (179), observed with respect to the groups of mice which had respectively received the administration of compounds (177) and (179) each at the dose of 50 mg/kg (in terms of paclitaxel), was significantly excellent, as compared to the antitumor activity of paclitaxel, observed with respect to the group of mice which had received the administration of paclitaxel as such. The magnitudes of the antitumor activity were in the order of (177)/(179)>(181)>(183)/paclitaxel.

Example 152

Production of 20-Gly-camptothecin Hydrochloride (201)

(Step 1) 263 mg (1.5 mmol) of BOC-Gly, 122 mg (1.0 mmol) of DMAP and 174 mg (0.5 mmol) of (S)-(+)-camptothecin (manufactured and sold by Tokyo Kasei Kogyo Co., Ltd., Japan) were dissolved in 20 ml of methylene chloride to obtain a solution. To the obtained solution was added 189 mg (1.5 mmol) of DIPC, followed by stirring at room temperature for 3.5 hours to effect a reaction, thereby obtaining a reaction mixture. The obtained reaction mixture was washed with 0.1 N aqueous hydrochloric acid and saturated saline and, then, the solvents were distilled off from the washed reaction mixture under reduced pressure. The resultant residue was purified by silica gel column chromatography (silica gel: Art No. 9385, Silica gel 60, 200-400 mesh, manufactured and sold by Merck KGaA, Germany; column: 4.0×30 cm; eluent: methylene chloride/acetonitrile ratio=70/30), thereby obtaining 311 mg of 20-BOC-Gly-camptothecin (202).

(Step 2) 300 mg of the above-obtained 20-BOC-Gly-camptothecin (202) was dissolved in 5 ml of methylene chloride, followed by addition thereto of 2 ml of TFA at room temperature, to obtain a mixture. The obtained mixture was stirred for 5 minutes to thereby remove the BOC group. The solvents were distilled off from the resultant product under reduced pressure. The resultant residue was purified by silica gel column chromatography (silica gel: Art No. 9385, Silica gel 60, 200-400 mesh, manufactured and sold by Merck KGBA, Germany; column: 4.0×50 cm; eluent: acetonitrile/methanol/methylene chloride ratio=Oct. 10, 1990), followed by treatment with an anion exchange resin, thereby obtaining 211 mg of 20-Gly-camptothecin hydrochloride (201).

$^1$H-NMR (solvent: DMSO-d6; reference standard: TMS): δ0.97 (s, 3H) 2.20 (m, 2H) 4.08, 4.34 (dd, 2H) 5.32 (s, 2H) 5.56 (s, 2H) 7.32 (s, 1H) 7.73 (t, 1H) 7.88 (t, 1H) 8.15 (d, 1H) 8.17 (d, 1H) 8.56 (brs, 2H) 8.72 (s, 1H)

$^{13}$C-NMR (solvent: DMSO-d6; reference standard: TMS): 7.53, 30.18, 38.6 to 40.2, 50.10, 66.29, 77.42, 95.51, 118.78, 127.63, 127.82, 128.45, 128.66, 129.49, 130.43, 131.58, 144.72, 145.97, 147.77, 152.13, 156.39, 166.77

Example 153

Production of Carboxymethylated polyether-20-Gly-camptothecin (203)

1.0 g of carboxymethylated polyether (175) obtained in step 1 of Example 132 was dissolved in 20 ml of water. To the resultant solution was added 20 ml of DMF while cooling over ice. To the resultant mixture were added 8 ml of a solution obtained by dissolving 200 mg of 20-Gly-camptothecin hydrochloride (201) obtained in Example 152 in an aqueous DMF (water:DMF ratio=1:1), and 5 ml of a solution obtained by dissolving 1.0 g of WSC.HCl in DMF, followed by stirring at room temperature for 6 hours, to thereby obtain a reaction mixture. The obtained reaction mixture was dialyzed for 2 days against purified water at 4° C. using a dialysis membrane (molecular weight cutoff: 12,000 to 14,000, manufactured and sold by Spectrum Laboratories Inc., U.S.A.). The resultant dialyzate was filtered through a membrane filter (pore size: 0.22 µm), and the resultant filtrate was lyophilized, thereby obtaining 950 mg of carboxymethylated polyether-20-Gly-camptothecin (203) (hereinafter referred to simply as "compound (203)"). The amount of camptothecin introduced in compound (203) was calculated from the absorbance of compound (203) at 254 nm and the weight of compound (203). The amount of the introduced camptothecin was 3.5% by weight, based on the weight of compound (203).

Example 154

Production of 20-Gly-Gly-Phe-Gly-camptothecin Hydrochloride (204)

(Step 1) 1,736 mg (3 mmol) of Trt-Gly-Gly-Phe-Gly obtained in step 4 of Example 139, 244 mg (2 mmol) of DMAP and 348 mg (1 mmol) of (S)-(+)-camptothecin were dissolved in 100 ml of methylene chloride to obtain a solution. To the obtained solution was added 378 mg (3 mmol) of DIPC, followed by stirring overnight at room temperature to effect a reaction, thereby obtaining a reaction mixture. The obtained reaction mixture was washed with 0.1 N aqueous hydrochloric acid and saturated saline and, then, the solvents were distilled off from the washed reaction mixture under reduced pressure. The resultant residue was purified by silica gel column chromatography (silica gel: Art No. 9385, Silica gel 60, 200-400 mesh, manufactured and sold by Merck KGaA, Germany; column: 4.0×30 cm; eluent: methylene chloride/acetonitrile ratio=70/30), thereby obtaining 750 mg of 20-20-Trt-Gly-Gly-Phe-Gly-camptothecin (205).

(Step 2) 700 mg of the above-obtained 20-20-Trt-Gly-Gly-Phe-Gly-camptothecin (205) was dissolved in 8 ml of a 75% acetic acid to obtain a solution containing an acetate. The obtained solution was stirred for 20 minutes to thereby remove the Trt group. The solvents were distilled off from the resultant product under reduced pressure. The resultant residue was converted from an acetate to a corresponding hydrochloride with an anion exchange resin (AG1-X8; manufactured and sold by Bio-Rad Laboratories, Inc., Japan), and subsequently purified by silica gel column chromatography (silica gel: Art No. 9385, Silica gel 60, 200-400 mesh, manufactured and sold by Merck KGaA, Germany; column: 4.0×

50 cm; eluent: methanol/methylene chloride ratio=15/85), thereby obtaining 532 mg of 20-Gly-Gly-Phe-Gly-camptothecin hydrochloride (204).

$^1$H-NMR (solvent: DMSO-d6; reference standard: TMS): δ0.93 (t, 3H) 2.32 (m, 2H) 2.77, 3.06 (dd, dd, 2H) 3.27 (s, 2H) 3.61, 3.76 (d, d, 2H) 4.11, 4.21 (dd, dd, 2H) 4.55 (m, 1H) 5.27 (s, 2H) 5.51 (s, 2H) 7.15 (m, 1H) 7.19 (s, 1H) 7.22 (m, 4H) 7.71 (t, 1H) 7.87 (t, 1H) 8.12 (d, 1H) 8.17 (d, 1H) 8.23 (brs, 1H) 8.31 (d, 1H) 8.68 (s, 1H) 8.68 (brs, 2H)

$^{13}$C-NMR (solvent: DMSO-d6; reference standard: TMS): 7.52, 30.42, 37.43, 40.41, 41.64, 42.21, 50.08, 53.96, 66.28, 76.27, 95.20, 118.87, 126.20, 127.59, 127.80, 128.01, 128.39, 128.79, 129.06, 129.50, 130.37, 131.49, 137.82, 145.11, 145.87, 147.72, 152.12, 156.41, 167.00, 168.35, 168.84, 171.68

Example 155

Production of Carboxymethylated polyether-20-Gly-Gly-Phe-Gly-camptothecin (206)

1.0 g of carboxymethylated polyether (175) obtained in step 1 of Example 132 was dissolved in 20 ml of water. To the resultant solution was added 20 ml of DMF while cooling over ice. To the resultant mixture were added 8 ml of a solution obtained by dissolving 200 mg of 20-Gly-Gly-Phe-Gly-camptothecin hydrochloride (204) obtained in Example 154 in an aqueous DMF (water:DMF ratio=1:1), and 5 ml of a solution obtained by dissolving 1.0 g of WSC.HCl in DMF, followed by stirring at room temperature for 6 hours, to thereby obtain a reaction mixture. The obtained reaction mixture was dialyzed for 2 days against purified water at 4° C. using a dialysis membrane (molecular weight cutoff: 12,000 to 14,000, manufactured and sold by Spectrum Laboratories Inc., U.S.A.). The resultant dialyzate was filtered through a membrane filter (pore size: 0.22 μm), and the resultant filtrate was lyophilized, thereby obtaining 1 g of carboxymethylated polyether-20-Gly-Gly-Phe-Gly-camptothecin (206) (hereinafter referred to simply as "compound (206)"). The amount of camptothecin introduced in compound (206) was calculated from the absorbance of compound (206) at 254 nm and the weight of compound (206). The amount of the introduced camptothecin was 4.5% by weight, based on the weight of compound (206).

Example 156

Production of 21-Ala-dexamethasone Hydrochloride (207)

(Step 1) 568 mg (3 mmol) of BOC-Ala, 244 mg (2 mmol) of DMAP and 392 mg (1 mmol) of dexamethasone were dissolved in 30 ml of methylene chloride to obtain a solution. To the obtained solution was added 252 mg (2 mmol) of DIPC, followed by stirring at room temperature for 0.5 hour to effect a reaction, thereby obtaining a reaction mixture. The obtained reaction mixture was washed with 0.1 N aqueous hydrochloric acid and saturated saline and, then, the solvents were distilled off from the washed reaction mixture under reduced pressure. The resultant residue was purified by silica gel column chromatography (silica gel: Art No. 9385, Silica gel 60, 200-400 mesh, manufactured and sold by Merck KGaA, Germany; column: 4.0×30 cm; eluent: methylene chloride/acetonitrile ratio=80/20), thereby obtaining 550 mg of 21-BOC-Ala-dexamethasone (208).

(Step 2) 500 mg of the above-obtained 21-BOC-Ala-dexamethasone (208) was dissolved in 10 ml of methylene chloride, followed by addition thereto of 1 ml of TFA at room temperature, to obtain a mixture. The obtained mixture was stirred for 2 hours to thereby remove the BOC group. The solvents were distilled off from the resultant product under reduced pressure. The resultant residue was purified by silica gel column chromatography (silica gel: Art No. 9385, Silica gel 60, 200-400 mesh, manufactured and sold by Merck KGaA, Germany; column: 4.0×50 cm; eluent: acetonitrile/methanol/methylene chloride ratio=May 15, 1985), followed by treatment with an anion exchange resin, thereby obtaining 410 mg of 21-Ala-dexamethasone hydrochloride (207).

$^1$H-NMR (solvent: DMSO-d6; reference standard: TMS): δ0.80 (d, 3H) 0.90 (s, 3H) 1.09 (s, 1H) 1.33 to 1.79 (m, 4H) 1.49 (s, 3H) 1.50 (d, 3H) 2.08 to 2.91 (m, 6H) 3.35 (brs, 1H) 4.17 (m, 1H) 4.24 (q, 1H) 4.95 (d, 1H) 5.20 (d, 1H) 5.27 (s, 1H) 5.53 (d, 1H) 6.01 (s, 1H) 6.23 (dd, 1H) 7.33 (d, 1H) 8.46 (brs, 1H)

$^{13}$C-NMR (solvent: DMSO-d6; reference standard: TMS): 15.20, 16.09, 16.29, 23.08, 27.41, 30.41, 32.05, 33.70, 35.61, 35.83, 43.42, 47.80, 48.05, 48.25, 69.38, 70.41, 90.61, 101.42, 124.19, 129.03, 152.94, 167.17, 169.98, 185.41, 204.30

Example 157

Production of Carboxymethylated polyether-21-Ala-dexamethasone (209)

1.0 g of carboxymethylated polyether (175) obtained in step 1 of Example 132 was dissolved in 20 ml of water. To the resultant solution was added 20 ml of DMF while cooling over ice. To the resultant mixture were added 8 ml of a solution obtained by dissolving 200 mg of 21-Ala-dexamethasone hydrochloride (207) obtained in Example 156 in an aqueous DMF (water:DMF ratio=1:1), and 5 ml of a solution obtained by dissolving 1.0 g of WSC.HCl in DMF, followed by stirring at room temperature for 6 hours, to thereby obtain a reaction mixture. The obtained reaction mixture was dialyzed for 2 days against purified water at 4° C. using a dialysis membrane (molecular weight cutoff: 12,000 to 14,000, manufactured and sold by Spectrum Laboratories Inc., U.S.A.). The resultant dialyzate was filtered through a membrane filter (pore size: 0.22 μm), and the resultant filtrate was lyophilized, thereby obtaining 0.95 g of carboxymethylated polyether-21-Ala-dexamethasone (209) (hereinafter referred to simply as "compound (209)"). The amount of dexamethasone introduced in compound (209) was calculated from the absorbance of compound (209) at 240 nm and the weight of compound (209). The amount of the introduced dexamethasone was 3.5% by weight, based on the weight of compound (209).

Example 158

Production of 21-Leu-dexamethasone Hydrochloride (210)

(Step 1) 747 mg (3 mmol) of BOC-Leu.H$_2$O, 244 mg (2 mmol) of DMAP and 392 mg (1 mmol) of dexamethasone were dissolved in 30 ml of methylene chloride to obtain a solution. To the obtained solution was added 252 mg (2 mmol) of DIPC, followed by stirring at room temperature for 13 hours to effect a reaction, thereby obtaining a reaction mixture. The obtained reaction mixture was washed with 0.1 N aqueous hydrochloric acid and saturated saline and, then, the solvents were distilled off from the washed reaction mixture under reduced pressure. The resultant residue was purified by silica gel column chromatography (silica gel: Art No. 9385, Silica gel 60, 200-400 mesh, manufactured and sold by Merck KGaA, Germany; column: 4.0×30 cm; eluent: methylene chloride/acetonitrile ratio=80/20), thereby obtaining 600 mg of 20-BOC-Leu-dexamethasone (211).

(Step 2) 500 mg of the above-obtained 20-BOC-Leu-dexamethasone (211) was dissolved in 5 ml of methylene chloride, followed by addition thereto of 1 ml of TFA at room temperature, to obtain a mixture. The obtained mixture was stirred for 2 hours to thereby remove the BOC group. The solvents were distilled off from the resultant product under reduced pressure. The resultant residue was purified by silica gel column chromatography (silica gel: Art No. 9385, Silica gel 60, 200-400 mesh, manufactured and sold by Merck KGaA, Germany; column: 4.0×50 cm; eluent: acetonitrile/methanol/methylene chloride ratio=May 15, 1985), followed by treatment with an anion exchange resin, thereby obtaining 510 mg of 21-Leu-dexamethasone hydrochloride (210).

$^1$H-NMR (solvent: DMSO-d6; reference standard: TMS): δ0.79 (d, 3H) 0.88 (d, 3H) 0.89 (s, 3H) 0.92 (d, 3H) 1.08 (m, 1H) 1.34 to 1.81 (m, 6H) 1.49 (s, 3H) 1.86 (m, 1H) 2.12 to 2.88 (m, 6H) 3.35 (s, 2H) 3.44 (q, 1H) 4.16 (m, 1H) 4.85 (d, 1H) 5.02 (d, 1H) 5.17 (s, 1H) 5.47 (d, 1H) 6.01 (s, 1H) 6.23 (dd, 1H) 7.31 (d, 1H)

$^{13}$C-NMR (solvent: DMSO-d6; reference standard: TMS): 15.27, 16.30, 21.87, 23.11, 23.15, 24.15, 27.46, 30.50, 32.13, 33.79, 35.52, 35.79, 43.46, 43.56, 48.15, 48.16, 52.16, 68.21, 70.62, 90.67, 101.47, 124.24, 129.06, 153.04, 167.27, 175.47, 185.48, 204.90

Example 159

Production of Carboxymethylated polyether-21-Leu-dexamethasone (212)

1.0 g of carboxymethylated polyether (175) obtained in step 1 of Example 132 was dissolved in 20 ml of water. To the resultant solution was added 20 ml of DMF while cooling over ice. To the resultant mixture were added 8 ml of a solution obtained by dissolving 200 mg of 21-Leu-dexamethasone hydrochloride (210) obtained in Example 158 in an aqueous DMF (water:DMF ratio=1:1), and 5 ml of a solution obtained by dissolving 1.0 g of WSC.HCl in DMF, followed by stirring at room temperature for 6 hours, to thereby obtain a reaction mixture. The obtained reaction mixture was dialyzed for 2 days against purified water at 4° C. using a dialysis membrane (molecular weight cut-off: 12,000 to 14,000, manufactured and sold by Spectrum Laboratories Inc., U.S.A.). The resultant dialyzate was filtered through a membrane filter (pore size: 0.22 μm), and the resultant filtrate was lyophilized, thereby obtaining 1 g of carboxymethylated polyether-21-Leu-dexamethasone (212) (hereinafter referred to simply as "compound (212)"). The amount of dexamethasone introduced in compound (212) was calculated from the absorbance of compound (212) at 240 nm and the weight of compound (212). The amount of the introduced dexamethasone was 4.0% by weight, based on the weight of compound (212).

Example 160

Production of 21-Ile-dexamethasone Hydrochloride (213)

(Step 1) 1,040 mg (4.5 mmol) of BOC-Ile, 366 mg (3 mmol) of DMAP and 588 mg (1.5 mmol) of dexamethasone were dissolved in 30 ml of methylene chloride to obtain a solution. To the obtained solution was added 378 mg (3 mmol) of DIPC, followed by stirring at room temperature for 14 hours to effect a reaction, thereby obtaining a reaction mixture. The obtained reaction mixture was washed with 0.1 N aqueous hydrochloric acid and saturated saline and, then, the solvents were distilled off from the washed reaction mixture under reduced pressure. The resultant residue was purified by silica gel column chromatography (silica gel: Art No. 9385, Silica gel 60, 200-400 mesh, manufactured and sold by Merck KGaA, Germany; column: 4.0×30 cm; eluent: methylene chloride/acetonitrile ratio=80/20), thereby obtaining 620 mg of 20-BOC-Ile-dexamethasone (214).

(Step 2) 600 mg of the above-obtained 20-BOC-Ile-dexamethasone (214) was dissolved in 5 ml of methylene chloride, followed by addition thereto of 1 ml of TPA at room temperature, to obtain a mixture. The obtained mixture was stirred for 2 hours to thereby remove the BOC group. The solvents were distilled off from the resultant product under reduced pressure. The resultant residue was purified by silica gel column chromatography (silica gel: Art No. 9385, Silica gel 60, 200-400 mesh, manufactured and sold by Merck KGaA, Germany; column: 4.0×50 cm; eluent: acetonitrile/methanol/methylene chloride ratio=May 15, 1985), followed by treatment with an anion exchange resin, thereby obtaining 580 mg of 21-Ile-dexamethasone hydrochloride (213).

$^1$H-NMR (solvent: DMSO-d6; reference standard: TMS): δ0.80 (d, 3H) 0.90 (s, 3H) 0.93 (t, 3H) 1.03 (d, 3H) 1.08 (m, 1H) 1.33 to 1.86 (m, 6H) 1.49 (s, 3H) 1.50 (d, 1H) 2.13 to 2.91 (m, 6H) 4.11 (d, 1H) 4.16 (m, 1H) 4.99 (d, 1H) 5.17 (d, 1H) 5.26 (s, 1H) 5.55 (d, 1H) 6.01 (s, 1H) 6.23 (dd, 1H) 7.34 (d, 1H) 8.44 (s, 1H)

$^{13}$C-NMR (solvent: DMSO-d6; reference standard: TMS): 11.69, 13.69, 15.21, 16.21, 23.09, 25.02, 27.44, 30.45, 32.08, 33.72, 35.81, 35.61, 36.34, 43.44, 48.08, 48.22, 56.15, 69.54, 70.41, 90.72, 101.46, 124.19, 129.00, 152.96, 167.18, 168.66, 185.41, 204.40

Example 161

Production of Carboxymethylated polyether-21-Ile-dexamethasone (215)

1.0 g of carboxymethylated polyether (175) obtained in step 1 of Example 132 was dissolved in 20 ml of water. To the resultant solution was added 20 ml of DMF while cooling over ice. To the resultant mixture were added 8 ml of a solution obtained by dissolving 200 mg of 21-Ile-dexamethasone hydrochloride (213) obtained in Example 160 in an aqueous DMF (water:DMF ratio=1:1), and 5 ml of a solution obtained by dissolving 1.0 g of WSC.HCl in DMF, followed by stirring at room temperature for 6 hours, to thereby obtain a reaction mixture. The obtained reaction mixture was dialyzed for 2 days against purified water at 4° C. using a dialysis membrane (molecular weight cutoff: 12,000 to 14,000, manufactured and sold by Spectrum Laboratories Inc., U.S.A.). The resultant dialyzate was filtered through a membrane filter (pore size: 0.22 μm), and the resultant filtrate was lyophilized, thereby obtaining 0.95 g of carboxymethylated polyether-21-Ile-dexamethasone (215) (hereinafter referred to simply as "compound (215)"). The amount of dexamethasone introduced in compound (215) was calculated from the absorbance of compound (215) at 240 nm and the weight of compound (215). The amount of the introduced dexamethasone was 3.0% by weight, based on the weight of compound (215).

Example 162

Solubility of Compounds (203), (206), (209), (212) and (215) in Physiological Saline Compound (203) obtained in Example 153 and compound (206) obtained in Example 155, which are carboxymethylated polyethers having camptothecin bonded thereto through a linker, and compound (209) obtained in Example 157, compound (212) obtained in Example 159 and compound (215) obtained Example 161, which are carboxymethylated polyethers having dexamethasone bonded thereto through a linker, were individually evaluated in the following manner.

10 mg of each of compounds (203) and (206) was precisely weighed and individually added to 0.1 ml of physiological saline. As a result, each compound completely dissolved in physiological saline. This means that the dissolution ratios of compounds (203) and (206) in terms of camptothecin were 3.5 mg/ml (physiological saline) and 4.5 mg/ml (physiological saline), respectively. Further, 10 mg of each of compounds (209), (212) and (215) was precisely weighed and individually added to 0.1 ml of physiological saline. As a result, each compound completely dissolved in physiological saline. This means that the dissolution ratios of compounds (209), (212) and (215) in terms of dexamethasone were 3.5 mg/ml (physiological saline), 4.0 mg/ml (physiological saline) and 3.0 mg/ml (physiological saline), respectively.

Example 163

Evaluation of the Release of Dexamethasone from Compounds (209), (212) and (215) in Mouse Plasma Compound (209) obtained in Example 157, compound (212) obtained in Example 159 and compound (215) obtained in Example 161, which are carboxymethylated polyethers having dexamethasone bonded thereto through a linker, were individually evaluated in the following manner.

Each of compounds (209), (212) and (215) was individually dissolved in physiological saline so that the final concentration of the compound in terms of dexamethasone was 80 µg/ml, thereby obtaining three solutions. 50 µl of each of the above-obtained three solutions was individually added to 250 µl of mouse plasma to obtain a dexamethasone-containing plasma, and the amounts of dexamethasone released from the respective compounds at 37° C. were determined. Recovery of dexamethasone from the plasma by solid-phase extraction and subsequent determination of the amount of dexamethasone released from each of compounds (209), (212) and (215) in plasma by HPLC were performed as follows. To 250 µl of the dexamethasone-containing plasma obtained above was added 250 µl of a phosphate buffer solution (pH value: 7.4), followed by an addition of 3 ml of an internal standard which is an acetonitrile-methanol solution of hydrocortisone acetate (acetonitrile:methanol ratio=4:1; hydrocortisone acetate concentration: 10 ng/ml), to obtain a mixture. The obtained mixture was subjected to centrifugation (3000 rpm, 10 minutes, 4° C.) to thereby obtain a supernatant containing dexamethasone. To 700 µl of the obtained supernatant was added 700 µl of distilled water, and the resultant mixture was filtered through a membrane filter (pour size: 0.4 µm), thereby obtaining a sample solution. The obtained sample solution was analyzed by means of HPLC under the following conditions to determine the amount of dexamethasone released from the compound in plasma.

Conditions for HPLC:
  Column: Asahipak HIKARISIL C18 (4.6×150 mm),
  Flow rate: 1.0 ml/min,
  Column temperature: 25° C.,
  Detection wavelength: 240 nm, and
  Mobile phase: Linear gradient
    0 min: 20% aqueous acetonitrile (20% $CH_3CN/H_2O$)
    20 min: 50% aqueous acetonitrile (50% $CH_3CN/H_2O$).

Figure 61:
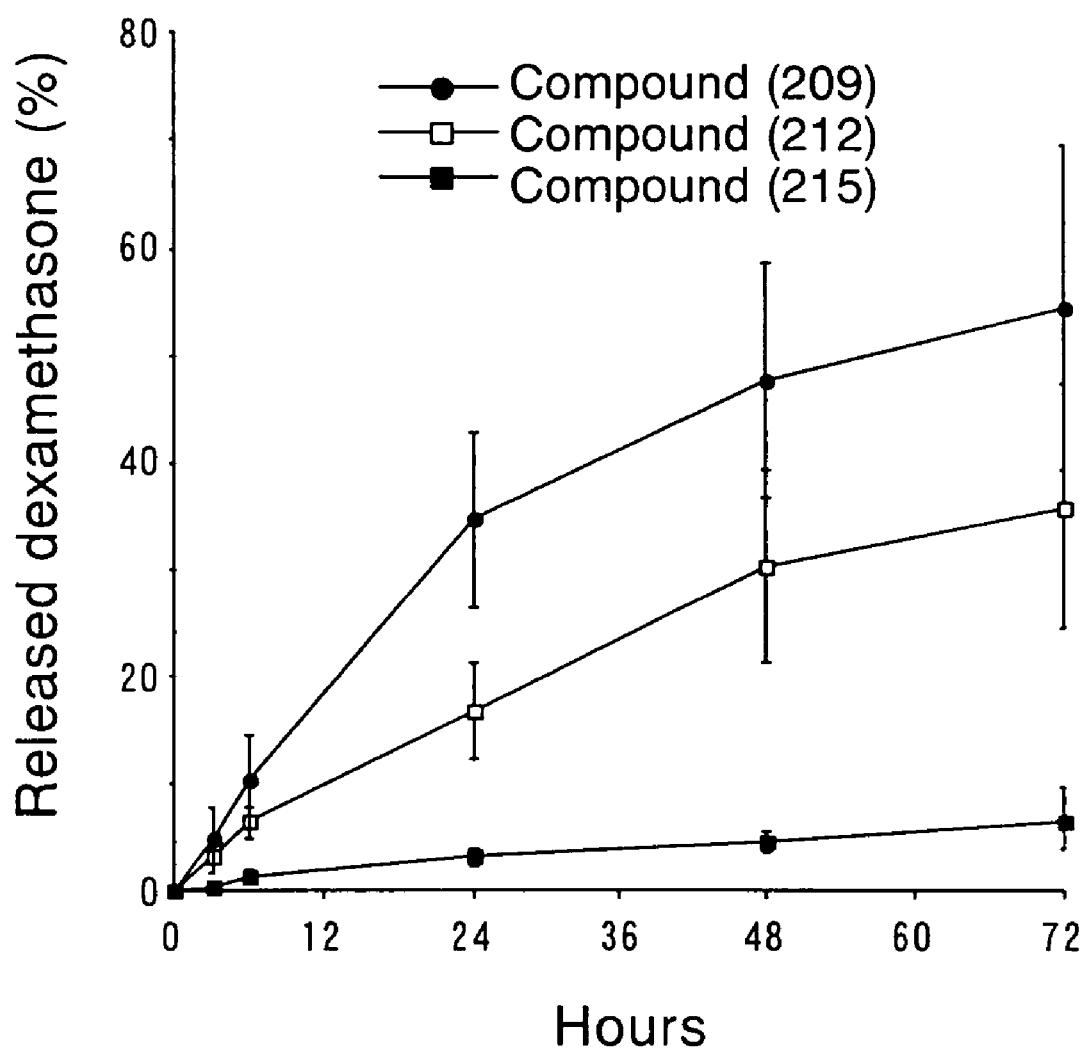
FIG. 61 is a graph showing the change with the lapse of time in the amount of the drug isolated from each of compound (209), compound (212) and compound (215) in a mouse plasma having a temperature of 37° C., which change is evaluated in Example 163.

The changes (with the lapse of time) of the release of dexamethasone from each of the compounds in mouse plasma are shown in FIG. 61. The magnitudes of the rates of the release of dexamethasone from the respective compounds were in the order of (209)>(212)>(215). The rate of the release of dexamethasone had a correlation with the magnitude of the steric hindrance of the amino acid used as a linker in the compound.

Example 164 and Comparative Example 4

(1) Production of poly(2-methoxyethyl)acrylate 2.6 g of 2-methoxyethyl acrylate was dissolved in 20 ml of dioxane under an argon atmosphere and, then, a solution obtained by dissolving 0.33 g of 2,2'-azobisisobutyronitrile (AIBN) in 2 ml of dioxane was added thereto, followed by stirring at 75° C. overnight, to thereby effect a reaction. The resultant reaction mixture was added to 200 ml of hexane, thereby obtaining a precipitate. The obtained precipitate was dissolved in 10 ml of tetrahydrofuran (THF) and, then, poured into 200 ml of hexane, thereby obtaining a precipitate. The obtained precipitate was washed with ether, thereby obtaining poly(2-methoxyethyl) acrylate (hereinafter referred to as "pMEA") in an amount of 2.4 g.

(2) Evaluation of Plasma Protein Adsorption

Copolymer (139) produced in Example 99, copolymer (142) produced in Example 100, and two types of acrylate resins (namely pMEA obtained above and a conventional poly(2-hydroxymethyl)methacrylate (pHEMA)) were individually evaluated in the following manner, wherein copolymers (139) and (142) were used for Example 164, and PMEA and pHEMA were used for Comparative Example 4.

Resin solutions respectively having resin concentrations of 10, 1, 0.1, 0.01 and 0.001 mg/ml were prepared by dissolving different amounts of a resin individually in an aqueous 70% ethanol solution. 0.2 ml of each of the obtained resin solutions was individually dispensed into a well of Coaster 96-well EIA plate (Product No. 3590, manufactured and sold by Corning Incorporated, U.S.A.). Then, the EIA plate was allowed to stand still at 4° C. overnight to thereby cause the wells (containing the resin solutions) to be coated with the resin. Subsequently, the resin solutions were removed by suction, followed by drying, to thereby obtain an EIA plate having resin-coated wells. Adhesion of fibrinogen to the resin-coated wells was evaluated as follows.

0.1 ml of a fibrinogen solution containing 5 µg/ml of a human fibrinogen (manufactured and sold by Biogenesis Inc., U.S.A.) was dispensed into the resin-coated wells of the above-obtained EIA plate, and was allowed to remain in contact with the surfaces of the wells at 37° C. for 2 hours. Subsequently, the amounts of human fibrinogen adsorbed on the surfaces of the wells were determined by enzyme-linked immunosorbent assay (ELISA) using a horseradish peroxidase (HRP)-conjugated goat IgG fraction to human fibrinogen (manufactured and sold by EY Laboratories, Inc., U.S.A.).

Figure 62:
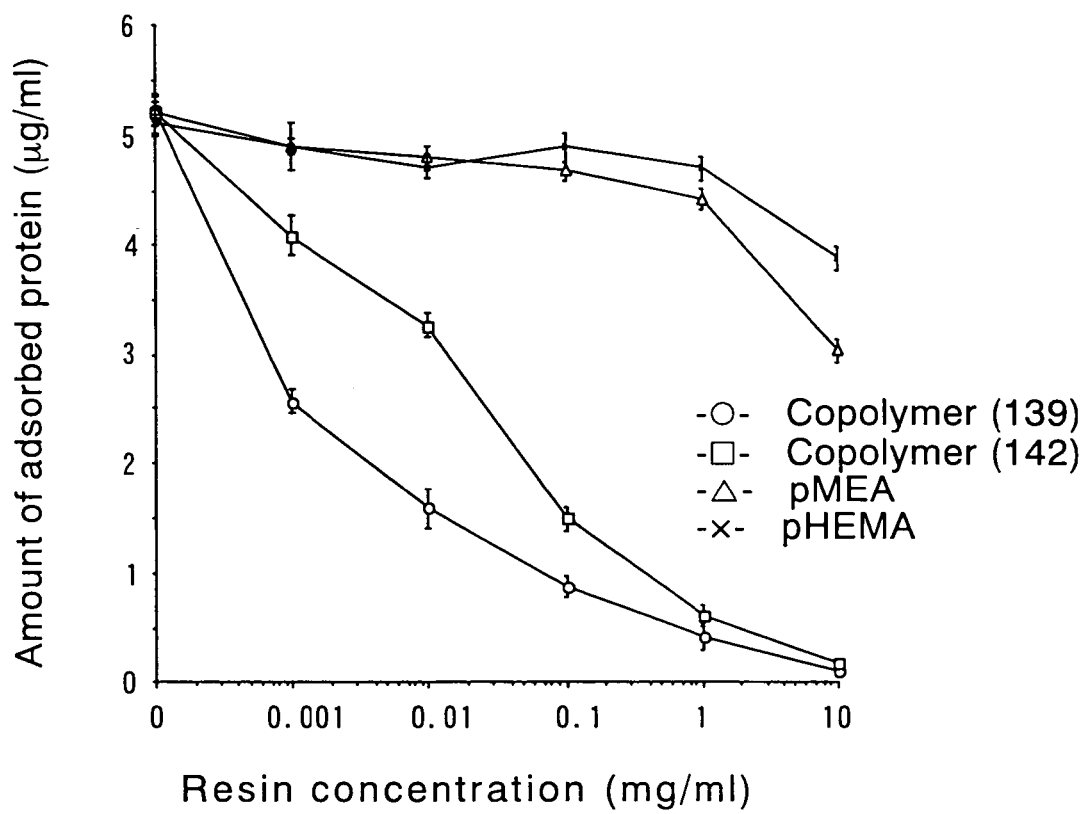
FIG. 62 is a graph showing the results of the evaluation of human fibrinogen adhesion, which evaluation is made in Example 164.

The results are shown in FIG. 62. The determination of the amounts of fibrinogen adsorbed on the wells of the EIA plate was performed using a calibration curve prepared by a method in which fibrinogen standard solutions having known fibrinogen concentrations are dispensed into wells of an EIA plate which is the same as used above, and the amounts of fibrinogen adsorbed on the surfaces of the wells are measured.

FIG. 62 shows that copolymers (139) and (142) were greatly effective for inhibiting human fibrinogen adsorption to the wells of the EIA plate than, as compared to the acrylate resins (namely pHEMA and pMEA).

INDUSTRIAL APPLICABILITY

The body fluid compatible and biocompatible resin of the present invention is advantageous not only in that the adhesion of biological substances (such as a biological tissue, a cell and a platelet) to the resin can be suppressed, and the activation of a platelet, a complement and the like by the resin can also be suppressed, but also in that the resin of the present invention is highly safe for living organisms and remains stable in a body fluid for a long time. Therefore, the body fluid compatible and biocompatible resin of the present invention can be advantageously used as a molding material or a coating material in the production of various biological and medical products. Specific examples of biological and medical products include a membrane for an artificial kidney, a plasma separation membrane, a membrane for an artificial lung, an artificial blood vessel, an anti-adhesion membrane, a wound dressing, an artificial skin and a leukocyte removal membrane. By virtue of the above-mentioned excellent characteristics of the resin of the present invention, even when a portion of the resin of the present invention is separated from the above-mentioned biological and medical products and released into a body fluid (for example, because the biological and medical products produced from the resin of the present invention are used for a long time), it is possible to suppress damage to an organ since the resin of the present invention has not only less interaction with a living organism but also less accumulation in an organ.

Further, when a compound having a pharmaceutical activity is bonded to the resin of the present invention through an amino acid or a peptide (i.e., the so-called "linker") to form a drug complex, such a drug complex enables the delivery of the compound having a pharmaceutical activity to a target tissue without being recognized by a biological tissue when the drug complex is administered to a living body. The drug complex enables an adjustment of the drug release rate. Furthermore, the drug complex improves the dissolution of a drug bonded to the resin of the present invention through a linker in physiological saline as compared to the case where a drug per se is dissolved in physiological saline and, hence, the drug complex enables an intravenous administration of a drug without using an adjuvant.

The invention claimed is:

1. A body fluid compatible and biocompatible resin for use in a medical treatment involving a contact of said resin with at least one member selected from the group consisting of a body fluid and a biological tissue, which comprises a random copolymer that is represented by the following formula (4):

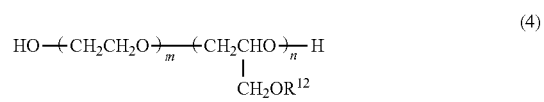

(4)

wherein:
each $R^{12}$ independently represents a —$CH_2COOH$ group, a —$CH_2COONa$ group or a —$CH_2COOR^{13}$ group, wherein each $R^{13}$ represents a group comprising an amino acid or peptide having chemically bonded thereto a compound having a pharmaceutical activity;
m and n are integers,
said random copolymer having a weight average molecular weight in the range of from 27,000 to 65,000, as determined by GPC using a calibration curve obtained with respect to standard polyethylene glycol (PEG) samples, each having a narrow molecular weight distribution.

2. The body fluid compatible and biocompatible resin according to claim 1, wherein said compound having a pharmaceutical activity is a compound having an anticancer activity.

3. The body fluid compatible and biocompatible resin according to claim 1 wherein said compound having a pharmaceutical activity is an adrenocortical hormone, a vasodilator or an enzyme inhibitor.

* * * * *